United States Patent
McGowan et al.

(10) Patent No.: US 11,786,532 B2
(45) Date of Patent: Oct. 17, 2023

(54) 2-PYRIDONES AND METHODS OF USE THEREOF

(71) Applicant: ALIGOS THERAPEUTICS, INC., South San Francisco, CA (US)

(72) Inventors: David Craig McGowan, Brussels (BE); Pierre Jean-Marie Bernard Raboisson, Wavre (BE); Koen Vandyck, Beringen (BE); Jerome Deval, El Granada, CA (US); Leonid Beigelman, San Mateo, CA (US)

(73) Assignee: Aligos Therapeutics, Inc., South San Francisco, CA (US)

(*) Notice: Subject to any disclaimer, the term of this patent is extended or adjusted under 35 U.S.C. 154(b) by 0 days.

(21) Appl. No.: 17/520,173

(22) Filed: Nov. 5, 2021

(65) Prior Publication Data

US 2022/0143032 A1    May 12, 2022

Related U.S. Application Data

(60) Provisional application No. 63/195,962, filed on Jun. 2, 2021, provisional application No. 63/110,812, filed on Nov. 6, 2020.

(51) Int. Cl.
| | |
|---|---|
| *A61K 31/53* | (2006.01) |
| *A61P 1/16* | (2006.01) |
| *A61P 3/04* | (2006.01) |
| *A61K 31/4439* | (2006.01) |
| *A61K 45/06* | (2006.01) |
| *C07D 401/12* | (2006.01) |
| *C07D 401/14* | (2006.01) |
| *C07D 413/12* | (2006.01) |
| *C07D 471/04* | (2006.01) |

(52) U.S. Cl.
CPC .......... *A61K 31/53* (2013.01); *A61K 31/4439* (2013.01); *A61K 45/06* (2013.01); *A61P 1/16* (2018.01); *A61P 3/04* (2018.01); *C07D 401/12* (2013.01); *C07D 401/14* (2013.01); *C07D 413/12* (2013.01); *C07D 471/04* (2013.01)

(58) Field of Classification Search
CPC .... A61K 31/53; A61K 31/4439; A61K 45/06; A61P 1/16; A61P 3/04; C07D 401/12; C07D 401/14; C07D 413/12; C07D 471/04
See application file for complete search history.

(56) References Cited

FOREIGN PATENT DOCUMENTS

| WO | WO-2016/037578 A1 | 3/2016 |
|---|---|---|
| WO | WO-2020/169069 A1 | 8/2020 |
| WO | WO-2021/057791 A1 | 4/2021 |
| WO | WO-2021/121210 A1 | 6/2021 |
| WO | WO-2021/143706 A1 | 7/2021 |

OTHER PUBLICATIONS

International Search Report and Written Opinion dated Apr. 25, 2022 in PCT/US2021/058300.
Aleiwi et al., "A reliable Pd-mediated hydrogenolytic deprotection of BOM group of uridine ureido nitrogen," Tetrahedron Letters, 2012, 53:3758-3762.
Bookout et al., "Anatomical Profiling of Nuclear Receptor Expression Reveals a Hierarchical Transcriptional Network," Cell, Aug. 25, 2006, 126(4):789-799.
Chalasani et al., "The Diagnosis and Management of Non-alcoholic Fatty Liver Disease: Practice Guideline by the American Gastroenterological Association, American Association for the Study of Liver Diseases, and American College of Gastroenterology," Gastroenterology, 2012, 142(7):1592-1609.
Drummond et al., "Evaluation and Synthesis of Aminohydroxyisoxazoles and Pyrazoles as Potential Glycine Agonists," J. Med. Chem., 1989, 32(9):2116-2128.
Dulai et al., "Increased Risk of Mortality by Fibrosis Stage in Nonalcoholic Fatty Liver Disease: Systematic Review and Meta-Analysis," Hepatology, May 2017, 65(5):1557-1565.
Erion et al., "Targeting thyroid hormone receptor-B agonists to the liver reduces cholesterol and triglycerides and improves the therapeutic index," PNAS, Sep. 25, 2007, 104(39):15490-15495.
Flamant et al., "International Union of Pharmacology. LIX. The Pharmacology and Classification of the Nuclear Receptor Superfamily: Thyroid Hormone Receptors," Pharmacological Reviews, 2006, 58(4):705-711.
Haning et al., "Novel heterocyclic thryomimetics," Bioorganic & Medicinal Chemistry Letters, Apr. 1, 2005, 15(7):1835-1840.

(Continued)

*Primary Examiner* — Joseph K McKane
*Assistant Examiner* — Jed A Kucharczk
(74) *Attorney, Agent, or Firm* — Foley & Lardner LLP

(57) ABSTRACT

Disclosed herein are compounds of Formula I":

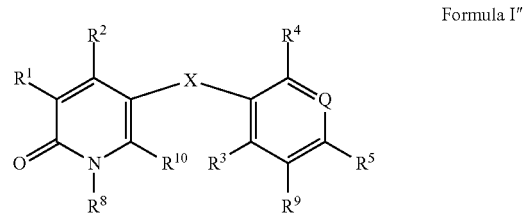

Formula I"

or a stereoisomer or a tautomer thereof, or a pharmaceutically acceptable salt thereof, pharmaceutical compositions comprising such compounds, and methods of treating disease by administering or contacting a subject with one or more of the above compounds.

19 Claims, No Drawings

(56) References Cited

OTHER PUBLICATIONS

Hartley et al., "A Thyroid Hormone-Based Strategy for Correcting the Biochemical Abnormality in X-Linked Adrenoleukodystrophy," Endocrinology, May 2017, 158(5):1328-1338.
Harvey et al., "Mechanism of Thyroid Hormone Action," Thyroid, Jun. 2002, 12(6):441-446.
Hirano et al., "Thyromimetics: a review of recent reports and patents (2004-2009)," Expert Opin. Ther. Pat., Feb. 2010, 20(2):213-228.
Iikuni et al., "Development of the 99mTc-Hydroxamamide Complex as a Probe Targeting Carbonic Anhydrase IX," Molecular Pharmaceutics, 2019, 16(4):1489-1497.
Katane et al., "Identification of Novel D-Amino Acid Oxidase Inhibitors by in Silico Screening and Their Functional Characterization in Vitro," J. Med. Chem., 2013, 56(5):1894-1907.
Kowalik et al., "Thyroid Hormones, Thyromimetics and Their Metabolites in the Treatment of Liver Disease," Frontiers in Endocrinology, Jul. 10, 2018, 9:382, 11 pages.
Lavery et al., "Pd2dba3/Bippyphos: A Robust Catalyst System for the Hydroxylation of Aryl Halides with Broad Substrate Scope," Advanced Synthesis & Catalysis, 2013, 355(5):981-987.
Lazo et al., "Nonalcoholic Fatty Liver disease (NAFLD): Is It Really a Serious Condition?", Hepatology, Oct. 2012, 56(4):1580-1584.
Li et al., "Highly Chemoselective, Transition-Metal-Free Transamidation of Unactivated Amides and Direct Amidation of Alkyl Esters by N—C/O—C Cleavage," J. Am. Chem. Soc. 2019, 141:11161-11172.
Liljebris et al., "Investigation of Potential Bioisosteric Replacements for the Carboxyl Groups of Peptidomimetic Inhibitors of Protein Tyrosine Phosphatase 1B: Identification of a Tetrazole-Containing Inhibitor with Cellular Activity," J. Med. Chem. 2002, 45(9):1785-1798.
Micale et al., "Development of peptidomimetic boronates as proteasome inhibitors," European Journal of Medicinal Chemistry, 2013, 64:23-34.
Milanesi et al., "Beam Me in: Thyroid Hormone Analog Targets Alternative Transporter in Mouse Model of X-Linked Adrenoleukodystrophy," Endocrinology, May 2017, 158:1116-1119.
Rigby et al., "Vinyl Isocyanates as Aza Diene Equivalents. A Method for the Synthesis of Functionalized 4-Hydroxy-2-(1H)-pyridones," J. Org. Chem., 1986, 51(5):1374-1376.
Sakata et al., "Regioselectivity in the Iridium-Catalyzed [2+2+2]Cycloaddition of Unsymmetrical alpha,omega-Diynes with Nitrile: A DFT Study," Organometallics, 2020, 39(11):2091-2101.
Serfaty et al., "Definition and natural history of metabolic steatosis: clinical aspects of NAFLD, NASH and cirrhosis," Diabetes and Metabolism, 2008, 34:634-637.
Sorensen et al., "A Novel Route to 5-Substituted 3-Isoxazolols. Cyclization of N,O-DiBoc Beta-keto Hydroxamic Aids Synthesized via Acyl Meldrum's Acids," J. Org. Chem., 2000, 65(4):1003-1007.
Ushkov et al., "Rational Catalysis Design on the Basis of Mechanistic Understanding: Highly Efficient PD-Catalyzed Cyanation of Aryl Bromides with NaCN in Recyclable Solvents," J. Am. Chem. Soc., 2011, 133:10999-11005.
Yang et al., "Synthesis of conformationally restricted nicotine analogues by intramolecular [3+2] cycloaddition," Tetrahedron, 2006, 62(10):2240-2246.
Younossi et al., "Current and Future Therapeutic Regimens for Nonalcoholic Fatty Liver Disease and Nonalcoholic Steatohepatitis," Hepatology, Jul. 2018, 68(1):361-371.
Younossi et al., "Global Epidemiology of Nonalcoholic Fatty Liver Disease—Meta-Analytic Assessment of Prevalence, Incidence and Outcomes," Hepatology, Jul. 2016, 64(1):73-84.
Zhai et al., "A Facile Synthesis of cis-1-Methyl-1,2,3,3a,4,8b-hexahydropyrrolo[3,2-f]pyrindine, an Annulated Nicotine Analog," Organic Letters, 2002, 4(25):4385-4386.
Zhi-Qiang et al., "Palladium-Catalyzed Hydroxylation of Aryl Halides with Boric Acid," Organic Letters, 2020, 22:8470-8474.

2-PYRIDONES AND METHODS OF USE THEREOF

CROSS-REFERENCE TO RELATED APPLICATIONS

This application claims the benefit of priority to U.S. Provisional Patent Application Ser. No. 63/110,812, filed on Nov. 6, 2020, and U.S. Provisional Patent Application Ser. No. 63/195,962, filed on Jun. 2, 2021, the entire disclosures of which are hereby incorporated by reference herein.

FIELD OF THE DISCLOSURE

The present disclosure is in the field of pharmaceutical compounds and preparations and method of their use in the treatment of disease. In particular, the present disclosure is in the field of THR-β modulators and their use.

BACKGROUND OF THE DISCLOSURE

In parallel with the global increase in obesity, nonalcoholic fatty liver disease (NAFLD) is becoming the leading cause of chronic liver disease and liver transplantation worldwide [1,2]. NAFLD is believed to affect 30% of the adult population and 70-80% of individuals who are obese and diabetic. NAFLD is defined as excess liver fat accumulation greater than 5% induced by causes other than alcohol intake. NAFLD progresses to liver inflammation (nonalcoholic steatohepatitis, NASH) and fibrosis in a variable proportion of individuals, ultimately leading to liver failure and hepatocellular carcinoma (HCC) in susceptible individuals [3].

In the United States alone, NASH is the third most common indication for liver transplantation and is on a trajectory to become the most common [4]. The most important medical need in patients with NAFLD and NASH is an effective treatment to halt the progression and possibly reverse fibrosis, which is the main predictor of liver disease evolution [5,6].

Thyroid hormone (TH) is essential for normal development, growth and metabolism of all vertebrates. Its effects are mediated principally through triiodothyronine (T3), which acts as a ligand for the TH receptors (TRs, or THRs) β1, β2 and α1 [7]. In the absence of ligand, TR first binds as a heterodimer or homodimer on TH response elements (TRE) located in the promoter regions of target genes, where it interacts with corepressors. Upon ligand binding, the TR homodimers are dissociated in favor of heterodimer formation with the retinoid-X receptor (RXR), resulting in release of the corepressors and recruitment of coactivators. This new complex attracts a large number of proteins which engage the RNA polymerase II in the transcription of the targeted genes.

Two different genetic loci, denoted THRA and THRB, are responsible for encoding multiple interrelated TR isoforms that have distinct tissue distributions and biological functions. The two major isoforms with the broadest level of tissue expression are TRα1 and TRβ1 [8]. While TRα1 is expressed first during fetal development and is widely expressed in adult tissues, TRβ1 appears later in development and displays highest expression in the adult liver, kidney, and lung [9]. TRα1 is a key regulator of cardiac output, whereas TRβ1 helps in the control of metabolism in the liver. Importantly, the natural thyroid hormone T3 activates both TRα1 and TRβ1 without any significant selectivity.

Design of thyromimetic small molecule agents led to the identification of TR (or THR) agonists with varying levels of TRβ selectivity despite high structural similarity between the ligand-binding domains for TRβ and TRα. TRβ selectivity achieved by some of these compounds resulted in an improved therapeutic index for lipid lowering relative to cardiac effects such as heart rate, cardiac hypertrophy, and contractility [10-12].

Another strategy to avoid activation of TRα in cardiac tissue is to design prodrugs of phosphonate-containing TR agonists that are specifically converted to the active agonist in the liver but remain stable as an inactive prodrug in blood and extrahepatic tissues, including the heart [13]. TRα and TRβ agonists are also used in indications other than liver-related disorders, as has been known in the art. For example, TRβ selective agonists may be useful in the treatment of X-linked adrenoleukodystrophy [14, 15].

SUMMARY

Provided herein, in one aspect, are compounds of Formula I''

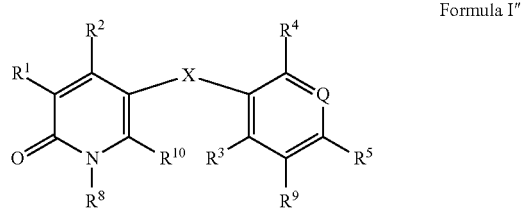

or a stereoisomer or a tautomer thereof, or a pharmaceutically acceptable salt thereof, wherein $R^1$ and $R^2$ are each independently selected from H, halogen, $-NR^aR^b$, $-C(O)NR^aR^b$, optionally substituted $C_1$-$C_6$ alkyl, optionally substituted $C_3$-$C_6$ cycloalkyl, and an optionally substituted non-aromatic bicyclic ring, wherein $R^1$ and $R^2$ cannot both be H; or $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, $-CN$, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

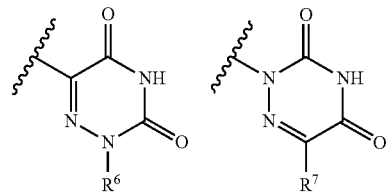

-continued

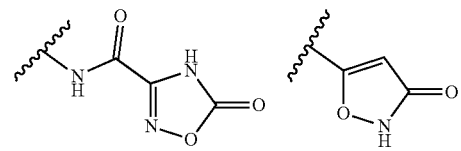

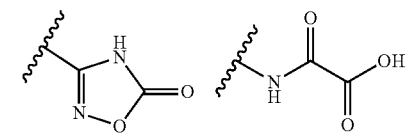

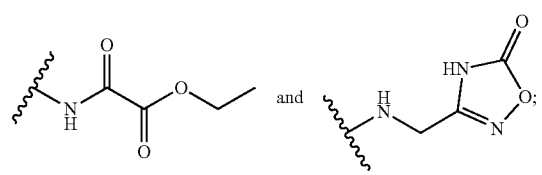

$R^6$ is H or $C_1$-$C_3$ alkyl;

$R^7$ is selected from H, —CN, CH$_3$, and —NH$_2$;

$R^8$ is H, $C_1$-$C_3$ alkyl optionally substituted with 1-5 halogens, or $C_3$-$C_6$ cycloalkyl optionally substituted with 1-6 halogens;

$R^9$ is selected from H, halogen, —CN, optionally substituted $C_1$-$C_3$ alkyl, and optionally substituted $C_1$-$C_2$ alkoxy; or $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

$R^{10}$ is selected from H, halogen, and optionally substituted $C_1$-$C_3$ alkyl, or $R^8$ and $R^{10}$ together with the atoms to which they are attached form 4- to 6-membered cyclic ring optionally substituted with 1 to 3 substituents independently selected from $C_1$-$C_3$ alkyl and halogen;

$R^a$ and $R^b$ are each independently selected from H, optionally substituted $C_1$-$C_6$ alkyl and optionally substituted $C_3$-$C_6$ cycloalkyl; or $R^a$ and $R^b$ together with the nitrogen atom to which they are attached form a 4- to 6-membered cyclic ring optionally substituted with 1 to 3 substituents independently selected from $C_1$-$C_3$ alkyl, halogen, and =O;

Q is selected from N, CH, and CF; and

X is O or CH$_2$;

wherein 0 to 10 hydrogen atoms that are attached to one or more carbon atoms are replaced with deuterium atom(s);

with the proviso that when $R^1$ and $R^2$ are each independently selected from H, halogen, optionally substituted $C_1$-$C_6$ alkyl, optionally substituted $C_3$-$C_6$ cycloalkyl, and an optionally substituted non-aromatic bicyclic ring; or when $R^1$ and $R^2$ together with the carbon atoms to which they are attached form a 4-membered monocyclic ring optionally substituted with 1 to 3 substituents independently selected from halogen and $C_1$-$C_6$ alkyl; then $R^7$ is H or —NH$_2$.

Provided herein, in another aspect, are compounds of Formula I':

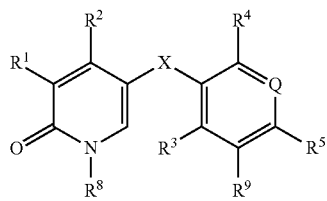

Formula I' or a stereoisomer or a tautomer thereof, or a pharmaceutically acceptable salt thereof, wherein $R^1$ and $R^2$ are each independently selected from H, halogen, —NR$^a$R$^b$, —C(O)NR$^a$R$^b$, optionally substituted $C_1$-$C_6$ alkyl, optionally substituted $C_3$-$C_6$ cycloalkyl, and an optionally substituted non-aromatic bicyclic ring, wherein $R^1$ and $R^2$ cannot both be H; or $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

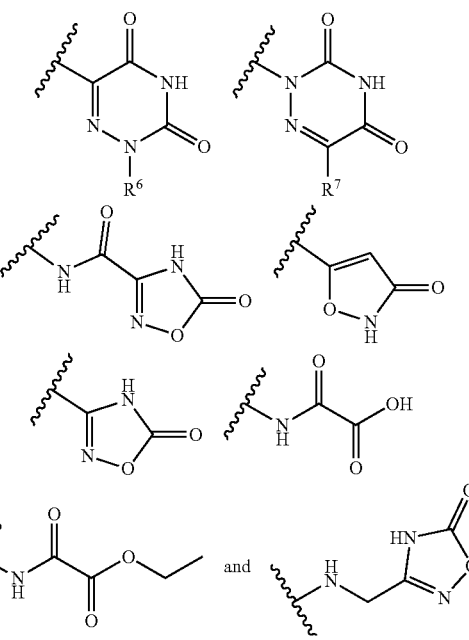

$R^6$ is H or $C_1$-$C_3$ alkyl;

$R^7$ is selected from H, —CN, CH$_3$, and —NH$_2$;

$R^8$ is H or $C_1$-$C_3$ alkyl optionally substituted with 1-5 halogens;

$R^9$ is selected from H, halogen, —CN, optionally substituted $C_1$-$C_3$ alkyl, and optionally substituted $C_1$-$C_2$ alkoxy; or $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

$R^a$ and $R^b$ are each independently selected from H, optionally substituted $C_1$-$C_6$ alkyl and optionally substituted $C_3$-$C_6$ cycloalkyl; or $R^a$ and $R^b$ together with the nitrogen atom to which they are attached form a 4- to 6-membered cyclic ring optionally substituted with 1 to 3 substituents independently selected from $C_1$-$C_3$ alkyl and halogen;

Q is selected from N, CH, and CF; and

X is O or $CH_2$;

wherein 0 to 10 hydrogen atoms that are attached to one or more carbon atoms are replaced with deuterium atom(s);

with the proviso that when $R^1$ and $R^2$ are each independently selected from H, halogen, optionally substituted $C_1$-$C_6$ alkyl, optionally substituted $C_3$-$C_6$ cycloalkyl, and an optionally substituted non-aromatic bicyclic ring; or when $R^1$ and $R^2$ together with the carbon atoms to which they are attached form a 4-membered monocyclic ring optionally substituted with 1 to 3 substituents independently selected from halogen and $C_1$-$C_6$ alkyl; then $R^7$ is H or —$NH_2$.

In some embodiments, $R^1$ is independently selected from H, halogen, —$NR^aR^b$, —$C(O)NR^aR^b$, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and a non-aromatic bicyclic ring optionally substituted with 1-6 halogens. In some embodiments, $R^2$ is independently selected from H, halogen, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and a non-aromatic bicyclic ring optionally substituted with 1-6 halogens. In some embodiments, $R^1$ is independently selected from H, optionally substituted $C_1$-$C_6$ alkyl, optionally substituted $C_3$-$C_6$ cycloalkyl, and an optionally substituted non-aromatic bicyclic ring; and $R^2$ is independently selected from H, halogen, optionally substituted $C_1$-$C_6$ alkyl, optionally substituted $C_3$-$C_6$ cycloalkyl, and an optionally substituted non-aromatic bicyclic ring. In some embodiments, $R^1$ is independently selected from H, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and a non-aromatic bicyclic ring optionally substituted with 1-6 halogens; and $R^2$ is independently selected from H, halogen, $C_1$-$C_6$ alkyl optionally substituted with 1-6 halogens, $C_3$-$C_6$ cycloalkyl optionally substituted with 1-6 halogens, and a non-aromatic bicyclic ring optionally substituted with 1-6 halogens. In some embodiments, $R^1$ is —$NR^aR^b$ or optionally substituted $C_1$-$C_6$ alkyl. In some embodiments, $R^1$ is —$NR^aR^b$ or $C_1$-$C_6$ alkyl optionally substituted with 1 to 5 substituents independently selected from halogen and $C_3$-$C_4$ cycloalkyl. In some embodiments, $R^1$ is —$NR^aR^b$ or $C_1$-$C_6$ alkyl optionally substituted with 1 to 5 halogens. In some embodiments, $R^1$ is —$C(O)NR^aR^b$. In some embodiments, $R^a$ and $R^b$ are each independently selected from $C_1$-$C_3$ alkyl. In some embodiments, $R^a$ is H; and $R^b$ is $C_1$-$C_3$ alkyl optionally substituted with 1 to 3 halogens, or $C_3$-$C_6$ cycloalkyl optionally substituted with 1-5 halogens. In some embodiments, $R^a$ and $R^b$ together with the nitrogen atom to which they are attached form a 4- to 6-membered cyclic ring optionally substituted with 1 to 3 substituents independently selected from $C_1$-$C_3$ alkyl and halogen.

Provided herein, in another aspect, are compounds of Formula I:

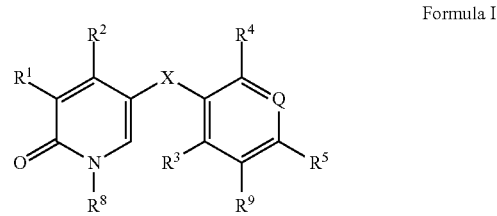

Formula I or a stereoisomer or a tautomer thereof, or a pharmaceutically acceptable salt thereof, wherein $R^1$ and $R^2$ are each independently selected from H, optionally substituted $C_1$-$C_6$ alkyl, optionally substituted $C_3$-$C_6$ cycloalkyl, and an optionally substituted non-aromatic bicyclic ring, wherein $R^1$ and $R^2$ cannot both be H; or $R^1$ and $R^2$ together with the carbon atoms to which they are attached form a $C_4$-$C_7$ monocyclic ring optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

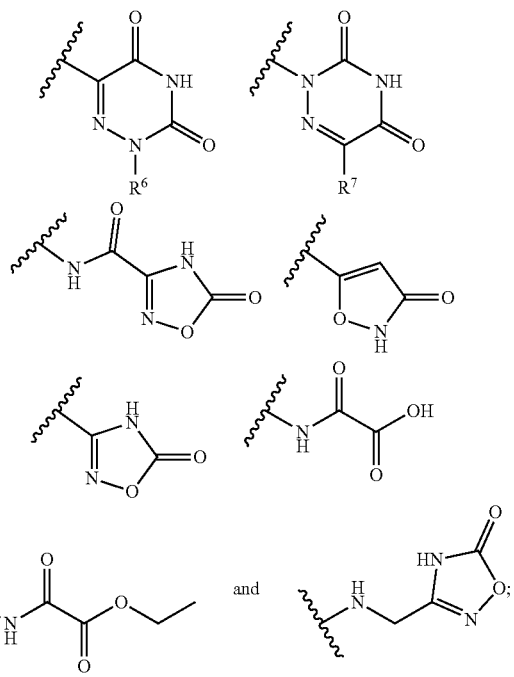

$R^6$ is H or $C_1$-$C_3$ alkyl;

$R^7$ is selected from H, —CN, $CH_3$, and —$NH_2$;

$R^8$ is H or $C_1$-$C_3$ alkyl optionally substituted with 1-5 halogens;

$R^9$ is selected from H, halogen, —CN, optionally substituted $C_1$-$C_3$ alkyl, and optionally substituted $C_1$-$C_2$ alkoxy; or $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

Q is selected from N, CH, and CF; and

X is O or $CH_2$;

wherein 0 to 10 hydrogen atoms that are attached to one or more carbon atoms are replaced with deuterium atom(s);

with the proviso that when $R^1$ and $R^2$ together with the carbon atoms to which they are attached do not form a $C_5$-$C_7$ monocyclic ring or a polycyclic ring, then $R^7$ is H or —$NH_2$.

In some embodiments, $R^8$ is hydrogen.

Provided herein, in another aspect, are compounds of Formula IA":

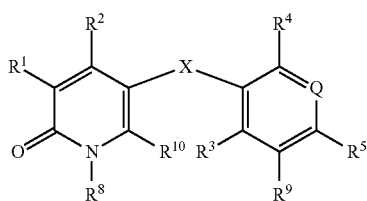

Formula IA"

or a stereoisomer or a tautomer thereof, or a pharmaceutically acceptable salt thereof, wherein $R^1$ and $R^2$ are each independently selected from H, halogen, —$NR^aR^b$, —$C(O)NR^aR^b$, optionally substituted $C_1$-$C_6$ alkyl, optionally substituted $C_3$-$C_6$ cycloalkyl, and an optionally substituted non-aromatic bicyclic ring; or $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

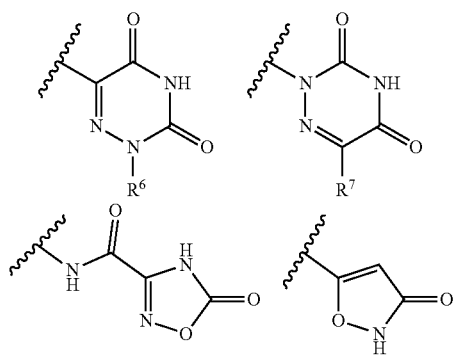

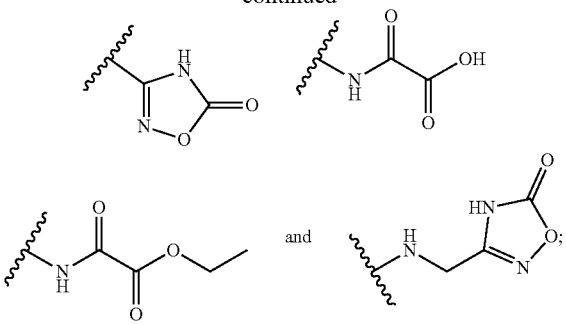

$R^6$ is H or $C_1$-$C_3$ alkyl;

$R^7$ is selected from H, —CN, $CH_3$, and —$NH_2$;

$R^8$ is $C_1$-$C_3$ alkyl optionally substituted with 1-5 halogens or optionally substituted $C_3$-$C_5$ cycloalkyl, or $C_3$-$C_6$ cycloalkyl optionally substituted with 1-6 halogens;

$R^9$ is selected from H, halogen, —CN, optionally substituted $C_1$-$C_3$ alkyl, and optionally substituted $C_1$-$C_2$ alkoxy; or $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

$R^{10}$ is selected from H, halogen, and optionally substituted $C_1$-$C_3$ alkyl, or $R^8$ and $R^{10}$ together with the atoms to which they are attached form 4- to 6-membered cyclic ring optionally substituted with 1 to 3 substituents independently selected from $C_1$-$C_3$ alkyl and halogen;

$R^a$ and $R^b$ are each independently selected from H, optionally substituted $C_1$-$C_6$ alkyl and optionally substituted $C_3$-$C_6$ cycloalkyl; or $R^a$ and $R^b$ together with the nitrogen atom to which they are attached form a 4- to 6-membered cyclic ring optionally substituted with 1 to 3 substituents independently selected from $C_1$-$C_3$ alkyl, halogen, and =O;

Q is selected from N, CH, and CF; and

X is O or $CH_2$;

wherein 0 to 10 hydrogen atoms that are attached to one or more carbon atoms are replaced with deuterium atom(s); with the proviso that the compound is not:

2-(3,5-dichloro-4-((1-isopropyl-6-oxo-1,6-dihydropyridin-3-yl)oxy)phenyl)-1,2,4-triazine-3,5(2H,4H)-dione;

2-(3,5-dichloro-4-((1-isopropyl-6-oxo-1,6-dihydropyridin-3-yl)oxy)phenyl)-3,5-dioxo-2,3,4,5-tetrahydro-1,2,4-triazine-6-carbonitrile; or 2-(3,5-dichloro-4-((1-cyclopropyl-6-oxo-1,6-dihydropyridin-3-yl)oxy)phenyl)-3,5-dioxo-2,3,4,5-tetrahydro-1,2,4-triazine-6-carbonitrile.

Provided herein, in another aspect, are compounds of Formula IA:

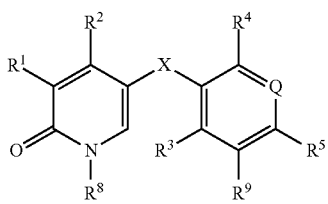

Formula IA or a stereoisomer or a tautomer thereof, or a pharmaceutically acceptable salt thereof, wherein $R^1$ and $R^2$ are each independently selected from H, halogen, —$NR^aR^b$, —$C(O)NR^aR^b$, optionally substituted $C_1$-$C_6$ alkyl, optionally substituted $C_3$-$C_6$ cycloalkyl, and an optionally substituted non-aromatic bicyclic ring; or $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

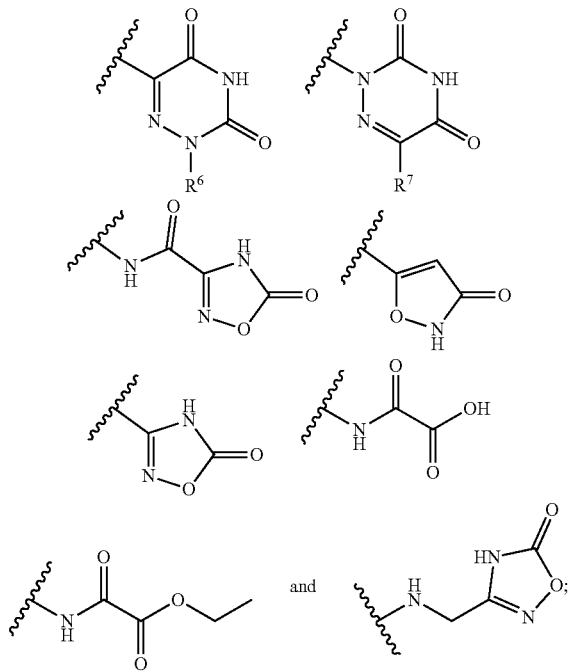

$R^6$ is H or $C_1$-$C_3$ alkyl;

$R^7$ is selected from H, —CN, $CH_3$, and —$NH_2$;

$R^8$ is $C_1$-$C_3$ alkyl optionally substituted with 1-5 halogens or optionally substituted $C_3$-$C_5$ cycloalkyl;

$R^9$ is selected from H, halogen, —CN, optionally substituted $C_1$-$C_3$ alkyl, and optionally substituted $C_1$-$C_2$ alkoxy; or $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

$R^a$ and $R^b$ are each independently selected from H, optionally substituted $C_1$-$C_6$ alkyl and optionally substituted $C_3$-$C_6$ cycloalkyl; or $R^a$ and $R^b$ together with the nitrogen atom to which they are attached form a 4- to 6-membered cyclic ring optionally substituted with 1 to 3 substituents independently selected from $C_1$-$C_3$ alkyl and halogen;

Q is selected from N, CH, and CF; and

X is O or $CH_2$;

wherein 0 to 10 hydrogen atoms that are attached to one or more carbon atoms are replaced with deuterium atom(s);

with the proviso that the compound is not:

2-(3,5-dichloro-4-((1-isopropyl-6-oxo-1,6-dihydropyridin-3-yl)oxy)phenyl)-1,2,4-triazine-3,5(2H,4H)-dione; or 2-(3,5-dichloro-4-((1-isopropyl-6-oxo-1,6-dihydropyridin-3-yl)oxy)phenyl)-3,5-dioxo-2,3,4,5-tetrahydro-1,2,4-triazine-6-carbonitrile.

In some embodiments, the compound has the chemical structure of:

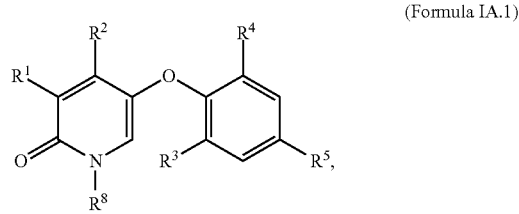

(Formula IA.1)

or a stereoisomer or a tautomer thereof, or a pharmaceutically acceptable salt thereof. In some embodiments, $R^8$ is H. In some embodiments, $R^8$ is $C_1$-$C_3$ alkyl optionally substituted with 1-5 halogens. In some embodiments, $R^8$ is $C_3$-$C_6$ cycloalkyl optionally substituted with 1-6 halogens. In some embodiments, $R^1$ and $R^2$ are each independently selected from H, halogen, —$NR^aR^b$, optionally substituted $C_1$-$C_6$ alkyl, optionally substituted $C_3$-$C_6$ cycloalkyl, and an optionally substituted non-aromatic bicyclic ring. In some embodiments, $R^1$ is independently selected from H, halogen, —$NR^aR^b$, —$C(O)NR^aR^b$, $C_1$-$C_6$ alkyl optionally substituted with 1-6 substituents independently selected from halogen and $C_3$-$C_4$ cycloalkyl optionally substituted with 1-6 halogens, $C_3$-$C_6$ cycloalkyl optionally substituted with 1-6 halogens, and a non-aromatic bicyclic ring optionally substituted with 1-6 halogens. In some embodiments, $R^2$ is independently selected from H, halogen, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and a non-aromatic bicyclic ring optionally substituted with 1-6 halogens. In some embodiments, $R^2$ is H. In some embodiments, $R^1$ is independently selected from H, optionally substituted $C_1$-$C_6$ alkyl, optionally substituted $C_3$-$C_6$ cycloalkyl, and an optionally substituted non-aromatic bicyclic ring; and $R^2$ is independently selected from H, halogen, optionally substituted $C_1$-$C_6$ alkyl, optionally substituted $C_3$-$C_6$ cycloalkyl, and an optionally substituted non-aromatic bicyclic ring. In some embodiments, $R^1$ is independently selected from H, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and a non-aromatic bicyclic ring optionally substituted with 1-6 halogens; and $R^2$ is independently selected from H, halogen, $C_1$-$C_6$ alkyl optionally substituted with 1-6 halogens, $C_3$-$C_6$ cycloalkyl optionally substituted with 1-6 halogens, and a non-aromatic bicyclic ring optionally substituted with 1-6 halogens. In some embodiments, $R^1$ is —$NR^aR^b$ or $C_1$-$C_6$ alkyl optionally substituted with 1 to 5 substituents independently selected from halogen and $C_3$-$C_4$ cycloalkyl. In some embodiments, $R^1$ is —$NR^aR^b$ or $C_1$-$C_6$ alkyl optionally substituted with 1 to 5 halogens. In some embodiments, $R^1$ is $C_1$-$C_6$ alkyl. In some embodiments, $R^1$ is halogen. In some embodiments, $R^1$ is $C_3$-$C_6$ cycloalkyl optionally substituted with 1-6 halogens. In some embodiments, $R^1$ is —C(O)NR$^a$R$^b$. In some embodiments, R$^a$ and R$^b$ are each independently selected from $C_1$-$C_3$ alkyl. In some embodiments, R$^a$ is H; and R$^b$ is $C_1$-$C_3$ alkyl optionally substituted with 1 to 3 halogens, or $C_3$-$C_6$ cycloalkyl optionally substituted with 1-5 halogens. In some embodiments, R$^a$ is H; and R$^b$ is a 4- to 6-membered cyclic ring optionally substituted with 2 halogens. In some embodiments, R$^a$ and R$^b$ together with the nitrogen atom to which they are attached form a 4- to 6-membered cyclic ring optionally substituted with 1 to 3 substituents independently selected from $C_1$-$C_3$ alkyl, halogen, and =O. In some embodiments, R$^a$ and R$^b$ together with the nitrogen atom to which they are attached form a 4- to 6-membered cyclic ring optionally substituted with 1 to 3 substituents independently selected from $C_1$-$C_3$ alkyl and halogen. In some embodiments, $R^1$ and $R^2$ are H; $R^5$ is

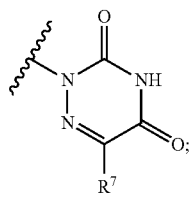

$R^7$ is —NH$_2$; and $R^8$ is isopropyl, optionally substituted with 1-5 halogens. In some embodiments, $R^1$ and $R^2$ are each independently $C_1$-$C_6$ alkyl, $C_3$-$C_6$ cycloalkyl, or a non-aromatic bicyclic ring. In some embodiments, $R^5$ is

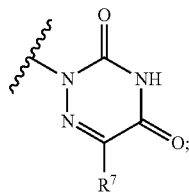

$R^7$ is CH$_3$ or —NH$_2$; and $R^8$ is $C_1$-$C_3$ alkyl. In some embodiments, the compound has the chemical structure of:

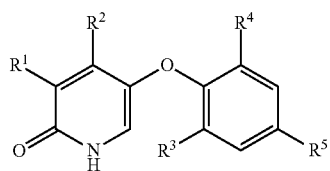

(Formula I.1)

or a stereoisomer or a tautomer thereof, or a pharmaceutically acceptable salt thereof. In some embodiments, $R^1$ is CH$_3$; $R^8$ is isopropyl; $R^5$ is

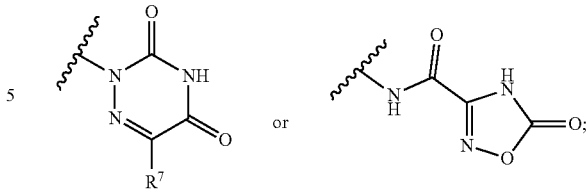

and $R^7$ is —NH$_2$. In some embodiments, $R^1$ and $R^2$ are each optionally substituted with 1 to 3 substituents independently selected from optionally substituted $C_3$-$C_4$ cycloalkyl, optionally substituted bicyclic ring, and halogen; or $R^1$ or $R^2$ are H, but $R^1$ and $R^2$ cannot both be H. In some embodiments, $R^1$ and $R^2$ are each independently $C_1$-$C_6$ alkyl, $C_3$-$C_6$ cycloalkyl, or a non-aromatic bicyclic ring, wherein $R^1$ and $R^2$ are each optionally substituted with 1 to 3 substituents independently selected from $C_3$-$C_4$ cycloalkyl optionally substituted with 1 to 3 substituents independently selected from halogen and $C_1$-$C_3$ alkyl; bicyclic ring optionally substituted with 1 to 3 substituents independently selected from halogen and $C_1$-$C_3$ alkyl; and halogen; or $R^1$ or $R^2$ are H, but $R^1$ and $R^2$ cannot both be H. In some embodiments, $R^1$ is $C_1$-$C_6$ alkyl. In some embodiments, $R^2$ is H. In some embodiments, $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl. In some embodiments, $R^1$ and $R^2$ together with the carbon atoms to which they are attached form a $C_4$-$C_7$ monocyclic ring optionally substituted with 1 to 3 substituents independently selected from halogen and $C_1$-$C_6$ alkyl. In some embodiments, $R^1$ and $R^2$ together with the carbon atoms to which they are attached form a polycyclic ring optionally substituted with 1 to 3 substituents independently selected from $C_1$-$C_6$ alkyl. In some embodiments, $R^3$ and $R^4$ are each independently selected from halogen; —CN; $C_1$-$C_3$ alkyl optionally substituted with 1 to 3 substituents independently selected from halogen and $C_1$-$C_6$ alkoxy; $C_1$-$C_2$ alkoxy optionally substituted with 1 to 3 substituents independently selected from halogen; and $C_2$-$C_3$ alkenyl optionally substituted with 1 to 3 substituents independently selected from halogen and $C_1$-$C_6$ alkoxy; and cyclopropyl. In some embodiments, $R^3$ and $R^4$ are each independently selected from halogen and $C_1$-$C_3$ alkyl. In some embodiments, $R^3$ and $R^4$ are both halogen. In some embodiments, $R^3$ and $R^4$ are both —Cl. In some embodiments, $R^3$ and $R^4$ are both methyl. In some embodiments, $R^9$ is selected from H; halogen; —CN; $C_1$-$C_3$ alkyl optionally substituted with 1 to 3 substituents independently selected from halogen and $C_1$-$C_2$ alkoxy; and $C_1$-$C_2$ alkoxy optionally substituted with 1 to 3 substituents independently selected from halogen. In some embodiments, $R^9$ is H. In some embodiments, $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring. In some embodiments, $R^5$ is

13

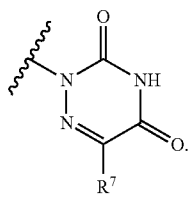

In some embodiments, $R^5$ is

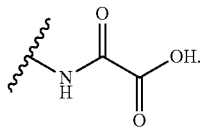 [SMILES: *NC(=O)C(=O)O]

In some embodiments, $R^5$ is

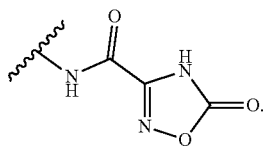 [SMILES: *NC(=O)c1noc(=O)[nH]1]

In some embodiments, $R^7$ is H. In some embodiments, $R^7$ is —NH$_2$. In some embodiments, $R^7$ is CH$_3$. In some embodiments, $R^7$ is —CN. In some embodiments, Q is CH. In some embodiments, X is CH$_2$. In some embodiments, X is O. In some embodiments, $R^8$ is H. In some embodiments, $R^8$ is $C_1$-$C_3$ alkyl optionally substituted with 1-5 halogens.

Provided herein, in another aspect, is a compound selected from the group consisting of:

6-amino-2-(3,5-dichloro-4-((7-methyl-1-oxo-2,5,6,7-tetrahydro-1H-cyclopenta[c]pyridin-4-yl)oxy)phenyl)-1,2,4-triazine-3,5(2H,4H)-dione;

6-amino-2-(4-chloro-5-((7-methyl-1-oxo-2,5,6,7-tetrahydro-1H-cyclopenta[c]pyridin-4-yl)oxy)bicyclo[4.2.0]octa-1,3,5-trien-2-yl)-1,2,4-triazine-3,5(2H,4H)-dione;

2-((4-chloro-5-((7-methyl-1-oxo-2,5,6,7-tetrahydro-1H-cyclopenta[c]pyridin-4-yl)oxy)bicyclo[4.2.0]octa-1,3,5-trien-2-yl)amino)-2-oxoacetic acid;

2-((7-((7-cyclopropyl-1-oxo-2,5,6,7-tetrahydro-1H-cyclopenta[c]pyridin-4-yl)oxy)-6-methyl-2,3-dihydro-1H-inden-4-yl)amino)-2-oxoacetic acid;

6-amino-2-(3,5-dichloro-4-((5-isopropyl-6-oxo-1,6-dihydropyridin-3-yl)oxy)phenyl)-1,2,4-triazine-3,5(2H,4H)-dione;

2-(3,5-dichloro-4-((7-methyl-1-oxo-2,5,6,7-tetrahydro-1H-cyclopenta[c]pyridin-4-yl)oxy)phenyl)-3,5-dioxo-2,3,4,5-tetrahydro-1,2,4-triazine-6-carbonitrile;

6-(3,5-dichloro-4-((5-isopropyl-6-oxo-1,6-dihydropyridin-3-yl)oxy)phenyl)-2-methyl-1,2,4-triazine-3,5(2H,4H)-dione;

6-amino-2-(3,5-dichloro-4-((5-(1-cyclopropylethyl)-6-hydroxypyridin-3-yl)oxy)phenyl)-1,2,4-triazine-3,5(2H,4H)-dione;

6-amino-2-(3,5-dichloro-4-((5-(1-(3,3-difluorocyclobutyl)ethyl)-6-hydroxypyridin-3-yl)oxy)phenyl)-1,2,4-triazine-3,5(2H,4H)-dione;

6-amino-2-(4-((5-(1-(bicyclo[1.1.1]pentan-2-yl)ethyl)-6-hydroxypyridin-3-yl)oxy)-3,5-dichlorophenyl)-1,2,4-triazine-3,5(2H,4H)-dione;

14

6-amino-2-(3,5-dichloro-4-((5-(6,6-difluorospiro[3.3]heptan-1-yl)-6-hydroxypyridin-3-yl)oxy)phenyl)-1,2,4-triazine-3,5(2H,4H)-dione;

6-amino-2-(3,5-dichloro-4-((6-hydroxy-5-(spiro[2.3]hexan-4-yl)pyridin-3-yl)oxy)phenyl)-1,2,4-triazine-3,5(2H,4H)-dione;

6-amino-2-(4-chloro-5-((6-hydroxy-5-isopropylpyridin-3-yl)oxy)-6-methylpyridin-2-yl)-1,2,4-triazine-3,5(2H,4H)-dione;

6-amino-2-(3,5-dichloro-4-((5-(1-cyclopropylethyl)-6-hydroxypyridin-3-yl)oxy)phenyl-2-d)-1,2,4-triazine-3,5(2H,4H)-dione;

6-amino-2-(3,5-dichloro-4-((6-hydroxy-5-isopropylpyridin-3-yl)oxy)phenyl-2-d)-1,2,4-triazine-3,5(2H,4H)-dione;

6-amino-2-(3,5-dichloro-4-((5-(1-cyclopropylethyl)-6-hydroxypyridin-3-yl)oxy)-2-fluorophenyl)-1,2,4-triazine-3,5(2H,4H)-dione;

6-amino-2-(3,5-dichloro-4-((8-methyl-1-oxo-1,2,5,6,7,8-hexahydro-5,8-ethanoisoquinolin-4-yl)oxy)phenyl)-1,2,4-triazine-3,5(2H,4H)-dione;

6-amino-2-(3,5-dichloro-4-((8-methyl-1-oxo-1,2,5,6,7,8-hexahydro-5,7-methanoisoquinolin-4-yl)oxy)phenyl)-1,2,4-triazine-3,5(2H,4H)-dione;

6-amino-2-(3,5-dichloro-4-((1-oxo-1,2,5,5a,6,6a-hexahydrocyclopropa[4,5]cyclopenta[1,2-c]pyridin-4-yl)oxy)phenyl)-1,2,4-triazine-3,5(2H,4H)-dione;

6-amino-2-(4-((5-isopropyl-6-oxo-1,6-dihydropyridin-3-yl)oxy)-3,5-dimethylphenyl)-1,2,4-triazine-3,5(2H,4H)-dione;

6-amino-2-(4-((5-isopropyl-6-oxo-1,6-dihydropyridin-3-yl)methyl)-3,5-dimethylphenyl)-1,2,4-triazine-3,5(2H,4H)-dione;

2-(3,5-dichloro-4-((5-isopropyl-6-oxo-1,6-dihydropyridin-3-yl)oxy)phenyl)-1,2,4-triazine-3,5(2H,4H)-dione;

2-(4-((5-isopropyl-6-oxo-1,6-dihydropyridin-3-yl)methyl)-3,5-dimethylphenyl)-1,2,4-triazine-3,5(2H,4H)-dione;

2-((3,5-dichloro-4-((5-isopropyl-6-oxo-1,6-dihydropyridin-3-yl)oxy)phenyl)amino)-2-oxoacetic acid;

N-(3,5-dichloro-4-((5-isopropyl-6-oxo-1,6-dihydropyridin-3-yl)oxy)phenyl)-5-oxo-4,5-dihydro-1,2,4-oxadiazole-3-carboxamide;

N-(3,5-dichloro-4-((1-isopropyl-6-oxo-1,6-dihydropyridin-3-yl)oxy)phenyl)-5-oxo-4,5-dihydro-1,2,4-oxadiazole-3-carboxamide;

6-amino-2-(3,5-dichloro-4-((1-isopropyl-6-oxo-1,6-dihydropyridin-3-yl)oxy)phenyl)-1,2,4-triazine-3,5(2H,4H)-dione;

6-amino-2-(3,5-dichloro-4-((5-(1-cyclopropylethyl)-6-oxo-1,6-dihydropyridin-3-yl)oxy)phenyl)-1,2,4-triazine-3,5(2H,4H)-dione;

6-amino-2-(3,5-dichloro-4-((5-(isopropyl(methyl)amino)-6-oxo-1,6-dihydropyridin-3-yl)oxy)phenyl)-1,2,4-triazine-3,5(2H,4H)-dione;

6-amino-2-(3,5-dichloro-4-((5-(dimethylamino)-6-oxo-1,6-dihydropyridin-3-yl)oxy)phenyl)-1,2,4-triazine-3,5(2H,4H)-dione;

6-amino-2-(3,5-dichloro-4-((5-isopropyl-1-methyl-6-oxo-1,6-dihydropyridin-3-yl)oxy)phenyl)-1,2,4-triazine-3,5(2H,4H)-dione;

6-amino-2-(3,5-dichloro-4-((4-fluoro-5-isopropyl-6-oxo-1,6-dihydropyridin-3-yl)oxy)phenyl)-1,2,4-triazine-3,5(2H,4H)-dione;

6-amino-2-(3,5-dichloro-4-((5-isopropyl-4-methyl-6-oxo-1,6-dihydropyridin-3-yl)oxy)phenyl)-1,2,4-triazine-3,5(2H,4H)-dione;

6-amino-2-(3,5-dichloro-4-((1-isopropyl-5-methyl-6-oxo-1,6-dihydropyridin-3-yl)oxy)phenyl)-1,2,4-triazine-3,5(2H,4H)-dione;
6-amino-2-(3,5-dichloro-4-((5-ethyl-1-isopropyl-6-oxo-1,6-dihydropyridin-3-yl)oxy)phenyl)-1,2,4-triazine-3,5(2H,4H)-dione;
6-amino-2-(3,5-dichloro-4-((1-isopropyl-6-oxo-5-propyl-1,6-dihydropyridin-3-yl)oxy)phenyl)-1,2,4-triazine-3,5(2H,4H)-dione;
6-amino-2-(3,5-dichloro-4-((5-fluoro-1-isopropyl-6-oxo-1,6-dihydropyridin-3-yl)oxy)phenyl)-1,2,4-triazine-3,5(2H,4H)-dione;
6-amino-2-(3,5-dichloro-4-((5-chloro-1-isopropyl-6-oxo-1,6-dihydropyridin-3-yl)oxy)phenyl)-1,2,4-triazine-3,5(2H,4H)-dione;
6-amino-2-(3,5-dichloro-4-((5-cyclobutyl-6-oxo-1,6-dihydropyridin-3-yl)oxy)phenyl)-1,2,4-triazine-3,5(2H,4H)-dione;
6-amino-2-(3,5-dichloro-4-((5-cyclopentyl-6-oxo-1,6-dihydropyridin-3-yl)oxy)phenyl)-1,2,4-triazine-3,5(2H,4H)-dione;
5-(4-(6-amino-3,5-dioxo-4,5-dihydro-1,2,4-triazin-2(3H)-yl)-2,6-dichlorophenoxy)-N-methyl-2-oxo-1,2-dihydropyridine-3-carboxamide;
5-(4-(6-amino-3,5-dioxo-4,5-dihydro-1,2,4-triazin-2(3H)-yl)-2,6-dichlorophenoxy)-N-(3,3-difluorocyclobutyl)-2-oxo-1,2-dihydropyridine-3-carboxamide;
N-(3,5-dichloro-4-((5-(methylcarbamoyl)-6-oxo-1,6-dihydropyridin-3-yl)oxy)phenyl)-5-oxo-4,5-dihydro-1,2,4-oxadiazole-3-carboxamide;
N-(3,5-dichloro-4-((5-((3,3-difluorocyclobutyl)carbamoyl)-6-oxo-1,6-dihydropyridin-3-yl)oxy)phenyl)-5-oxo-4,5-dihydro-1,2,4-oxadiazole-3-carboxamide;
6-amino-2-(3,5-dichloro-4-((1-cyclobutyl-6-oxo-1,6-dihydropyridin-3-yl)oxy)phenyl)-1,2,4-triazine-3,5(2H,4H)-dione;
6-amino-2-(3,5-dichloro-4-((1-cyclopropyl-6-oxo-1,6-dihydropyridin-3-yl)oxy)phenyl)-1,2,4-triazine-3,5(2H,4H)-dione;
6-amino-2-(3,5-dichloro-4-((6-oxo-1-(1,1,1-trifluoropropan-2-yl)-1,6-dihydropyridin-3-yl)oxy)phenyl)-1,2,4-triazine-3,5(2H,4H)-dione;
2-(3,5-dichloro-4-((3-methyl-5-oxo-1,2,3,5-tetrahydroindolizin-8-yl)oxy)phenyl)-3,5-dioxo-2,3,4,5-tetrahydro-1,2,4-triazine-6-carbonitrile;
6-amino-2-(3,5-dichloro-4-((3-methyl-5-oxo-1,2,3,5-tetrahydroindolizin-8-yl)oxy)phenyl)-1,2,4-triazine-3,5(2H,4H)-dione;
(S)-6-amino-2-(3,5-dichloro-4-((3-methyl-5-oxo-1,2,3,5-tetrahydroindolizin-8-yl)oxy)phenyl)-1,2,4-triazine-3,5(2H,4H)-dione;
(R)-6-amino-2-(3,5-dichloro-4-((3-methyl-5-oxo-1,2,3,5-tetrahydroindolizin-8-yl)oxy)phenyl)-1,2,4-triazine-3,5(2H,4H)-dione; and
6-amino-2-(3,5-dichloro-4-((6-oxo-5-(2-oxopyrrolidin-1-yl)-1,6-dihydropyridin-3-yl)oxy)phenyl)-1,2,4-triazine-3,5(2H,4H)-dione;
or a stereoisomer or a tautomer thereof, or a pharmaceutically acceptable salt thereof.

Provided herein, in another aspect, is a pharmaceutical composition comprising a compound disclosed herein and at least one pharmaceutically acceptable excipient.

Provided herein, in another aspect, is a method of treating a disorder or disease in a subject in need thereof, the method comprising administering to the subject a therapeutically effective amount of a compound disclosed herein or a therapeutically effective amount of the pharmaceutical composition disclosed herein, wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Provided herein, in another aspect, is a use of a compound disclosed herein for the manufacture of a medicament for the treatment of a disorder or disease selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Provided herein, in another aspect, is a compound disclosed herein for use in treating a disorder or disease selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Provided herein, in another aspect, is a composition disclosed herein for use in treating a disorder or disease selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Provided herein, in another aspect, is a method of treating a thyroid hormone receptor related disorder in a patient, the method comprising the steps of identifying a patient in need of treatment for the thyroid hormone receptor related disorder, and administering to the patient, or contacting the patient with, a compound disclosed herein or a therapeutically effective amount of a pharmaceutical composition disclosed herein. In some embodiments, the thyroid hormone receptor related disorder is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Provided herein, in another aspect, is a method of selectively modulating the activity of a thyroid hormone receptor beta (THR-β) comprising contacting a compound disclosed herein with the thyroid hormone receptor. In some embodiments, the contacting is in vitro or ex vivo. In some embodiments, the contacting is in vivo.

Provided herein, in another aspect, is a compound disclosed herein for use in selectively modulating the activity of a thyroid hormone receptor beta (THR-β).

Provided herein, in another aspect, is a composition disclosed herein for use in selectively modulating the activity of a thyroid hormone receptor beta (THR-β).

DETAILED DESCRIPTION

Definitions

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In the definition of chemical substituents, each of $R_x$ and $R_y$ is independently hydrogen, alkyl, carbocyclic ring, heterocyclic ring, aryl, or heteroaryl, all of which, except hydrogen, are optionally substituted.

Unless otherwise indicated, the abbreviations "TR" and "THR" refer to thyroid hormone receptors.

As used herein, "pharmaceutically acceptable salt" refers to a salt of a compound that does not cause significant irritation to a patient to which it is administered and does not abrogate the biological activity and properties of the compound. Pharmaceutical salts can be obtained by reaction of a compound disclosed herein with an acid or base. Base-formed salts include, without limitation, ammonium salt ($NH_4^+$); alkali metal, such as, without limitation, sodium or potassium, salts; alkaline earth, such as, without limitation, calcium or magnesium, salts; salts of organic bases such as, without limitation, dicyclohexylamine, N-methyl-D-glucamine, tris(hydroxymethyl)methylamine; and salts with the amino group of amino acids such as, without limitation, arginine and lysine. Useful acid-based salts include, without limitation, hydrochlorides, hydrobromides, sulfates, nitrates, phosphates, methane-sulfonates, ethanesulfonates, p-toluenesulfonates and salicylates.

As used herein, "pharmaceutically acceptable ester" refers to an ester of a compound that does not cause significant irritation to a patient to which it is administered. The ester is metabolized in the body to result in the parent compound, e.g., the claimed compound. Accordingly, the ester does not abrogate the biological activity and properties of the compound. Pharmaceutical esters can be obtained by reaction of a compound disclosed herein with an alcohol. Methyl, ethyl, and isopropyl esters are some of the common esters to be prepared. Other esters suitable are well-known to those skilled in the art (see, for example Wuts, P. G. M., Greene's Protective Groups in Organic Synthesis, 5$^{th}$ Ed., John Wiley & Sons, New York, N.Y., 2014, which is incorporated herein by reference in its entirety).

Where the compounds disclosed herein have at least one chiral center, they may exist as a racemate or as individual enantiomers. It should be noted that all such isomers and mixtures thereof are included in the scope of the present disclosure. Thus, the illustration of a chiral center without a designation of R or S signifies that the scope of the disclosure includes the R isomer, the S isomer, the racemic mixture of the isomers, or mixtures where one isomer is present in greater abundance than the other.

Where the processes for the preparation of the compounds disclosed herein give rise to mixtures of stereoisomers, such isomers may be separated by conventional techniques such as preparative chiral chromatography. The compounds may be prepared in racemic form or individual enantiomers may be prepared by stereoselective synthesis or by resolution. The compounds may be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides followed by chromatographic separation and removal of the chiral auxiliary.

Unless otherwise indicated, when a substituent is deemed to be "optionally substituted" it is meant that the substituent is a group that may be substituted with one or more (e.g., 1 to 2, or 1 to 3, or 1 to 4, or 1 to 5, or 1 to 6) group(s) individually and independently selected, without limitation, from alkyl, alkenyl, alkynyl, cycloalkyl, aryl, heteroaryl, heterocycloalkyl, hydroxy, alkoxy, aryloxy, mercapto, alkylthio, arylthio, cyano, halo, carbonyl, thiocarbonyl, O-carbamoyl, N-carbamoyl, O-thiocarbamoyl, N-thiocarbamoyl, C-amido, N-amido, S-sulfonamido, N-sulfonamido, C-carboxy, O-carboxy, is O-cyanato, thiocyanato, isothiocyanato, nitro, silyl, trihalomethanesulfonyl, and amino (e.g., $-NR_xR_y$), including mono- and di-substituted amino groups, and the protected derivatives thereof. The protecting groups that may form the protective derivatives of the above substituents are known to those of skill in the art and may be found in references such as Wuts, above.

As used herein, a "carbocyclic ring" is an aromatic or non-aromatic ring structure in which all the atoms in the ring are carbon atoms. As such, the ring structure may be fully saturated, fully unsaturated, or partially saturated. If any of the atoms in the ring is anything other than a carbon atom, then the ring is a "heterocyclic ring." Examples of atoms that are within a ring include sulfur, oxygen, and nitrogen. A carbocyclic ring or a heterocyclic ring may be polycyclic, e.g., a fused ring system, a spirocyclic ring system, or a bridged ring system. These polycyclic rings include, for example, adamantyl, norbornyl (i.e., bicyclo[2.2.1]heptanyl), norbornenyl, decalinyl, 7,7-dimethyl-bicyclo[2.2.1] heptanyl, and the like. Additional non-limiting examples include bicyclic rings such as but not limited to:

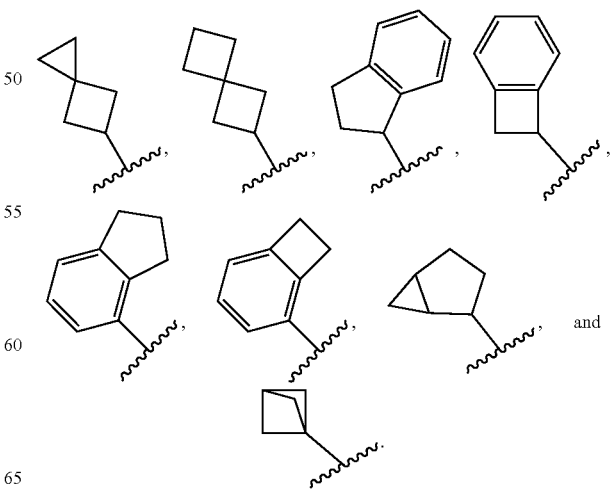

As used herein, "aryl" refers to a carbocyclic (all carbon) ring that has a fully delocalized pi-electron system. The "aryl" group can be made up of two or more fused rings (rings that share two adjacent carbon atoms). When the aryl is a fused ring system, then the ring that is connected to the rest of the molecule has a fully delocalized pi-electron system. The other ring(s) in the fused ring system may or may not have a fully delocalized pi-electron system. Further, the other ring(s) may or may not contain one or more heteroatoms (e.g., O, N, or S). Examples of aryl groups include, without limitation, the radicals of benzene, naphthalene and azulene. Additional non-limiting examples include:

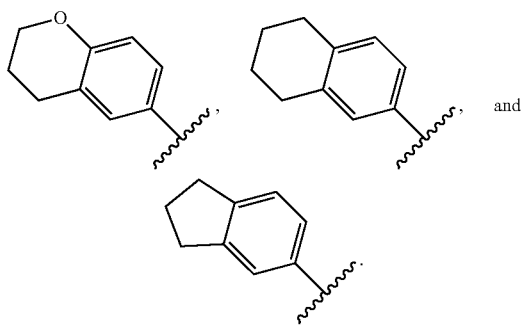

As used herein, "heteroaryl" refers to a ring that has a fully delocalized pi-electron system and contains one or more heteroatoms selected from the group consisting of nitrogen, oxygen, and sulfur in the ring. The "heteroaryl" group can be made up of two or more fused rings (rings that share two adjacent carbon atoms). When the heteroaryl is a fused ring system, then the ring that is connected to the rest of the molecule has a fully delocalized pi-electron system. The other ring(s) in the fused ring system may or may not have a fully delocalized pi-electron system. Examples of heteroaryl rings include, without limitation, furan, thiophene, phthalazinone, pyrrole, oxazole, thiazole, imidazole, pyrazole, isoxazole, isothiazole, triazole, thiadiazole, pyridine, pyridazine, pyrimidine, pyrazine and triazine.

Wherever "hetero" is used it is intended to mean a group as specified, such as an alkyl or an aryl group, where at least one carbon atom has been replaced with a heteroatom selected from nitrogen, oxygen and sulfur.

As used herein, "alkyl" refers to a straight or branched chain fully saturated (no double or triple bonds) hydrocarbon group. An alkyl group of the presently disclosed compounds may comprise from 1 to 20 carbon atoms. An alkyl group herein may also be of medium size having 1 to 10 carbon atoms. An alkyl group herein may also be a lower alkyl having 1 to 5 carbon atoms or 1 to 6 carbon atoms. Examples of alkyl groups include, without limitation, methyl, ethyl, n-propyl, isopropyl, n-butyl, i-butyl, sec-butyl, t-butyl, amyl, t-amyl, hexyl, heptyl, octyl, nonyl, decyl, undecyl and dodecyl.

An alkyl group of the presently disclosed compounds may be substituted or unsubstituted. When substituted, the substituent group(s) can be one or more group(s) independently selected from cycloalkyl, aryl, heteroaryl, heterocycloalkyl, hydroxy, protected hydroxy, alkoxy, aryloxy, mercapto, alkylthio, arylthio, cyano, halogen, carbonyl, thiocarbonyl, O-carbamoyl, N-carbamoyl, O-thiocarbamoyl, N-thiocarbamoyl, C-amido, N-amido, S-sulfonamido, N-sulfonamido, C-carboxy, protected C-carboxy, O-carboxy, isocyanato, thiocyanato, isothiocyanato, nitro, silyl, trihalomethanesulfonyl, amino (e.g., —NR$_x$R$_y$), and protected amino.

As used herein, "alkenyl" refers to an alkyl group that contains in the straight or branched hydrocarbon chain one or more double bonds. An alkenyl group of the presently disclosed compounds may comprise from 2 to 20 carbon atoms. An alkenyl group herein may also be of medium size having 2 to 10 carbon atoms. An alkenyl group herein may also be a lower alkenyl having 2 to 5 carbon atoms or 2 to 6 carbon atoms. An alkenyl group of the presently disclosed compounds may be unsubstituted or substituted. When substituted, the substituent(s) may be selected from the same groups disclosed above regarding alkyl group substitution, or with regard to optional substitution.

As used herein, "alkynyl" refers to an alkyl group that contains in the straight or branched hydrocarbon chain one or more triple bonds. An alkynyl group of the presently disclosed compounds may comprise from 2 to 20 carbon atoms. An alkynyl group herein may also be of medium size having 2 to 10 carbon atoms. An alkynyl group herein may also be a lower alkynyl having 2 to 5 carbon atoms or 2 to 6 carbon atoms. An alkynyl group of the presently disclosed compounds may be unsubstituted or substituted. When substituted, the substituent(s) may be selected from the same groups disclosed above regarding alkyl group substitution, or with regard to optional substitution.

As used herein, "alkoxy" refers to an "—O-(alkyl)" group, wherein "alkyl" is as defined above.

As used herein, "acyl" refers to an "R$_x$C(=O)—" group.

As used herein, "cycloalkyl" refers to a completely saturated (no double bonds) hydrocarbon ring. In some embodiments, cycloalkyl refers to a hydrocarbon ring containing no double bonds or one or more double bonds provided that they do not form a fully delocalized pi-electron system in the ring. Cycloalkyl groups of the presently disclosed compounds may range from $C_3$ to $C_8$. A cycloalkyl group may be unsubstituted or substituted. If substituted, the substituent(s) may be selected from those indicated above regarding substitution of an alkyl group. The "cycloalkyl" group can be made up of two or more fused rings (rings that share two adjacent carbon atoms). When the cycloalkyl is a fused ring system, then the ring that is connected to the rest of the molecule is a cycloalkyl as defined above. The other ring(s) in the fused ring system may be a cycloalkyl, a cycloalkenyl, an aryl, a heteroaryl, or a heterocycloalkyl.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). A cycloalkenyl group of the presently disclosed compounds may unsubstituted or substituted. When substituted, the substituent(s) may be selected from the same groups disclosed above regarding alkyl group substitution. The "cycloalkenyl" group can be made up of two or more fused rings (rings that share two adjacent carbon atoms). When the cycloalkenyl is a fused ring system, then the ring that is connected to the rest of the molecule is a cycloalkenyl as defined above. The other ring(s) in the fused ring system may be a cycloalkyl, a cycloalkenyl, an aryl, a heteroaryl, or a heterocycloalkyl.

The term "alkylene" refers to an alkyl group, as defined herein, which is a biradical and is connected to two other moieties. Thus, methylene (—CH$_2$—), ethylene (—CH$_2$CH$_2$—), propylene (—CH$_2$CH$_2$CH$_2$—), isopropylene (IUPAC: (methyl)ethylene) (—CH$_2$—CH(CH$_3$)—), and isobutylene (IUPAC: 2-(methyl)propylene) (—CH$_2$—CH (CH$_3$)—CH$_2$—) are examples, without limitation, of an alkylene group. Similarly, the term "cycloalkylene" refers to a cycloalkyl group, as defined here, which binds in an analogous way to two other moieties. If the alkyl and cycloalkyl groups contain unsaturated carbons, the terms "alkenylene" and "cycloalkenylene" are used.

As used herein, "heterocycloalkyl," "heteroalicyclic," or "heteroali-cyclyl" refers to a ring having in the ring system one or more heteroatoms independently selected from nitrogen, oxygen and sulfur. The ring may also contain one or more double bonds provided that they do not form a fully delocalized pi-electron system in the rings. The ring defined herein can be a stable 3- to 18-membered ring that consists of carbon atoms and from one to five heteroatoms selected from the group consisting of nitrogen, oxygen, and sulfur. Heterocycloalkyl groups of the presently disclosed compounds may be unsubstituted or substituted. When substituted, the substituent(s) may be one or more groups independently selected from the group consisting of halogen, hydroxy, protected hydroxy, cyano, nitro, alkyl, alkoxy, acyl, acyloxy, carboxy, protected carboxy, amino, protected amino, carboxamide, protected carboxamide, alkylsulfonamido and trifluoromethane-sulfonamido. The "heterocycloalkyl" group can be made up of two or more fused rings (rings that share two adjacent carbon atoms). When the heterocycloalkyl is a fused ring system, then the ring that is connected to the rest of the molecule is a heterocycloalkyl as defined above. The other ring(s) in the fused ring system may be a cycloalkyl, a cycloalkenyl, an aryl, a heteroaryl, or a heterocycloalkyl.

As used herein, "aralkyl" refers to an alkylene substituted with an aryl group.

As used herein, "(carbocyclic)alkyl" refers to an alkylene substituted with a carbocyclic group.

As used herein, (heterocyclic)alkyl" refers to an alkylene substituted with a heterocyclic group.

As used herein, "(heteroaryl)alkyl" refers to an alkylene substituted with a heteroaryl group.

An "O-carboxy" group refers to a "R$_x$C(=O)O—" group.
A "C-carboxy" group refers to a "—C(=O)OR$_x$" group.
An "acetyl" group refers to a CH$_3$C(=O)— group.
A "C-amido" group refers to a "—C(=O)NR$_x$R$_y$" group.
An "N-amido" group refers to a "R$_y$C(=O)NR$_x$—" group.

The term "perhaloalkyl" refers to an alkyl group in which all the hydrogen atoms are replaced by halogen atoms.

Any unsubstituted or monosubstituted amine group on a compound herein can be converted to an amide, any hydroxy group can be converted to an ester and any carboxyl group can be converted to either an amide or ester using techniques well-known to those skilled in the art (see, for example Wuts, above).

It is understood that, in any compound of the presently disclosed compounds having one or more chiral centers, if an absolute stereochemistry is not expressly indicated, then each center may independently be R or S or a mixture thereof. In addition, it is understood that, in any compound of the presently disclosed compounds having one or more double bond(s) generating geometrical isomers that can be defined as E or Z each double bond may independently be E or Z, or a mixture thereof.

It is understood that the disclosure of a compound herein inherently includes the disclosure of a tautomer thereof, if applicable. For instance, the disclosure of:

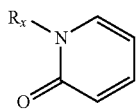

(wherein R$_x$ is H)
also includes the disclosure of:

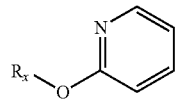

and vice versa, even if only one of the two structures is disclosed.

Throughout the present disclosure, when a compound is illustrated or named, it is understood that the isotopically enriched analogs of the compound are also contemplated. For example, a compound may have a deuterium incorporated instead of a hydrogen, or a carbon-13 instead of carbon with natural isotopic distribution. The isotopic enrichment may be in one location on the compound, i.e., only one hydrogen is replaced by a deuterium, or in more than one location. The present disclosure also encompasses compounds where all the similar atoms are replaced by their less common isotope, for example, a perdeutero compound where all the hydrogen atoms are replaced by a deuterium. The isotopically enriched compounds are useful when obtaining NMR spectra or when making use of an isotope effect in managing the kinetics of the reaction the compound undergoing.

The term "pharmaceutical composition" refers to a mixture of one or more compounds disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example, dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

In certain embodiments, the same substance can act as a carrier, diluent, or excipient, or have any of the two roles, or have all three roles. Thus, a single additive to the pharmaceutical composition can have multiple functions.

The term "pharmaceutically acceptable" defines a carrier or diluent that does not abrogate the biological activity and properties of the compound.

Compounds

Provided herein, in one aspect, are compounds of Formula I":

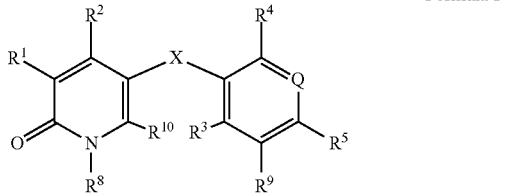

Formula I"

or a stereoisomer or a tautomer thereof, or a pharmaceutically acceptable salt thereof, wherein $R^1$ and $R^2$ are each independently selected from H, halogen, —$NR^aR^b$, —$C(O)NR^aR^b$, optionally substituted $C_1$-$C_6$ alkyl, optionally substituted $C_3$-$C_6$ cycloalkyl, and an optionally substituted non-aromatic bicyclic ring, wherein $R^1$ and $R^2$ cannot both be H; or $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

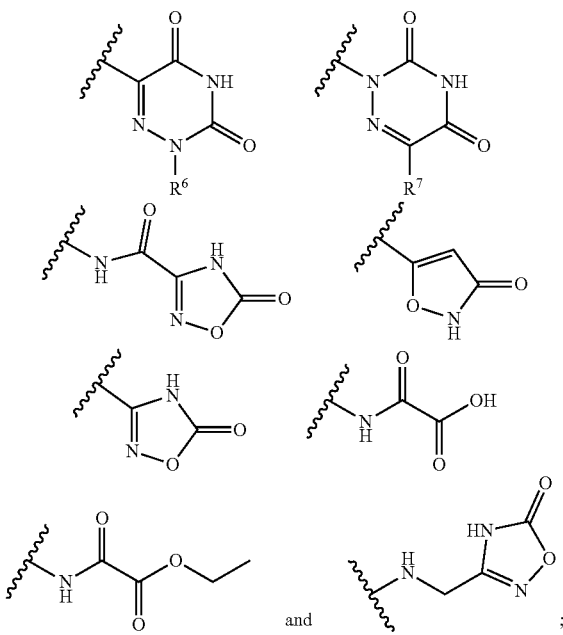

$R^6$ is H or $C_1$-$C_3$ alkyl;
$R^7$ is selected from H, —CN, $CH_3$, and —$NH_2$;

$R^8$ is H, $C_1$-$C_3$ alkyl optionally substituted with 1-5 halogens, or $C_3$-$C_6$ cycloalkyl optionally substituted with 1-6 halogens;

$R^9$ is selected from H, halogen, —CN, optionally substituted $C_1$-$C_3$ alkyl, and optionally substituted $C_1$-$C_2$ alkoxy; or $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

$R^{10}$ is selected from H, halogen, and optionally substituted $C_1$-$C_3$ alkyl, or $R^8$ and $R^{10}$ together with the atoms to which they are attached form 4- to 6-membered cyclic ring optionally substituted with 1 to 3 substituents independently selected from $C_1$-$C_3$ alkyl and halogen;

$R^a$ and $R^b$ are each independently selected from H, optionally substituted $C_1$-$C_6$ alkyl and optionally substituted $C_3$-$C_6$ cycloalkyl; or $R^a$ and $R^b$ together with the nitrogen atom to which they are attached form a 4- to 6-membered cyclic ring optionally substituted with 1 to 3 substituents independently selected from $C_1$-$C_3$ alkyl, halogen, and =O;

Q is selected from N, CH, and CF; and

X is O or $CH_2$;

wherein 0 to 10 hydrogen atoms that are attached to one or more carbon atoms are replaced with deuterium atom(s);

with the proviso that when $R^1$ and $R^2$ are each independently selected from H, halogen, optionally substituted $C_1$-$C_6$ alkyl, optionally substituted $C_3$-$C_6$ cycloalkyl, and an optionally substituted non-aromatic bicyclic ring; or when $R^1$ and $R^2$ together with the carbon atoms to which they are attached form a 4-membered monocyclic ring optionally substituted with 1 to 3 substituents independently selected from halogen and $C_1$-$C_6$ alkyl; then $R^7$ is H or —$NH_2$.

Provided herein, in another aspect, are compounds of Formula I':

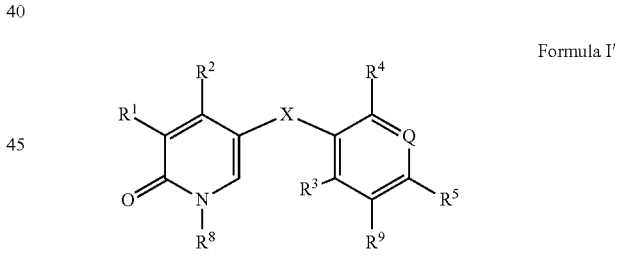

Formula I' or a stereoisomer or a tautomer thereof, or a pharmaceutically acceptable salt thereof, wherein $R^1$ and $R^2$ are each independently selected from H, halogen, —$NR^aR^b$, —$C(O)NR^aR^b$, optionally substituted $C_1$-$C_6$ alkyl, optionally substituted $C_3$-$C_6$ cycloalkyl, and an optionally substituted non-aromatic bicyclic ring, wherein $R^1$ and $R^2$ cannot both be H; or $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

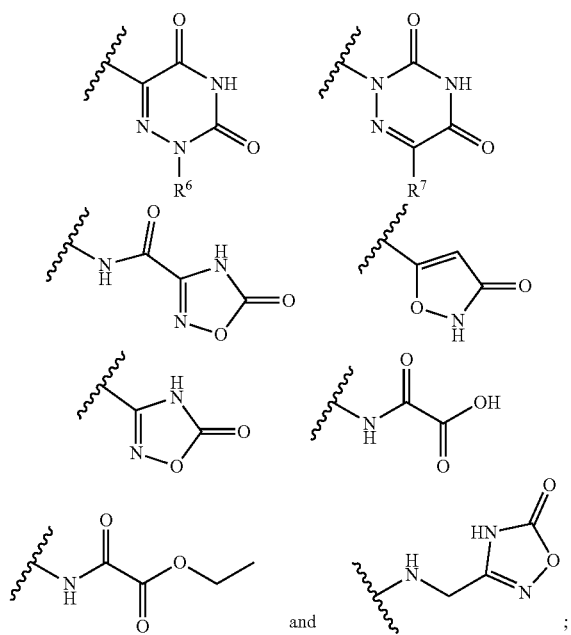

$R^6$ is H or $C_1$-$C_3$ alkyl;

$R^7$ is selected from H, —CN, $CH_3$, and —$NH_2$;

$R^8$ is H or $C_1$-$C_3$ alkyl optionally substituted with 1-5 halogens;

$R^9$ is selected from H, halogen, —CN, optionally substituted $C_1$-$C_3$ alkyl, and optionally substituted $C_1$-$C_2$ alkoxy; or $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

$R^a$ and $R^b$ are each independently selected from H, optionally substituted $C_1$-$C_6$ alkyl and optionally substituted $C_3$-$C_6$ cycloalkyl; or $R^a$ and $R^b$ together with the nitrogen atom to which they are attached form a 4- to 6-membered cyclic ring optionally substituted with 1 to 3 substituents independently selected from $C_1$-$C_3$ alkyl and halogen;

Q is selected from N, CH, and CF; and

X is O or $CH_2$;

wherein 0 to 10 hydrogen atoms that are attached to one or more carbon atoms are replaced with deuterium atom(s);

with the proviso that when $R^1$ and $R^2$ are each independently selected from H, halogen, optionally substituted $C_1$-$C_6$ alkyl, optionally substituted $C_3$-$C_6$ cycloalkyl, and an optionally substituted non-aromatic bicyclic ring; or when $R^1$ and $R^2$ together with the carbon atoms to which they are attached form a 4-membered monocyclic ring optionally substituted with 1 to 3 substituents independently selected from halogen and $C_1$-$C_6$ alkyl; then $R^7$ is H or —$NH_2$.

In some embodiments, $R^1$ is independently selected from H, halogen, —$NR^aR^b$, —$C(O)NR^aR^b$, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and a non-aromatic bicyclic ring optionally substituted with 1-6 halogens.

In some embodiments, $R^2$ is independently selected from H, halogen, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and a non-aromatic bicyclic ring optionally substituted with 1-6 halogens.

In some embodiments, $R^1$ is independently selected from H, optionally substituted $C_1$-$C_6$ alkyl, optionally substituted $C_3$-$C_6$ cycloalkyl, and an optionally substituted non-aromatic bicyclic ring; and $R^2$ is independently selected from H, halogen, optionally substituted $C_1$-$C_6$ alkyl, optionally substituted $C_3$-$C_6$ cycloalkyl, and an optionally substituted non-aromatic bicyclic ring. In some embodiments, $R^1$ is independently selected from H, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and a non-aromatic bicyclic ring optionally substituted with 1-6 halogens; and $R^2$ is independently selected from H, halogen, $C_1$-$C_6$ alkyl optionally substituted with 1-6 halogens, $C_3$-$C_6$ cycloalkyl optionally substituted with 1-6 halogens, and a non-aromatic bicyclic ring optionally substituted with 1-6 halogens.

In some embodiments, $R^1$ is —$NR^aR^b$ or optionally substituted $C_1$-$C_6$ alkyl.

In some embodiments, $R^1$ is —$NR^aR^b$ or $C_1$-$C_6$ alkyl optionally substituted with 1 to 5 substituents independently selected from halogen and $C_3$-$C_4$ cycloalkyl.

In some embodiments, $R^1$ is —$C(O)NR^aR^b$.

In some embodiments, $R^a$ and $R^b$ are each independently selected from $C_1$-$C_3$ alkyl.

In some embodiments, $R^a$ is H; and $R^b$ is $C_1$-$C_3$ alkyl optionally substituted with 1 to 3 halogens, or $C_3$-$C_6$ cycloalkyl optionally substituted with 1-5 halogens.

In some embodiments, $R^a$ and $R^b$ together with the nitrogen atom to which they are attached form a 4- to 6-membered cyclic ring optionally substituted with 1 to 3 substituents independently selected from $C_1$-$C_3$ alkyl and halogen.

In another aspect, provided herein are compounds of Formula I:

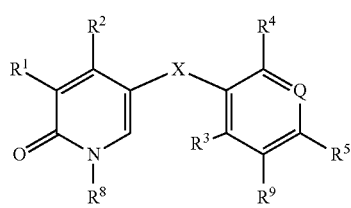

Formula I or a stereoisomer or a tautomer thereof, or a pharmaceutically acceptable salt thereof, wherein $R^1$ and $R^2$ are each independently selected from H, optionally substituted $C_1$-$C_6$ alkyl, optionally substituted $C_3$-$C_6$ cycloalkyl, and an optionally substituted non-aromatic bicyclic ring, wherein $R^1$ and $R^2$ cannot both be H; or $R^1$ and $R^2$ together with the carbon atoms to which they are attached form a $C_4$-$C_7$ monocyclic ring optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

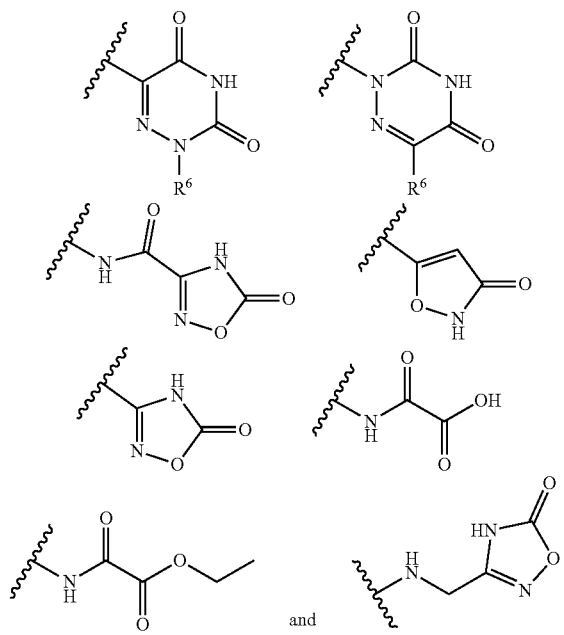

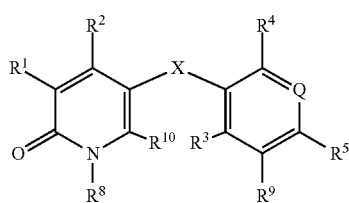

and $R^6$ is H or $C_1$-$C_3$ alkyl;
$R^7$ is selected from H, —CN, $CH_3$, and —$NH_2$;
$R^8$ is H or $C_1$-$C_3$ alkyl optionally substituted with 1-5 halogens;
$R^9$ is selected from H, halogen, —CN, optionally substituted $C_1$-$C_3$ alkyl, and optionally substituted $C_1$-$C_2$ alkoxy; or $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

Q is selected from N, CH, and CF; and

X is O or $CH_2$;

wherein 0 to 10 hydrogen atoms that are attached to one or more carbon atoms are replaced with deuterium atom(s);

with the proviso that when $R^1$ and $R^2$ together with the carbon atoms to which they are attached do not form a $C_5$-$C_7$ monocyclic ring or a polycyclic ring, then $R^7$ is H or —$NH_2$. In some embodiments, $R^8$ is hydrogen.

Provided herein, in another aspect, are compounds of Formula IA″:

Formula IA″

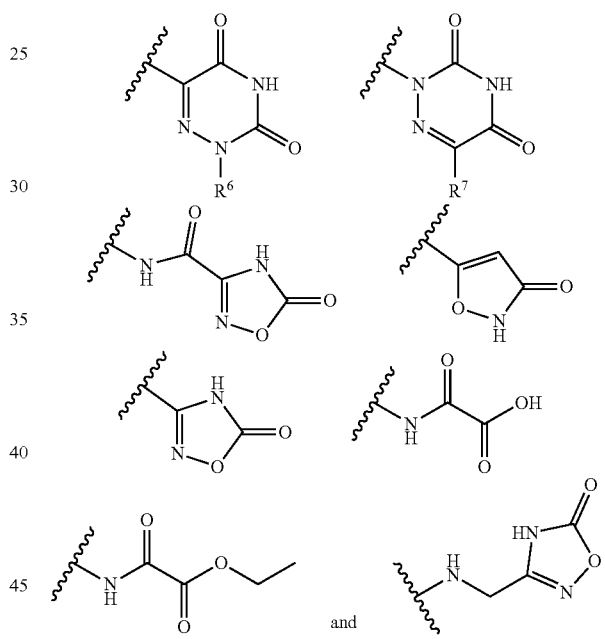

or a stereoisomer or a tautomer thereof, or a pharmaceutically acceptable salt thereof, wherein $R^1$ and $R^2$ are each independently selected from H, halogen, —$NR^aR^b$, —C(O)$NR^aR^b$, optionally substituted $C_1$-$C_6$ alkyl, optionally substituted $C_3$-$C_6$ cycloalkyl, and an optionally substituted non-aromatic bicyclic ring; or $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

$R^6$ is H or $C_1$-$C_3$ alkyl;
$R^7$ is selected from H, —CN, $CH_3$, and —$NH_2$;
$R^8$ is $C_1$-$C_3$ alkyl optionally substituted with 1-5 halogens or optionally substituted $C_3$-$C_5$ cycloalkyl, or $C_3$-$C_6$ cycloalkyl optionally substituted with 1-6 halogens;
$R^9$ is selected from H, halogen, —CN, optionally substituted $C_1$-$C_3$ alkyl, and optionally substituted $C_1$-$C_2$ alkoxy; or $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

$R^{10}$ is selected from H, halogen, and optionally substituted $C_1$-$C_3$ alkyl, or $R^8$ and $R^{10}$ together with the atoms to which they are attached form 4- to 6-membered cyclic ring optionally substituted with 1 to 3 substituents independently selected from $C_1$-$C_3$ alkyl and halogen;

$R^a$ and $R^b$ are each independently selected from H, optionally substituted $C_1$-$C_6$ alkyl and optionally substituted $C_3$-$C_6$ cycloalkyl; or $R^a$ and $R^b$ together with the nitrogen atom to which they are attached form a 4- to 6-membered cyclic ring optionally substituted with 1 to 3 substituents independently selected from $C_1$-$C_3$ alkyl, halogen, and =O;

Q is selected from N, CH, and CF; and

X is O or $CH_2$;

wherein 0 to 10 hydrogen atoms that are attached to one or more carbon atoms are replaced with deuterium atom(s);

with the proviso that the compound is not:

2-(3,5-dichloro-4-((1-isopropyl-6-oxo-1,6-dihydropyridin-3-yl)oxy)phenyl)-1,2,4-triazine-3,5(2H,4H)-dione;

2-(3,5-dichloro-4-((1-isopropyl-6-oxo-1,6-dihydropyridin-3-yl)oxy)phenyl)-3,5-dioxo-2,3,4,5-tetrahydro-1,2,4-triazine-6-carbonitrile; or 2-(3,5-dichloro-4-((1-cyclopropyl-6-oxo-1,6-dihydropyridin-3-yl)oxy)phenyl)-3,5-dioxo-2,3,4,5-tetrahydro-1,2,4-triazine-6-carbonitrile.

In another aspect, provided herein are compounds of Formula IA:

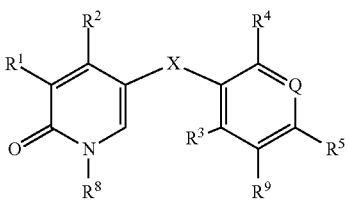

Formula IA or a stereoisomer or a tautomer thereof, or a pharmaceutically acceptable salt thereof, wherein $R^1$ and $R^2$ are each independently selected from H, halogen, —$NR^aR^b$, —$C(O)NR^aR^b$, optionally substituted $C_1$-$C_6$ alkyl, optionally substituted $C_3$-$C_6$ cycloalkyl, and an optionally substituted non-aromatic bicyclic ring; or $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

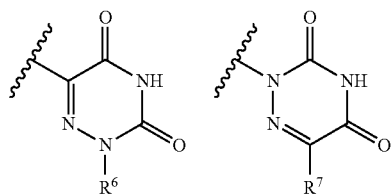

-continued

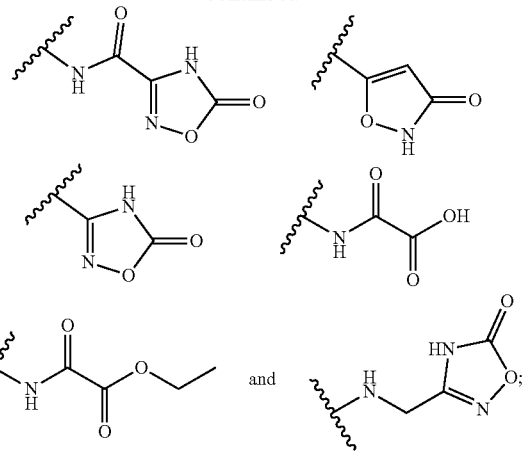

$R^6$ is H or $C_1$-$C_3$ alkyl;

$R^7$ is selected from H, —CN, $CH_3$, and —$NH_2$;

$R^8$ is $C_1$-$C_3$ alkyl optionally substituted with 1-5 halogens or optionally substituted $C_3$-$C_5$ cycloalkyl;

$R^9$ is selected from H, halogen, —CN, optionally substituted $C_1$-$C_3$ alkyl, and optionally substituted $C_1$-$C_2$ alkoxy; or $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

$R^a$ and $R^b$ are each independently selected from H, optionally substituted $C_1$-$C_6$ alkyl and optionally substituted $C_3$-$C_6$ cycloalkyl; or $R^a$ and $R^b$ together with the nitrogen atom to which they are attached form a 4- to 6-membered cyclic ring optionally substituted with 1 to 3 substituents independently selected from $C_1$-$C_3$ alkyl and halogen;

Q is selected from N, CH, and CF; and

X is O or $CH_2$;

wherein 0 to 10 hydrogen atoms that are attached to one or more carbon atoms are replaced with deuterium atom(s);

with the proviso that the compound is not:

2-(3,5-dichloro-4-((1-isopropyl-6-oxo-1,6-dihydropyridin-3-yl)oxy)phenyl)-1,2,4-triazine-3,5(2H,4H)-dione; or 2-(3,5-dichloro-4-((1-isopropyl-6-oxo-1,6-dihydropyridin-3-yl)oxy)phenyl)-3,5-dioxo-2,3,4,5-tetrahydro-1,2,4-triazine-6-carbonitrile.

In some embodiments, the compound has the chemical structure of:

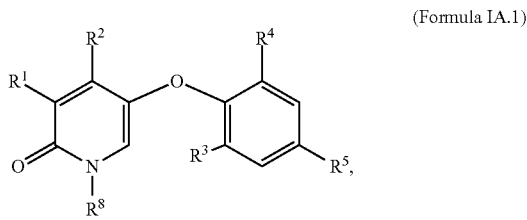

(Formula IA.1)

or a stereoisomer or a tautomer thereof, or a pharmaceutically acceptable salt thereof.

In some embodiments, $R^8$ is H.

In some embodiments, $R^8$ is $C_1$-$C_3$ alkyl optionally substituted with 1-5 halogens. In some embodiments, $R^8$ is $C_3$-$C_6$ cycloalkyl optionally substituted with 1-6 halogens.

In some embodiments, $R^1$ and $R^2$ are each independently selected from H, halogen, $-NR^aR^b$, optionally substituted $C_1$-$C_6$ alkyl, optionally substituted $C_3$-$C_6$ cycloalkyl, and an optionally substituted non-aromatic bicyclic ring.

In some embodiments, $R^1$ is independently selected from H, halogen, $-NR^aR^b$, $-C(O)NR^aR^b$, $C_1$-$C_6$ alkyl optionally substituted with 1-6 substituents independently selected from halogen and $C_3$-$C_4$ cycloalkyl optionally substituted with 1-6 halogens, $C_3$-$C_6$ cycloalkyl optionally substituted with 1-6 halogens, and a non-aromatic bicyclic ring optionally substituted with 1-6 halogens.

In some embodiments, $R^2$ is independently selected from H, halogen, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and a non-aromatic bicyclic ring optionally substituted with 1-6 halogens.

In some embodiments, $R^2$ is independently selected from H, halogen, $C_1$-$C_6$ alkyl optionally substituted with 1-6 substituents independently selected from halogen and $C_3$-$C_4$ cycloalkyl optionally substituted with 1-6 halogens, $C_3$-$C_6$ cycloalkyl, and a non-aromatic bicyclic ring optionally substituted with 1-6 halogens.

In some embodiments, $R^2$ is H.

In some embodiments, $R^1$ is independently selected from H, optionally substituted $C_1$-$C_6$ alkyl, optionally substituted $C_3$-$C_6$ cycloalkyl, and an optionally substituted non-aromatic bicyclic ring; and $R^2$ is independently selected from H, halogen, optionally substituted $C_1$-$C_6$ alkyl, optionally substituted $C_3$-$C_6$ cycloalkyl, and an optionally substituted non-aromatic bicyclic ring.

In some embodiments, $R^1$ is independently selected from H, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and a non-aromatic bicyclic ring optionally substituted with 1-6 halogens; and $R^2$ is independently selected from H, halogen, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and a non-aromatic bicyclic ring optionally substituted with 1-6 halogens.

In some embodiments, $R^1$ is $-NR^aR^b$ or $C_1$-$C_6$ alkyl optionally substituted with 1 to 5 halogens.

In some embodiments, $R^1$ is $C_1$-$C_6$ alkyl.

In some embodiments, $R^1$ is halogen.

In some embodiments, $R^1$ is $C_3$-$C_6$ cycloalkyl optionally substituted with 1-6 halogens.

In some embodiments, $R^1$ is $-C(O)NR^aR^b$.

In some embodiments, $R^a$ and $R^b$ are each independently selected from $C_1$-$C_3$ alkyl.

In some embodiments, $R^a$ is H; and $R^b$ is $C_1$-$C_3$ alkyl optionally substituted with 1 to 3 halogens, or $C_3$-$C_6$ cycloalkyl optionally substituted with 1-5 halogens.

In some embodiments, $R^a$ is H; and $R^b$ is a 4- to 6-membered cyclic ring optionally substituted with 2 halogens.

In some embodiments, $R^a$ and $R^b$ together with the nitrogen atom to which they are attached form a 4- to 6-membered cyclic ring optionally substituted with 1 to 3 substituents independently selected from $C_1$-$C_3$ alkyl, halogen, and =O. In some embodiments, $R^a$ and $R^b$ together with the nitrogen atom to which they are attached form a 4- to 6-membered cyclic ring substituted with =O.

In some embodiments, $R^a$ and $R^b$ together with the nitrogen atom to which they are attached form a 4- to 6-membered cyclic ring optionally substituted with 1 to 3 substituents independently selected from $C_1$-$C_3$ alkyl and halogen.

In some embodiments, $R^1$ and $R^2$ are H; $R^5$ is

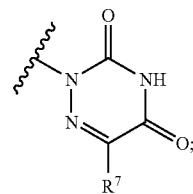

$R^7$ is $-NH_2$; and $R^8$ is isopropyl, optionally substituted with 1-5 halogens.

In some embodiments, $R^5$ is

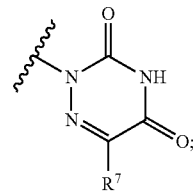

$R^7$ is $CH_3$ or $-NH_2$; and $R^8$ is $C_1$-$C_3$ alkyl.

In some embodiments, the compound has the chemical structure of:

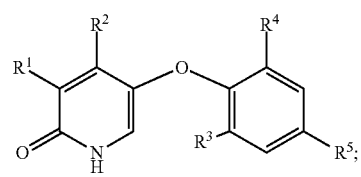

(Formula I.1)

or a stereoisomer or a tautomer thereof, or a pharmaceutically acceptable salt thereof.

In some embodiments, $R^1$ is $CH_3$; $R^8$ is isopropyl; $R^5$ is

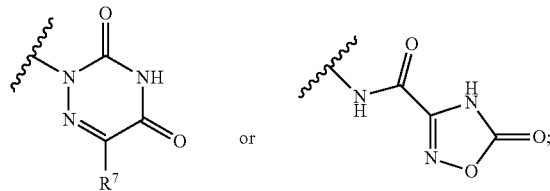

and $R^7$ is $-NH_2$.

In some embodiments, $R^1$ and $R^2$ are each independently $C_1$-$C_6$ alkyl, $C_3$-$C_6$ cycloalkyl, or a non-aromatic bicyclic ring, wherein $R^1$ and $R^2$ are each optionally substituted with 1 to 3 substituents independently selected from optionally substituted $C_3$-$C_4$ cycloalkyl, optionally substituted bicyclic ring, and halogen; or $R^1$ or $R^2$ are H, but $R^1$ and $R^2$ cannot both be H. In some embodiments, $R^1$ and $R^2$ are each independently $C_1$-$C_6$ alkyl, $C_3$-$C_6$ cycloalkyl, or a non-aromatic bicyclic ring, wherein $R^1$ and $R^2$ are each optionally substituted with 1 to 3 substituents independently selected from $C_3$-$C_4$ cycloalkyl optionally substituted with 1 to 3 substituents independently selected from halogen and $C_1$-$C_3$ alkyl; bicyclic ring optionally substituted with 1 to 3 substituents independently selected from halogen and $C_1$-$C_3$ alkyl; and halogen; or $R^1$ or $R^2$ are H, but $R^1$ and $R^2$ cannot both be H. In some embodiments, $R^1$ and $R^2$ are each independently $C_1$-$C_6$ alkyl, $C_3$-$C_6$ cycloalkyl, or a non-aromatic bicyclic ring, wherein $R^1$ and $R^2$ are each optionally substituted with 1 to 3 substituents independently selected from halogen, $C_3$-$C_4$ cycloalkyl, and a bicyclic ring, wherein the $C_3$-$C_4$ cycloalkyl and the bicyclic ring are optionally substituted with 1 to 3 substituents independently selected from $C_1$-$C_3$ alkyl and halogen; or $R^1$ or $R^2$ are H, but $R^1$ and $R^2$ cannot both be H. In some embodiments, the bicyclic ring is a spirocyclic ring system. In some embodiments, the bicyclic ring is a fused ring system. In some embodiments, the bicyclic ring is a bridged ring system.

In some embodiments, $R^1$ is $C_1$-$C_6$ alkyl.

In some embodiments, $R^2$ is H.

In some embodiments, $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl. In some embodiments, $R^1$ and $R^2$ together with the carbon atoms to which they are attached form a $C_4$-$C_7$ monocyclic ring optionally substituted with 1 to 3 substituents independently selected from halogen and $C_1$-$C_6$ alkyl.

In some embodiments, $R^1$ and $R^2$ together with the carbon atoms to which they are attached form a polycyclic ring optionally substituted with 1 to 3 substituents independently selected from $C_1$-$C_6$ alkyl. In some embodiments, the polycyclic ring is a spirocyclic ring system. In some embodiments, the polycyclic ring is a fused ring system. In some embodiments, the polycyclic ring is a bridged ring system.

In some embodiments, $R^3$ and $R^4$ are each independently selected from halogen; —CN; $C_1$-$C_3$ alkyl optionally substituted with 1 to 3 substituents independently selected from halogen and $C_1$-$C_6$ alkoxy; $C_1$-$C_2$ alkoxy optionally substituted with 1 to 3 substituents independently selected from halogen; and $C_2$-$C_3$ alkenyl optionally substituted with 1 to 3 substituents independently selected from halogen and $C_1$-$C_6$ alkoxy; and cyclopropyl. In some embodiments, $R^3$ and $R^4$ are each independently selected from Cl; —CN; $C_1$-$C_3$ alkyl optionally substituted with 1 to 3 substituents independently selected from halogen and $C_1$-$C_6$ alkoxy; $C_1$-$C_2$ alkoxy optionally substituted with 1 to 3 substituents independently selected from halogen; and $C_2$-$C_3$ alkenyl optionally substituted with 1 to 3 substituents independently selected from halogen and $C_1$-$C_6$ alkoxy; and cyclopropyl. In some embodiments, $R^3$ and $R^4$ are each independently selected from halogen and $C_1$-$C_3$ alkyl. In some embodiments, $R^3$ and $R^4$ are both halogen. In some embodiments, $R^3$ and $R^4$ are both Cl. In some embodiments, $R^3$ and $R^4$ are both methyl.

In some embodiments, $R^5$ is

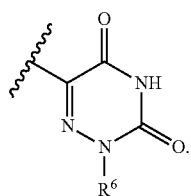

In some embodiments, $R^5$ is

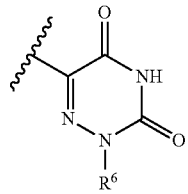

and $R^6$ is H or $C_1$-$C_3$ alkyl. In some embodiments, $R^5$ is

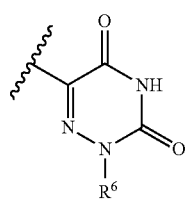

and $R^6$ is H. In some embodiments, $R^5$ is

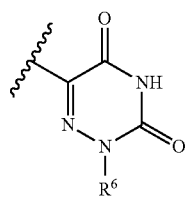

and $R^6$ is $C_1$-$C_3$ alkyl.

In some embodiments, $R^6$ is H. In some embodiments, $R^6$ is $C_1$-$C_3$ alkyl.

In some embodiments, $R^5$ is

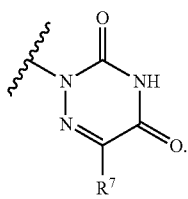

In some embodiments, $R^5$ is

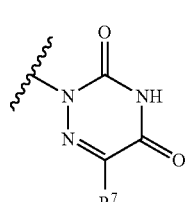

and $R^7$ is H or —$NH_2$. In some embodiments, $R^5$ is

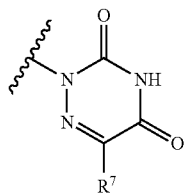

and $R^7$ is H. In some embodiments, $R^5$ is

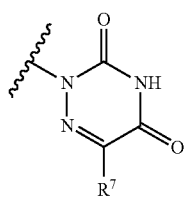

and $R^7$ is —$NH_2$. In some embodiments, $R^5$ is

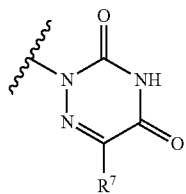

and $R^7$ is $CH_3$. In some embodiments, $R^5$ is

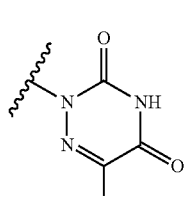

and $R^7$ is —CN.

In some embodiments, $R^7$ is H or —$NH_2$. In some embodiments, $R^7$ is H. In some embodiments, $R^7$ is —$NH_2$. In some embodiments, $R^7$ is —CN. In some embodiments, $R^7$ is $CH_3$.

In some embodiments, $R^5$ is

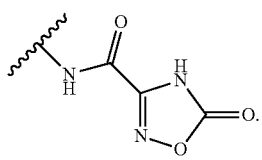 [SMILES: *NC(=O)c1noc(=O)[nH]1]

In some embodiments, $R^5$ is

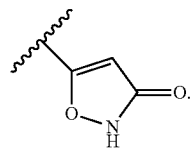 [SMILES: *c1cc(=O)[nH]o1]

In some embodiments, $R^5$ is

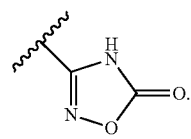 [SMILES: *c1noc(=O)[nH]1]

In some embodiments, $R^5$ is

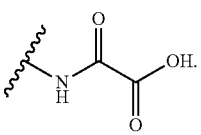 [SMILES: *NC(=O)C(=O)O]

In some embodiments, $R^5$ is

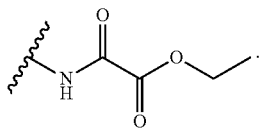 [SMILES: *NC(=O)C(=O)OCC]

In some embodiments, $R^5$ is

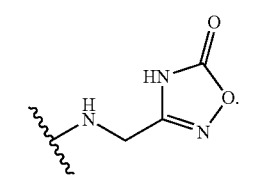 [SMILES: *NCc1noc(=O)[nH]1]

In some embodiments, Q is CH, CD, or CF. In some embodiments, Q is CH. In some embodiments, Q is CD. In some embodiments, Q is CF. In some embodiments, Q is N.

In some embodiments, X is $CH_2$. In some embodiments, X is O.

In some embodiments, $R^8$ is H. In some embodiments, $R^8$ is $C_1$-$C_3$ alkyl optionally substituted with 1-5 halogens. In some embodiments, $R^8$ is $C_1$-$C_3$ alkyl.

In some embodiments, $R^8$ and $R^{10}$ together with the atoms to which they are attached form 4- to 6-membered cyclic ring optionally substituted with 1 to 3 substituents independently selected from $C_1$-$C_3$ alkyl and halogen.

In some embodiments, $R^9$ is selected from H; halogen; —CN; $C_1$-$C_3$ alkyl optionally substituted with 1 to 3 substituents independently selected from halogen and $C_1$-$C_2$ alkoxy; and $C_1$-$C_2$ alkoxy optionally substituted with 1 to 3 substituents independently selected from halogen. In some embodiments, $R^9$ is hydrogen or $C_1$-$C_3$ alkyl. In some embodiments, $R^9$ is hydrogen.

In some embodiments, $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring. In some embodiments, $R^3$ and $R^9$ together with the carbon atoms to which they are attached form a 4-, 5-, or 6-membered partially unsaturated carbocyclic ring. In some embodiments, $R^3$ and $R^9$ together with the carbon atoms to which they are attached form a 4-, 5-, or 6-membered partially unsaturated heterocyclic ring. In some embodiments, $R^3$ and $R^9$ together with the carbon atoms to which they are attached form a $C_6$-$C_{10}$ aryl ring. In some embodiments, $R^3$ and $R^9$ together with the carbon atoms to which they are attached form a 5- or 6-membered heteroaryl ring.

In some embodiments, $R^{10}$ is selected from H, halogen, and $C_1$-$C_3$ alkyl optionally substituted with 1-5 halogens.

In some embodiments, the compound of Formula I", I', I, IA", or IA have the chemical structure of:

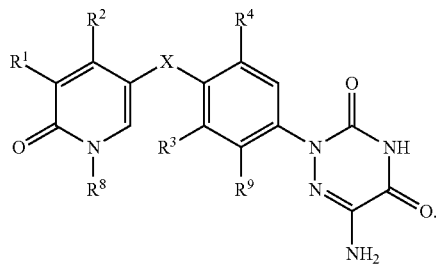

In some embodiments, the compound of Formula I", I', I, IA", or IA have the chemical structure of:

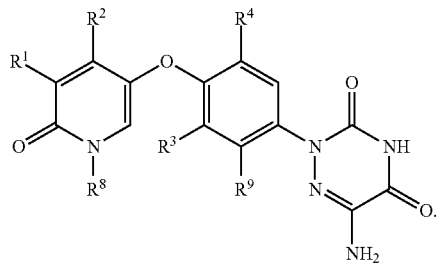

In some embodiments, the compound of Formula I", I', I, IA", or IA have the chemical structure of:

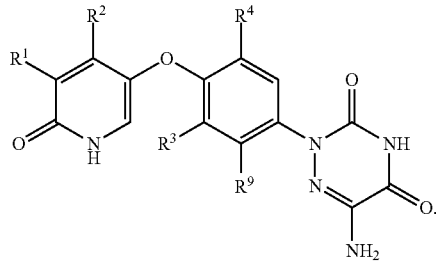

In some embodiments, the compound of Formula I", I', I, IA", or IA have the chemical structure of:

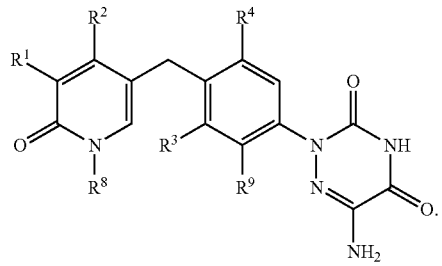

In some embodiments, the compound of Formula I", I', I, IA", or IA have the chemical structure of:

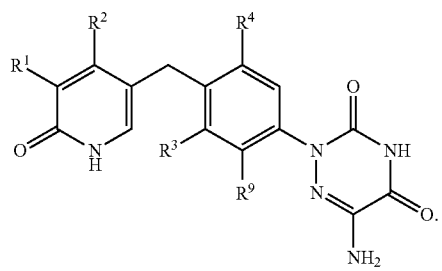

In some embodiments, the compound of Formula I" or IA" have the chemical structure of:

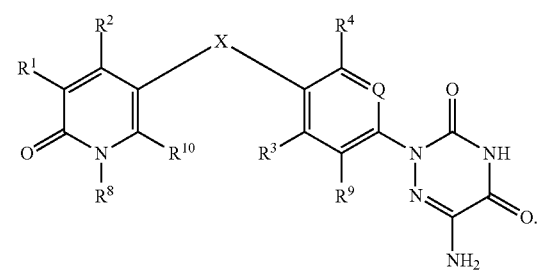

In some embodiments, the compound of Formula I" or IA" have the chemical structure of:

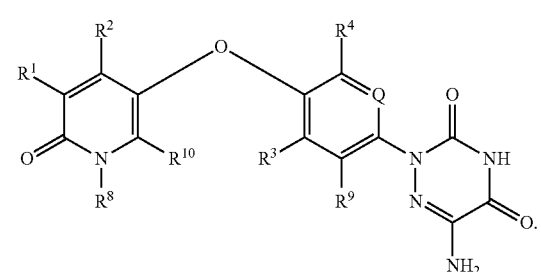

In some embodiments, the compound of Formula I" or IA" have the chemical structure of:

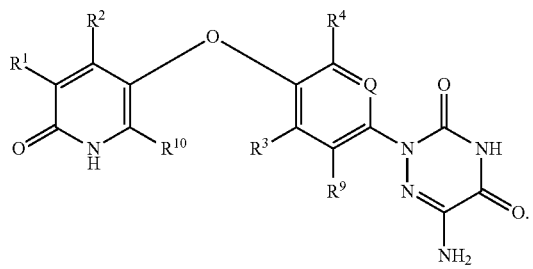

In some embodiments, the compound of Formula I" or IA" have the chemical structure of:

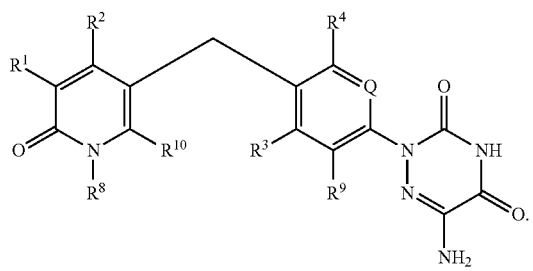

In some embodiments, the compound of Formula I" or IA" have the chemical structure of:

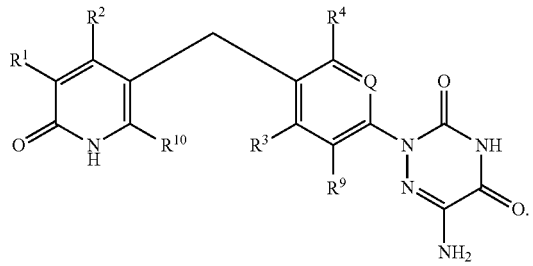

In some embodiments, the compound of Formula I', I, or IA have the chemical structure of:

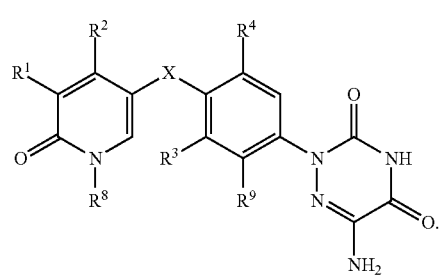

In some embodiments, the compound of Formula I', I, or IA have the chemical structure of:

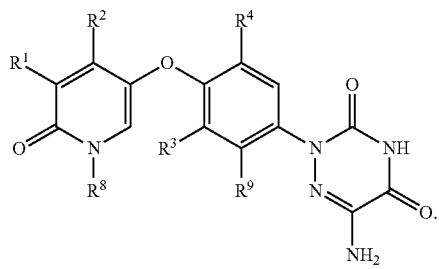

In some embodiments, the compound of Formula I', I, or IA have the chemical structure of:

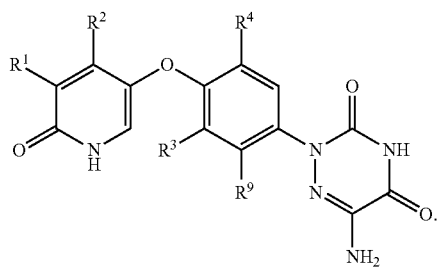

In some embodiments, the compound of Formula I', I, or IA have the chemical structure of:

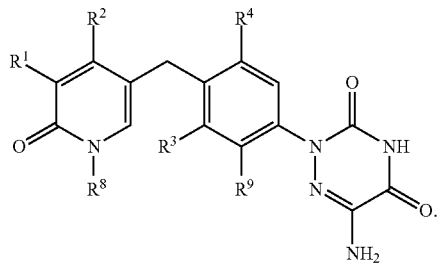

In some embodiments, the compound of Formula I', I, or IA have the chemical structure of:

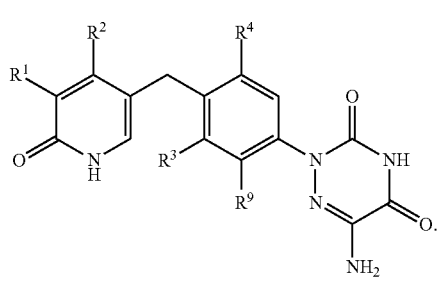

In some embodiments, the compound of Formula I" or IA" have the chemical structure of:

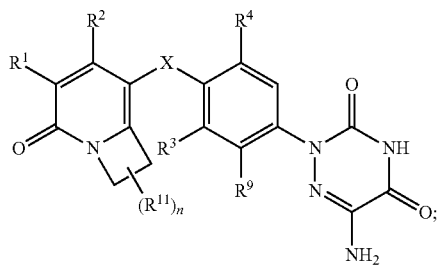

wherein each $R^{11}$ is independently selected from $C_1$-$C_3$ alkyl and halogen; and n is 0, 1, 2 or 3.

In some embodiments, the compound of Formula I" or IA" have the chemical structure of:

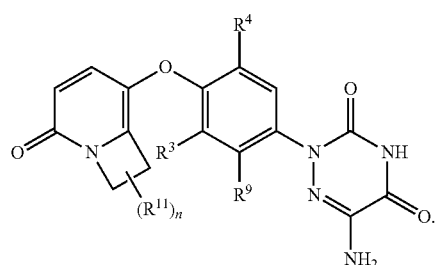

In some embodiments, the compound of Formula I" or IA" have the chemical structure of:

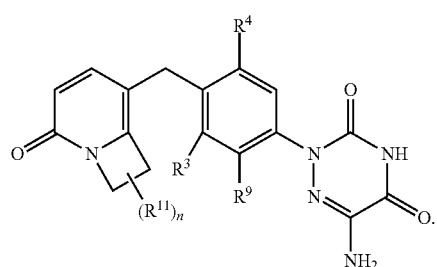

In some embodiments, the compound of Formula I" or IA" have the chemical structure of:

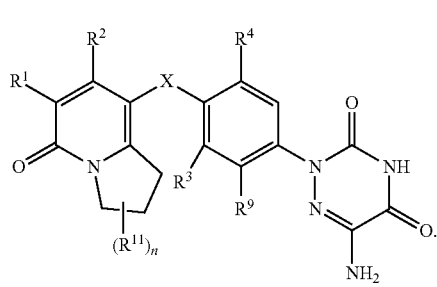

In some embodiments, the compound of Formula I" or IA" have the chemical structure of:

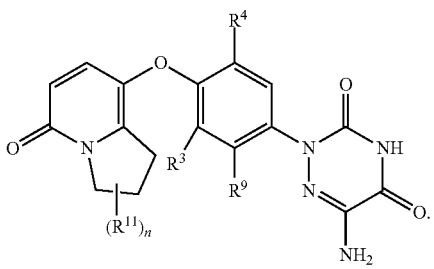

In some embodiments, the compound of Formula I" or IA" have the chemical structure of:

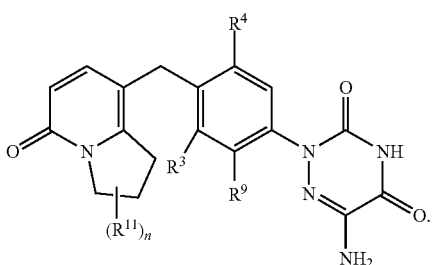

In some embodiments, the compound of Formula I" or IA" have the chemical structure of:

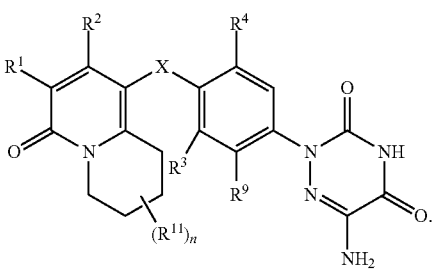

In some embodiments, the compound of Formula I" or IA" have the chemical structure of:

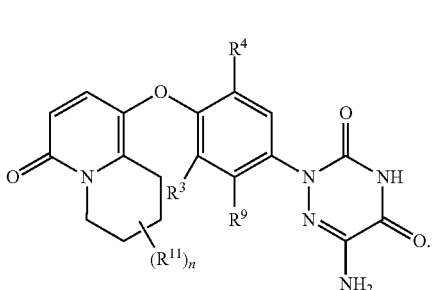

In some embodiments, the compound of Formula I" or IA" have the chemical structure of:

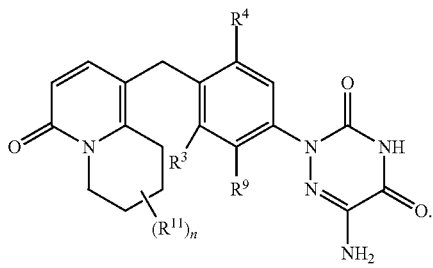

In some embodiments, each $R^{11}$ is independently selected from —$CH_3$, —$CH_2CH_3$, —F, Cl, and —Br. In some embodiments, $R^{11}$ is —$CH_3$. In some embodiments, $R^{11}$ is —F.

In some embodiments, n is 0. In some embodiments, n is 1. In some embodiments, n is 2. In some embodiments, n is 3.

In another aspect, disclosed herein is a compound selected from the group consisting of:

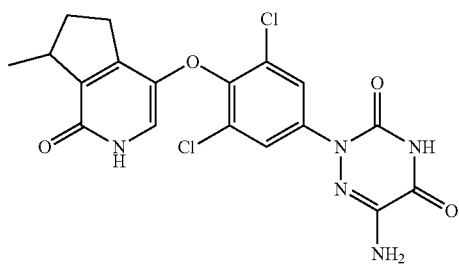

6-amino-2-(3,5-dichloro-4-((7-methyl-1-oxo-2,5,6,7-tetrahydro-1H-cyclopenta[c]pyridin-4-yl)oxy)phenyl)-1,2,4-triazine-3,5(2H,4H)-dione;

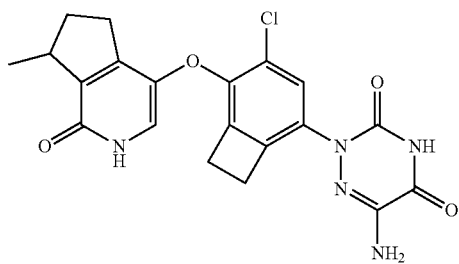 [SMILES: CC1CCc2c(Oc3c(Cl)cc(-n4nc(N)c(=O)[nH]c4=O)c4c3CC4)c[nH]c(=O)c21]

6-amino-2-(4-chloro-5-((7-methyl-1-oxo-2,5,6,7-tetrahydro-1H-cyclopenta[c]pyridin-4-yl)oxy)bicyclo[4.2.0]octa-1,3,5-trien-2-yl)-1,2,4-triazine-3,5(2H,4H)-dione;

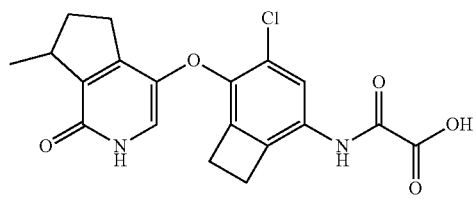 [SMILES: CC1CCc2c(Oc3c(Cl)cc(NC(=O)C(=O)O)c4c3CC4)c[nH]c(=O)c21]

2-((4-chloro-5-((7-methyl-1-oxo-2,5,6,7-tetrahydro-1H-cyclopenta[c]pyridin-4-yl)oxy)bicyclo[4.2.0]octa-1,3,5-trien-2-yl)amino)-2-oxoacetic acid;

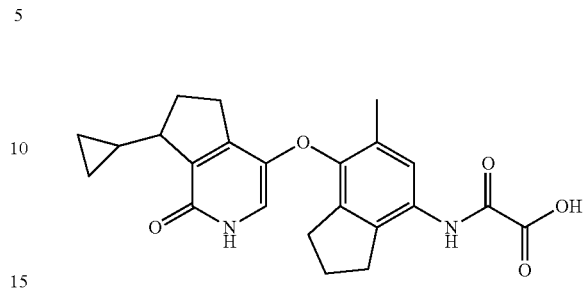

2-((7-((7-cyclopropyl-1-oxo-2,5,6,7-tetrahydro-1H-cyclopenta[c]pyridin-4-yl)oxy)-6-methyl-2,3-dihydro-1H-inden-4-yl)amino)-2-oxoacetic acid;

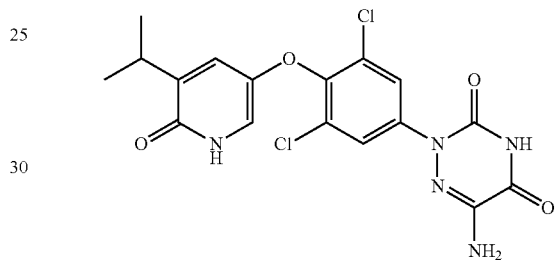

6-amino-2-(3,5-dichloro-4-((5-isopropyl-6-oxo-1,6-dihydropyridin-3-yl)oxy)phenyl)-1,2,4-triazine-3,5(2H,4H)-dione;

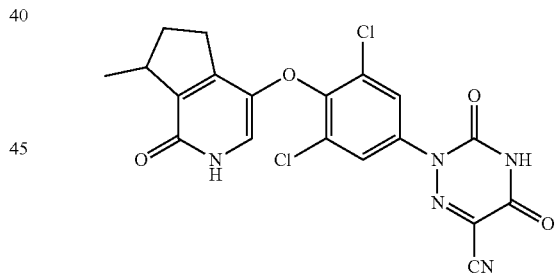

2-(3,5-dichloro-4-((7-methyl-1-oxo-2,5,6,7-tetrahydro-1H-cyclopenta[c]pyridin-4-yl)oxy)phenyl)-3,5-dioxo-2,3,4,5-tetrahydro-1,2,4-triazine-6-carbonitrile;

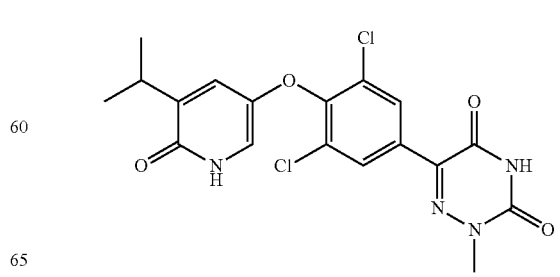

6-(3,5-dichloro-4-((5-isopropyl-6-oxo-1,6-dihydropyridin-3-yl)oxy)phenyl)-2-methyl-1,2,4-triazine-3,5(2H,4H)-dione;

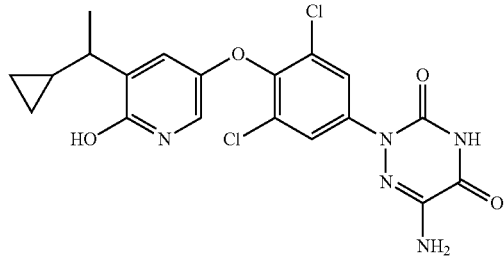

6-amino-2-(3,5-dichloro-4-((5-(1-cyclopropylethyl)-6-hydroxypyridin-3-yl)oxy)phenyl)-1,2,4-triazine-3,5(2H,4H)-dione;

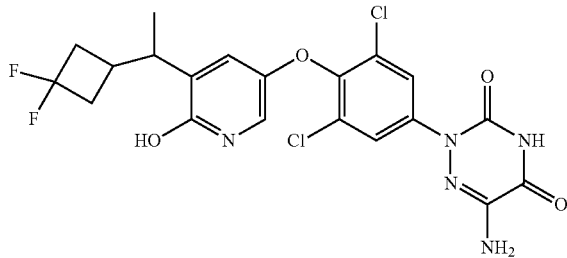 [SMILES: CC(c1cc(Oc2c(Cl)cc(-n3nc(N)c(=O)[nH]c3=O)cc2Cl)cnc1O)C1CC(F)(F)C1]

6-amino-2-(3,5-dichloro-4-((5-(1-(3,3-difluorocyclobutyl)ethyl)-6-hydroxypyridin-3-yl)oxy)phenyl)-1,2,4-triazine-3,5(2H,4H)-dione;

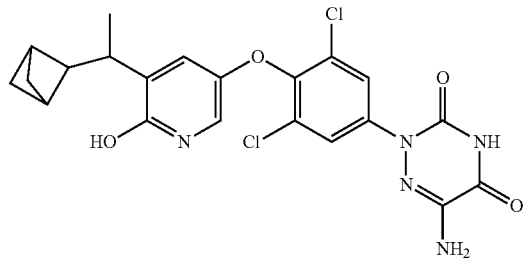 [SMILES: CC(c1cc(Oc2c(Cl)cc(-n3nc(N)c(=O)[nH]c3=O)cc2Cl)cnc1O)C1C2CC1C2]

6-amino-2-(4-((5-(1-(bicyclo[1.1.1]pentan-2-yl)ethyl)-6-hydroxypyridin-3-yl)oxy)-3,5-dichlorophenyl)-1,2,4-triazine-3,5(2H,4H)-dione;

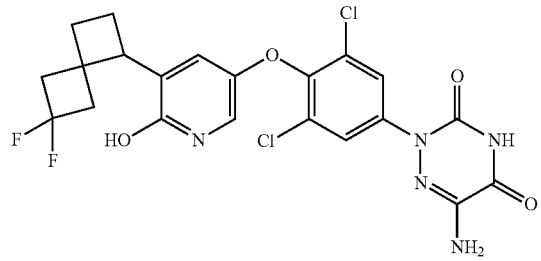 [SMILES: Nc1nn(-c2cc(Cl)c(Oc3cnc(O)c(C4CCC45CC(F)(F)C5)c3)c(Cl)c2)c(=O)[nH]c1=O]

6-amino-2-(3,5-dichloro-4-((5-(6,6-difluorospiro[3.3]heptan-1-yl)-6-hydroxypyridin-3-yl)oxy)phenyl)-1,2,4-triazine-3,5(2H,4H)-dione;

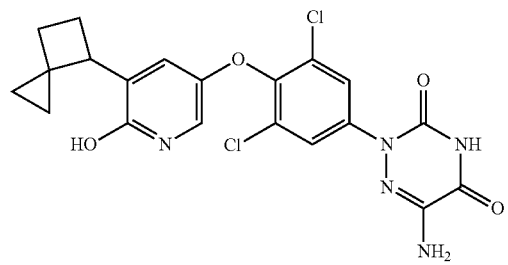 [SMILES: Nc1nn(-c2cc(Cl)c(Oc3cnc(O)c(C4CCC45CC5)c3)c(Cl)c2)c(=O)[nH]c1=O]

6-amino-2-(3,5-dichloro-4-((6-hydroxy-5-(spiro[2.3]hexan-4-yl)pyridin-3-yl)oxy)phenyl)-1,2,4-triazine-3,5(2H,4H)-dione;

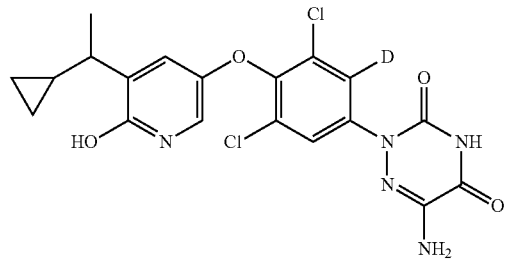

6-amino-2-(4-chloro-5-((6-hydroxy-5-isopropylpyridin-3-yl)oxy)-6-methylpyridin-2-yl)-1,2,4-triazine-3,5(2H,4H)-dione;

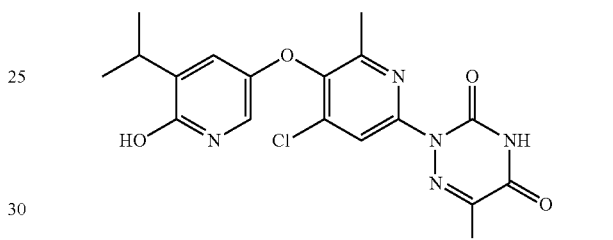

6-amino-2-(3,5-dichloro-4-((5-(1-cyclopropylethyl)-6-hydroxypyridin-3-yl)oxy)phenyl-2-d)-1,2,4-triazine-3,5(2H,4H)-dione;

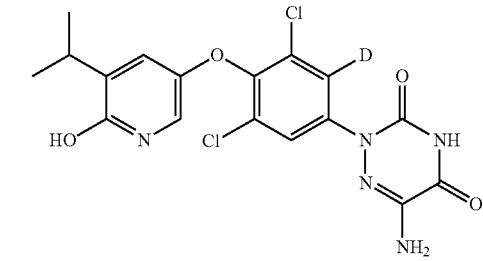 [SMILES: [2H]c1c(-n2nc(N)c(=O)[nH]c2=O)cc(Cl)c(Oc2cnc(O)c(C(C)C)c2)c1Cl]

6-amino-2-(3,5-dichloro-4-((6-hydroxy-5-isopropylpyridin-3-yl)oxy)phenyl-2-d)-1,2,4-triazine-3,5(2H,4H)-dione;

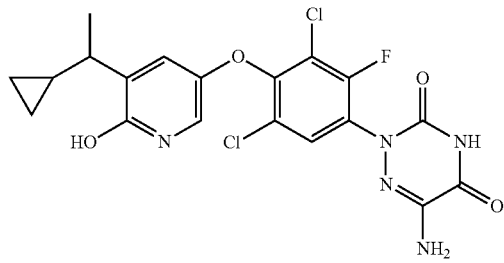 [SMILES: CC(c1cc(Oc2c(Cl)cc(-n3nc(N)c(=O)[nH]c3=O)c(F)c2Cl)cnc1O)C1CC1]

6-amino-2-(3,5-dichloro-4-((5-(1-cyclopropylethyl)-6-hydroxypyridin-3-yl)oxy)-2-fluorophenyl)-1,2,4-triazine-3,5(2H,4H)-dione;

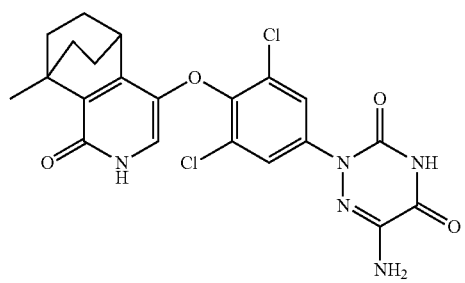 [SMILES: CC12CCC(CC1)c1c(Oc3c(Cl)cc(-n4nc(N)c(=O)[nH]c4=O)cc3Cl)c[nH]c(=O)c12]

6-amino-2-(3,5-dichloro-4-((8-methyl-1-oxo-1,2,5,6,7,8-hexahydro-5,8-ethanoisoquinolin-4-yl)oxy)phenyl)-1,2,4-triazine-3,5(2H,4H)-dione;

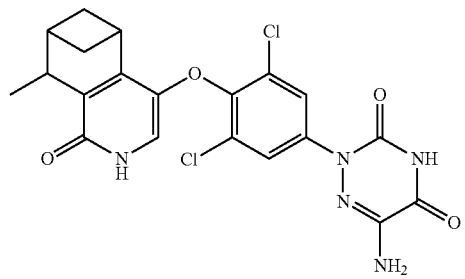 [SMILES: CC1c2c(c(Oc3c(Cl)cc(-n4nc(N)c(=O)[nH]c4=O)cc3Cl)c[nH]c2=O)C2CC1C2]

6-amino-2-(3,5-dichloro-4-((8-methyl-1-oxo-1,2,5,6,7,8-hexahydro-5,7-methanoisoquinolin-4-yl)oxy)phenyl)-1,2,4-triazine-3,5(2H,4H)-dione;

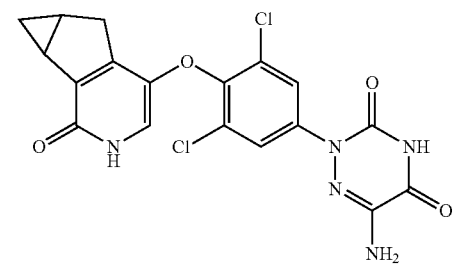 [SMILES: Nc1nn(-c2cc(Cl)c(Oc3c[nH]c(=O)c4c3CC3CC43)c(Cl)c2)c(=O)[nH]c1=O]

6-amino-2-(3,5-dichloro-4-((1-oxo-1,2,5,5a,6,6a-hexahydrocyclopropa[4,5]cyclopenta[1,2-c]pyridin-4-yl)oxy)phenyl)-1,2,4-triazine-3,5(2H,4H)-dione;

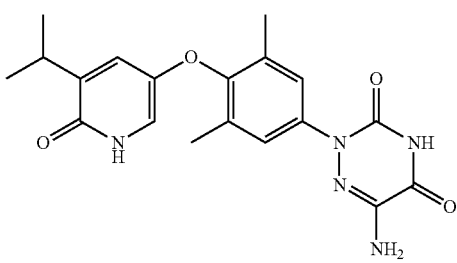

6-amino-2-(4-((5-isopropyl-6-oxo-1,6-dihydropyridin-3-yl)oxy)-3,5-dimethylphenyl)-1,2,4-triazine-3,5(2H,4H)-dione;

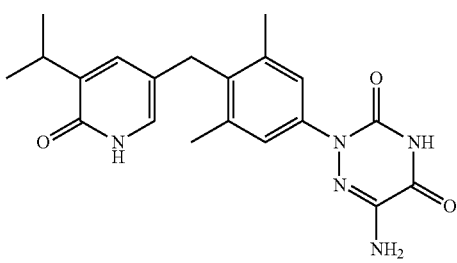

6-amino-2-(4-((5-isopropyl-6-oxo-1,6-dihydropyridin-3-yl)methyl)-3,5-dimethylphenyl)-1,2,4-triazine-3,5(2H,4H)-dione;

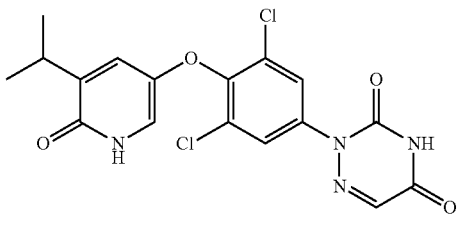 [SMILES: CC(C)c1cc(Oc2c(Cl)cc(-n3ncc(=O)[nH]c3=O)cc2Cl)c[nH]c1=O]

2-(3,5-dichloro-4-((5-isopropyl-6-oxo-1,6-dihydropyridin-3-yl)oxy)phenyl)-1,2,4-triazine-3,5(2H,4H)-dione; and

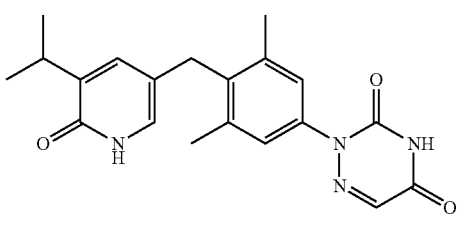 [SMILES: Cc1cc(-n2ncc(=O)[nH]c2=O)cc(C)c1Cc1c[nH]c(=O)c(C(C)C)c1]

2-(4-((5-isopropyl-6-oxo-1,6-dihydropyridin-3-yl)methyl)-3,5-dimethylphenyl)-1,2,4-triazine-3,5(2H,4H)-dione;

or a stereoisomer or a tautomer thereof, or a pharmaceutically acceptable salt thereof.

In another aspect, disclosed herein is a compound of Formula I'' or IA'' selected from the group consisting of:

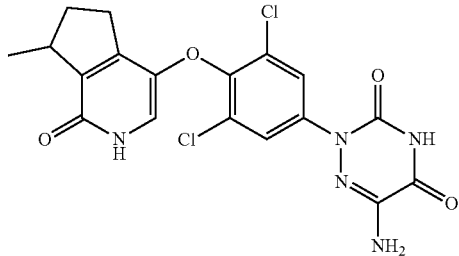 [SMILES: CC1CCc2c(Oc3c(Cl)cc(-n4nc(N)c(=O)[nH]c4=O)cc3Cl)c[nH]c(=O)c21]

6-amino-2-(3,5-dichloro-4-((7-methyl-1-oxo-2,5,6,7-tetrahydro-1H-cyclopenta[c]pyridin-4-yl)oxy)phenyl)-1,2,4-triazine-3,5(2H,4H)-dione;

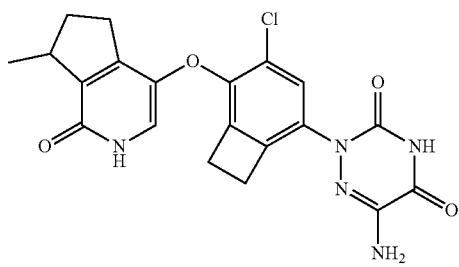 [SMILES: CC1CCc2c(Oc3c(Cl)cc(-n4nc(N)c(=O)[nH]c4=O)c4c3CC4)c[nH]c(=O)c21]

6-amino-2-(4-chloro-5-((7-methyl-1-oxo-2,5,6,7-tetrahydro-1H-cyclopenta[c]pyridin-4-yl)oxy)bicyclo[4.2.0]octa-1,3,5-trien-2-yl)-1,2,4-triazine-3,5(2H,4H)-dione;

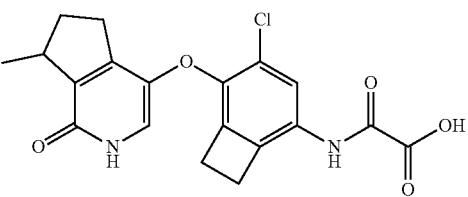 [SMILES: CC1CCc2c(Oc3c(Cl)cc(NC(=O)C(=O)O)c4c3CC4)c[nH]c(=O)c21]

2-((4-chloro-5-((7-methyl-1-oxo-2,5,6,7-tetrahydro-1H-cyclopenta[c]pyridin-4-yl)oxy)bicyclo[4.2.0]octa-1,3,5-trien-2-yl)amino)-2-oxoacetic acid;

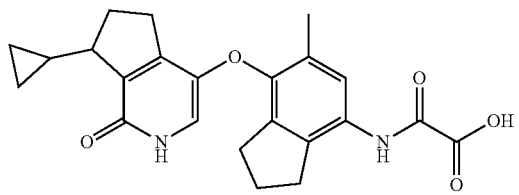 [SMILES: Cc1cc(NC(=O)C(=O)O)c2c(c1Oc1c[nH]c(=O)c3c1CCC3C1CC1)CCC2]

2-((7-((7-cyclopropyl-1-oxo-2,5,6,7-tetrahydro-1H-cyclopenta[c]pyridin-4-yl)oxy)-6-methyl-2,3-dihydro-1H-inden-4-yl)amino)-2-oxoacetic acid;

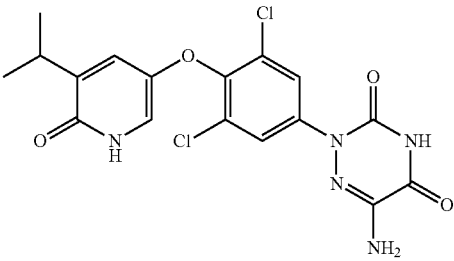

6-amino-2-(3,5-dichloro-4-((5-isopropyl-6-oxo-1,6-dihydropyridin-3-yl)oxy)phenyl)-1,2,4-triazine-3,5(2H,4H)-dione;

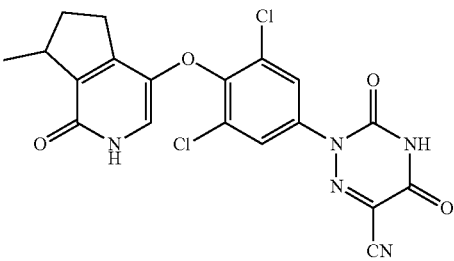 [SMILES: CC1CCc2c(Oc3c(Cl)cc(-n4nc(C#N)c(=O)[nH]c4=O)cc3Cl)c[nH]c(=O)c21]

2-(3,5-dichloro-4-((7-methyl-1-oxo-2,5,6,7-tetrahydro-1H-cyclopenta[c]pyridin-4-yl)oxy)phenyl)-3,5-dioxo-2,3,4,5-tetrahydro-1,2,4-triazine-6-carbonitrile;

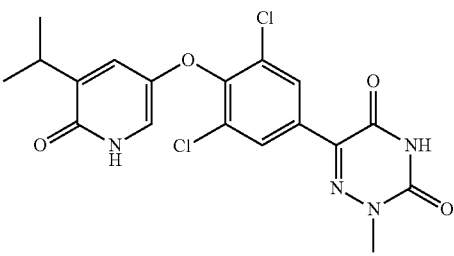 [SMILES: CC(C)c1cc(Oc2c(Cl)cc(-c3nn(C)c(=O)[nH]c3=O)cc2Cl)c[nH]c1=O]

6-(3,5-dichloro-4-((5-isopropyl-6-oxo-1,6-dihydropyridin-3-yl)oxy)phenyl)-2-methyl-1,2,4-triazine-3,5(2H,4H)-dione;

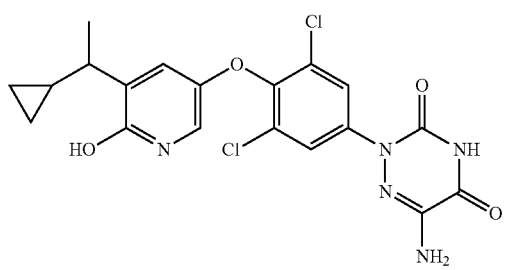 [SMILES: CC(c1cc(Oc2c(Cl)cc(-n3nc(N)c(=O)[nH]c3=O)cc2Cl)cnc1O)C1CC1]

6-amino-2-(3,5-dichloro-4-((5-(1-cyclopropylethyl)-6-hydroxypyridin-3-yl)oxy)phenyl)-1,2,4-triazine-3,5(2H,4H)-dione;

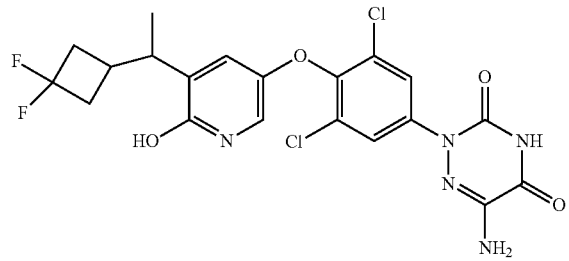 [SMILES: CC(c1cc(Oc2c(Cl)cc(-n3nc(N)c(=O)[nH]c3=O)cc2Cl)cnc1O)C1CC(F)(F)C1]

6-amino-2-(3,5-dichloro-4-((5-(1-(3,3-difluorocyclobutyl)ethyl)-6-hydroxypyridin-3-yl)oxy)phenyl)-1,2,4-triazine-3,5(2H,4H)-dione;

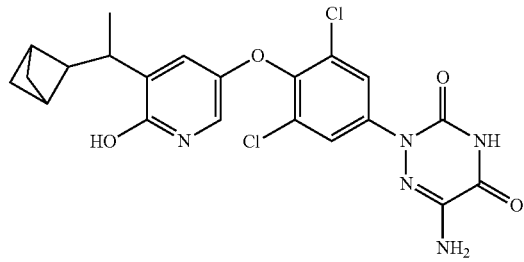 [SMILES: CC(c1cc(Oc2c(Cl)cc(-n3nc(N)c(=O)[nH]c3=O)cc2Cl)cnc1O)C1C2CC1C2]

6-amino-2-(4-((5-(1-(bicyclo[1.1.1]pentan-2-yl)ethyl)-6-hydroxypyridin-3-yl)oxy)-3,5-dichlorophenyl)-1,2,4-triazine-3,5(2H,4H)-dione;

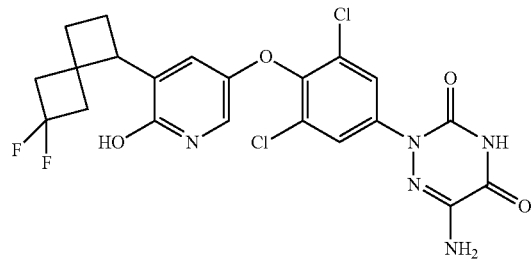 [SMILES: Nc1nn(-c2cc(Cl)c(Oc3cnc(O)c(C4CCC45CC(F)(F)C5)c3)c(Cl)c2)c(=O)[nH]c1=O]

6-amino-2-(3,5-dichloro-4-((5-(6,6-difluorospiro[3.3]heptan-1-yl)-6-hydroxypyridin-3-yl)oxy)phenyl)-1,2,4-triazine-3,5(2H,4H)-dione;

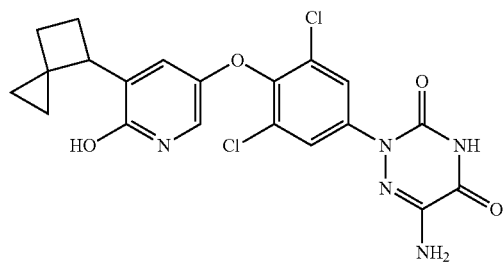 [SMILES: Nc1nn(-c2cc(Cl)c(Oc3cnc(O)c(C4CCC45CC5)c3)c(Cl)c2)c(=O)[nH]c1=O]

6-amino-2-(3,5-dichloro-4-((6-hydroxy-5-(spiro[2.3]hexan-4-yl)pyridin-3-yl)oxy)phenyl)-1,2,4-triazine-3,5(2H,4H)-dione;

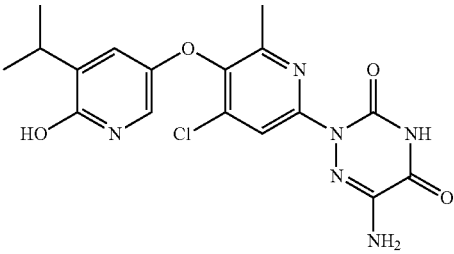 [SMILES: Cc1nc(-n2nc(N)c(=O)[nH]c2=O)cc(Cl)c1Oc1cnc(O)c(C(C)C)c1]

6-amino-2-(4-chloro-5-((6-hydroxy-5-isopropylpyridin-3-yl)oxy)-6-methylpyridin-2-yl)-1,2,4-triazine-3,5(2H,4H)-dione;

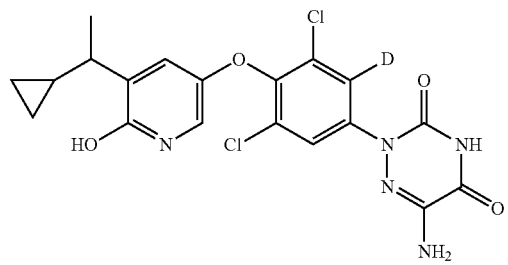

6-amino-2-(3,5-dichloro-4-((5-(1-cyclopropylethyl)-6-hydroxypyridin-3-yl)oxy)phenyl-2-d)-1,2,4-triazine-3,5(2H,4H)-dione;

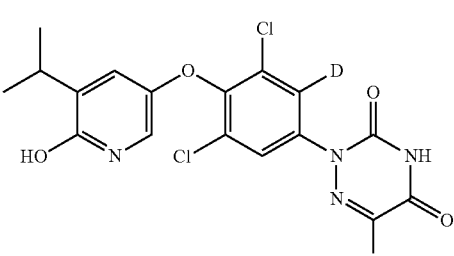

6-amino-2-(3,5-dichloro-4-((6-hydroxy-5-isopropylpyridin-3-yl)oxy)phenyl-2-d)-1,2,4-triazine-3,5(2H,4H)-dione;

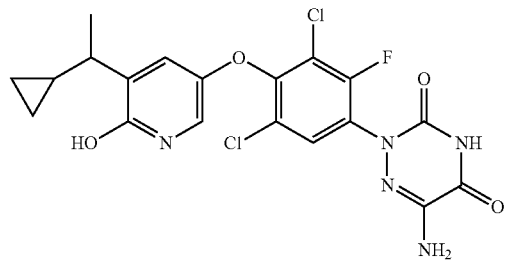 [SMILES: CC(c1cc(Oc2c(Cl)cc(-n3nc(N)c(=O)[nH]c3=O)c(F)c2Cl)cnc1O)C1CC1]

6-amino-2-(3,5-dichloro-4-((5-(1-cyclopropylethyl)-6-hydroxypyridin-3-yl)oxy)-2-fluorophenyl)-1,2,4-triazine-3,5(2H,4H)-dione;

6-amino-2-(4-((5-isopropyl-6-oxo-1,6-dihydropyridin-3-yl)oxy)-3,5-dimethylphenyl)-1,2,4-triazine-3,5(2H,4H)-dione;

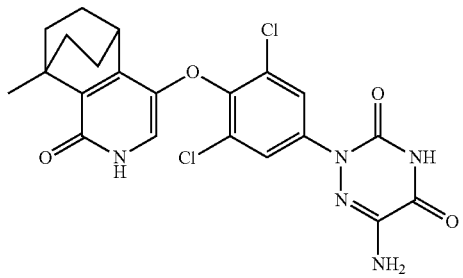 [SMILES: CC12CCC(CC1)c1c(Oc3c(Cl)cc(-n4nc(N)c(=O)[nH]c4=O)cc3Cl)c[nH]c(=O)c12]

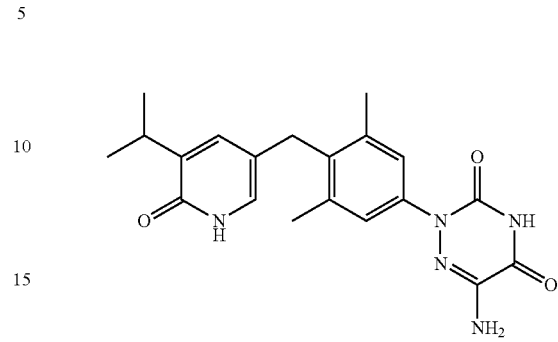

6-amino-2-(3,5-dichloro-4-((8-methyl-1-oxo-1,2,5,6,7,8-hexahydro-5,8-ethanoisoquinolin-4-yl)oxy)phenyl)-1,2,4-triazine-3,5(2H,4H)-dione;

6-amino-2-(4-((5-isopropyl-6-oxo-1,6-dihydropyridin-3-yl)methyl)-3,5-dimethylphenyl)-1,2,4-triazine-3,5(2H,4H)-dione;

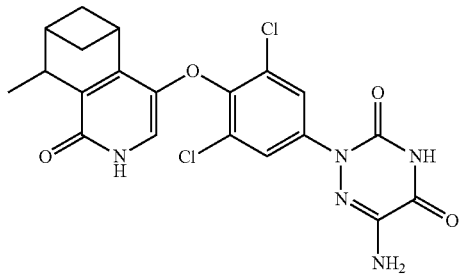 [SMILES: CC1c2c(c(Oc3c(Cl)cc(-n4nc(N)c(=O)[nH]c4=O)cc3Cl)c[nH]c2=O)C2CC1C2]

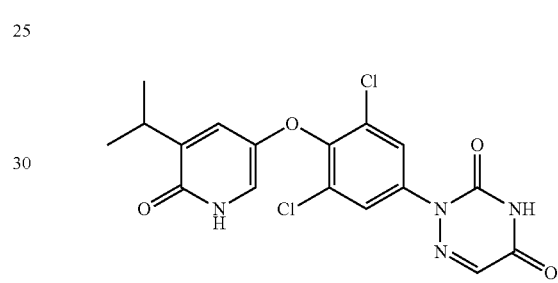

6-amino-2-(3,5-dichloro-4-((8-methyl-1-oxo-1,2,5,6,7,8-hexahydro-5,7-methanoisoquinolin-4-yl)oxy)phenyl)-1,2,4-triazine-3,5(2H,4H)-dione;

2-(3,5-dichloro-4-((5-isopropyl-6-oxo-1,6-dihydropyridin-3-yl)oxy)phenyl)-1,2,4-triazine-3,5(2H,4H)-dione; and

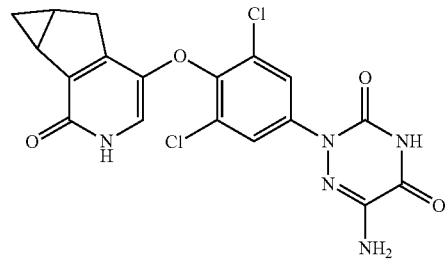 [SMILES: Nc1nn(-c2cc(Cl)c(Oc3c[nH]c(=O)c4c3CC3CC43)c(Cl)c2)c(=O)[nH]c1=O]

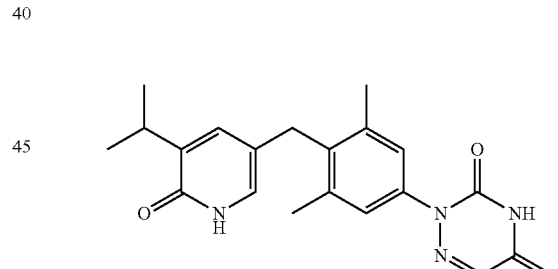

6-amino-2-(3,5-dichloro-4-((1-oxo-1,2,5,5a,6,6a-hexahydrocyclopropa[4,5]cyclopenta[1,2-c]pyridin-4-yl)oxy)phenyl)-1,2,4-triazine-3,5(2H,4H)-dione;

2-(4-((5-isopropyl-6-oxo-1,6-dihydropyridin-3-yl)methyl)-3,5-dimethylphenyl)-1,2,4-triazine-3,5(2H,4H)-dione;

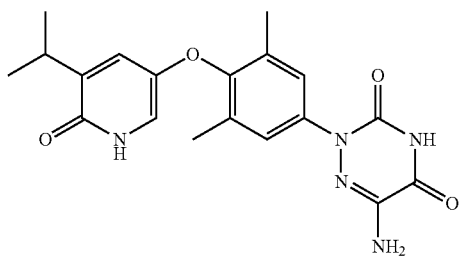 [SMILES: Cc1cc(-n2nc(N)c(=O)[nH]c2=O)cc(C)c1Oc1c[nH]c(=O)c(C(C)C)c1]

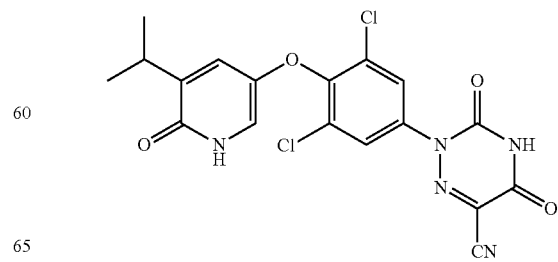

2-(3,5-dichloro-4-((5-isopropyl-6-oxo-1,6-dihydropyridin-3-yl)oxy)phenyl)-3,5-dioxo-2,3,4,5-tetrahydro-1,2,4-triazine-6-carbonitrile;

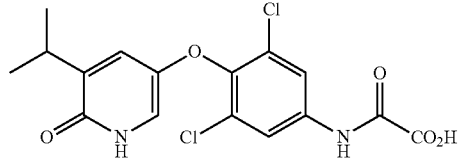 [SMILES: CC(C)c1cc(Oc2c(Cl)cc(NC(=O)C(=O)O)cc2Cl)c[nH]c1=O]

2-((3,5-dichloro-4-((5-isopropyl-6-oxo-1,6-dihydropyridin-3-yl)oxy)phenyl)amino)-2-oxoacetic acid;

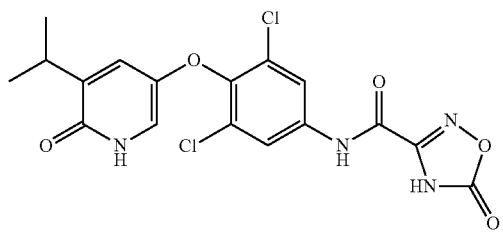 [SMILES: CC(C)c1cc(Oc2c(Cl)cc(NC(=O)c3noc(=O)[nH]3)cc2Cl)c[nH]c1=O]

N-(3,5-dichloro-4-((5-isopropyl-6-oxo-1,6-dihydropyridin-3-yl)oxy)phenyl)-5-oxo-4,5-dihydro-1,2,4-oxadiazole-3-carboxamide;

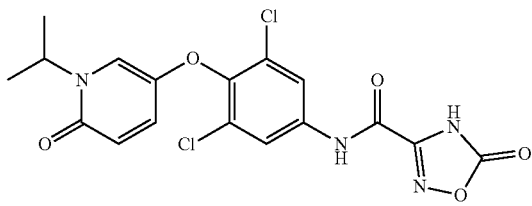 [SMILES: CC(C)n1cc(Oc2c(Cl)cc(NC(=O)c3noc(=O)[nH]3)cc2Cl)ccc1=O]

N-(3,5-dichloro-4-((1-isopropyl-6-oxo-1,6-dihydropyridin-3-yl)oxy)phenyl)-5-oxo-4,5-dihydro-1,2,4-oxadiazole-3-carboxamide; and

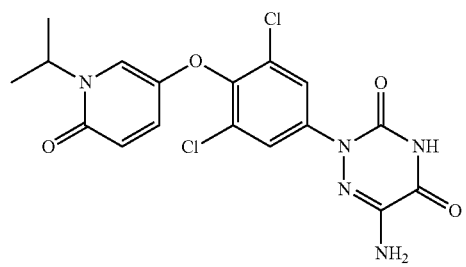 [SMILES: CC(C)n1cc(Oc2c(Cl)cc(-n3nc(N)c(=O)[nH]c3=O)cc2Cl)ccc1=O]

6-amino-2-(3,5-dichloro-4-((1-isopropyl-6-oxo-1,6-dihydropyridin-3-yl)oxy)phenyl)-1,2,4-triazine-3,5(2H,4H)-dione;

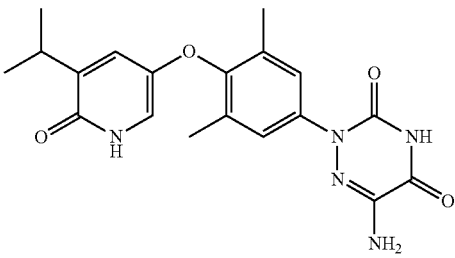

6-amino-2-(4-((5-isopropyl-6-oxo-1,6-dihydropyridin-3-yl)oxy)-3,5-dimethylphenyl)-1,2,4-triazine-3,5(2H,4H)-dione;

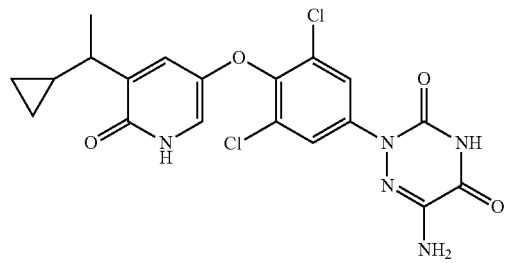 [SMILES: CC(c1cc(Oc2c(Cl)cc(-n3nc(N)c(=O)[nH]c3=O)cc2Cl)c[nH]c1=O)C1CC1]

6-amino-2-(3,5-dichloro-4-((5-(1-cyclopropylethyl)-6-oxo-1,6-dihydropyridin-3-yl)oxy)phenyl)-1,2,4-triazine-3,5(2H,4H)-dione;

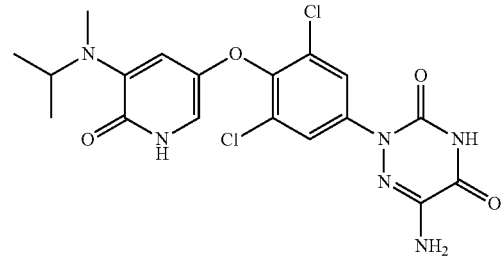 [SMILES: CC(C)N(C)c1cc(Oc2c(Cl)cc(-n3nc(N)c(=O)[nH]c3=O)cc2Cl)c[nH]c1=O]

6-amino-2-(3,5-dichloro-4-((5-(isopropyl(methyl)amino)-6-oxo-1,6-dihydropyridin-3-yl)oxy)phenyl)-1,2,4-triazine-3,5(2H,4H)-dione;

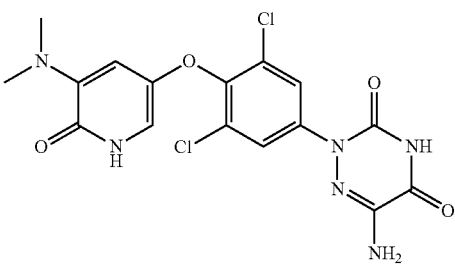 [SMILES: CN(C)c1cc(Oc2c(Cl)cc(-n3nc(N)c(=O)[nH]c3=O)cc2Cl)c[nH]c1=O]

57

6-amino-2-(3,5-dichloro-4-((5-(dimethylamino)-6-oxo-1,6-dihydropyridin-3-yl)oxy)phenyl)-1,2,4-triazine-3,5(2H,4H)-dione;

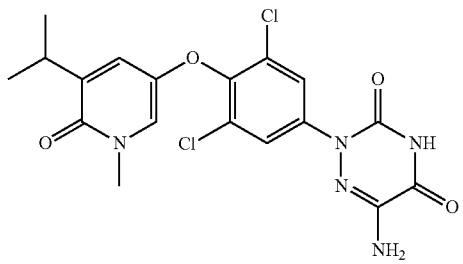 [SMILES: CC(C)c1cc(Oc2c(Cl)cc(-n3nc(N)c(=O)[nH]c3=O)cc2Cl)cn(C)c1=O]

6-amino-2-(3,5-dichloro-4-((5-isopropyl-1-methyl-6-oxo-1,6-dihydropyridin-3-yl)oxy)phenyl)-1,2,4-triazine-3,5(2H,4H)-dione;

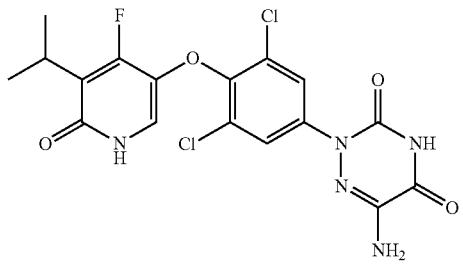 [SMILES: CC(C)c1c(F)c(Oc2c(Cl)cc(-n3nc(N)c(=O)[nH]c3=O)cc2Cl)c[nH]c1=O]

6-amino-2-(3,5-dichloro-4-((4-fluoro-5-isopropyl-6-oxo-1,6-dihydropyridin-3-yl)oxy)phenyl)-1,2,4-triazine-3,5(2H,4H)-dione;

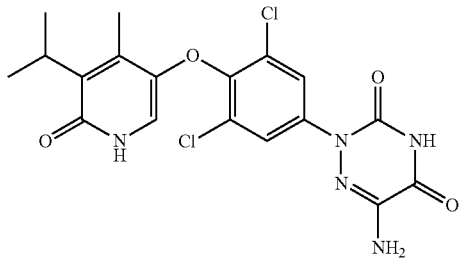

6-amino-2-(3,5-dichloro-4-((5-isopropyl-4-methyl-6-oxo-1,6-dihydropyridin-3-yl)oxy)phenyl)-1,2,4-triazine-3,5(2H,4H)-dione;

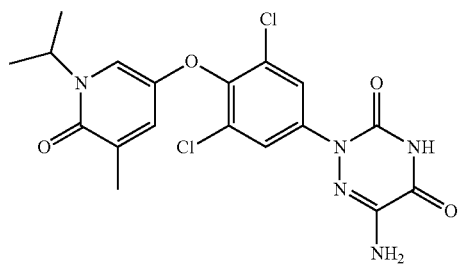

58

6-amino-2-(3,5-dichloro-4-((1-isopropyl-5-methyl-6-oxo-1,6-dihydropyridin-3-yl)oxy)phenyl)-1,2,4-triazine-3,5(2H,4H)-dione;

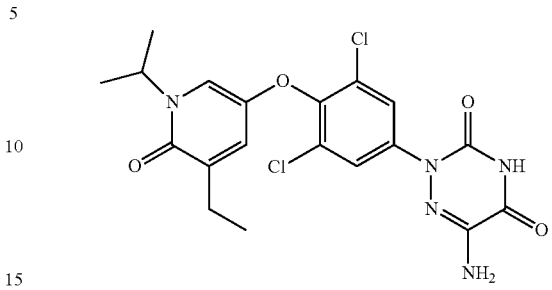

6-amino-2-(3,5-dichloro-4-((5-ethyl-1-isopropyl-6-oxo-1,6-dihydropyridin-3-yl)oxy)phenyl)-1,2,4-triazine-3,5(2H,4H)-dione;

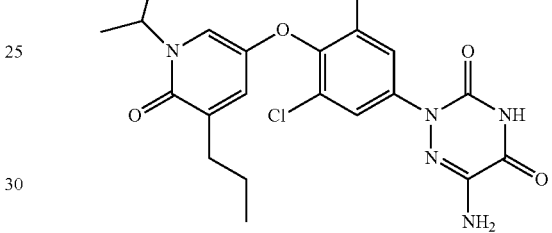

6-amino-2-(3,5-dichloro-4-((1-isopropyl-6-oxo-5-propyl-1,6-dihydropyridin-3-yl)oxy)phenyl)-1,2,4-triazine-3,5(2H,4H)-dione;

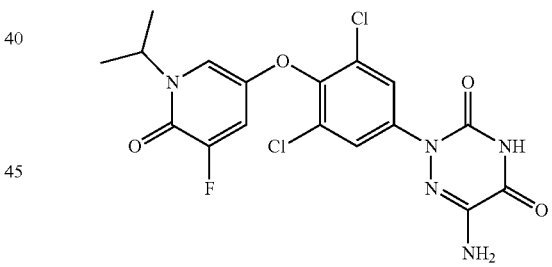

6-amino-2-(3,5-dichloro-4-((5-fluoro-1-isopropyl-6-oxo-1,6-dihydropyridin-3-yl)oxy)phenyl)-1,2,4-triazine-3,5(2H,4H)-dione;

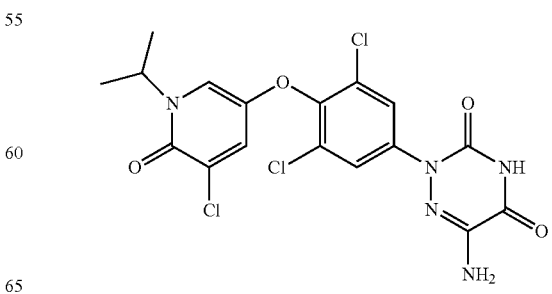

6-amino-2-(3,5-dichloro-4-((5-chloro-1-isopropyl-6-oxo-1,6-dihydropyridin-3-yl)oxy)phenyl)-1,2,4-triazine-3,5(2H,4H)-dione;

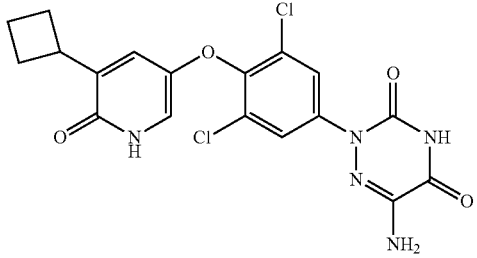 [SMILES: Nc1nn(-c2cc(Cl)c(Oc3c[nH]c(=O)c(C4CCC4)c3)c(Cl)c2)c(=O)[nH]c1=O]

6-amino-2-(3,5-dichloro-4-((5-cyclobutyl-6-oxo-1,6-dihydropyridin-3-yl)oxy)phenyl)-1,2,4-triazine-3,5(2H,4H)-dione;

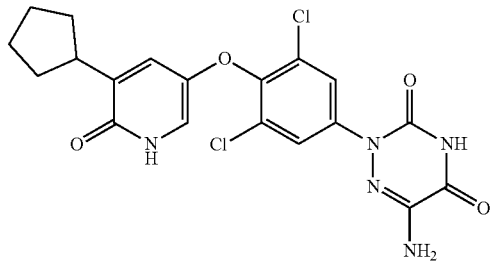 [SMILES: Nc1nn(-c2cc(Cl)c(Oc3c[nH]c(=O)c(C4CCCC4)c3)c(Cl)c2)c(=O)[nH]c1=O]

6-amino-2-(3,5-dichloro-4-((5-cyclopentyl-6-oxo-1,6-dihydropyridin-3-yl)oxy)phenyl)-1,2,4-triazine-3,5(2H,4H)-dione;

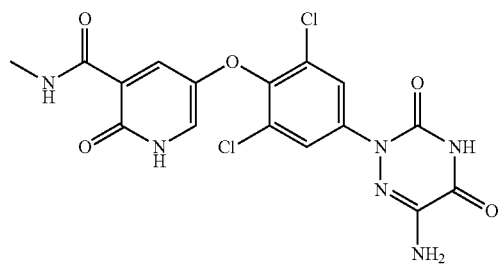 [SMILES: CNC(=O)c1cc(Oc2c(Cl)cc(-n3nc(N)c(=O)[nH]c3=O)cc2Cl)c[nH]c1=O]

5-(4-(6-amino-3,5-dioxo-4,5-dihydro-1,2,4-triazin-2(3H)-yl)-2,6-dichlorophenoxy)-N-methyl-2-oxo-1,2-dihydropyridine-3-carboxamide;

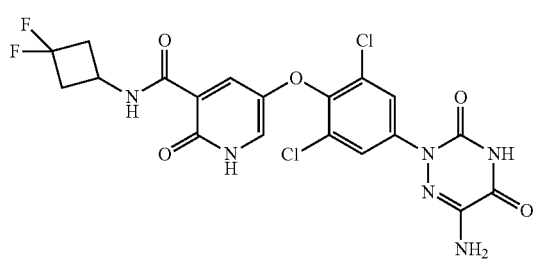 [SMILES: Nc1nn(-c2cc(Cl)c(Oc3c[nH]c(=O)c(C(=O)NC4CC(F)(F)C4)c3)c(Cl)c2)c(=O)[nH]c1=O]

5-(4-(6-amino-3,5-dioxo-4,5-dihydro-1,2,4-triazin-2(3H)-yl)-2,6-dichlorophenoxy)-N-(3,3-difluorocyclobutyl)-2-oxo-1,2-dihydropyridine-3-carboxamide;

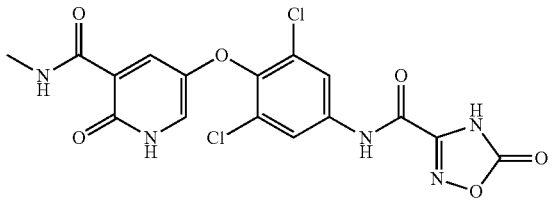 [SMILES: CNC(=O)c1cc(Oc2c(Cl)cc(NC(=O)c3noc(=O)[nH]3)cc2Cl)c[nH]c1=O]

N-(3,5-dichloro-4-((5-(methylcarbamoyl)-6-oxo-1,6-dihydropyridin-3-yl)oxy)phenyl)-5-oxo-4,5-dihydro-1,2,4-oxadiazole-3-carboxamide;

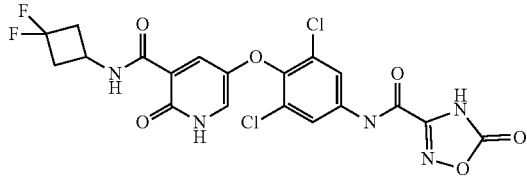 [SMILES: O=C(Nc1cc(Cl)c(Oc2c[nH]c(=O)c(C(=O)NC3CC(F)(F)C3)c2)c(Cl)c1)c1noc(=O)[nH]1]

N-(3,5-dichloro-4-((5-((3,3-difluorocyclobutyl)carbamoyl)-6-oxo-1,6-dihydropyridin-3-yl)oxy)phenyl)-5-oxo-4,5-dihydro-1,2,4-oxadiazole-3-carboxamide;

or a stereoisomer or a tautomer thereof, or a pharmaceutically acceptable salt thereof.

In another aspect, disclosed herein is a compound selected from the group consisting of:

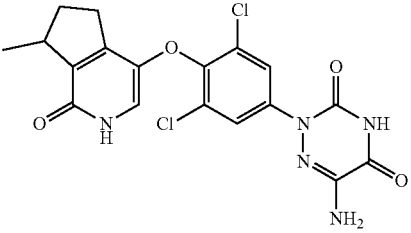 [SMILES: CC1CCc2c(Oc3c(Cl)cc(-n4nc(N)c(=O)[nH]c4=O)cc3Cl)c[nH]c(=O)c21]

6-amino-2-(3,5-dichloro-4-((7-methyl-1-oxo-2,5,6,7-tetrahydro-1H-cyclopenta[c]pyridin-4-yl)oxy)phenyl)-1,2,4-triazine-3,5(2H,4H)-dione;

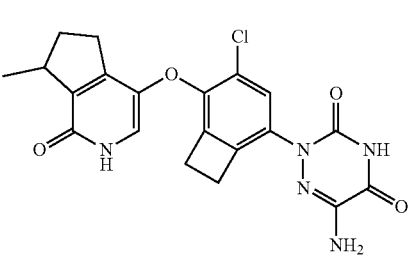 [SMILES: CC1CCc2c(Oc3c(Cl)cc(-n4nc(N)c(=O)[nH]c4=O)c4c3CC4)c[nH]c(=O)c21]

6-amino-2-(4-chloro-5-((7-methyl-1-oxo-2,5,6,7-tetra-hydro-1H-cyclopenta[c]pyridin-4-yl)oxy)bicyclo[4.2.0]octa-1,3,5-trien-2-yl)-1,2,4-triazine-3,5(2H,4H)-dione;

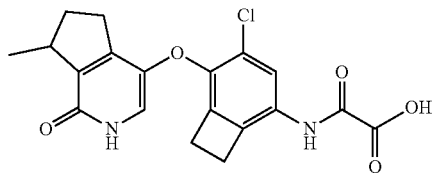 [SMILES: CC1CCc2c(Oc3c(Cl)cc(NC(=O)C(=O)O)c4c3CC4)c[nH]c(=O)c21]

2-((4-chloro-5-((7-methyl-1-oxo-2,5,6,7-tetrahydro-1H-cyclopenta[c]pyridin-4-yl)oxy)bicyclo[4.2.0]octa-1,3,5-trien-2-yl)amino)-2-oxoacetic acid;

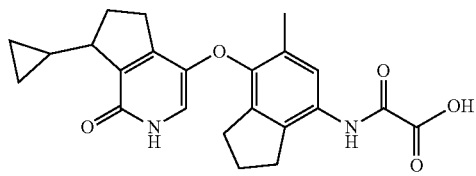 [SMILES: Cc1cc(NC(=O)C(=O)O)c2c(c1Oc1c[nH]c(=O)c3c1CCC3C1CC1)CCC2]

2-((7-((7-cyclopropyl-1-oxo-2,5,6,7-tetrahydro-1H-cyclopenta[c]pyridin-4-yl)oxy)-6-methyl-2,3-dihydro-1H-inden-4-yl)amino)-2-oxoacetic acid;

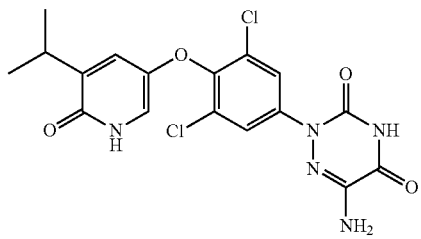 [SMILES: CC(C)c1cc(Oc2c(Cl)cc(-n3nc(N)c(=O)[nH]c3=O)cc2Cl)c[nH]c1=O]

6-amino-2-(3,5-dichloro-4-((5-isopropyl-6-oxo-1,6-dihydropyridin-3-yl)oxy)phenyl)-1,2,4-triazine-3,5(2H,4H)-dione;

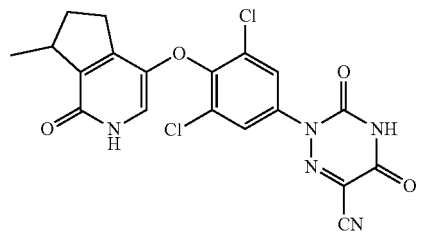 [SMILES: CC1CCc2c(Oc3c(Cl)cc(-n4nc(C#N)c(=O)[nH]c4=O)cc3Cl)c[nH]c(=O)c21]

2-(3,5-dichloro-4-((7-methyl-1-oxo-2,5,6,7-tetrahydro-1H-cyclopenta[c]pyridin-4-yl)oxy)phenyl)-3,5-dioxo-2,3,4,5-tetrahydro-1,2,4-triazine-6-carbonitrile;

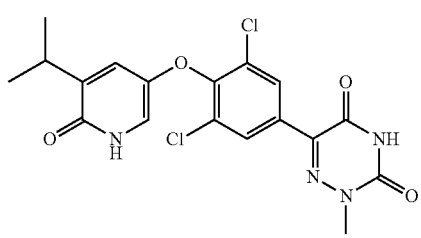 [SMILES: CC(C)c1cc(Oc2c(Cl)cc(-c3nn(C)c(=O)[nH]c3=O)cc2Cl)c[nH]c1=O]

6-(3,5-dichloro-4-((5-isopropyl-6-oxo-1,6-dihydropyridin-3-yl)oxy)phenyl)-2-methyl-1,2,4-triazine-3,5(2H,4H)-dione;

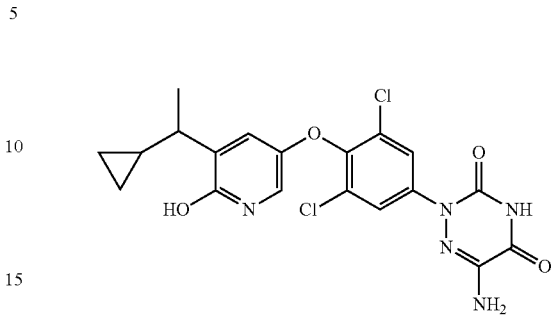

6-amino-2-(3,5-dichloro-4-((5-(1-cyclopropylethyl)-6-hydroxypyridin-3-yl)oxy)phenyl)-1,2,4-triazine-3,5(2H,4H)-dione;

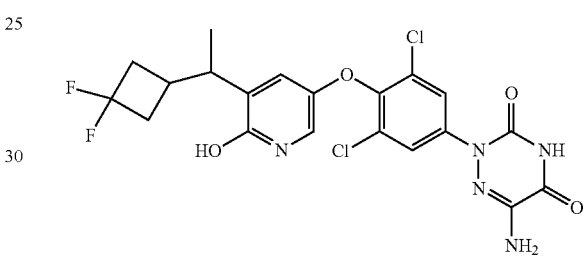

6-amino-2-(3,5-dichloro-4-((5-(1-(3,3-difluorocyclobutyl)ethyl)-6-hydroxypyridin-3-yl)oxy)phenyl)-1,2,4-triazine-3,5(2H,4H)-dione;

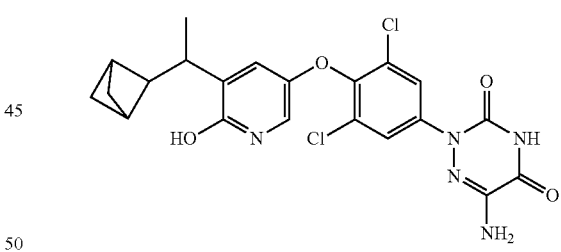

6-amino-2-(4-((5-(1-(bicyclo[1.1.1]pentan-2-yl)ethyl)-6-hydroxypyridin-3-yl)oxy)-3,5-dichlorophenyl)-1,2,4-triazine-3,5(2H,4H)-dione;

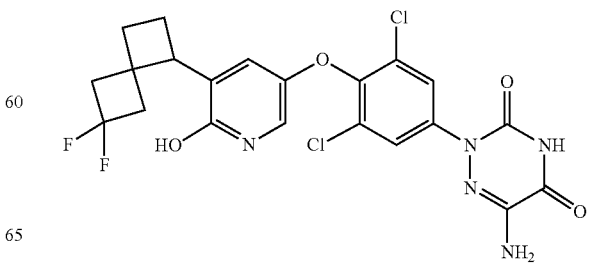

6-amino-2-(3,5-dichloro-4-((5-(6,6-difluorospiro[3.3]heptan-1-yl)-6-hydroxypyridin-3-yl)oxy)phenyl)-1,2,4-triazine-3,5(2H,4H)-dione;

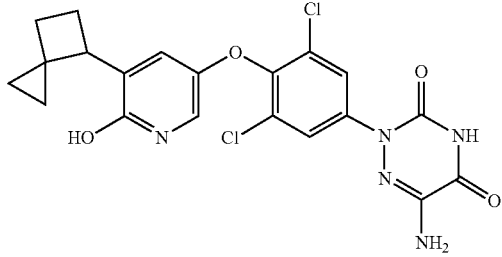 [SMILES: Nc1nn(-c2cc(Cl)c(Oc3cnc(O)c(C4CCC45CC5)c3)c(Cl)c2)c(=O)[nH]c1=O]

6-amino-2-(3,5-dichloro-4-((6-hydroxy-5-(spiro[2.3]hexan-4-yl)pyridin-3-yl)oxy)phenyl)-1,2,4-triazine-3,5(2H,4H)-dione;

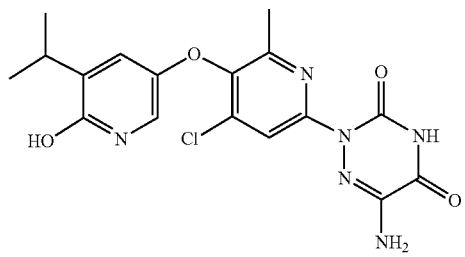 [SMILES: Cc1nc(-n2nc(N)c(=O)[nH]c2=O)cc(Cl)c1Oc1cnc(O)c(C(C)C)c1]

6-amino-2-(4-chloro-5-((6-hydroxy-5-isopropylpyridin-3-yl)oxy)-6-methylpyridin-2-yl)-1,2,4-triazine-3,5(2H,4H)-dione;

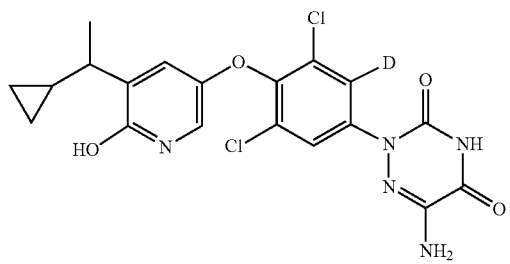 [SMILES: [2H]c1c(-n2nc(N)c(=O)[nH]c2=O)cc(Cl)c(Oc2cnc(O)c(C(C)C3CC3)c2)c1Cl]

6-amino-2-(3,5-dichloro-4-((5-(1-cyclopropylethyl)-6-hydroxypyridin-3-yl)oxy)phenyl-2-d)-1,2,4-triazine-3,5(2H,4H)-dione;

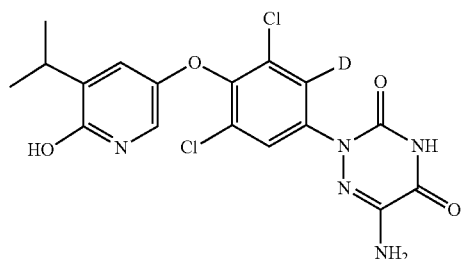

6-amino-2-(3,5-dichloro-4-((6-hydroxy-5-isopropylpyridin-3-yl)oxy)phenyl-2-d)-1,2,4-triazine-3,5(2H,4H)-dione;

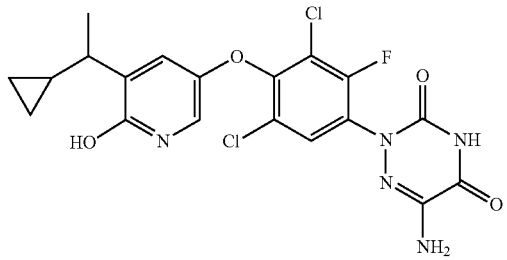 [SMILES: CC(c1cc(Oc2c(Cl)cc(-n3nc(N)c(=O)[nH]c3=O)c(F)c2Cl)cnc1O)C1CC1]

6-amino-2-(3,5-dichloro-4-((5-(1-cyclopropylethyl)-6-hydroxypyridin-3-yl)oxy)-2-fluorophenyl)-1,2,4-triazine-3,5(2H,4H)-dione;

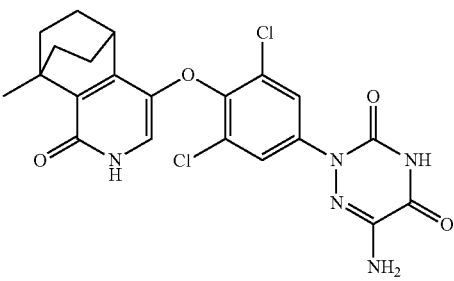 [SMILES: CC12CCC(CC1)c1c(Oc3c(Cl)cc(-n4nc(N)c(=O)[nH]c4=O)cc3Cl)c[nH]c(=O)c12]

6-amino-2-(3,5-dichloro-4-((8-methyl-1-oxo-1,2,5,6,7,8-hexahydro-5,8-ethanoisoquinolin-4-yl)oxy)phenyl)-1,2,4-triazine-3,5(2H,4H)-dione;

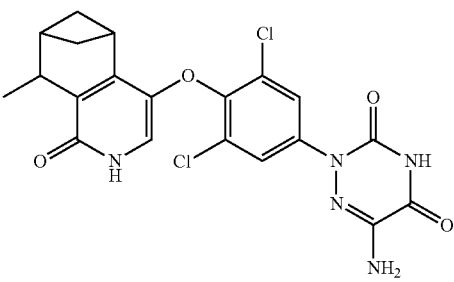 [SMILES: CC1c2c(c(Oc3c(Cl)cc(-n4nc(N)c(=O)[nH]c4=O)cc3Cl)c[nH]c2=O)C2CC1C2]

6-amino-2-(3,5-dichloro-4-((8-methyl-1-oxo-1,2,5,6,7,8-hexahydro-5,7-methanoisoquinolin-4-yl)oxy)phenyl)-1,2,4-triazine-3,5(2H,4H)-dione;

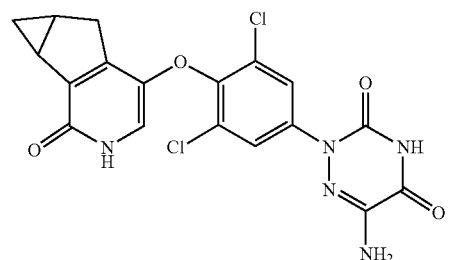

6-amino-2-(3,5-dichloro-4-((1-oxo-1,2,5,5a,6,6a-hexahydrocyclopropa[4,5]cyclopenta[1,2-c]pyridin-4-yl)oxy)phenyl)-1,2,4-triazine-3,5(2H,4H)-dione;

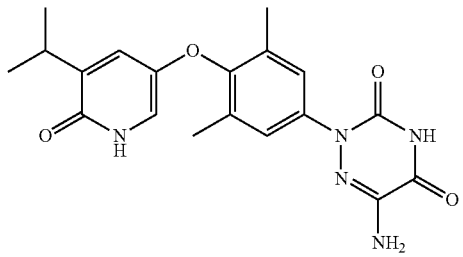

6-amino-2-(4-((5-isopropyl-6-oxo-1,6-dihydropyridin-3-yl)oxy)-3,5-dimethylphenyl)-1,2,4-triazine-3,5(2H,4H)-dione;

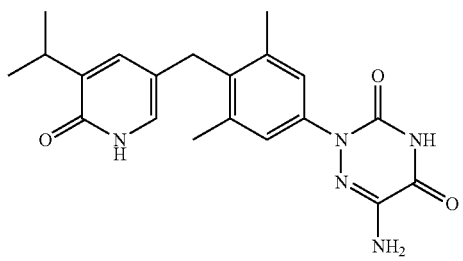

6-amino-2-(4-((5-isopropyl-6-oxo-1,6-dihydropyridin-3-yl)methyl)-3,5-dimethylphenyl)-1,2,4-triazine-3,5(2H,4H)-dione;

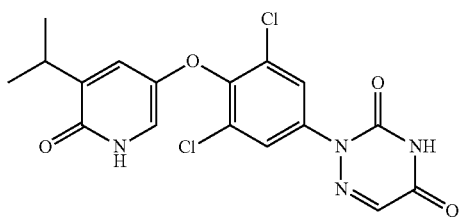 [SMILES: CC(C)c1cc(Oc2c(Cl)cc(-n3ncc(=O)[nH]c3=O)cc2Cl)c[nH]c1=O]

2-(3,5-dichloro-4-((5-isopropyl-6-oxo-1,6-dihydropyridin-3-yl)oxy)phenyl)-1,2,4-triazine-3,5(2H,4H)-dione; and

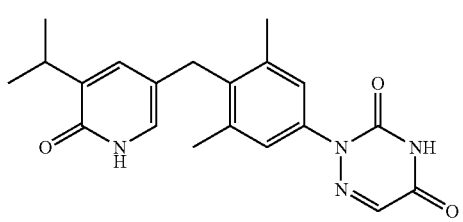 [SMILES: Cc1cc(-n2ncc(=O)[nH]c2=O)cc(C)c1Cc1c[nH]c(=O)c(C(C)C)c1]

2-(4-((5-isopropyl-6-oxo-1,6-dihydropyridin-3-yl)methyl)-3,5-dimethylphenyl)-1,2,4-triazine-3,5(2H,4H)-dione;

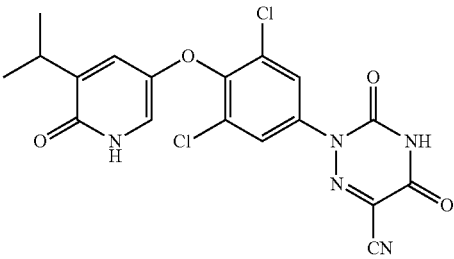 [SMILES: CC(C)c1cc(Oc2c(Cl)cc(-n3nc(C#N)c(=O)[nH]c3=O)cc2Cl)c[nH]c1=O]

2-(3,5-dichloro-4-((5-isopropyl-6-oxo-1,6-dihydropyridin-3-yl)oxy)phenyl)-3,5-dioxo-2,3,4,5-tetrahydro-1,2,4-triazine-6-carbonitrile;

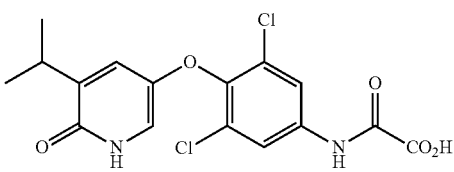 [SMILES: CC(C)c1cc(Oc2c(Cl)cc(NC(=O)C(=O)O)cc2Cl)c[nH]c1=O]

2-((3,5-dichloro-4-((5-isopropyl-6-oxo-1,6-dihydropyridin-3-yl)oxy)phenyl)amino)-2-oxoacetic acid;

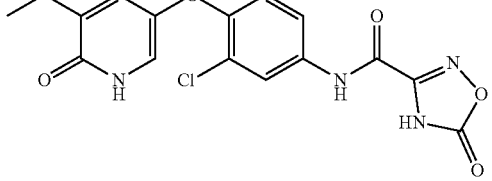

N-(3,5-dichloro-4-((5-isopropyl-6-oxo-1,6-dihydropyridin-3-yl)oxy)phenyl)-5-oxo-4,5-dihydro-1,2,4-oxadiazole-3-carboxamide;

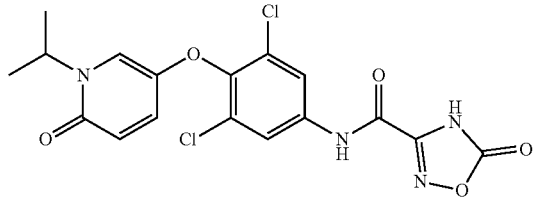 [SMILES: CC(C)n1cc(Oc2c(Cl)cc(NC(=O)c3noc(=O)[nH]3)cc2Cl)ccc1=O]

N-(3,5-dichloro-4-((1-isopropyl-6-oxo-1,6-dihydropyridin-3-yl)oxy)phenyl)-5-oxo-4,5-dihydro-1,2,4-oxadiazole-3-carboxamide; and

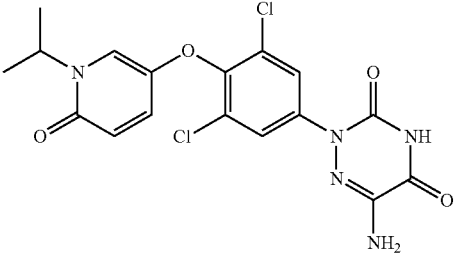 [SMILES: CC(C)n1cc(Oc2c(Cl)cc(-n3nc(N)c(=O)[nH]c3=O)cc2Cl)ccc1=O]

6-amino-2-(3,5-dichloro-4-((1-isopropyl-6-oxo-1,6-dihydropyridin-3-yl)oxy)phenyl)-1,2,4-triazine-3,5(2H,4H)-dione;

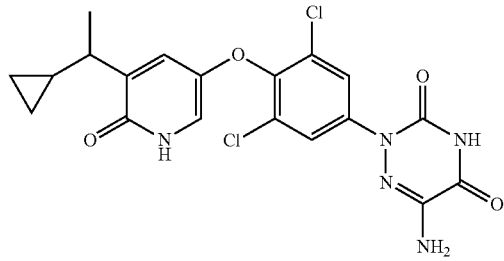 [SMILES: CC(c1cc(Oc2c(Cl)cc(-n3nc(N)c(=O)[nH]c3=O)cc2Cl)c[nH]c1=O)C1CC1]

6-amino-2-(3,5-dichloro-4-((5-(1-cyclopropylethyl)-6-oxo-1,6-dihydropyridin-3-yl)oxy)phenyl)-1,2,4-triazine-3,5(2H,4H)-dione;

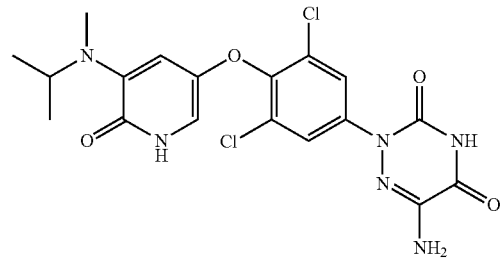 [SMILES: CC(C)N(C)c1cc(Oc2c(Cl)cc(-n3nc(N)c(=O)[nH]c3=O)cc2Cl)c[nH]c1=O]

6-amino-2-(3,5-dichloro-4-((5-(isopropyl(methyl)amino)-6-oxo-1,6-dihydropyridin-3-yl)oxy)phenyl)-1,2,4-triazine-3,5(2H,4H)-dione;

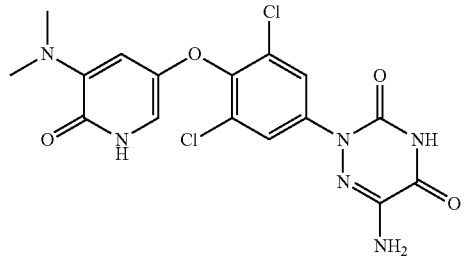

6-amino-2-(3,5-dichloro-4-((5-(dimethylamino)-6-oxo-1,6-dihydropyridin-3-yl)oxy)phenyl)-1,2,4-triazine-3,5(2H,4H)-dione;

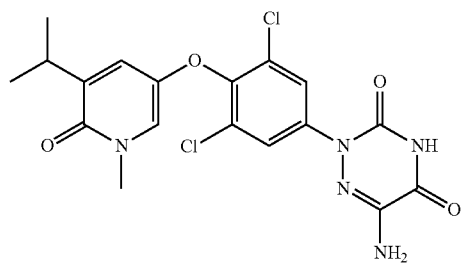 [SMILES: CC(C)c1cc(Oc2c(Cl)cc(-n3nc(N)c(=O)[nH]c3=O)cc2Cl)cn(C)c1=O]

6-amino-2-(3,5-dichloro-4-((5-isopropyl-1-methyl-6-oxo-1,6-dihydropyridin-3-yl)oxy)phenyl)-1,2,4-triazine-3,5(2H,4H)-dione;

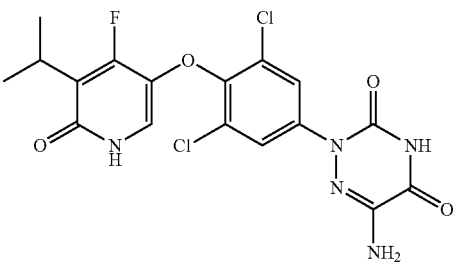

6-amino-2-(3,5-dichloro-4-((4-fluoro-5-isopropyl-6-oxo-1,6-dihydropyridin-3-yl)oxy)phenyl)-1,2,4-triazine-3,5(2H,4H)-dione;

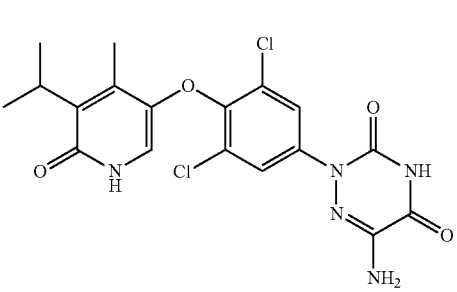 [SMILES: Cc1c(Oc2c(Cl)cc(-n3nc(N)c(=O)[nH]c3=O)cc2Cl)c[nH]c(=O)c1C(C)C]

6-amino-2-(3,5-dichloro-4-((5-isopropyl-4-methyl-6-oxo-1,6-dihydropyridin-3-yl)oxy)phenyl)-1,2,4-triazine-3,5(2H,4H)-dione;

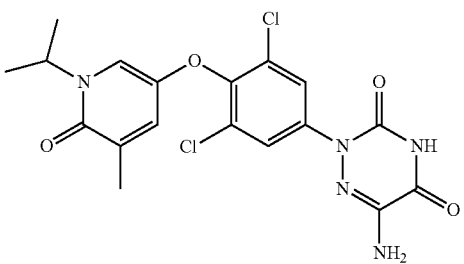 [SMILES: Cc1cc(Oc2c(Cl)cc(-n3nc(N)c(=O)[nH]c3=O)cc2Cl)cn(C(C)C)c1=O]

6-amino-2-(3,5-dichloro-4-((1-isopropyl-5-methyl-6-oxo-1,6-dihydropyridin-3-yl)oxy)phenyl)-1,2,4-triazine-3,5(2H,4H)-dione;

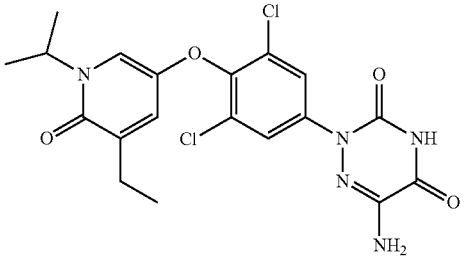 [SMILES: CCc1cc(Oc2c(Cl)cc(-n3nc(N)c(=O)[nH]c3=O)cc2Cl)cn(C(C)C)c1=O]

6-amino-2-(3,5-dichloro-4-((5-ethyl-1-isopropyl-6-oxo-1,6-dihydropyridin-3-yl)oxy)phenyl)-1,2,4-triazine-3,5(2H,4H)-dione;

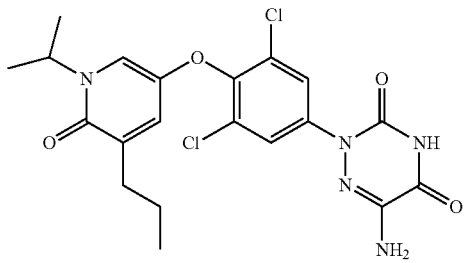 [SMILES: CCCc1cc(Oc2c(Cl)cc(-n3nc(N)c(=O)[nH]c3=O)cc2Cl)cn(C(C)C)c1=O]

6-amino-2-(3,5-dichloro-4-((1-isopropyl-6-oxo-5-propyl-1,6-dihydropyridin-3-yl)oxy)phenyl)-1,2,4-triazine-3,5(2H,4H)-dione;

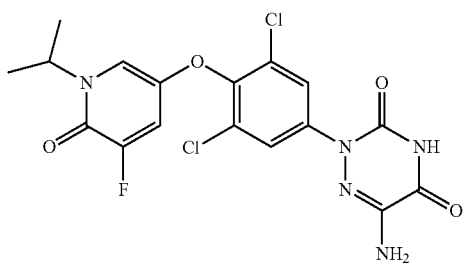

6-amino-2-(3,5-dichloro-4-((5-fluoro-1-isopropyl-6-oxo-1,6-dihydropyridin-3-yl)oxy)phenyl)-1,2,4-triazine-3,5(2H,4H)-dione;

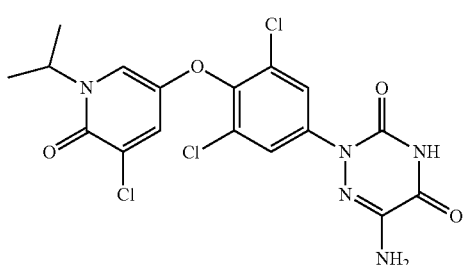

6-amino-2-(3,5-dichloro-4-((5-chloro-1-isopropyl-6-oxo-1,6-dihydropyridin-3-yl)oxy)phenyl)-1,2,4-triazine-3,5(2H,4H)-dione;

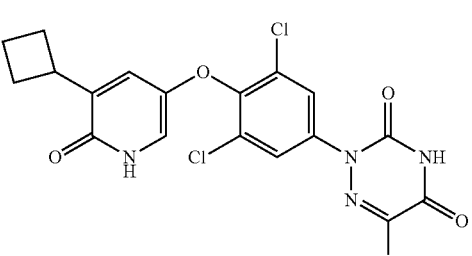

6-amino-2-(3,5-dichloro-4-((5-cyclobutyl-6-oxo-1,6-dihydropyridin-3-yl)oxy)phenyl)-1,2,4-triazine-3,5(2H,4H)-dione;

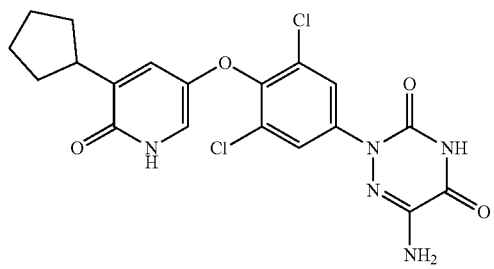 [SMILES: Nc1nn(-c2cc(Cl)c(Oc3c[nH]c(=O)c(C4CCCC4)c3)c(Cl)c2)c(=O)[nH]c1=O]

6-amino-2-(3,5-dichloro-4-((5-cyclopentyl-6-oxo-1,6-dihydropyridin-3-yl)oxy)phenyl)-1,2,4-triazine-3,5(2H,4H)-dione;

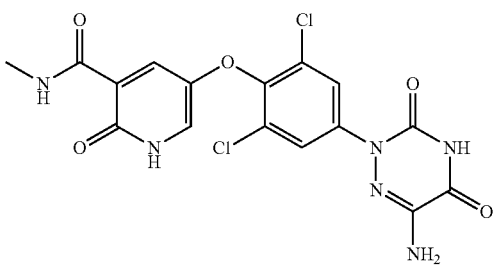 [SMILES: CNC(=O)c1cc(Oc2c(Cl)cc(-n3nc(N)c(=O)[nH]c3=O)cc2Cl)c[nH]c1=O]

5-(4-(6-amino-3,5-dioxo-4,5-dihydro-1,2,4-triazin-2(3H)-yl)-2,6-dichlorophenoxy)-N-methyl-2-oxo-1,2-dihydropyridine-3-carboxamide;

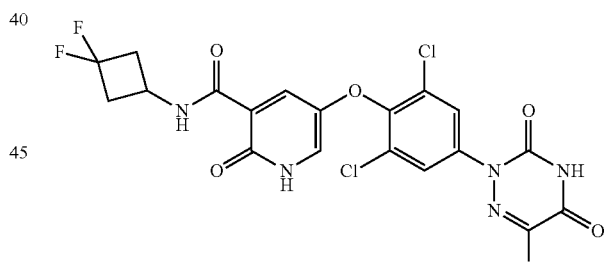

5-(4-(6-amino-3,5-dioxo-4,5-dihydro-1,2,4-triazin-2(3H)-yl)-2,6-dichlorophenoxy)-N-(3,3-difluorocyclobutyl)-2-oxo-1,2-dihydropyridine-3-carboxamide;

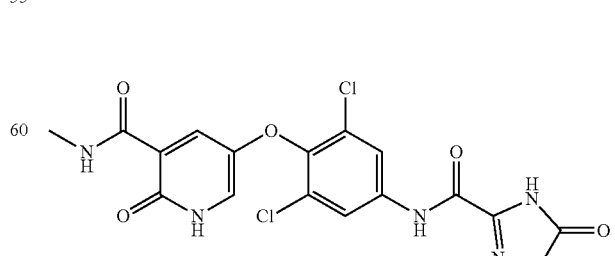

N-(3,5-dichloro-4-((5-(methylcarbamoyl)-6-oxo-1,6-dihydropyridin-3-yl)oxy)phenyl)-5-oxo-4,5-dihydro-1,2,4-oxadiazole-3-carboxamide;

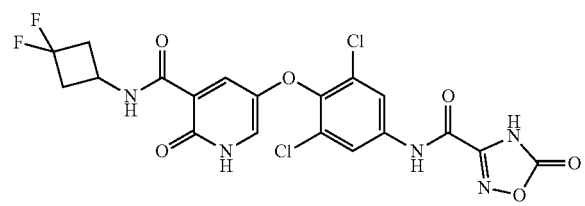 [SMILES: O=C(Nc1cc(Cl)c(Oc2c[nH]c(=O)c(C(=O)NC3CC(F)(F)C3)c2)c(Cl)c1)c1noc(=O)[nH]1]

N-(3,5-dichloro-4-((5-((3,3-difluorocyclobutyl)carbamoyl)-6-oxo-1,6-dihydropyridin-3-yl)oxy)phenyl)-5-oxo-4,5-dihydro-1,2,4-oxadiazole-3-carboxamide;

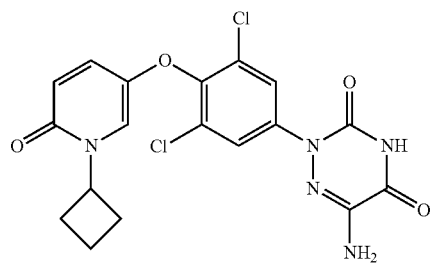 [SMILES: Nc1nn(-c2cc(Cl)c(Oc3ccc(=O)n(C4CCC4)c3)c(Cl)c2)c(=O)[nH]c1=O]

6-amino-2-(3,5-dichloro-4-((1-cyclobutyl-6-oxo-1,6-dihydropyridin-3-yl)oxy)phenyl)-1,2,4-triazine-3,5(2H,4H)-dione;

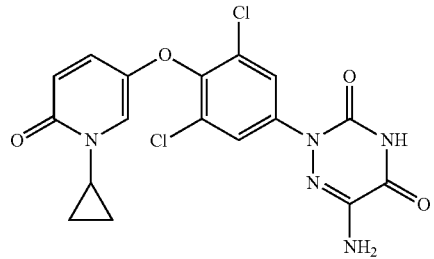 [SMILES: Nc1nn(-c2cc(Cl)c(Oc3ccc(=O)n(C4CC4)c3)c(Cl)c2)c(=O)[nH]c1=O]

6-amino-2-(3,5-dichloro-4-((1-cyclopropyl-6-oxo-1,6-dihydropyridin-3-yl)oxy)phenyl)-1,2,4-triazine-3,5(2H,4H)-dione;

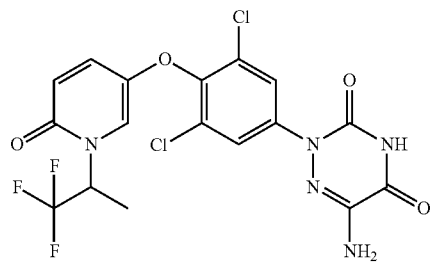 [SMILES: CC(n1cc(Oc2c(Cl)cc(-n3nc(N)c(=O)[nH]c3=O)cc2Cl)ccc1=O)C(F)(F)F]

6-amino-2-(3,5-dichloro-4-((6-oxo-1-(1,1,1-trifluoropropan-2-yl)-1,6-dihydropyridin-3-yl)oxy)phenyl)-1,2,4-triazine-3,5(2H,4H)-dione;

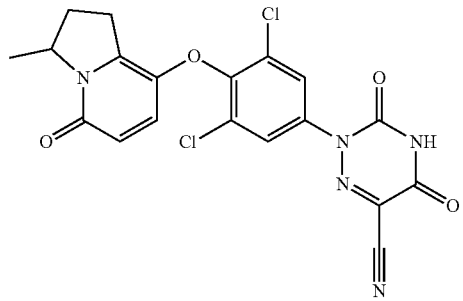 [SMILES: CC1CCc2c(Oc3c(Cl)cc(-n4nc(C#N)c(=O)[nH]c4=O)cc3Cl)ccc(=O)n21]

2-(3,5-dichloro-4-((3-methyl-5-oxo-1,2,3,5-tetrahydroindolizin-8-yl)oxy)phenyl)-3,5-dioxo-2,3,4,5-tetrahydro-1,2,4-triazine-6-carbonitrile;

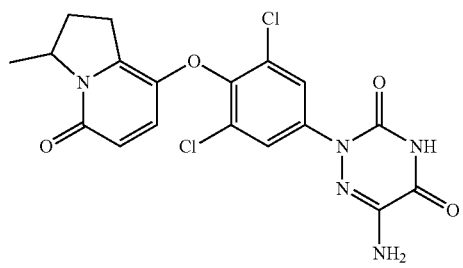 [SMILES: CC1CCc2c(Oc3c(Cl)cc(-n4nc(N)c(=O)[nH]c4=O)cc3Cl)ccc(=O)n21]

6-amino-2-(3,5-dichloro-4-((3-methyl-5-oxo-1,2,3,5-tetrahydroindolizin-8-yl)oxy)phenyl)-1,2,4-triazine-3,5(2H,4H)-dione;

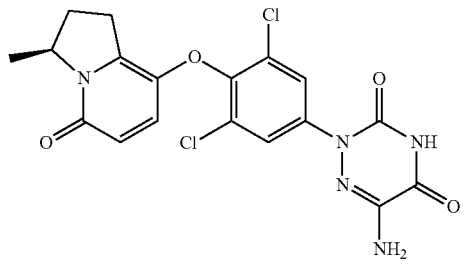 [SMILES: C[C@H]1CCc2c(Oc3c(Cl)cc(-n4nc(N)c(=O)[nH]c4=O)cc3Cl)ccc(=O)n21]

(S)-6-amino-2-(3,5-dichloro-4-((3-methyl-5-oxo-1,2,3,5-tetrahydroindolizin-8-yl)oxy)phenyl)-1,2,4-triazine-3,5(2H,4H)-dione;

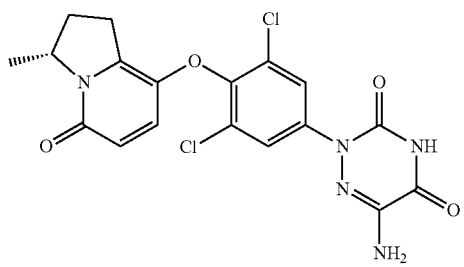

(R)-6-amino-2-(3,5-dichloro-4-((3-methyl-5-oxo-1,2,3,5-tetrahydroindolizin-8-yl)oxy)phenyl)-1,2,4-triazine-3,5(2H,4H)-dione; and

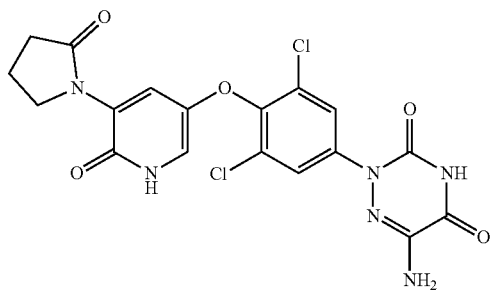 [SMILES: Nc1nn(-c2cc(Cl)c(Oc3c[nH]c(=O)c(N4CCCC4=O)c3)c(Cl)c2)c(=O)[nH]c1=O]

6-amino-2-(3,5-dichloro-4-((6-oxo-5-(2-oxopyrrolidin-1-yl)-1,6-dihydropyridin-3-yl)oxy)phenyl)-1,2,4-triazine-3,5(2H,4H)-dione;

or a stereoisomer or a tautomer thereof, or a pharmaceutically acceptable salt thereof.

Synthesis of the Compounds

The presently disclosed compounds were synthesized using the general synthetic procedures set forth in Schemes below. The carrying out of each individual illustrated step is within the skill of an ordinary artisan, who also knows how to modify the synthetic procedures of the below schemes to synthesize the full scope of the compounds disclosed herein. The synthetic procedure for individual compounds is provided in the Examples section, below.

In Scheme 1, 2-methoxy pyridine (A1) may be first brominated in the position $R^1$ then reacted with an alkyl or vinyl boronic acid or trifluoroborate under basic conditions with an appropriate Pd catalyst to afford compounds of formula A2. Optional reduction of a double bond can proceed via standard catalytic hydrogenation conditions. Bromination can occur with a standard brominating agent in an appropriate solvent (e.g., polar aprotic solvent) to afford compounds of formula A4. Subsequent formation of a boronic acid under conditions described in the literature to form boronic acid compounds of formula A5. Compounds of formula A5 can then be transformed to the corresponding aromatic alcohol of formula A6 using described methods (e.g., using acetic acid and hydrogen peroxide). Alternatively, aryl bromides of formula A4 can be converted directly to the aromatic alcohols of type A6 using a method described in the literature (e.g., Zhi-Qiang et al. Organic Letters 2020, doi.org/10.1021/acs.orglett.0c03069).

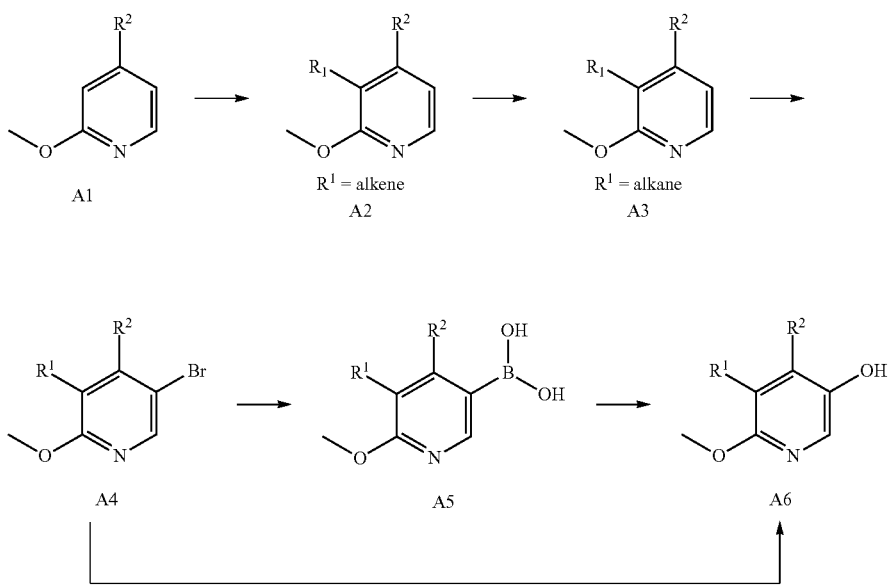

Scheme 1a outlines the synthesis of intermediates A13 and A14. Starting from pyridines of the Formula A10 [see the following literature references for generation of highly substituted/fused ring pyridines: (a) J. Org. Chem., Vol. 51, No. 5, 1986. (b) Organic Letters, 4(25), 4385-4386; 2002 (c) Tetrahedron, 62(10), 2240-2246; 2006 (d) Organometallics (2020), 39(11), 2091-2101] N-oxidation can occur using typical oxidizing agents (e.g. m-CPBA) to afford compounds of formula A11. 2-Chloropyridines of the formula A12 can be made after reacting compounds A11 with $POCl_3$. Hydrolysis of chloropyridines of formula A12 under described conditions (e.g., Advanced Synthesis & Catalysis, 355(5), 981-987; 2013 and European Journal of Medicinal Chemistry, 64, 23-34; 2013) affords 2-hydroxypyridines (or 2-pyridones) of the formula A13. The oxygen of these products can be alkylated to afford compounds of formula A14, or compounds of formula A13 can be brominated using a typical brominated agent (NBS, or bromine in acetic acid).

Scheme 1a.

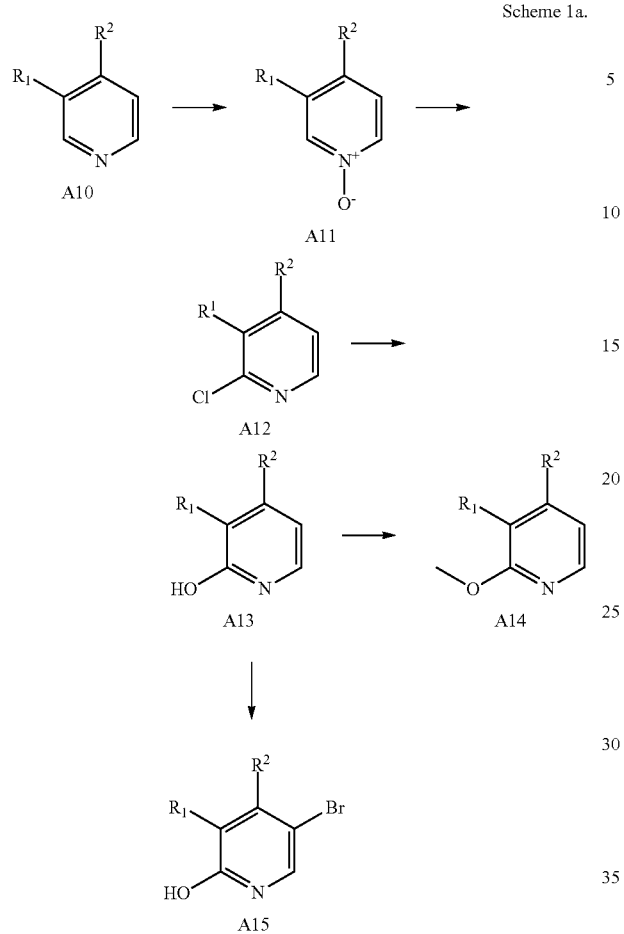

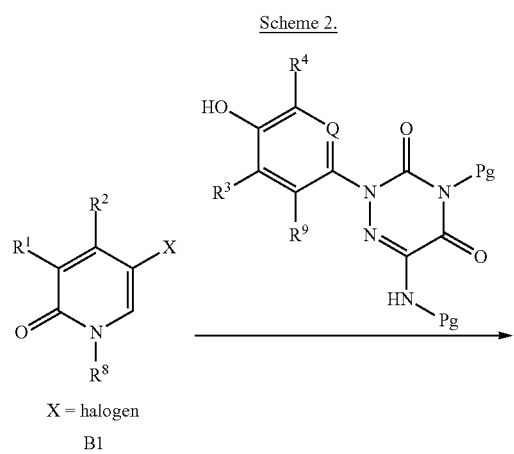

Scheme 2 describes the synthesis of compounds of Formula B3. Compounds of formula B1 (X=halogen), may be coupled with the phenolic compounds of formula B1a under a copper or palladium mediated reaction to afford intermediates of type B2. Subsequent deprotection of the protecting groups (Pg) leads to the formation of compounds of B3. $R^8$ in this scheme may be a protecting group (Pg). The chemistry described in this scheme is also valid when $R^8$ is H.

As described in Scheme 3, an aromatic amine compound of Formula C1 can be converted to an aza-uracil compound of Formula C2, first by generating the corresponding diazonium salt, followed by reaction with an N-(2-cyanoacetyl)-carbamate, and then cyclization, results in the formation of a compound of Formula C2. Subsequent hydrolysis of the nitrile of Formula C2 to a carboxylic acid compound of Formula E3 can be performed using described conditions. The compounds of Formula C4 can be afforded from the acid compounds C3 proceeding through an acyl azide intermediate and subsequent Curtius rearrangement. Subsequent deprotection (of the protecting group Pg) of the compound of Formula C4, (for example if Pg is boc, using HCl or TFA), leads to compounds of formula C5. $R^8$ in this scheme may be a protecting group (Pg). The chemistry described in this scheme is also valid when $R^8$ is H.

-continued

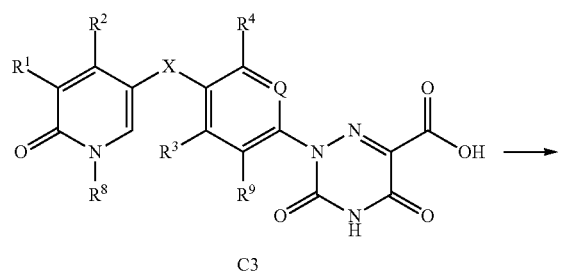

C3

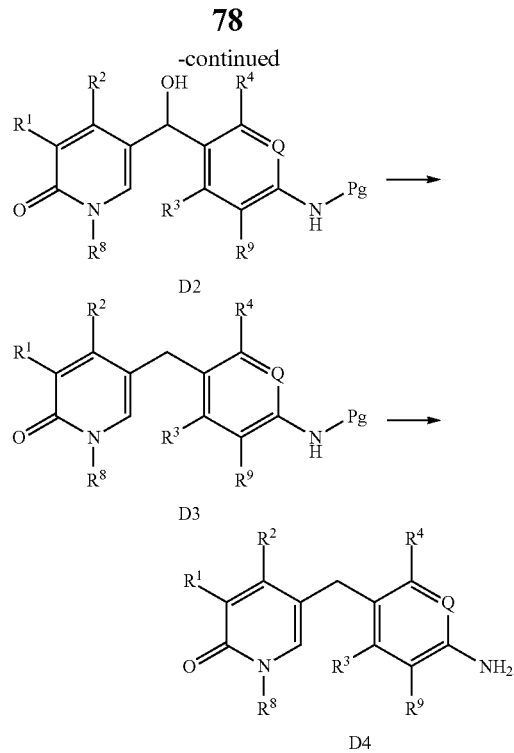

D2

D3

D4

Scheme 5 describes boronic acid compounds of Formula E1 are coupled to bromide compounds of formula E1a under typical Suzuki-Miyaura cross-coupling reaction conditions to afford compounds of formula E2. $R^8$ in this scheme may be a protecting group (Pg). The chemistry described in this scheme is also valid when $R^8$ is H.

C4

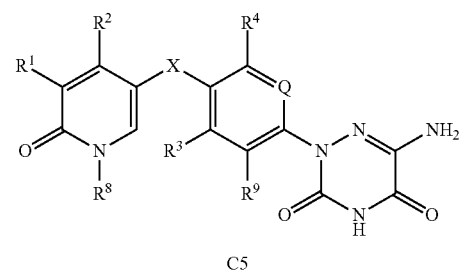

C5

Scheme 4 describes the synthesis of a compound of Formula D4. A transmetalation reaction of a compound of Formula D1 (e.g., X is Br or I) is followed by an addition to the aldehyde of general formula D1a affording the alcohol compound of Formula D2, which is then reduced to a compound of Formula D3. Deprotection of Pg of the compound of Formula D3 results in the formation of a compound of Formula D4. $R^8$ in this scheme may be a protecting group (Pg). The chemistry described in this scheme is also valid when $R^8$ is H.

Scheme 4.

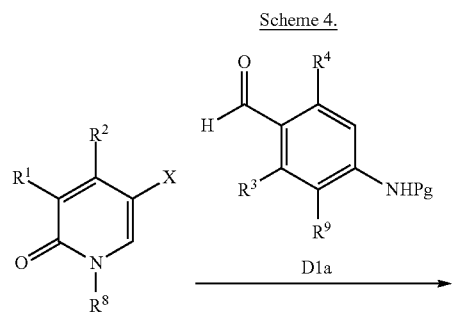

X = halogen

B1

Scheme 5

E1

E1a

E2

Scheme 6 depicts the synthesis of a compound of formula F2 from a compound of formula F1 in a Suzuki-Miyaura type coupling reaction with 4,4,5,5-tetramethyl-2-[(4,4,5,5-tetramethyl-1,3,2-dioxaborolan-2-yl)methyl]-1,3,2-dioxaborolane. An appropriate protecting group (Pg), or groups, may be required.

literature (e.g., Fe, NH$_4$Cl) to afford compounds of formula H12. The chemistry described in this scheme is also valid when R$^8$ is H.

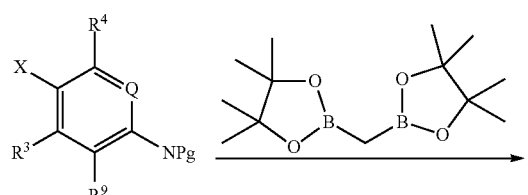

X = halogen
F1

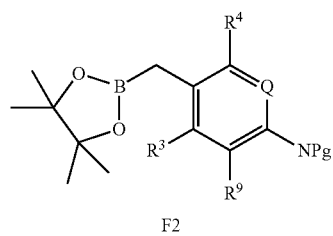

F2

A compound of Formula G2 may be obtained by coupling a boronic acid compound of Formula G1 with an azauracil compound of Formula G1a, as described in Scheme 7. The benzyloxymethyl acetal can then be deprotected using a variety of methods described in the literature (e.g., Tetrahedron Letters 2012, 53, pages 3758-3762). The chemistry described in this scheme is also valid when R$^8$ is H.

Scheme 7.

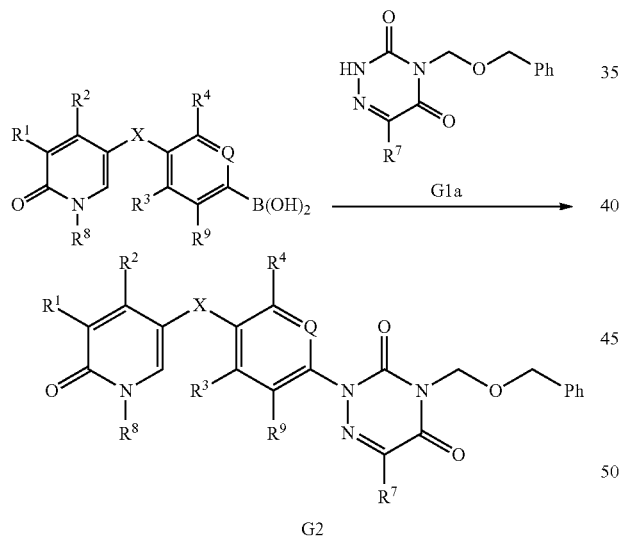

Described in scheme 8 is the reaction of compounds of formula H1, (where R$^8$ is optionally present, or is a protecting group (Pg)) with nitroaromatic compounds of formula H1a under basic conditions in a suitable solvent, perhaps at elevated temperature to afford compounds of formula H2. The nitro group can then be reduced using methods described in the literature (e.g., Fe, NH$_4$Cl) to afford compounds of formula H3. Alternatively, alkoxy pyridine compounds of formula H10 (where alkoxy is methoxy) are reacted with nitroaromatic compounds of formula H1a under basic conditions in a suitable solvent, perhaps at elevated temperature to afford compounds of formula H11. The nitro group can then be reduced using methods described in the Scheme 8.

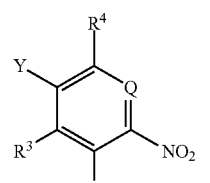

Y = e.g. F, Cl
H1a

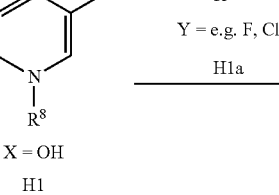

X = OH
H1

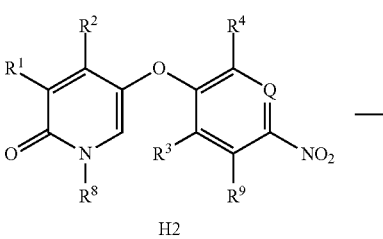

H2

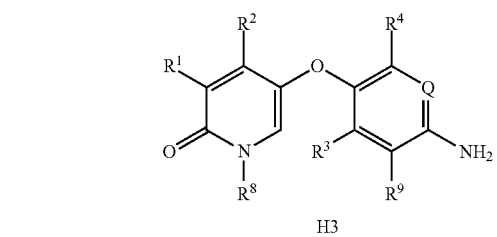

H3

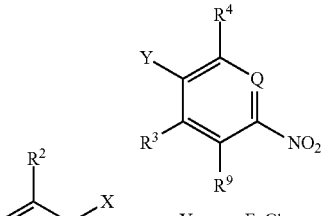

Y = e.g. F, Cl
H1a

X = OH
H10

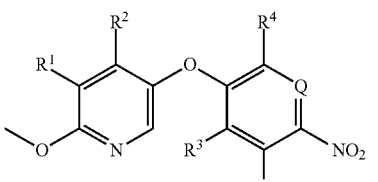

H11

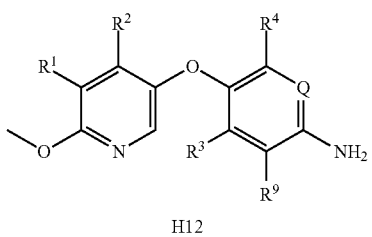

H12

A compound of Formula K1 (Scheme 9) can be formed by reacting the aromatic amine of formula H3 with ethyl 2-chloro-2-oxoacetate in the presence of an organic base, in an appropriate organic solvent. Standard hydrolysis conditions are performed to afford compounds of formula K2. Compounds of the formula H3 may also be reacted with 5-oxo-4,5-dihydro-1,2,4-oxadiazole-3-carbonyl chloride in a non-polar organic solvent in the presence of a base to afford compounds of the formula K3. Alternatively, compounds of the formula H3 may also be reacted with 5-oxo-4,5-dihydro-1,2,4-oxadiazole-3-carboxylic acid in a polar aprotic solvent in the presence of a base and coupling agent to afford compounds of the formula K3. Compounds of the formula K4 may be produced by reaction of compounds of formula C4 with 5-oxo-4,5-dihydro-1,2,4-oxadiazole-3-carbaldehyde under standard reductive amination conditions. Alternatively, compounds of the formula K4 may be produced by reaction of compounds of formula C1 with 3-(bromomethyl)-1,2,4-oxadiazol-5(4H)-one (or, for example, 3-(chloromethyl)-1,2,4-oxadiazol-5(4H)-one) under basic conditions with optional heating. The chemistry described in this scheme is also valid when $R^8$ is H.

Scheme 9.

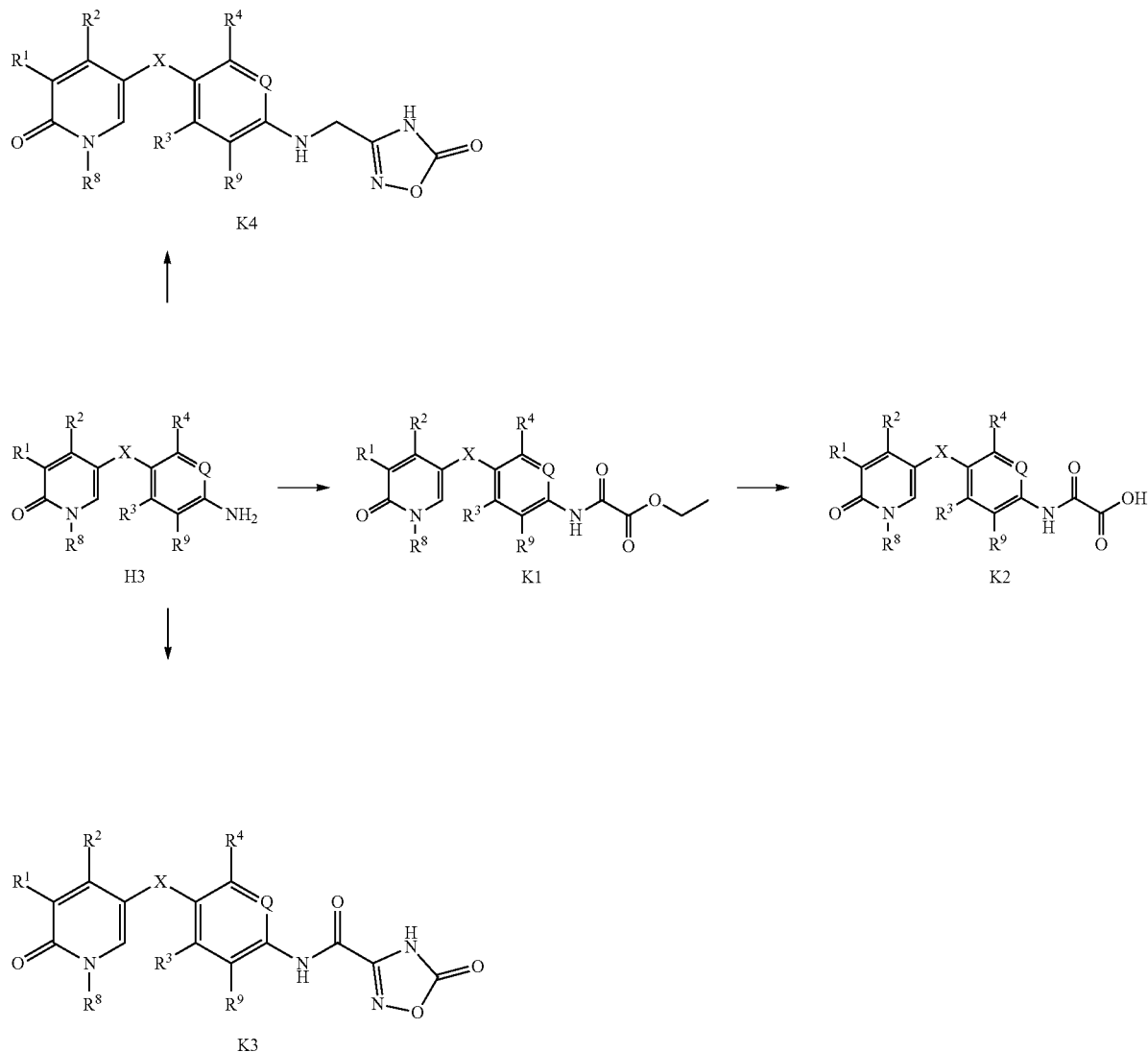

Scheme 10 depicts the synthesis of compounds of formula M3. The aryl halide compounds M1 are reacted with methyl propiolate under typical Sonogoshira conditions to afford compounds of formula M2. Cyclization towards heterocycles of the formula M3 occurs under conditions described in the literature (e.g., J. Med. Chem. 2002, 45, 9, 1785-1798; J. Med. Chem. 2013, 56, 5, 1894-1907). Compounds of formula M3 can alternatively be generated via other described methods (e.g., J. Org. Chem. 2000, 65, 4, 1003-1007; J. Med. Chem. 1989, 32, 9, 2116-2128). The chemistry described in this scheme is also valid when $R^8$ is H.

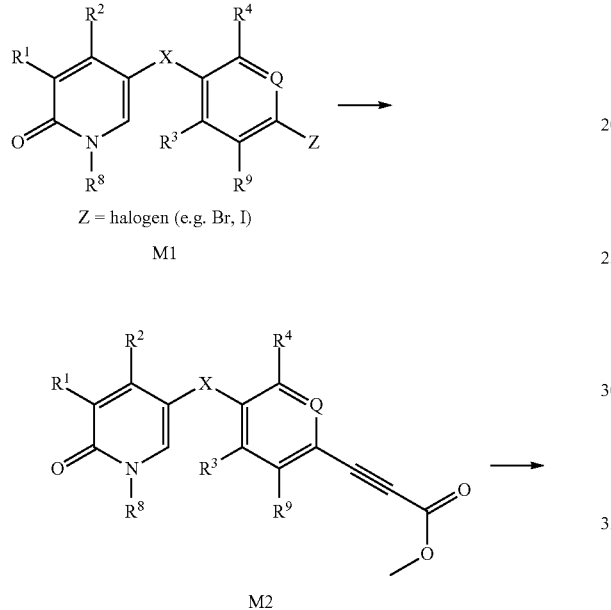

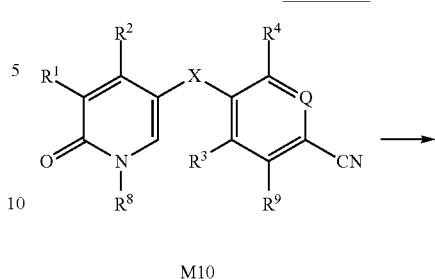

Scheme 11 describes the synthesis of compounds of formula M12. Aryl cyanide compounds M10 can be transformed to compounds of formula M11 via the addition of hydroxylamine. Further conversion to compounds of formula M12 proceeds via the addition of carbonyl diimidazole with base in an appropriate solvent, often at elevated temperature (see, e.g., Molecular Pharmaceutics, 16(4), 1489-1497; 2019). Compounds of the formula M10 may be synthesized from the aryl halides M1 via several described methods using either a copper catalyst (known as the Rosenmund-von Braun reaction) or alternatively using a Pd catalyst (see, e.g., J. Am. Chem. Soc., 2011, 133, 10999-11005). The aryl cyanides of formula M10 may also be generated from the amine using the Sandmeyer reaction. The chemistry described in this scheme is also valid when $R^8$ is H.

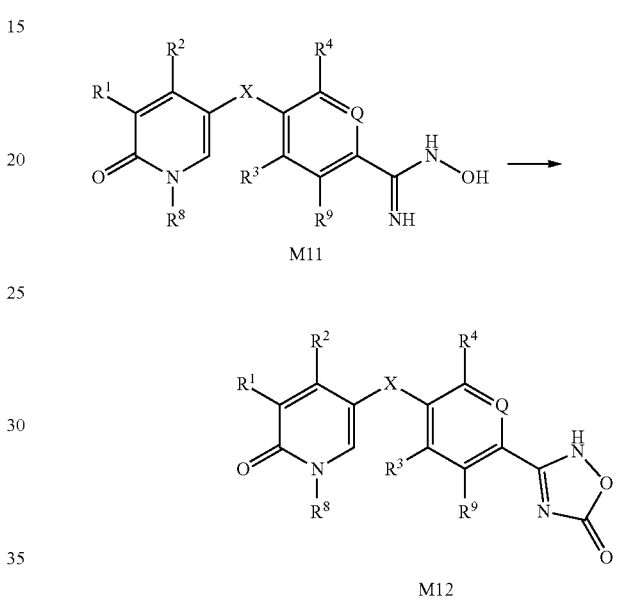

An alternative synthesis of compounds of the formula K3 involves the reaction of anilines H3 with ethyl 5-oxo-4,5-dihydro-1,2,4-oxadiazole-3-carboxylate in an organic solvent (e.g. THF), in the presence of one or more equivalents of LiHMDS (reference: J. Am. Chem. Soc. 2019, 141, 11161-11172).

Scheme 12 describes a variation on Scheme 8 where compounds of formula N1 can be alkylated under standard conditions described in literature, for example compounds of formula N1 can be alkylated via an alkyl halide, a base, in a polar solvent to afford compounds of formula H2. Alternatively, typical Mitsunobu conditions can be used with a C1-C3 alcohol to also afford products H2. Compounds of the formula H3 can be afforded by reduction of the nitro group under standard conditions (e.g. Fe, NH$_4$Cl).

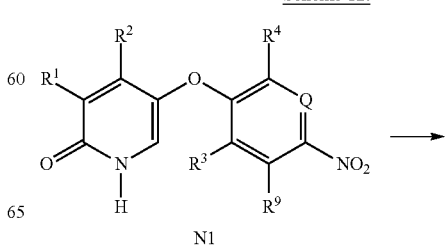

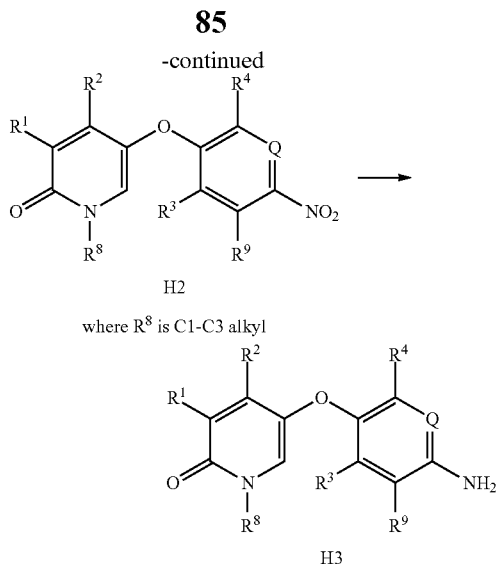

H2 where R⁸ is C1-C3 alkyl

H3

Scheme 13 exemplifies methods to produce compounds where R¹ is NRᵃRᵇ. Nitropyridines of the formula H10 can be converted to anilines of the formula H11 by a variety of methods described in the chemical literature (e.g. iron, in aqueous and alcoholic media). The anilines can be protected to form compounds of formula H12 where the boc protecting group is shown as an example. Alternatively, compounds H11 can be converted to compounds of the formula H13 by alkylation of the amine by alkyl halides for example, or functionalization could take place under reductive amination conditions, or any number of other conditions described in the literature. Compounds of the formula H12 can be optionally functionalized to produce compounds of the formula H14, possibly using methods described to form compounds of the formula H13, or compounds H12 can proceed to a later stage in the synthesis, starting with the conversion of the boronate to the phenol (as in Scheme 14), where then Rᵃ and Rᵇ may be installed.

In Scheme 14, commercially available methoxynicotinic acids of the formula H20, can be coupled with amines using conditions described in the literature (e.g. using a coupling agent, in a polar aprotic solvent, with base) to form amides of the formula H21. Alternatively, the amine can be reacted with the corresponding carboxylic acid chloride of H20, preferably using a base in an organic solvent, to afford amides of the formula H21. In a subsequent reaction, boronic acids or esters of the formula H22 (where a boronic ester is exemplified) can be formed using a plethora of methods described in the literature from the aryl bromide H21. Boronates (or boronic acids) of the formula H22 may then be converted to the phenol by oxidative means using one of several methods described in the literature (e.g. $H_2O_2$ in acetic acid) to afford phenolic compounds of the formula H23. Compounds of the formula H23 can then proceed to subsequent steps toward final products in a manner similar to that described in Scheme 8.

Scheme 14.

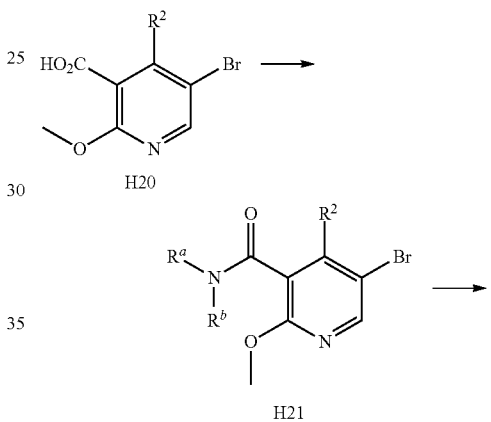

Scheme 13.

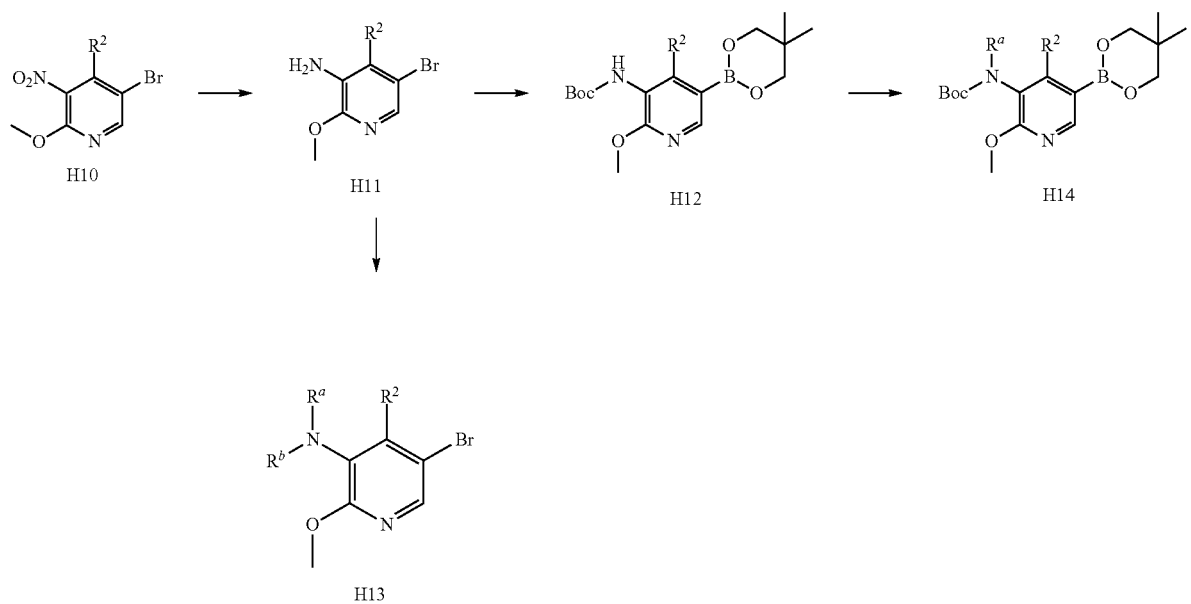

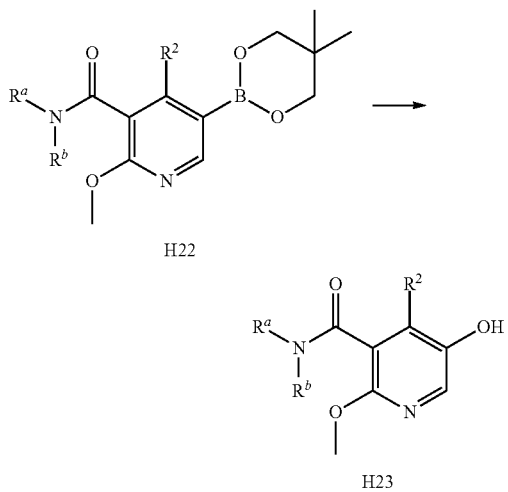

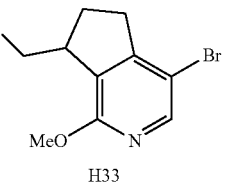

Compounds of the formula H33 may be made using analogous procedures to those described in WO2016037578. Alternatively, the compounds maybe formed as described in Scheme 15. Compounds of formula H30 are reacted with an allyl bromide under basic conditions (e.g. LDA, in THF at −78 C) to form compounds of the formula H31. In a subsequent step, radical cyclization can occur using conditions typically described for this transformation (e.g. tributyl tin hydride, benzoyl peroxide, at elevated temperature in toluene) to afford intermediates of the formula H32. Compounds of formula H33 are formed using typical bromination conditions (e.g. NBS in acetonitrile).

Scheme 15.

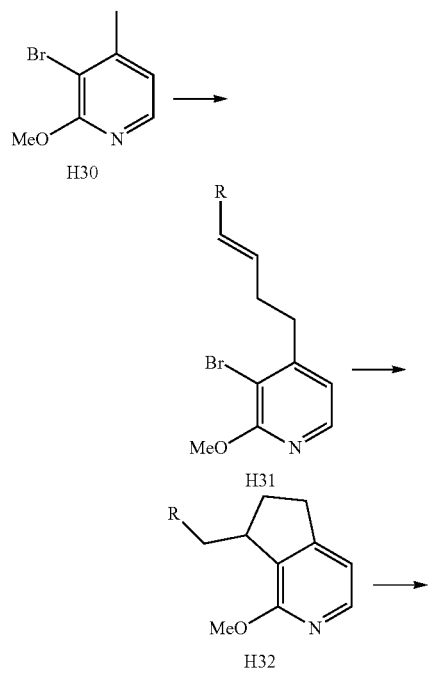

Scheme 16 describes the synthesis of intermediates of the formula J4 where $R^1$ is a cycloalkyl. Compounds of formula J1, in the presence of an alkyl lithium, may undergo lithium halogen exchange. The aryl lithium species formed could then react, as a nucleophile, with a cyclic or acyclic ketone to afford compounds of the formula J2. Elimination of the OH group of J2 can be optionally performed for example in triethylsilane in TFA, and dichloromethane to afford compounds J3. Bromination of J3, using conditions typically described in the literature (e.g. NBS in acetonitrile), would lead to the brominated compounds of formula J4.

Scheme 16.

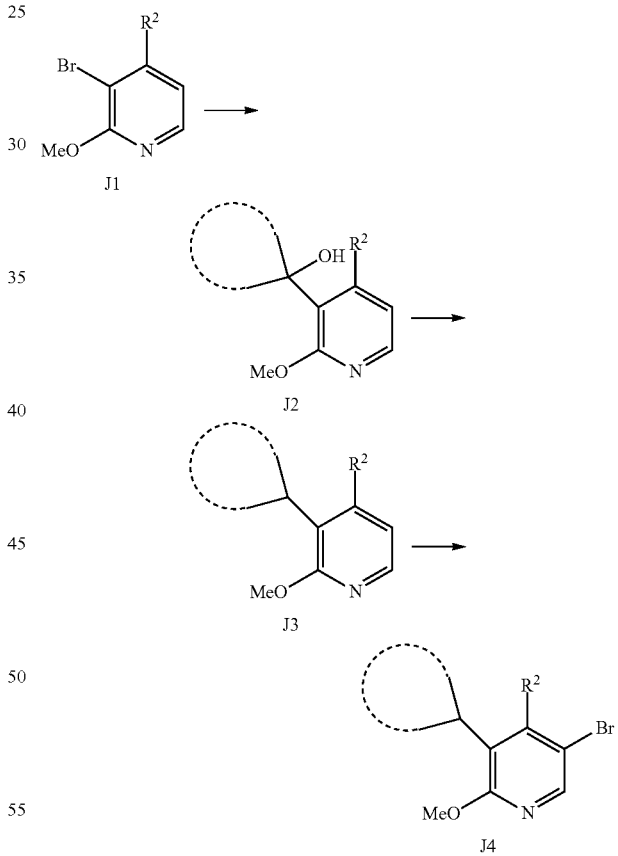

Pharmaceutical Compositions

In another aspect, disclosed herein are pharmaceutical compositions comprising, consisting essentially of, or consisting of a compound as described herein, and at least one pharmaceutically acceptable excipient.

In another aspect, disclosed herein are pharmaceutical compositions comprising, consisting essentially of, or consisting of a compound of Formula I, as described herein, and at least one pharmaceutically acceptable excipient.

In another aspect, disclosed herein are pharmaceutical compositions comprising, consisting essentially of, or consisting of a compound of Formulas I', I, or IA as described herein, and at least one pharmaceutically acceptable excipient.

In another aspect, disclosed herein are pharmaceutical compositions comprising, consisting essentially of, or consisting of a compound of Formulas I", I', I, IA", or IA as described herein, and at least one pharmaceutically acceptable excipient.

The pharmaceutical composition disclosed herein may comprise a pharmaceutically acceptable carrier, such as diluents, disintegrants, sweetening agents, glidants, or flavoring agents and may be formulated into an oral dosage form such as tablets, capsules, powders, granules, suspensions, emulsions, or syrups; or a parenteral dosage form such as liquids for external use, suspensions for external use, emulsions for external use, gels (ointments or the like), inhaling agents, spraying agents, injections, etc. Said dosage forms may be formulated in various forms, e.g., a dosage form for single administration or for multiple administrations.

The pharmaceutical composition disclosed herein may include excipients such as lactose, corn starch, or the like, glidants such as magnesium stearate, etc., emulsifying agents, suspending agents, stabilizers, and isotonic agents, etc. If desired, a sweetening agent and/or a flavoring agent may be added. Exemplary excipients include, without limitation, polyethylene glycol (PEG), hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Inorganic salt or buffers include, but are not limited to, citric acid, sodium chloride, potassium chloride, sodium sulfate, potassium nitrate, sodium phosphate monobasic, sodium phosphate dibasic, and combinations thereof.

Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition disclosed herein may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Non-limiting examples of suitable bases include bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the role of the excipient, the dosage requirements of the active agent components, and particular needs of the composition. Generally, however, the excipient will be present in the composition in an amount of about 1% to about 99% by weight, preferably from about 5% to about 98% by weight, more preferably from about 15 to about 95% by weight of the excipient. In general, the amount of excipient present in a composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, transdermal, rectal, transmucosal, or intestinal administration; parenteral delivery, including intramuscular, subcutaneous, intravenous, intramedullary injections, as well as inhalation, intrathecal, direct intraventricular, intraperitoneal, intranasal, or intraocular injections.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. These pharmaceutical compositions, then, may be formulated in a conventional manner using one or more known physiologically acceptable carriers comprising excipients and/or auxiliaries, which facilitate processing of the active compounds into preparations that can be used pharmaceutically. Any of the well-known techniques, carriers, and excipients may be used as suitable and as understood in the art; e.g., in Remington's Pharmaceutical Sciences, above.

Pharmaceutical compositions suitable for use in the presently disclosed formulations include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. In some embodiments, a therapeutically effective amount means an amount of compound effective to alleviate or ameliorate symptoms of disease or prolong the survival of the subject being treated.

Although the exact dosage can be determined on a drug-by-drug basis, in most cases, some generalizations regarding the dosage can be made. The daily dosage regimen for an adult human patient may be, for example, an oral dose of between 0.001 mg and 1000 mg of each ingredient, preferably between 0.01 mg and 500 mg, for example, 1 to 200 mg or each active ingredient of the pharmaceutical compositions disclosed herein or a pharmaceutically acceptable salt thereof calculated as the free base or free acid, the composition being administered 1 to 4 times per day or per week. Alternatively, the compositions disclosed herein may be administered by continuous such as sustained, delayed, or extended release, preferably at a dose of each ingredient up to 500 mg per day. Thus, the total daily dosage by oral administration of each ingredient will typically be in the range 0.1 mg to 2000 mg.

Methods of Treatment

In another aspect, disclosed herein are methods of treating a thyroid hormone receptor related disorder in a patient, the method comprising, consisting essentially of, or consisting of the steps of identifying a patient in need of treatment for the thyroid hormone receptor related disorder, and administering to the patient, or contacting the patient with, a compound as described herein.

In another aspect, disclosed herein are methods of treating a thyroid hormone receptor related disorder in a patient, the method comprising, consisting essentially of, or consisting of the steps of identifying a patient in need of treatment for the thyroid hormone receptor related disorder, and administering to the patient, or contacting the patient with, a compound of Formula I, as described herein.

In some embodiments, a health care professional, such as a physician, physician's assistant, nurse practitioner, or the like, identifies an individual as being in need of treatment for the thyroid hormone receptor related disorder, and/or a candidate for treatment with a compound disclosed herein. The identification may be based on medical test results, non-responsiveness to other, first-line therapies, the specific nature of the particular liver disorder, or the like.

In some embodiments, the thyroid hormone receptor related disorder is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

In another aspect, disclosed herein are methods of treating a disorder or disease in a subject in need thereof, the method comprising, consisting essentially of, or consisting of administering to the subject a therapeutically effective amount of a compound or composition disclosed herein, wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

In another aspect, disclosed herein are methods of treating NASH in a subject in need thereof, the method comprising, consisting essentially of, or consisting of administering to the subject a therapeutically effective amount of a compound or composition disclosed herein.

In another aspect, disclosed herein are methods of treating obesity in a subject in need thereof, the method comprising, consisting essentially of, or consisting of administering to the subject a therapeutically effective amount of a compound or composition disclosed herein.

In another aspect, disclosed herein are methods of treating hyperlipidemia in a subject in need thereof, the method comprising, consisting essentially of, or consisting of administering to the subject a therapeutically effective amount of a compound or composition disclosed herein.

In another aspect, disclosed herein are methods of treating hypercholesterolemia in a subject in need thereof, the method comprising, consisting essentially of, or consisting of administering to the subject a therapeutically effective amount of a compound or composition disclosed herein.

In another aspect, disclosed herein are methods of treating diabetes in a subject in need thereof, the method comprising, consisting essentially of, or consisting of administering to the subject a therapeutically effective amount of a compound or composition disclosed herein.

In another aspect, disclosed herein are methods of treating liver steatosis in a subject in need thereof, the method comprising, consisting essentially of, or consisting of administering to the subject a therapeutically effective amount of a compound or composition disclosed herein.

In some embodiments, the compound as described herein, or the stereoisomer or the tautomer thereof, or the pharmaceutically acceptable salt thereof, or a therapeutically effective amount of the pharmaceutical composition; is administered in combination with a KHK inhibitor, an FXR agonist, a SSAO inhibitor, a FASN inhibitor, or a SCD1 modulator. In some embodiments, the KHK inhibitor is PF-06835919; the FXR agonist is TERN-101 (LY2562175), Tropifexor, obeticholic acid (OCA), or ASC42; the SSAO inhibitor is TERN-201; the FASN inhibitor is ASC40; and the SCD1 modulator is aramchol.

In another aspect, disclosed herein are methods of selectively modulating the activity of a thyroid hormone receptor beta (THR-β) comprising, consisting essentially of, or consisting of contacting a compound as described herein, with a thyroid hormone receptor. In some embodiments, the contacting is in vitro or ex vivo, whereas in other embodiments, the contacting is in vivo.

In another aspect, disclosed herein are methods of selectively modulating the activity of a thyroid hormone receptor beta (THR-β) comprising, consisting essentially of, or consisting of contacting a compound of Formula I, as described herein, with a thyroid hormone receptor. In some embodiments, the contacting is in vitro or ex vivo, whereas in other embodiments, the contacting is in vivo.

In another aspect, disclosed herein are methods of selectively modulating the activity of a thyroid hormone receptor beta (THR-β) comprising, consisting essentially of, or consisting of contacting a composition described herein, with a thyroid hormone receptor. In some embodiments, the contacting is in vitro or ex vivo, whereas in other embodiments, the contacting is in vivo.

| Table of abbreviations | |
|---|---|
| Abbreviation | Meaning |
| EtOAc, or EA | Ethyl Acetate |
| CyH | Cyclohexane |
| DCM | dichloromethane |
| ACN or MeCN | acetonitrile |
| AcOH | Acetic acid |
| MeCN | acetonitrile |
| EtOH | ethanol |
| rt | Room temperature |
| DPPA | Diphenyl phosphoryl azide |

EXAMPLES

Example 1

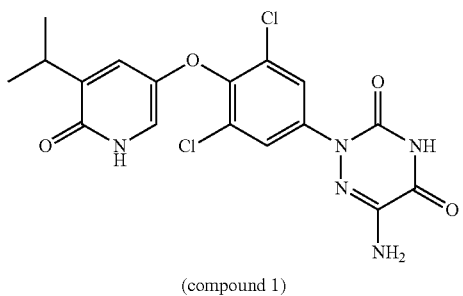

(compound 1)

Compound 1 can be made via the following guidelines. First, 5-isopropyl-6-methoxypyridin-3-ol may be prepared according to procedures outlined in Scheme 1. Then, Scheme 8 can be followed to synthesize 3,5-dichloro-4-((5-isopropyl-6-methoxypyridin-3-yl)oxy)aniline. Finally, transformation to the aminoazauracil can proceed via according to Scheme 3 to afford Compound 1.

Alternatively, compound 1 was made in the following manner:

Potassium trifluoro(prop-1-en-2-yl)borate (11.81 g, 79.78 mmol), Pd(dppf)Cl$_2$ (3.89 g, 5.32 mmol) and K$_2$CO$_3$ (36.75 g, 265.92 mmol) were added to a mixture of 3-bromo-2-methoxypyridine (10 g, 53.18 mmol) in DME (100 mL) and H$_2$O (20 mL). The reaction mixture was purged with N$_2$ and stirred at 90° C. for 2 h. The reaction mixture was cooled to room temperature, diluted with water and extracted with EtOAc (3×). Combined organic layers were washed with brine and dried over MgSO$_4$. The solids were removed by filtration and the filtrate was evaporated to dryness. The crude mixture was purified by flash chromatography on silica gel (0% to 10% EtOAc in CyH) to give 2-methoxy-3-(prop-1-en-2-yl)pyridine 2 (7.80 g, 89%) as a yellow oil. $^1$H-NMR (DMSO-d$_6$, 400 MHz): 2.05 (s, 3H), 3.87 (s, 3H), 5.18-5.21 (m, 2H), 6.97 (dd, J=7.2 Hz, 4.8 Hz, 1H), 7.57 (dd, J=7.2 Hz, 2.0 Hz, 1H), 8.08 (dd, J=4.8 Hz, 2.0 Hz, 1H) ppm. LC-MS: C$_9$H$_{11}$NO [M+H]$^+$: 150.

A mixture of 10% Pd/C (1.67 g) and 2-methoxy-3-(prop-1-en-2-yl)pyridine 2 (7.8 g, 52.28 mmol) in CH$_3$OH (120 mL) was stirred at room temperature under a balloon of H$_2$ for 2 h. The reaction mixture was then filtered on a pad of celite. The filtrate was evaporated to dryness to give 3-isopropyl-2-methoxypyridine (4.50 g, 58%) as a colorless oil. $^1$H-NMR (DMSO-d$_6$, 400 MHz): 1.15 (d, J=6.8 Hz, 6H), 3.10 (m, J=6.8 Hz, 1H), 3.87 (s, 3H), 6.93 (dd, J=7.2 Hz, 4.8 Hz, 1H), 7.55 (dd, J=7.2 Hz, 2.0 Hz, 1H), 7.99 (dd, J=4.8 Hz, 2.0 Hz, 1H) ppm. LC-MS: C$_9$H$_{13}$NO [M+H]$^+$: 152.

NBS (6.89 g, 38.69 mmol) was added to a solution of 3-isopropyl-2-methoxypyridine 3 (4.5 g, 29.76 mmol) in anhydrous acetonitrile (90 mL). The reaction mixture was refluxed for 2 h under N$_2$, cooled to room temperature, then evaporated to dryness. The residue was dissolved in AcOEt (50 mL) and washed with water (50 mL). The aqueous phase was extracted with AcOEt (2×). Combined organic layers were washed with brine and dried over MgSO$_4$. The solids were removed by filtration and the filtrate was evaporated to dryness. The crude mixture was purified by flash chromatography on silica gel (0% to 10% EtOAc in CyH) to give 5-bromo-3-isopropyl-2-methoxypyridine (5.35 g, 78%) as a colorless oil. $^1$H-NMR (DMSO-d$_6$, 300 MHz): 1.16 (d, J=6.8 Hz, 6H), 3.07 (m, J=6.8 Hz, 1H), 3.87 (s, 3H), 7.72 (d, J=2.1 Hz, 1H), 8.11 (d, J=2.1 Hz, 1H) ppm. LC-MS: C$_9$H$_{12}$BrNO [M+H]$^+$: 230/232

Bis(neopentyl-glycolato)diboron (23.56 g, 104.3 mmol), KOAc (10.24 g, 104.3 mmol) and PdCl$_2$[P(o-Tol)$_3$]$_2$ (2.73 g, 3.48 mmol) were added to a solution of 5-bromo-3-isopropyl-2-methoxypyridine (8 g, 34.77 mmol) in anhydrous DMSO (200 mL) under N$_2$. The reaction mixture was stirred at 90° C. for 2 h. After cooling to room temperature, the reaction mixture was diluted with water and extracted with EtOAc (3×). The combined organic phases were washed with water (3×) and brine (2×) and dried over Na$_2$SO$_4$. The solids were removed by filtration and the filtrate was evaporated to dryness. The crude mixture was purified by flash chromatography on silica gel (0% to 20% EtOAc in CyH) to give 5-(5,5-dimethyl-1,3,2-dioxaborinan-2-yl)-3-isopropyl-2-methoxypyridine (4.68 g, 51%) as a white solid. $^1$H-NMR (DMSO-d$_6$, 400 MHz): 0.95 (s, 6H), 1.17 (d, J=6.8 Hz, 6H), 3.09 (m, J=6.8 Hz, 1H), 3.74 (s, 4H), 3.89 (s, 3H), 7.72 (d, J=1.6 Hz, 1H), 8.25 (d, J=1.6 Hz, 1H) ppm.

Acetic acid (26 mL) and H$_2$O$_2$ (30%, 46 mL) were added to a solution of 5-(5,5-dimethyl-1,3,2-dioxaborinan-2-yl)-3-isopropyl-2-methoxypyridine (4.7 g, 17.86 mmol) in THF (100 mL). The reaction mixture was stirred at room temperature for 18 h. It was then diluted with sat. aq. NaHCO$_3$ and extracted with EtOAc (3×). The combined organic layers were washed with brine and dried over Na$_2$SO$_4$. The solids were removed by filtration and the filtrate was evaporated to dryness. The crude mixture was purified by flash chromatography on silica gel (0% to 20% CH$_3$OH in DCM) to give 5-isopropyl-6-methoxypyridin-3-ol (2.90 g, 97%) as a yellow oil. $^1$H-NMR (DMSO-d$_6$, 300 MHz): 1.13 (d, J=6.8 Hz, 6H), 3.03 (m, J=6.8 Hz, 1H), 3.78 (s, 3H), 7.03 (d, J=2.4 Hz, 1H), 7.50 (d, J=2.4 Hz, 1H), 9.12 (br s, 1H) ppm. LC-MS: C$_9$H$_{13}$NO$_2$ [M+H]$^+$: 168.

1,3-dichloro-2-fluoro-5-nitrobenzene (4.37 g, 20.81 mmol) and K$_2$CO$_3$ (11.98 g, 86.72 mmol) were added to a solution of 5-isopropyl-6-methoxypyridin-3-ol (2.9 g, 17.34 mmol) in anhydrous DMF (130 mL) under N$_2$. The reaction mixture was then stirred at 80° C. for 1 h. After cooling to room temperature, the reaction mixture was diluted with water and extracted with EtOAc (3×). The combined organic phases were washed with water and brine and dried over Na$_2$SO$_4$. The solids were removed by filtration and the filtrate was evaporated to dryness. The crude mixture was purified by flash chromatography on silica gel (0% to 20% EtOAc in CyH) to give 5-(2,6-dichloro-4-nitrophenoxy)-3-isopropyl-2-methoxypyridine (5.89 g, 95%) as a yellow solid. LC-MS: C$_{15}$H$_{14}$Cl$_2$N$_2$O$_4$ [M+H]$^+$: 357.

Iron (1.63 g, 29.19 mmol) was added to a solution of 5-(2,6-dichloro-4-nitrophenoxy)-3-isopropyl-2-methoxypyridine (2.085 g, 5.84 mmol) and NH$_4$Cl (3.12 g, 58.38 mmol) in EtOH (30 mL) and water (20 mL) under N$_2$. The reaction mixture was stirred at 85° C. for 3 h. After cooling to room temperature, the reaction mixture was filtered over a celite pad and rinsed with EtOH. The filtrate was concentrated to remove EtOH and extracted with EtOAc (3×). The combined organic layers were washed with sat. aq. NaHCO$_3$ (2×) and brine (80 mL) and dried over Na$_2$SO$_4$. The solids were removed by filtration and the filtrate was evaporated to dryness to give 3,5-dichloro-4-((5-isopropyl-6-methoxy-pyridin-3-yl)oxy)aniline (1.57 g, 82%) as a yellow solid, which was used without further purification in the next step. $^1$H-NMR (DMSO-d$_6$, 300 MHz): 1.13 (d, J=6.8 Hz, 6H), 3.09 (m, J=6.8 Hz, 1H), 3.82 (s, 3H), 5.65 (s, 2H), 6.70 (s, 2H), 7.16 (d, J=2.4 Hz, 1H), 7.38 (d, J=2.4 Hz, 1H) ppm. LC-MS: $C_{15}H_{16}Cl_2N_2O_2$ [M+H]$^+$: 327

A solution of NaNO$_2$ (0.53 g, 7.70 mmol) in water (74 mL) was added to a solution of 3,5-dichloro-4-((5-isopropyl-6-methoxypyridin-3-yl)oxy)aniline (1.2 g, 3.67 mmol) in HCl (conc., 32 mL), acetic acid (95 mL) and water (74 mL) at 0° C. under N$_2$. The reaction mixture was stirred at 0° C. for 1 h. In parallel, a solution of ethyl N-(2-cyanoacetyl)carbamate (0.86 g, 5.50 mmol) in water (90 mL) and pyridine (32 mL) was stirred at 0° C. for 15 min. The first reaction mixture was quickly added to the second one and the resulting reaction mixture was stirred at 0° C. for 2 h. The reaction mixture was diluted in water (500 mL). The precipitate was filtered, washed with water (3×), dissolved in EtOAc and dried over Na$_2$SO$_4$. The solids were removed by filtration and the filtrate was evaporated to dryness to afford ethyl (2-cyano-2-(2-(3,5-dichloro-4-((5-isopropyl-6-methoxypyridin-3-yl)oxy)phenyl)hydrazineylidene)acetyl)carbamate (1.66 g, 92%) as an orange solid which was used without further purification in the next step. LC-MS: $C_{21}H_{21}Cl_2N_5O_5$ [M+H]$^+$: 494/495; [M–H]$^-$: 492/494.

A mixture of ethyl (2-cyano-2-(2-(3,5-dichloro-4-((5-isopropyl-6-methoxypyridin-3-yl)oxy)phenyl)hydrazineylidene)acetyl)carbamate (1.66 g, 3.36 mmol) and NaOAc (1.10 g, 13.43 mmol) in acetic acid (34 mL) under N$_2$ was stirred at 120° C. for 2 h. The reaction mixture was diluted in water (200 mL), filtered, and washed with water (3×). The precipitate was dissolved in EtOAc and dried over Na$_2$SO$_4$. The solids were removed by filtration and the filtrate was evaporated to dryness to give 2-(3,5-dichloro-4-((5-isopropyl-6-methoxypyridin-3-yl)oxy)phenyl)-3,5-dioxo-2,3,4,5-tetrahydro-1,2,4-triazine-6-carbonitrile (1.67 g, quant.) as an orange solid which was used without further purification in the next step. $^1$H-NMR (DMSO-d$_6$, 300 MHz): 1.16 (d, J=6.9 Hz, 6H), 3.09 (m, J=6.8 Hz, 1H), 3.84 (s, 3H), 7.32 (d, J=2.5 Hz, 1H), 7.49 (d, J=2.6 Hz, 1H), 7.81 (s, 2H), 13.25 (br s, 1H) ppm. LC-MS: $C_{19}H_{15}Cl_2N_5O_4$ [M+H]$^+$: 448/450; [M–H]$^-$: 446/448.

HBr (48% aq., 2.1 mL, 18.3 mmol) was added to a solution of 2-(3,5-dichloro-4-((5-isopropyl-6-methoxypyridin-3-yl)oxy)phenyl)-3,5-dioxo-2,3,4,5-tetrahydro-1,2,4-triazine-6-carbonitrile (1.64 g, 3.66 mmol) in anhydrous 1,4-dioxane (61 mL) under N$_2$. The reaction mixture was stirred at 60° C. for 3 h. The reaction mixture was diluted in EtOAc, washed with sat. aq. NaHCO$_3$ and washed with brine. The aqueous phases were extracted with EtOAc (2×). The combined organic phases were dried over Na$_2$SO$_4$. The solids were removed by filtration and the filtrate was evaporated to dryness. The crude mixture was purified by flash chromatography on silica gel using a DCM to CH$_3$OH in DCM gradient to afford 2-(3,5-dichloro-4-((5-isopropyl-6-oxo-1,6-dihydropyridin-3-yl)oxy)phenyl)-3,5-dioxo-2,3,4,5-tetrahydro-1,2,4-triazine-6-carbonitrile (compound 2) (670 mg, 42%) as an orange solid of which 50 mg was purified by preparative HPLC (2% to 100% Acetonitrile in 2 g/L NH$_4$HCO$_3$ aq.) to afford 2-(3,5-dichloro-4-((5-isopropyl-6-oxo-1,6-dihydropyridin-3-yl)oxy)phenyl)-3,5-dioxo-2,3,4,5-tetrahydro-1,2,4-triazine-6-carbonitrile (compound 2) (36 mg, 2%) as a light yellow solid. $^1$H-NMR (DMSO-d$_6$, 300 MHz): 1.13 (d, J=6.1 Hz, 6H), 2.99 (m, J=6.4 Hz, 1H), 6.66 (s, 1H), 7.26 (s, 1H), 7.78 (s, 2H), 11.12 (br s, 1H), 13.22 (br s, 1H) ppm. LC-MS: $C_{18}H_{13}Cl_2N_5O_4$ [M+H]$^+$: 434/436; [M–H]$^-$: 432/434.

A solution of 2-(3,5-dichloro-4-((5-isopropyl-6-oxo-1,6-dihydropyridin-3-yl)oxy)phenyl)-3,5-dioxo-2,3,4,5-tetrahydro-1,2,4-triazine-6-carbonitrile (1.22 g, 2.81 mmol) in HCl (conc., 22 mL) and acetic acid (45 mL) under N$_2$ was stirred at 120° C. for 1 h. The reaction mixture was cooled to room temperature and water (200 mL) was added. The precipitate was filtered, washed with water, dissolved in a mixture of EtOAc and THF and dried over Na$_2$SO$_4$. The solids were removed by filtration and the filtrate was evaporated to dryness to afford 2-(3,5-dichloro-4-((5-isopropyl-6-oxo-1,6-dihydropyridin-3-yl)oxy)phenyl)-3,5-dioxo-2,3,4,5-tetrahydro-1,2,4-triazine-6-carboxylic acid (1.18 g, 93%) as a yellow solid which was used without further purification in the next step. $^1$H-NMR (DMSO-d$_6$, 300 MHz): 1.12 (d, J=6.8 Hz, 6H), 2.99 (m, J=6.8 Hz, 1H), 6.67 (d, J=2.2 Hz, 1H), 7.27 (d, J=2.7 Hz, 1H), 7.82 (s, 2H) ppm. LC-MS: $C_{18}H_{14}Cl_2N_4O_6$ [M+H]$^+$: 453/455; [M–H]$^-$: 451/453.

Et$_3$N (1.5 mL, 10.4 mmol) and diphenyl phosphoryl azide (1.7 mL, 7.81 mmol) were added to a solution of 2-(3,5-dichloro-4-((5-isopropyl-6-oxo-1,6-dihydropyridin-3-yl)oxy)phenyl)-3,5-dioxo-2,3,4,5-tetrahydro-1,2,4-triazine-6-carboxylic acid (1.18 g, 2.60 mmol) in t-butanol (38 mL) under N$_2$. The resulting mixture was stirred at 85° C. for 2 h. The reaction mixture was quenched with NH$_4$Cl (sat., aq., 10 mL) and diluted in EtOAc. The organic phase was washed with NH$_4$Cl (sat., aq., 150 mL) and brine (2×) and dried over Na$_2$SO$_4$. The solids were removed by filtration and the filtrate was evaporated to dryness. The crude mixture was purified by flash chromatography on silica gel (0% to 5% CH$_3$OH in DCM) to give t-butyl (2-(3,5-dichloro-4-((5-isopropyl-6-oxo-1,6-dihydropyridin-3-yl)oxy)phenyl)-3,5-dioxo-2,3,4,5-tetrahydro-1,2,4-triazin-6-yl)carbamate (0.78 g, 57%) a yellow solid. $^1$H-NMR (DMSO-d$_6$, 300 MHz): 1.12 (d, J=6.7 Hz, 6H), 1.45 (s, 9H), 2.99 (m, J=6.9 Hz, 1H), 6.63 (d, J=2.7 Hz, 1H), 7.25 (d, J=3.1 Hz, 1H), 7.89 (s, 2H), 9.11 (s, 1H), 11.20 (br s, 1H), 12.61 (s, 1H) ppm. LC-MS: $C_{22}H_{23}Cl_2N_5O_6$ [M+H]$^+$: 524/526; [M–H]$^-$: 522/524.

A solution of t-butyl (2-(3,5-dichloro-4-((5-isopropyl-6-oxo-1,6-dihydropyridin-3-yl)oxy)phenyl)-3,5-dioxo-2,3,4,5-tetrahydro-1,2,4-triazin-6-yl)carbamate in 4N HCl in 1,4-dioxane (7.3 mL, 29.1 mmol) under N$_2$ was stirred at room temperature for 21 h. The reaction mixture was evaporated to dryness and the product was purified by flash chromatography on silica gel (4% to 10% CH$_3$OH in DCM) to afford 6-amino-2-(3,5-dichloro-4-((5-isopropyl-6-oxo-1,6-dihydropyridin-3-yl)oxy)phenyl)-1,2,4-triazine-3,5(2H,4H)-dione (compound 1) (310 mg, 50%) as a light yellow solid. $^1$H-NMR (DMSO-d$_6$, 300 MHz): 1.12 (d, J=6.7 Hz, 6H), 2.99 (m, J=6.6 Hz, 1H), 6.53 (s, 2H), 6.59 (d, J=2.2 Hz, 1H), 7.23 (d, J=1.9 Hz, 1H), 7.89 (s, 2H), 11.19 (br s, 1H), 12.28 (br s, 1H) ppm. LC-MS: $C_{17}H_{15}Cl_2N_5O_4$ [M+H]$^+$: 424/426; [M–H]$^-$: 422/424.

Example 3

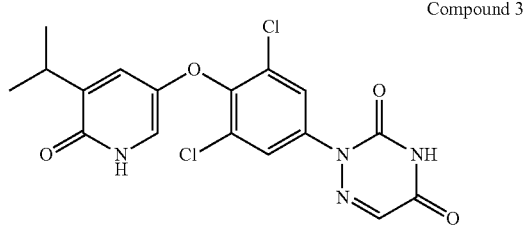 [SMILES: CC(C)c1cc(Oc2c(Cl)cc(-n3ncc(=O)[nH]c3=O)cc2Cl)c[nH]c1=O]

Compound 3

A solution of 2-(3,5-dichloro-4-((5-isopropyl-6-oxo-1,6-dihydropyridin-3-yl)oxy)phenyl)-3,5-dioxo-2,3,4,5-tetrahydro-1,2,4-triazine-6-carboxylic acid (740 mg, 1.63 mmol)

in mercaptoacetic acid (2.5 mL) under $N_2$ was stirred at 120° C. for 5 h. The reaction mixture was cooled to room temperature and water (30 mL) was added. The precipitate was isolated by filtration, washed with water, dissolved in $CH_3OH$ and evaporated to dryness. The crude mixture was purified by flash chromatography on silica gel (0% to 10% $CH_3OH$ in DCM) to give 2-(3,5-dichloro-4-((5-isopropyl-6-oxo-1,6-dihydropyridin-3-yl)oxy)phenyl)-1,2,4-triazine-3,5(2H,4H)-dione (compound 3) (507 mg, 76%) as white solid. $^1$H-NMR (DMSO-$d_6$, 400 MHz): 1.12 (d, J=6.9 Hz, 6H), 2.99 (m, J=6.8 Hz, 1H), 6.64 (d, J=3.2 Hz, 1H), 7.26 (d, J=3.3 Hz, 1H), 7.71 (s, 1H), 7.81 (s, 2H), 11.23 (br s, 1H), 12.49 (br s, 1H) ppm. LC-MS: $C_{17}H_{14}Cl_2N_4O_4$ [M+H]$^+$: 409/411; [M−H]$^−$: 407/409.

Example 4

Compound 4

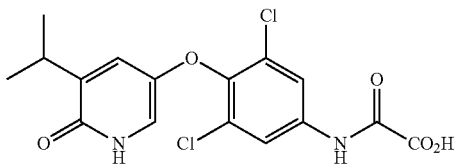

HBr (48% aq., 0.86 mL, 7.64 mmol) was added to a solution of 3,5-dichloro-4-((5-isopropyl-6-methoxypyridin-3-yl)oxy)aniline (500 mg, 1.53 mmol) in 1,4-Dioxane (15 mL) under $N_2$ and the reaction mixture was stirred at 65° C. for 3 h. Heating was stopped and the reaction mixture was stirred at room temperature overnight. Then, heating at 65° C. was resumed for 2 h to reach full conversion. The reaction mixture was diluted with water and sat. aq. $Na_2CO_3$ and DCM were added. The layers were separated and the aqueous layer was extracted with DCM (3×). The combined organic phases were washed with sat. aq. $Na_2CO_3$ (2×) and brine and dried over $Na_2SO_4$. The solids were removed by filtration and the filtrate was evaporated to dryness to give 5-(4-amino-2,6-dichlorophenoxy)-3-isopropylpyridin-2 (1H)-one (450 mg, 94%) as a yellow solid, which was used without any further purification. $^1$H-NMR (DMSO-$d_6$, 400 MHz): 1.11 (d, J=6.9 Hz, 6H), 2.97 (m, J=6.9 Hz, 1H), 5.65 (s, 2H), 6.43 (d, J=2.9 Hz, 1H), 6.68 (s, 2H), 7.15 (d, J=2.9 Hz, 1H), 11.10 (br s, 1H) ppm. LC-MS: $C_{14}H_{14}Cl_2N_2O_2$ [M+H]$^+$: 313.

Ethyl-2-chloro-2-oxoacetate (279.56 mg, 0.23 mL, 2.048 mmol) was added dropwise at 0° C. to a solution of 3,5-dichloro-4-((5-isopropyl-6-methoxypyridin-3-yl)oxy) aniline (670 mg, 2.048 mmol), DIPEA (291.11 mg, 0.37 mL, 2.25 mmol) and DMAP (25.016 mg, 0.205 mmol) in anhydrous DCM (20 mL) under $N_2$. The reaction mixture was allowed to warm and was further stirred at room temperature for 2 h, then diluted with water and extracted with DCM (3×). The combined organic layers were washed with brine (2×) and dried over $Na_2SO_4$. The solids were removed by filtration and the filtrate was evaporated to dryness. The crude mixture was purified by flash chromatography on silica gel (0% to 25% EtOAc in CyH) to afford ethyl 2-((3,5-dichloro-4-((5-isopropyl-6-methoxypyridin-3-yl) oxy)phenyl)amino)-2-oxoacetate (870 mg, 100%) as a yellow oil. $^1$H-NMR (DMSO-$d_6$, 300 MHz): 1.14 (d, J=6.8 Hz, 6H), 1.32 (t, J=4.2 Hz, 3H), 3.08 (m, J=6.8 Hz, 1H), 3.83 (s, 3H), 4.33 (q, J=4.2 Hz, 2H), 7.24 (d, J=2.4 Hz, 1H), 7.43 (d, J=2.4 Hz, 1H), 8.05 (s, 2H), 11.15 (s, 1H) ppm. LC-MS: $C_{19}H_{20}Cl_2N_2O_5$ [M−H]$^−$: 425.

HBr (48% aq., 0.66 mL, 4.68 mmol) was added to a solution of 2-((3,5-dichloro-4-((5-isopropyl-6-methoxypyridin-3-yl)oxy)phenyl)amino)-2-oxoacetate (400 mg, 0.94 mmol) in 1,4-Dioxane (8 mL) under $N_2$. The reaction mixture was stirred at room temperature for 72 h, then more HBr (48% aq., 0.66 mL, 4.68 mmol) was added and stirring at room temperature continued. After an additional 24 h period, more HBr (48% aq., 1.059 mL, 9.36 mmol) was added. The reaction mixture was stirred for an additional 24 h then brought to pH 12 by the addition of NaOH (6N). The resulting aqueous solution was washed with EtOAc (3×). The aqueous phase was then acidified to pH 2 with conc. HCl and extracted with EtOAc (3×). The combined organic phases were washed with water (2×) and brine and dried over $Na_2SO_4$. The solids were removed by filtration and the filtrate was evaporated to dryness. The crude mixture was purified by preparative HPLC (2% to 100% $CH_3CN$ in 2 g/L $NH_4HCO_3$ aq. solution) to give 2-((3,5-dichloro-4-((5-isopropyl-6-oxo-1,6-dihydropyridin-3-yl)oxy)phenyl)amino)-2-oxoacetic acid (compound 4) (54 mg, 15%) as a white solid. $^1$H-NMR (DMSO-$d_6$, 400 MHz): 1.11 (d, J=6.9 Hz, 6H), 2.98 (m, J=6.9 Hz, 1H), 6.55 (d, J=2.9 Hz, 1H), 7.20-7.22 (m, 1H), 8.08 (s, 2H), 10.60 (s, 1H), 11.20 (br s, 1H) ppm. LC-MS: $C_{16}H_{14}Cl_2N_2O_5$ [M+H]$^+$: 385.

Example 5

Compound 5

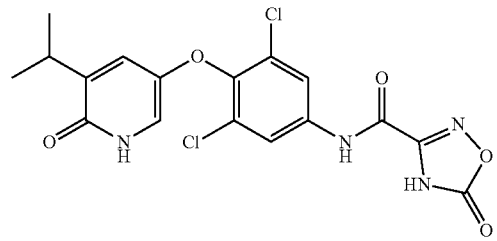

DBU (12.74 g, 12.5 mL, 83.67 mmol) and CDI (13.5 g, 83.26 mmol) were added to a solution of ethyl 2-(hydroxyamino)-2-iminoacetate (10 g, 75.69 mmol) in anhydrous dioxane (75 mL) under $N_2$. The reaction mixture was stirred at 80° C. for 16 h. After cooling to room temperature, the reaction mixture was acidified to pH=3 with HCl (1N, aq.) and extracted with AcOEt (3×). The combined organics layers were dried over $Na_2SO_4$. The solids were removed by filtration and the filtrate was evaporated to dryness. The product was purified by flash chromatography on silica gel (0% to 1% $CH_3OH$ in DCM) to give ethyl 5-oxo-4,5-dihydro-1,2,4-oxadiazole-3-carboxylate (5.60 g, 47%) as a colorless oil. $^1$H-NMR (DMSO-$d_6$, 300 MHz): 1.30 (t, J=7.2 Hz, 3H), 2.97 (q, J=7.2 Hz, 1H), 13.3 (br s, 1H) ppm. LC-MS: $C_5H_6N_2O_4$ [M+H]$^+$: 159

LiHMDS (1M in THF, 1.62 mL, 1.62 mmol) was added to a solution of ethyl 5-oxo-4,5-dihydro-1,2,4-oxadiazole-3-carboxylate (128.24 mg, 0.81 mmol) and 5-(4-amino-2,6-dichlorophenoxy)-3-isopropylpyridin-2(1H)-one (254 mg, 0.81 mmol) in anhydrous toluene (3.85 mL) and the reaction mixture was stirred at room temperature for 24 h under $N_2$. The reaction mixture was diluted with $CH_3OH$ and evaporated to dryness. The crude mixture was purified by flash chromatography on silica gel using $CH_3OH/NH_4OH$ in DCM gradient to afford N-(3,5-dichloro-4-((5-isopropyl-6-oxo-1,6-dihydropyridin-3-yl)oxy)phenyl)-5-oxo-4,5-dihydro-1,2,4-oxadiazole-3-carboxamide (compound 5) (79 mg, 23%) as a white solid. $^1$H-NMR (DMSO-$d_6$, 400 MHz): 1.12 (d, J=7.1 Hz, 6H), 2.98 (m, J=7.1 Hz, 1H), 6.60 (s, 1H), 7.22 (d, J=2.9 Hz, 1H), 8.03 (s, 2H), 11.04-11.34 (m, 2H), 13.39 (bs, 1H) ppm. LC-MS: $C_{17}H_{14}Cl_2N_4O_5$ [M+H]$^+$: 425.

Example 6

Compound 6

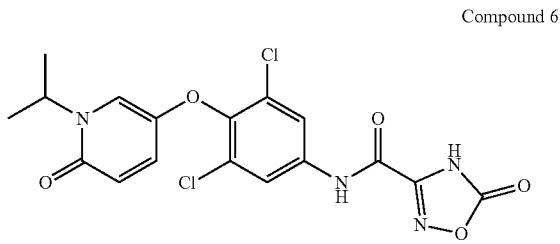 [SMILES: CC(C)n1cc(Oc2c(Cl)cc(NC(=O)c3noc(=O)[nH]3)cc2Cl)ccc1=O]

DIPEA (10.47 g, 13.4 mL, 81.008 mmol) and 1,3-dichloro-2-fluoro-5-nitrobenzene (8.505 g, 40.504 mmol) were added to a solution of 5-hydroxy-1,2-dihydropyridin-2-one 1 (4.5 g, 40.504 mmol) in anhydrous DMF (225 mL) under $N_2$. The reaction mixture was stirred at room temperature for 16 h. The reaction mixture was then diluted with water (150 mL). The resulting precipitate was filtered, washed with water and co-evaporated with toluene to give 5-(2,6-dichloro-4-nitrophenoxy)pyridin-2(1H)-one (10.42 g, 85%) as a beige solid which was used without further purification in the next step. $^1$H-NMR (DMSO-$d_6$, 300 MHz): 6.45 (d, J=9.6 Hz, 1H), 7.24 (d, J=3.0 Hz, 1H), 7.40 (dd, J=9.6 Hz, 3.0 Hz, 1H), 8.50 (s, 2H), 11.26 (br s, 1H) ppm. LC-MS: $C_{11}H_6Cl_2N_2O_4$ [M+H]$^+$: 301

$K_2CO_3$ (2.066 g, 14.95 mmol) was added to a solution of 5-(2,6-dichloro-4-nitrophenoxy)pyridin-2(1H)-one (3 g, 9.96 mmol) in anhydrous dioxane (60 mL) under $N_2$. After 10 min. of stirring at room temperature, 2-iodopropane (2.54 g, 1.49 mL, 14.95 mmol) was added and the reaction mixture was stirred at 120° C. for 16 h. After cooling to room temperature, the reaction mixture was filtered and the filtrate was evaporated to dryness. The crude mixture was purified by flash chromatography on silica gel (40% to 50% EtOAc in CyH) to give 5-(2,6-dichloro-4-nitrophenoxy)-1-isopropylpyridin-2(1H)-one (1.91 g, 56%) as a yellow solid. $^1$H-NMR (DMSO-$d_6$, 300 MHz): 1.25 (d, J=6.6 Hz, 6H), 4.94-5.08 (m, 1H), 6.41 (d, J=9.9 Hz, 1H), 7.30 (dd, J=9.9 Hz, 3.0 Hz, 1H), 7.49 (d, J=3.0 Hz, 1H), 8.51 (s, 2H) ppm. LC-MS: $C_{14}H_{12}Cl_2N_2O_4$ [M+H]$^+$: 343

Fe (1.55 g, 27.83 mmol) was added to a solution of 5-(2,6-dichloro-4-nitrophenoxy)-1-isopropylpyridin-2(1H)-one (1.91 g, 5.57 mmol) and $NH_4Cl$ (2.98 g, 55.66 mmol) in EtOH (38 mL) and water (21 mL) under $N_2$. The reaction mixture was stirred at 70° C. for 16 h. After cooling to room temperature, the reaction mixture was filtered over a pad of celite and the filtrate was diluted with AcOEt. The organic phase was collected, washed with brine (2x) and dried over $Na_2SO_4$. The solids were removed by filtration and the filtrate was evaporated to dryness. The crude mixture was purified by flash chromatography on silica gel (0% to 10% MeOH in DCM) to give 5-(4-amino-2,6-dichlorophenoxy)-1-isopropylpyridin-2(1H)-one (860 mg, 49%) as a yellow solid. $^1$H-NMR (DMSO-$d_6$, 300 MHz): 1.24 (d, J=6.6 Hz, 6H), 4.94-5.08 (m, 1H), 5.65 (br s, 2H), 6.37 (d, J=9.9 Hz, 1H), 6.70 (s, 2H), 7.13 (dd, J=9.9 Hz, 3.3 Hz, 1H), 7.26 (d, J=3.3 Hz, 1H) ppm. LC-MS: $C_{14}H_{14}Cl_2N_2O_2$ [M+H]$^+$: 313

LiHMDS (1M in THF, 2.75 mL, 2.75 mmol) was added to a solution of ethyl 5-oxo-4,5-dihydro-1,2,4-oxadiazole-3-carboxylate (108.55 mg, 0.69 mmol) and 5-(4-amino-2,6-dichlorophenoxy)-1-isopropylpyridin-2(1H)-one (215 mg, 0.69 mmol) in anhydrous THF (3 mL) under $N_2$. The reaction mixture was stirred at room temperature for 30 min. The reaction mixture was then diluted with MeOH and the mixture was evaporated to dryness. The crude product was purified by flash chromatography on silica gel (0% to 10% MeOH in DCM). The resulting solid was triturated in EtOH and co-evaporated with MeCN to give N-(3,5-dichloro-4-(((1-isopropyl-6-oxo-1,6-dihydropyridin-3-yl)oxy)phenyl)-5-oxo-4,5-dihydro-1,2,4-oxadiazole-3-carboxamide (compound 6) (155 mg, 53%) as a white solid. $^1$H-NMR (DMSO-$d_6$, 400 MHz): 1.24 (d, J=7.0 Hz, 6H), 4.96-5.03 (m, 1H), 6.36-6.38 (d, J=9.9 Hz, 1H), 7.20 (dd, J=9.9 Hz, 3.3 Hz, 1H), 7.41 (d, J=3.4 Hz, 1H), 8.04 (s, 2H), 11.39 (br, 1H) ppm. LC-MS: $C_{17}H_{14}Cl_2N_4O_5$ [M+H]$^+$: 425.

Example 7

Compound 7

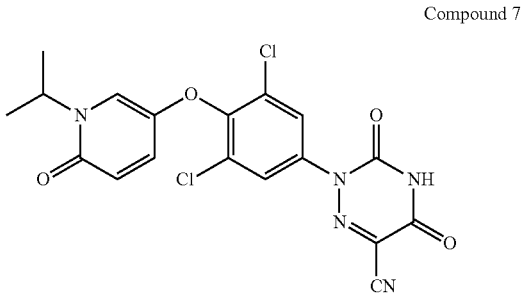 [SMILES: CC(C)n1cc(Oc2c(Cl)cc(-n3nc(C#N)c(=O)[nH]c3=O)cc2Cl)ccc1=O]

A solution of $NaNO_2$ (0.74 g, 10.73 mmol) in water (106 mL) was added dropwise to a solution of 5-(4-amino-2,6-dichlorophenoxy)-1-isopropylpyridin-2(1H)-one (1.6 g, 5.109 mmol) in HCl 37% (44.3 mL, 539.95 mmol), acetic acid (138 mL) and water (106 mL) at 0° C. under $N_2$. The reaction mixture was stirred at 0° C. for 1 h. In parallel, a solution of ethyl N-(2-cyanoacetyl)carbamate (1.2 g, 7.66 mmol) in water (127 mL) and pyridine (42 mL) was stirred at 0° C. for 15 min. The first reaction mixture was quickly added to the second one. The resulting reaction mixture was stirred at 0° C. for 2 h. Extra N-(2-cyanoacetyl)carbamate (1.2 g, 7.66 mmol) in pyridine (42 mL) and water (127 mL) was added and stirring was continued at 0° C. for 1 h. The reaction mixture was diluted with more water (250 mL). The precipitate was filtered, washed with water and dried under vacuum to give ethyl (2-cyano-2-(2-(3,5-dichloro-4-((1-isopropyl-6-oxo-1,6-dihydropyridin-3-yl)oxy)phenyl)hydrazineylidene)acetyl)carbamate (2.04 g, 83%) as an orange solid. LC-MS: $C_{20}H_{19}Cl_2N_5O_5$ [M+H]$^+$: 480.

Procedure 1

Sodium acetate (1.093 g, 0.013 mol) was added to a solution of ethyl (2-cyano-2-(2-(3,5-dichloro-4-((1-isopropyl-6-oxo-1,6-dihydropyridin-3-yl)oxy)phenyl)hydrazineylidene)acetyl)carbamate (1.6 g, 0.0033 mol) in acetic acid (29 mL) under $N_2$. The reaction mixture was stirred at 120° C. for 2 h. The reaction mixture was then cooled to 0° C., water (150 mL) was added and the mixture was stirred for 30 min. The resulting precipitate was filtered and purified by flash chromatography on silica gel (0 to 5% MeOH in DCM). Two fractions containing the product were obtained. The first one was repurified by preparative HPLC (2% to 100% MeCN in 2 g/L NH$_4$HCO$_3$ aq.) to give 2-(3,5-dichloro-4-((1-isopropyl-6-oxo-1,6-dihydropyridin-3-yl)oxy)phenyl)-3,5-dioxo-2,3,4,5-tetrahydro-1,2,4-triazine-6-carbonitrile (7) (46 mg, 3%) as a white solid. The second fraction was repurified by flash chromatography on silica gel (50% to 70% AcOEt in CyH) to give (2-(3,5-dichloro-4-((1-isopropyl-6-oxo-1,6-dihydropyridin-3-yl)oxy)phenyl)-3,5-dioxo-2,3,4,5-tetrahydro-1,2,4-triazine-6-carbonitrile (compound 7) (488 mg, 34%) as a pink solid.

Procedure 2

Sodium acetate (2.79 g, 0.034 mol) was added to a solution of ethyl (2-cyano-2-(2-(3,5-dichloro-4-((1-isopropyl-6-oxo-1,6-dihydropyridin-3-yl)oxy)phenyl)hydrazinenylidene)acetyl)carbamate 5 (2.04 g, 0.0042 mol) in acetic acid (37 mL) under N$_2$. The reaction mixture was stirred at 120° C. for 2 h. The reaction mixture was then cooled to 0° C., water (150 mL) was added and the mixture was stirred for 30 min. The resulting precipitate was filtered to give 2-(3,5-dichloro-4-((1-isopropyl-6-oxo-1,6-dihydropyridin-3-yl)oxy)phenyl)-3,5-dioxo-2,3,4,5-tetrahydro-1,2,4-triazine-6-carbonitrile (compound 7) (1.24 g, 67%) as a pink solid, which was used as such in the next step. $^1$H-NMR (DMSO-d$_6$, 400 MHz): 1.26 (d, J=6.4 Hz, 6H), 4.96-5.06 (m, 1H), 6.37 (d, J=10.0 Hz, 1H), 6.53 (br, 2H), 7.20 (dd, J=10.0 Hz, 3.2 Hz, 1H), 7.52 (d, J=3.2 Hz, 1H), 7.79 (s, 2H) ppm. LC-MS: C$_{18}$H$_{13}$Cl$_2$N$_5$O$_4$ [M+H]$^+$: 434.

Example 8

The combined organic layers were washed with sat. aq. NaHCO$_3$ and brine and dried over Na$_2$SO$_4$. The solids were removed by filtration and the filtrate was evaporated to dryness. The crude mixture was purified by flash chromatography on silica gel (0% to 5% MeOH in DCM) to give t-butyl (2-(3,5-dichloro-4-((1-isopropyl-6-oxo-1,6-dihydropyridin-3-yl)oxy)phenyl)-3,5-dioxo-2,3,4,5-tetrahydro-1,2,4-triazin-6-yl)carbamate 7 (660 mg, 60%) as a yellow solid. $^1$H-NMR (DMSO-d$_6$, 300 MHz): 1.26 (d, J=6.6 Hz, 6H), 1.45 (s, 9H), 4.94-5.08 (m, 1H), 6.37 (d, J=9.9 Hz, 1H), 7.19 (dd, J=9.9 Hz, 3.0 Hz, 1H), 7.51 (d, J=3.0 Hz, 1H), 7.89 (s, 2H), 9.08 (s, 1H), 12.61 (br s, 1H) ppm. LC-MS: C$_{22}$H$_{23}$Cl$_2$N$_5$O$_6$ [M+H]$^+$: 524

TFA (1.73 mL, 23.27 mmol) was added to a solution of t-butyl (2-(3,5-dichloro-4-((1-isopropyl-6-oxo-1,6-dihydropyridin-3-yl)oxy)phenyl)-3,5-dioxo-2,3,4,5-tetrahydro-1,2,4-triazin-6-yl)carbamate (610 mg, 1.16 mmol) in anhydrous DCM (14.7 mL) under N$_2$. The reaction mixture was stirred at room temperature for 16 h, and then evaporated to dryness. The crude product was purified by flash chromatography on silica gel (0% to 10% [MeOH/NH$_4$OH 9:1] in DCM). The resulting solid was triturated in EtOH to afford 6-amino-2-(3,5-dichloro-4-((1-isopropyl-6-oxo-1,6-dihydropyridin-3-yl)oxy)phenyl)-1,2,4-triazine-3,5(2H,4H)-dione (compound 8) (131 mg, 27%) as a white solid. $^1$H-NMR (DMSO-d$_6$, 400 MHz): 1.24 (d, J=6.8 Hz, 6H), 4.99-5.03 (m, 1H), 6.39 (d, J=9.2 Hz, 1H), 6.53 (br s, 2H), 7.20 (dd, J=10.0 Hz, 3.3 Hz, 1H), 7.47 (d, J=3.3 Hz, 1H), 7.89 (s, 2H), 12.28 (br, 1H) ppm. LC-MS: C$_{17}$H$_{15}$Cl$_2$N$_5$O$_4$ [M+H]$^+$: 424.

Example 9

Compound 8

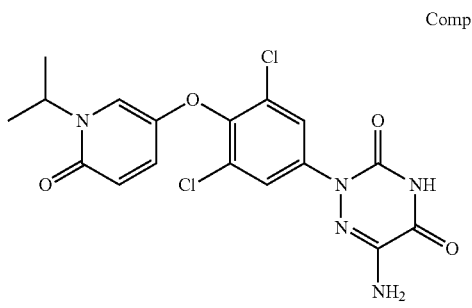

Compound 9

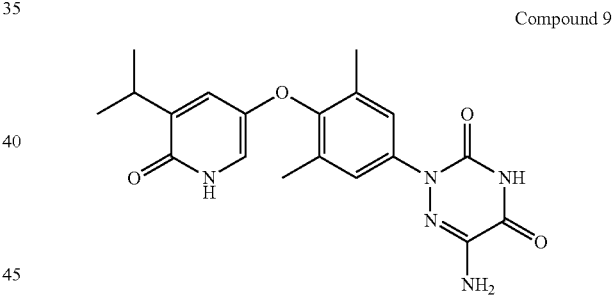

A mixture of 2-(3,5-dichloro-4-((1-isopropyl-6-oxo-1,6-dihydropyridin-3-yl)oxy)phenyl)-3,5-dioxo-2,3,4,5-tetrahydro-1,2,4-triazine-6-carbonitrile (1.62 g, 3.73 mmol), HCl 37% (2.76 mL, 33.58 mmol) and AcOH (5.56 mL, 97 mmol) under N$_2$ was stirred at 120° C. for 3 h. The reaction mixture was cooled to room temperature and water was added. The resulting precipitate was filtered, washed with water and co-evaporated with toluene to give 2-(3,5-dichloro-4-((1-isopropyl-6-oxo-1,6-dihydropyridin-3-yl)oxy)phenyl)-3,5-dioxo-2,3,4,5-tetrahydro-1,2,4-triazine-6-carboxylic acid (957 mg, 57%) which was used as such in the next step. LC-MS: C$_{18}$H$_{14}$Cl$_2$N$_4$O$_6$ [M+H]$^+$: 453.

Triethylamine (854.68 mg, 1.17 mL, 8.45 mmol) and diphenyl phosphoryl azide (1743.29 mg, 1.37 mL, 6.33 mmol) were added to a solution of 2-(3,5-dichloro-4-((1-isopropyl-6-oxo-1,6-dihydropyridin-3-yl)oxy)phenyl)-3,5-dioxo-2,3,4,5-tetrahydro-1,2,4-triazine-6-carboxylic acid (957 mg, 2.11 mmol) in t-butanol (31 mL) under N$_2$. The resulting mixture was stirred at 85° C. for 16 h. After cooling to room temperature, the reaction mixture was quenched with sat. aq. NaHCO$_3$ and was extracted with EtOAc (2×).

Cs$_2$CO$_3$ (7.01 g, 21.53 mmol) was added to a solution of 5-isopropyl-6-methoxypyridin-3-ol (1.8 g, 10.77 mmol) and 2-fluoro-1,3-dimethyl-5-nitrobenzene (1.82 g, 10.77 mmol) in anhydrous DMF (31 mL) under N$_2$. The reaction mixture was stirred at room temperature for 4 h. Cs$_2$CO$_3$ (7.01 g, 21.53 mmol) was added and stirring at room temperature was pursued for 16 h. Then, the reaction mixture was diluted with water and extracted with EA (3×). The combined organic layers were washed with water (2×) and brine (3×) and dried over Na$_2$SO$_4$. The solids were removed by filtration and the filtrate was evaporated to dryness. The crude mixture was purified by flash chromatography on silica gel (0% to 20% EA in CyH) and triturated with pentane to give 5-(2,6-dimethyl-4-nitrophenoxy)-3-isopropyl-2-methoxypyridine (1.70 g, 50%) as a white solid. LCMS: C$_{17}$H$_{20}$N$_2$O$_4$ [M+H]$^+$: 317

Fe (1.5 g, 26.87 mmol) was added to a solution of 5-(2,6-dimethyl-4-nitrophenoxy)-3-isopropyl-2-methoxypyridine (1.7 g, 5.37 mmol) and NH$_4$Cl (2.87 g, 53.74 mmol) in EtOH (37 mL) and water (20.6 mL) under N$_2$. The reaction mixture was stirred at 70° C. for 16 h. After cooling to room temperature, the reaction mixture was filtered through a pad of celite which was rinsed with EtOH. The filtrate was concentrated to removed EtOH and extracted with EA (3×). The combined organics layers were washed with sat. aq. NaHCO$_3$ and brine and dried over Na$_2$SO$_4$. The solids were removed by filtration and the filtrate was evaporated to dryness to give 4-((5-isopropyl-6-methoxypyridin-3-yl)oxy)-3,5-dimethylaniline (1.54 g, 100%) as a yellow solid which was used without further purification. $^1$H-NMR (DMSO-d$_6$, 300 MHz): 1.11 (d, J=6.9 Hz, 6H), 1.93 (s, 6H), 3.00-3.09 (m, 1H), 3.80 (s, 3H), 4.85 (s, 2H), 6.32 (s, 2H), 7.06 (d, J=2.4 Hz, 1H), 7.31 (d, J=2.4 Hz, 1H) ppm.

A solution of NaNO$_2$ (1.26 g, 18.33 mmol) in water (181 mL) was added dropwise to a solution of 4-((5-isopropyl-6-methoxypyridin-3-yl)oxy)-3,5-dimethylaniline (2.5 g, 8.73 mmol) in HCl 37% (75.8 mL, 922.64 mmol), acetic acid (230 mL) and water (180 mL) at 0° C. under N$_2$. The reaction mixture was stirred at 0° C. for 1 h. In parallel, a solution of ethyl N-(2-cyanoacetyl)carbamate (2.04 g, 13.09 mmol) in water (217 mL) and pyridine (72 mL) was stirred at 0° C. for 15 min. The first reaction mixture was quickly added to the second one. The resulting reaction mixture was then allowed to warm at room temperature for 16 h. The reaction mixture was diluted with water (1 L). The resulting precipitate was collected by filtration, washed with water and dried under vacuum to give ethyl (2-cyano-2-(2-(4-((5-isopropyl-6-methoxypyridin-3-yl)oxy)-3,5-dimethylphenyl)hydrazineylidene)acetyl)carbamate (1.5 g) as a yellow solid. NaOH 1N was added to the filtrate until pH ~6. The resulting precipitate was collected by filtration, washed with water and dried under vacuum to give more ethyl (2-cyano-2-(2-(4-((5-isopropyl-6-methoxypyridin-3-yl)oxy)-3,5-dimethylphenyl)hydrazineylidene)acetyl)carbamate (1.7 g) as a red solid. Both solids were used without further purification. $^1$H-NMR (DMSO-d$_6$, 300 MHz): 1.13 (d, J=6.9 Hz, 6H), 1.62 (t, J=7.2 Hz, 3H), 2.10 (s, 6H), 3.02-3.11 (m, 1H), 3.82 (s, 3H), 7.11 (d, J=2.7 Hz, 1H), 7.35 (d, J=2.7 Hz, 1H), 7.52 (s, 2H), 10.50 (s, 1H), 12.02 (br s, 1H) ppm.

Sodium acetate (3.91 g, 0.048 mol) was added to a solution of ethyl (2-cyano-2-(2-(4-((5-isopropyl-6-methoxypyridin-3-yl)oxy)-3,5-dimethylphenyl)hydrazineylidene)acetyl)carbamate (2.7 g, 0.006 mol) in acetic acid (50 mL). The reaction mixture was stirred at 120° C. under N$_2$ for 2 h. The reaction mixture was then cooled to 0° C. and diluted with water (300 mL). The mixture was stirred for 30 min at 0° C. The resulting precipitate was collected by filtration, washed with water and dissolved in EA. This solution was dried over Na$_2$SO$_4$. The solids were removed by filtration and the filtrate was evaporated to dryness to give 2-(4-((5-isopropyl-6-methoxypyridin-3-yl)oxy)-3,5-dimethylphenyl)-3,5-dioxo-2,3,4,5-tetrahydro-1,2,4-triazine-6-carbonitrile (2.26 g, 93%) as a pink solid which was used without further purification. $^1$H-NMR (DMSO-d$_6$, 300 MHz): 1.14 (d, J=6.9 Hz, 6H), 2.13 (s, 6H), 3.03-3.12 (m, 1H), 3.83 (s, 3H), 7.19 (d, J=3.0 Hz, 1H), 7.30 (s, 2H), 7.34 (d, J=3.0 Hz, 1H), 13.00 (br s, 1H) ppm. LCMS: C$_{21}$H$_{21}$N$_5$O$_4$ [M+H]$^+$: 408

HBr 48% in water (5.59 g, 3.75 mL, 33.13 mmol) was added to a solution of 2-(4-((5-isopropyl-6-methoxypyridin-3-yl)oxy)-3,5-dimethylphenyl)-3,5-dioxo-2,3,4,5-tetrahydro-1,2,4-triazine-6-carbonitrile (2.7 g, 6.63 mmol) in 1,4-dioxane (100 mL) under N$_2$. The reaction mixture was stirred at 60° C. for 4 h. After cooling to room temperature, the reaction mixture was diluted with EA (300 mL) and washed with sat. aq. NaHCO$_3$ (150 mL) and brine. The aqueous phases were re-extracted with EA (2×). The combined organic phases were dried over Na$_2$SO$_4$. The solids were removed by filtration and the filtrate was evaporated to dryness to give 2-(4-((5-isopropyl-6-oxo-1,6-dihydropyridin-3-yl)oxy)-3,5-dimethylphenyl)-3,5-dioxo-2,3,4,5-tetrahydro-1,2,4-triazine-6-carbonitrile (1.76 g, 68%) as a red solid which was used without further purification. LCMS: C$_{20}$H$_{19}$N$_5$O$_4$ [M+H]$^+$: 394

A solution of 2-(4-((5-isopropyl-6-oxo-1,6-dihydropyridin-3-yl)oxy)-3,5-dimethylphenyl)-3,5-dioxo-2,3,4,5-tetrahydro-1,2,4-triazine-6-carbonitrile (1.76 g, 4.47 mmol) in conc. HCl (3.31 mL, 40.26 mmol) and AcOH (6.67 mL, 116.32 mmol) was stirred at 120° C. under N$_2$ for 3 h. The reaction mixture was cooled to room temperature and water (150 mL) was added. The resulting precipitate was collected by filtration, washed with water and dried under vacuum to give 2-(4-((5-isopropyl-6-oxo-1,6-dihydropyridin-3-yl)oxy)-3,5-dimethylphenyl)-3,5-dioxo-2,3,4,5-tetrahydro-1,2,4-triazine-6-carboxylic acid (1.61 g, 87%) as a beige solid which was used without further purification. $^1$H-NMR (DMSO-d$_6$, 300 MHz): 1.13 (d, J=6.9 Hz, 6H), 2.15 (s, 6H), 2.95-3.04 (m, 1H), 6.30 (d, J=3.0 Hz, 1H), 7.23 (d, J=3.0 Hz, 1H), 7.30 (s, 2H), 12.5 (br s, 1H) ppm. LCMS: C$_{20}$H$_{20}$N$_4$O$_6$ [M+H]$^+$: 413

Triethylamine (1.35 mL, 9.7 mmol) and diphenyl phosphoryl azide (1.57 mL, 7.27 mmol) were added to a solution of 2-(4-((5-isopropyl-6-oxo-1,6-dihydropyridin-3-yl)oxy)-3,5-dimethylphenyl)-3,5-dioxo-2,3,4,5-tetrahydro-1,2,4-triazine-6-carboxylic acid (1 g, 2.42 mmol) in t-butanol (37 mL) under N$_2$. The reaction mixture was stirred at 85° C. for 18 h. The reaction mixture was quenched with sat. aq. NaHCO$_3$ (50 mL) and diluted with EA (150 mL). The organic phase was washed with sat. aq. NaHCO$_3$ (2×) and brine and dried over Na$_2$SO$_4$. The solids were removed by filtration and the filtrate was evaporated to dryness. The crude mixture was purified by flash chromatography on silica gel (0% to 5% MeOH in DCM) to give t-butyl (2-(4-((5-isopropyl-6-oxo-1,6-dihydropyridin-3-yl)oxy)-3,5-dimethylphenyl)-3,5-dioxo-2,3,4,5-tetrahydro-1,2,4-triazin-6-yl)carbamate (0.41 g, 35%) as an orange solid. $^1$H-NMR (DMSO-d$_6$, 300 MHz): 1.13 (d, J=6.9 Hz, 6H), 1.43 (s, 9H), 2.14 (s, 6H), 2.95-3.04 (m, 1H), 6.28 (d, J=3.0 Hz, 1H), 7.23 (d, J=3.0 Hz, 1H), 7.31 (s, 2H), 8.96 (s, 1H), 11.01 (br s, 1H), 12.45 (br s, 1H) ppm. LCMS: C$_{24}$H$_{29}$N$_5$O$_6$ [M+H]$^+$: 484

A solution of t-butyl (2-(4-((5-isopropyl-6-oxo-1,6-dihydropyridin-3-yl)oxy)-3,5-dimethylphenyl)-3,5-dioxo-2,3,4,5-tetrahydro-1,2,4-triazin-6-yl)carbamate (550 mg, 1.14 mmol) in HCl (4N in dioxane, 5.69 mL, 22.75 mmol) was stirred at room temperature under N$_2$ for 2 h. The reaction mixture was evaporated to dryness and purified by flash chromatography on silica gel (10% to 50% [MeOH/NH$_4$OH (9:1)] in DCM). The resulting solid was triturated in EtOH (4×) to afford 6-amino-2-(4-((5-isopropyl-6-oxo-1,6-dihydropyridin-3-yl)oxy)-3,5-dimethylphenyl)-1,2,4-triazine-3,5(2H,4H)-dione (compound 9) (260 mg, 60%) as a beige solid. $^1$H-NMR (DMSO-d$_6$, 400 MHz): 1.12 (d, J=6.9 Hz, 6H), 2.11 (s, 6H), 2.95-3.02 (m, 1H), 6.23 (br s, 1H), 6.33 (s, 2H), 7.22 (d, J=3.3 Hz, 1H), 7.30 (s, 2H), 11.05 (br s, 1H), 12.11 (s, 1H) ppm. LCMS: C$_{19}$H$_{21}$N$_5$O$_4$ [M+H]$^+$: 384.

Example 10

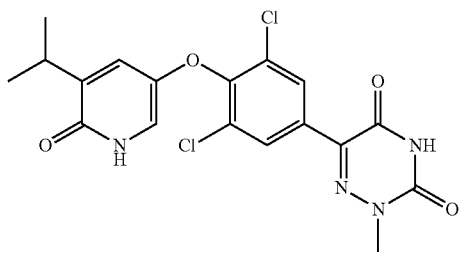

Compound 10

A solution of NaNO$_2$ (232 mg, 3.36 mmol) in water (6 mL) was added to a solution of 5-(4-amino-2,6-dichlorophenoxy)-3-isopropylpyridin-2(1H)-one (526 mg, 1.68 mmol) in MeOH (23 mL), water (6 mL), acetic acid (3 mL) and conc. HCl (8 mL) at 0° C. under N$_2$. The reaction mixture was stirred at 0° C. for 30 min. Then, tetrahydroxydiboron (1204 mg, 13.44 mmol) was added and the reaction mixture was stirred at 60° C. for 30 min. The reaction mixture was cooled to room temperature and diluted with more water (100 mL). The precipitate was collected by filtration, washed with water and dried under vacuum to give (3,5-dichloro-4-((5-isopropyl-6-oxo-1,6-dihydropyridin-3-yl)oxy)phenyl)boronic acid (426 mg, 74%) as a yellow solid which was used as such in the next step. LC-MS: C$_{14}$H$_{14}$BCl$_2$NO$_4$ [M+H]$^+$: 342.

Na$_2$CO$_3$ (2M aq., 2.50 mL, 4.98 mmol) was added to a solution of (3,5-dichloro-4-((5-isopropyl-6-oxo-1,6-dihydropyridin-3-yl)oxy)phenyl)boronic acid (426 mg, 1.25 mmol), 6-bromo-2-methyl-2,3,4,5-tetrahydro-1,2,4-triazine-3,5-dione (307.93 mg, 1.49 mmol) and Pd(dppf)Cl$_2$ (91.1 mg, 0.12 mmol) in 1,4-dioxane (9 mL) under N$_2$. The reaction mixture was stirred at 100° C. for 30 min. After cooling to room temperature, the reaction mixture was diluted with water. The resulting precipitate was collected by filtration. The filtrate was extracted with EA (2×). The combined organic layers were washed with brine and dried over Na$_2$SO$_4$. The solids were removed by filtration and the filtrate was evaporated to dryness. The resulting residue was combined with the solid obtained by precipitation and purified by prep. HPLC (15% to 100% MeCN in water [0.2% v/v NH$_3$]) to afford 6-(3,5-dichloro-4-((5-isopropyl-6-oxo-1,6-dihydropyridin-3-yl)oxy)phenyl)-2-methyl-1,2,4-triazine-3,5(2H,4H)-dione (10) (33 mg, 6%) as a white solid. $^1$H-NMR (DMSO-d$_6$, 400 MHz): 1.12 (d, J=8.0 Hz, 6H), 2.95-3.02 (m, 1H), 3.47 (s, 3H), 6.60 (d, J=3.4 Hz, 1H), 7.23 (d, J=3.6 Hz, 1H), 8.31 (s, 2H) ppm. LC-MS: C$_{18}$H$_{16}$Cl$_2$N$_4$O$_4$ [M+H]$^+$: 423.

The following compounds may be synthesized using methods similar to those described in the above examples or described in the general schemes.

Example 11

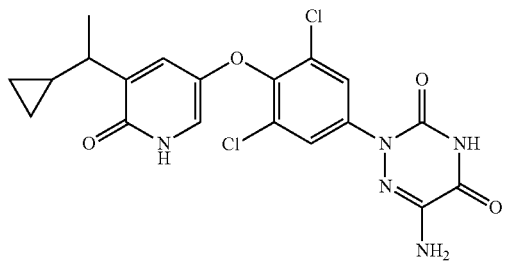

Compound 11

6-amino-2-(3,5-dichloro-4-((5-(1-cyclopropylethyl)-6-oxo-1,6-dihydropyridin-3-yl)oxy)phenyl)-1,2,4-triazine-3,5(2H,4H)-dione The titled compound could be prepared following the procedure used to form 6-amino-2-(3,5-dichloro-4-((5-isopropyl-6-oxo-1,6-dihydropyridin-3-yl)oxy)phenyl)-1,2,4-triazine-3,5(2H,4H)-dione with the exception that (1-cyclopropylvinyl)boronic acid (or corresponding boronic ester) could be used in the first step.

Example 12

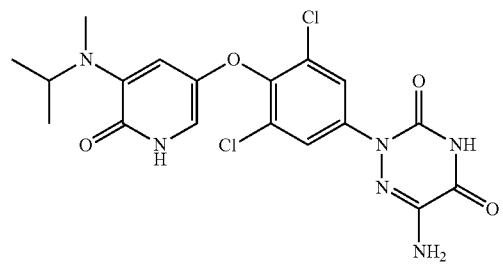

Compound 12

6-amino-2-(3,5-dichloro-4-((5-(isopropyl(methyl)amino)-6-oxo-1,6-dihydropyridin-3-yl)oxy)phenyl)-1,2,4-triazine-3,5(2H,4H)-dione The titled compound may be prepared following the procedure described for compound 13 with the exception of using acetone in the reductive alkylation step. Alternatively, alkylation could be done with the corresponding alkyl halides.

Example 13

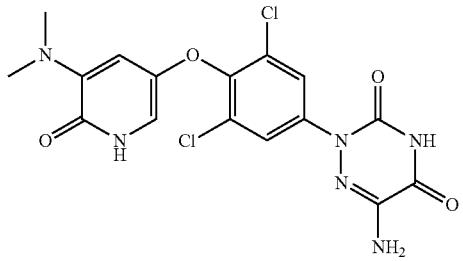

Compound 13

Triethylamine (4 eq., 12 mL, 86.19 mmol) and Diphenyl phosphoryl azide (3 eq., 17.79 g, 13.93 mL, 64.65 mmol) were added to a solution of 5-bromo-2-methoxypyridine-3-carboxylic acid (1 eq., 5 g, 21.55 mmol) in tert-butanol (312 mL) under $N_2$. The reaction mixture was stirred at 85° C. for 3 d. After cooling to rt, the reaction mixture was quenched with sat. aq. $NaHCO_3$ and extracted with EA. The organic layer was washed with sat. aq. $NaHCO_3$ and brine and dried over $Na_2SO_4$. The solids were removed by filtration and the filtrate was evaporated to dryness. The crude mixture was purified by flash chromatography on silica gel (0 to 20% EA in CyH) to give tert-butyl (5-bromo-2-methoxypyridin-3-yl)carbamate (6.05 g, 93%) as a colorless oil. $^1$H-NMR (DMSO-$d_6$, 300 MHz): 1.46 (s, 9H), 3.88 (s, 3H), 7.93 (d, J=2.1 Hz, 1H), 8.20 (d, J=2.1 Hz, 1H), 8.50 (br s, 1H) ppm. LC-MS: $C_{11}H_{15}BrN_2O_3$ [M+H]$^+$: 303/305.

Bis(neopentyl glycolato)diboron (5.86 g, 25.93 mmol), potassium acetate (7.83 g, 79.79 mmol) and Pd(dppf)Cl$_2$ (1.46 g, 1.99 mmol) were added to a solution of t-butyl (5-bromo-2-methoxypyridin-3-yl)carbamate (6.05 g, 19.95 mmol) in anhydrous DMSO (73 mL) under $N_2$. The reaction mixture was stirred at 80° C. for 3 h. After cooling to rt, the reaction mixture was diluted with EA and filtered on a pad of celite. The filtrate was diluted with sat. aq. $NaHCO_3$ and the layers were separated. The aqueous layer was reextracted with EA. The combined organic layers were washed with water (2×) and brine and dried over $Na_2SO_4$. The solids were removed by filtration and the filtrate was evaporated to dryness. The crude mixture was purified by flash chromatography on silica gel (10 to 20% EA in CyH) to give tert-butyl (5-(5,5-dimethyl-1,3,2-dioxaborinan-2-yl)-2-methoxypyridin-3-yl)carbamate 3 (4.60 g, 69%) as a white solid. LC-MS: $C_{16}H_{25}BN_2O_5$ [M(boronic acid)+H]$^+$: 269.

A solution of oxo(sodioperoxy)borane tetrahydrate (2.44 g, 15.83 mmol) in $H_2O$ (46 mL) was added to a solution of tert-butyl (5-(5,5-dimethyl-1,3,2-dioxaborinan-2-yl)-2-methoxypyridin-3-yl)carbamate 3 (1 eq., 2.66 g, 7.91 mmol) in THF (92 mL) under $N_2$. The reaction mixture was stirred at rt for 3 h. The reaction mixture was then saturated with solid NaCl and extracted with EA (2×). The combined organic layers were dried over $Na_2SO_4$. The solids were removed by filtration and the filtrate was evaporated to dryness. The crude product was purified by flash chromatography on silica gel (10% to 20% EA in CyH) to give tert-butyl (5-hydroxy-2-methoxypyridin-3-yl)carbamate (1.90 g, 100%) as a colorless oil. LCMS: $C_{11}H_{16}N_2O_4$ [M+H]$^+$: 241.

DIPEA (6.54 mL, 39.54 mmol) was added to a solution of tert-butyl (5-hydroxy-2-methoxypyridin-3-yl)carbamate (1.9 g, 7.91 mmol) and 1,3-dichloro-2-fluoro-5-nitrobenzene (1 eq., 1.66 g, 7.91 mmol) in anhydrous DMF (35 mL) under $N_2$. The reaction mixture was stirred at rt for 2 h. The reaction mixture was diluted with water and extracted with EA (3×). The combined organic layers were washed with brine (5×) and dried over $Na_2SO_4$. The solids were removed by filtration and the filtrate was evaporated to dryness. The crude mixture was purified by flash chromatography on silica gel (0% to 10% EA in CyH) to give tert-butyl (5-(2,6-dichloro-4-nitrophenoxy)-2-methoxypyridin-3-yl) carbamate (2.07 g, 61%) as a white solid. LC-MS: $C_{17}H_{17}Cl_2N_3O_6$ [M+H]$^+$: 430.

A solution of tert-butyl (5-(2,6-dichloro-4-nitrophenoxy)-2-methoxypyridin-3-yl)carbamate (1 eq., 2.63 g, 6.11 mmol) in HCl 4N in Dioxane (48 mL) was stirred at rt under $N_2$ for 5 h. The reaction mixture was quenched with sat. aq. $NaHCO_3$ and extracted with EA (2×). The combined organic layers were washed with brine and dried over $Na_2SO_4$. The solids were removed by filtration and the filtrate was evaporated to dryness. The crude mixture was purified by flash chromatography on silica gel (0% to 30% EA in CyH) to give 5-(2,6-dichloro-4-nitrophenoxy)-2-methoxypyridin-3-amine (1.40 g, 69%) as a yellow solid. $^1$H-NMR (DMSO-$d_6$, 300 MHz): 3.82 (s, 3H), 5.20 (s, 2H), 6.52 (d, J=2.4 Hz, 1H), 6.95 (d, J=2.1 Hz, 1H), 8.51 (s, 1H) ppm. LC-MS: $C_{12}H_9Cl_2N_3O_4$ [M+H]$^+$: 330.

TFAA (0.67 mL, 4.82 mmol) was added to a solution of 5-(2,6-dichloro-4-nitrophenoxy)-2-methoxypyridin-3-amine (1 eq., 796 mg, 2.41 mmol) in anhydrous DCM (18 mL) at 0° C. under $N_2$. The reaction mixture was stirred at rt for 1 h. The reaction mixture was diluted with water and extracted with DCM (3×). The combined organic layers were dried over $Na_2SO_4$. The solids were removed by filtration and evaporated to dryness to give N-(5-(2,6-dichloro-4-nitrophenoxy)-2-methoxypyridin-3-yl)-2,2,2-trifluoroacetamide 7 (659 mg, 64%) as a yellow oil. $^1$H-NMR (DMSO-$d_6$, 300 MHz): 3.89 (s, 3H), 7.67 (d, J=2.7 Hz, 1H), 7.90 (d, J=2.7 Hz, 1H), 8.56 (s, 1H), 11.04 (s, 1H) ppm. LC-MS: $C_{14}H_8Cl_2F_3N_3O_5$ [M+H]$^+$: 426.

A mixture of N-(5-(2,6-dichloro-4-nitrophenoxy)-2-methoxypyridin-3-yl)-2,2,2-trifluoroacetamide 7 (1 eq., 659 mg, 1.55 mmol), $NH_4Cl$ (10 eq., 827 mg, 15.46 mmol) and Fe (5 eq., 432 mg, 7.73 mmol) in EtOH (10 mL) and water (5 mL) was stirred at 70° C. under $N_2$ for 15 min. After cooling to rt, the reaction mixture was filtered over a pad of celite and the filtrate was extracted with EA (3×). The combined organic phases were washed with brine (2×) and dried over $Na_2SO_4$. The solids were removed by filtration and the filtrate was evaporated to dryness to give N-(5-(4-amino-2,6-dichlorophenoxy)-2-methoxypyridin-3-yl)-2,2,2-trifluoroacetamide (603 mg, 98%) as a white solid which was used as such in the next step. $^1$H-NMR (DMSO-$d_6$, 300 MHz): 3.88 (s, 3H), 5.70 (s, 2H), 6.71 (s, 2H), 7.47 (d, J=2.7 Hz, 1H), 7.74 (d, J=2.7 Hz, 1H), 10.90 (s, 1H) ppm. LC-MS: $C_{14}H_{10}Cl_2F_3N_3O_3$ [M+H]$^+$: 396.

A solution of $NaNO_2$ (2.1 eq., 331 mg, 4.80 mmol) in water (19 mL) was slowly added to a solution of N-(5-(4-amino-2,6-dichlorophenoxy)-2-methoxypyridin-3-yl)-2,2,2-trifluoroacetamide (1 eq., 906 mg, 2.29 mmol) in HCl 37% (7.9 mL), AcOH (23 mL) and water (19 mL) at 0° C. under $N_2$. The reaction mixture was stirred at 0° C. for 30 min. In parallel, a solution of ethyl N-(2-cyanoacetyl)carbamate (1.5 eq., 536 mg, 3.43 mmol) in water (23 mL) and pyridine (7.9 mL) was stirred at 0° C. for 15 min. The first reaction mixture was quickly added to the second one. The resulting reaction mixture was stirred at 0° C. for 30 min. The reaction mixture was diluted with more water. The precipitate was collected by filtration, washed with water (3×), dissolved in EA and dried over Na$_2$SO$_4$. The solids were removed by filtration and the filtrate was evaporated to dryness to give ethyl (2-cyano-2-(2-(3,5-dichloro-4-((6-methoxy-5-(2,2,2-trifluoroacetamido)pyridin-3-yl)oxy)phenyl)hydrazineylidene)acetyl)carbamate (1.25 g, 97%) as an orange solid which was used as such in the next step. LC-MS: C$_{20}$H$_{15}$Cl$_2$F$_3$N$_6$O$_6$ [M+H]$^+$: 563.

A mixture of ethyl (2-cyano-2-(2-(3,5-dichloro-4-((6-methoxy-5-(2,2,2-trifluoroacetamido)pyridin-3-yl)oxy)phenyl)hydrazineylidene)acetyl)carbamate (1 eq., 1.25 g, 2.23 mmol) and NaOAc (4 eq., 0.73 g, 8.91 mmol) in AcOH (22 mL) was stirred at 120° C. for 2 h under N$_2$. After cooling to rt, the reaction mixture was diluted with water. The resulting precipitate was collected by filtration, washed with water (3×), dissolved in EA and dried over Na$_2$SO$_4$. The solids were removed by filtration and the filtrate was evaporated to dryness to give N-(5-(2,6-dichloro-4-(6-cyano-3,5-dioxo-4,5-dihydro-1,2,4-triazin-2(3H)-yl)phenoxy)-2-methoxypyridin-3-yl)-2,2,2-trifluoroacetamide 10 (1.14 g, 99%) as an orange oil which was used as such in the next step. $^1$H-NMR (DMSO-d$_6$, 300 MHz): 3.90 (s, 3H), 7.62 (d, J=2.7 Hz, 1H), 7.82 (s, 2H), 7.89 (d, J=2.7 Hz, 1H), 10.909 (s, 1H), 13.24 (br s, 1H) ppm. LC-MS: C$_{18}$H$_9$Cl$_2$F$_3$N$_6$O$_5$ [M+H]$^+$: 517.

A solution of N-(5-(2,6-dichloro-4-(6-cyano-3,5-dioxo-4,5-dihydro-1,2,4-triazin-2(3H)-yl)phenoxy)-2-methoxypyridin-3-yl)-2,2,2-trifluoroacetamide (1.14 g, 2.21 mmol) in ammonia 7N in MeOH (45 mL) was stirred at 60° C. for 1 h under N$_2$. The reaction mixture was then evaporated to dryness to give 2-(4-((5-amino-6-methoxypyridin-3-yl)oxy)-3,5-dichlorophenyl)-3,5-dioxo-2,3,4,5-tetrahydro-1,2,4-triazine-6-carbonitrile (874 mg, 94%) as a red solid which was used as such in the next step. $^1$H-NMR (DMSO-d$_6$, 300 MHz): 3.82 (s, 3H), 5.19 (br s, 2H), 6.38 (d, J=2.4 Hz, 1H), 7.04 (d, J=2.4 Hz, 1H), 7.80 (s, 2H) ppm. LC-MS: C$_{16}$H$_{10}$Cl$_2$N$_6$O$_4$ [M+H]$^+$: 421.

Paraformaldehyde (6 eq., 374 mg, 12.45 mmol) and sodium triacetoxyborohydride (5 eq., 2.20 g, 10.38 mmol) were added to a solution of 2-(4-((5-amino-6-methoxypyridin-3-yl)oxy)-3,5-dichlorophenyl)-3,5-dioxo-2,3,4,5-tetrahydro-1,2,4-triazine-6-carbonitrile 11 (1 eq., 874 mg, 2.08 mmol) in anhydrous DCM (23 mL) under N$_2$. The reaction mixture was stirred at 40° C. for 5 h, at which point extra sodium triacetoxyborohydride (3 eq., 1.32 g, 6.23 mmol) and paraformaldehyde (4 eq., 249 mg, 8.3 mmol) were added and stirring at 40° C. was pursued for 16 h to reach full conversion. The reaction mixture was diluted with EA, washed with sat. aq. NaHCO$_3$ (2×) and brine and dried over Na$_2$SO$_4$. The solids were removed by filtration and the filtrate was evaporated to dryness to give 2-(3,5-dichloro-4-((5-(dimethylamino)-6-methoxypyridin-3-yl)oxy)phenyl)-3,5-dioxo-2,3,4,5-tetrahydro-1,2,4-triazine-6-carbonitrile (932 mg, 100%). $^1$H-NMR (DMSO-d$_6$, 300 MHz): 2.76 (s, 6H), 3.84 (s, 3H), 6.86 (d, J=2.4 Hz, 1H), 7.04 (d, J=2.4 Hz, 1H), 7.80 (s, 2H) ppm. LC-MS: C$_{18}$H$_{14}$Cl$_2$N$_6$O$_4$ [M+H]$^+$: 449.

A solution of 2-(3,5-dichloro-4-((5-(dimethylamino)-6-methoxypyridin-3-yl)oxy)phenyl)-3,5-dioxo-2,3,4,5-tetrahydro-1,2,4-triazine-6-carbonitrile (732 mg, 1.63 mmol) in HCl 37% (2.8 mL) and AcOH (7.3 mL) was stirred at 120° C. under N$_2$ for 1 h. After cooling to rt, the reaction mixture was diluted with water and washed with EA (2×). The aqueous phase was brought to pH 8 using aq. NaOH 1N and extracted with n-BuOH (6×). The combined organic phases were dried over Na$_2$SO$_4$. The solids were removed by filtration and the filtrate was evaporated to dryness to give 2-(3,5-dichloro-4-((5-(dimethylamino)-6-oxo-1,6-dihydropyridin-3-yl)oxy)phenyl)-3,5-dioxo-2,3,4,5-tetrahydro-1,2,4-triazine-6-carboxylic acid (553 mg, 75%) as a brown solid which was used as such in the next step. LC-MS: C$_{17}$H$_{13}$Cl$_2$N$_5$O$_6$ [M+H]$^+$: 454.

Triethylamine (4 eq., 0.68 mL, 4.87 mmol) and DPPA (3 eq., 0.79 mL, 3.65 mmol) were added to a solution of 2-(3,5-dichloro-4-((5-(dimethylamino)-6-oxo-1,6-dihydropyridin-3-yl)oxy)phenyl)-3,5-dioxo-2,3,4,5-tetrahydro-1,2,4-triazine-6-carboxylic acid (1 eq., 553 mg, 1.22 mmol) in tert-butanol (18 mL) under N$_2$. The resulting mixture was stirred at 85° C. for 18 h, at which point extra triethylamine (4 eq., 0.68 mL, 4.87 mmol) and DPPA (0.79 mL, 3.65 mmol) along with THF (8.3 mL) were added and stirring at 85° C. was pursued for 3 d. After cooling to rt, the reaction mixture was quenched with sat. aq. NaHCO$_3$ and extracted with EA. The organic layer was washed with sat. aq. NaHCO$_3$ and brine and dried over Na$_2$SO$_4$. The solids were removed by filtration and the filtrate was evaporated to dryness. The crude mixture was purified by flash chromatography on silica gel (0% to 10% MeOH in DCM) to afford tert-butyl (2-(3,5-dichloro-4-((5-(dimethylamino)-6-oxo-1,6-dihydropyridin-3-yl)oxy)phenyl)-3,5-dioxo-2,3,4,5-tetrahydro-1,2,4-triazin-6-yl)carbamate (203 mg, 32%) as a colorless oil. LC-MS: C$_{21}$H$_{22}$Cl$_2$N$_6$O$_6$ [M−H]$^-$: 523.

A solution of t-butyl (2-(3,5-dichloro-4-((5-(dimethylamino)-6-oxo-1,6-dihydropyridin-3-yl)oxy)phenyl)-3,5-dioxo-2,3,4,5-tetrahydro-1,2,4-triazin-6-yl)carbamate (203 mg, 0.39 mmol) in HCl 4N in Dioxane (5.8 mL) was stirred at rt for 16 h under N$_2$. The reaction mixture was quenched with sat. aq. NaHCO$_3$ and extracted with EA (3×). The combined organic layers were washed with brine and dried over Na$_2$SO$_4$. The solids were removed by filtration and the filtrate was evaporated to dryness. The crude mixture was purified by Prep. HPLC (5% to 100% MeCN in 0.2 wt % NH$_3$ solution in water) to give 6-amino-2-(3,5-dichloro-4-((5-(dimethylamino)-6-oxo-1,6-dihydropyridin-3-yl)oxy)phenyl)-1,2,4-triazine-3,5(2H,4H)-dione (13) (14 mg, 11%) as a white solid. $^1$H-NMR (DMSO-d$_6$, 400 MHz): 2.83 (s, 6H), 6.06 (br s, 1H), 6.43 (br s, 2H), 6.51 (d, J=2.8 Hz, 1H), 7.89 (s, 2H), 11.03 (s, 1H), 12.25 (br s, 1H) ppm. LC-MS: C$_{16}$H$_{14}$Cl$_2$N$_6$O$_4$ [M+H]$^+$: 425.

Example 14

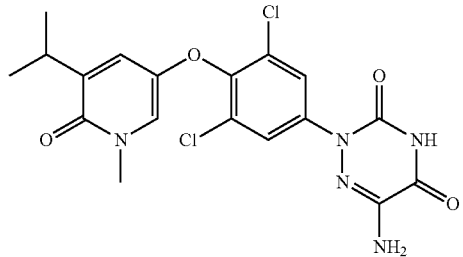

Compound 14

HBr 48% in water (2.02 mL, 17.83 mmol) was added to a solution of 5-(2,6-dichloro-4-nitrophenoxy)-3-isopropyl-2-methoxypyridine (910 mg, 2.55 mmol) in dioxane (25 mL) under N$_2$. The reaction mixture was stirred at 60° C. for 16 h. After cooling to rt, the reaction mixture was quenched with sat. aq. Na$_2$CO$_3$ until reaching pH 7 and extracted with EA (3×). The combined organic layers were washed with brine and dried over Na$_2$SO$_4$. The solids were removed by filtration and the filtrate was evaporated to dryness to give 5-(2,6-dichloro-4-nitrophenoxy)-3-isopropylpyridin-2(1H)-one (862 mg, 99%) as a yellow solid which was used without further purification in the next step. ¹H-NMR (DMSO-d₆, 300 MHz): 1.11 (d, J=6.8 Hz, 6H), 2.94-3.03 (m, 1H), 6.80 (d, J=3.0 Hz, 1H), 7.26 (d, J=3.0 Hz, 1H), 8.48 (s, 2H), 11.32 (br s, 1H) ppm. LC-MS: $C_{14}H_{12}Cl_2N_2O_4$ [M+H]⁺: 343.

K₂CO₃ (2 eq., 694 mg, 5.02 mmol) and MeI (6 eq., 0.94 mL, 15.07 mmol) were added to a solution of 5-(2,6-dichloro-4-nitrophenoxy)-3-isopropylpyridin-2(1H)-one (862 mg, 2.51 mmol) in anhydrous dioxane (9 mL) under N₂ and the reaction mixture was heated at 80° C. for 7 h. Heating was stopped and the reaction mixture was stirred at rt overnight. The reaction mixture was then filtered and the filtrate was evaporated to dryness. The crude product was purified by flash chromatography on silica gel (20% EA in CyH) to give 5-(2,6-dichloro-4-nitrophenoxy)-3-isopropyl-1-methylpyridin-2(1H)-one (0.78 g, 87%) as a yellow solid. ¹H-NMR (DMSO-d₆, 300 MHz): 1.13 (d, J=6.6 Hz, 6H), 2.99-3.09 (m, 1H), 3.34 (s, 3H), 7.20 (d, J=3.0 Hz, 1H), 7.29 (d, J=3.0 Hz, 1H), 8.53 (s, 2H) ppm. LC-MS: $C_{15}H_{14}Cl_2N_2O_4$ [M–H]⁻: 357.

Iron (0.67 g, 12.08 mmol) was added to a solution of 5-(2,6-dichloro-4-nitrophenoxy)-3-isopropyl-1-methylpyridin-2(1H)-one (0.86 g, 2.42 mmol) and Ammonium Chloride (1.29 g, 24.16 mmol) in EtOH (16.6 mL) and Water (9.2 mL) under N₂ and the reaction mixture was heated at 70° C. for 4 h and at 80° C. for 3 h. After cooling to rt, the reaction mixture was filtered over a pad of celite and the filtrate was concentrated under vacuum to remove EtOH. The residue was extracted with EA (3×). The combined organic layers were washed with water and brine and dried over Na₂SO₄. The solids were removed by filtration and the filtrate was evaporated to dryness to give 5-(4-amino-2,6-dichlorophenoxy)-3-isopropyl-1-methylpyridin-2(1H)-one (560 mg, 71%) as a yellow solid which was used without further purification in the next step. LC-MS: $C_{15}H_{16}Cl_2N_2O_2$ [M+H]⁺: 327.

A solution of NaNO₂ (248 mg, 3.59 mmol) in water (35 mL) was added dropwise to a solution of 5-(4-amino-2,6-dichlorophenoxy)-3-isopropyl-1-methylpyridin-2(1H)-one (560 mg, 1.71 mmol) in HCl 37% (105.7 eq., 14.8 mL, 180.88 mmol), acetic acid (46 mL) and water (35 mL) at 0° C. under N₂. The reaction mixture was stirred at 0° C. for 1 h. In parallel, a solution of ethyl N-(2-cyanoacetyl)carbamate (401 mg, 2.57 mmol) in water (42 mL) and pyridine (14 mL) was stirred at 0° C. for 15 min. The first reaction mixture was quickly added to the second one. The resulting reaction mixture was stirred at 0° C. for 1 h. The reaction mixture was then diluted with more water. The precipitate was collected by filtration, washed with water and dried under vacuum to give ethyl (2-cyano-2-(2-(3,5-dichloro-4-((5-isopropyl-1-methyl-6-oxo-1,6-dihydropyridin-3-yl)oxy)phenyl)hydrazineylidene)acetyl)carbamate (846 mg, 100%) as an orange solid which was used in the next step without further purification. LC-MS: $C_{21}H_{21}Cl_2N_5O_5$ [M+H]⁺: 494.

Sodium acetate (1.12 g, 0.014 mol) was added to a solution of (2-cyano-2-(2-(3,5-dichloro-4-((5-isopropyl-1-methyl-6-oxo-1,6-dihydropyridin-3-yl)oxy)phenyl)hydrazineylidene)acetyl)carbamate (846 mg, 0.0017 mol) in acetic acid (15 mL) under N₂. The reaction mixture was stirred at 120° C. for 2 h. The reaction mixture was then cooled at 0° C., diluted with water stirred for 30 min. The resulting precipitate was collected by filtration, washed with water and dried under vacuum to give 2-(3,5-dichloro-4-((5-isopropyl-1-methyl-6-oxo-1,6-dihydropyridin-3-yl)oxy)phenyl)-3,5-dioxo-2,3,4,5-tetrahydro-1,2,4-triazine-6-carbonitrile (706 mg, 92%) as a pink solid which was used as such in the next step. LC-MS: $C_{19}H_{15}Cl_2N_5O_4$ [M+H]⁺: 448.

A solution of 2-(3,5-dichloro-4-((5-isopropyl-1-methyl-6-oxo-1,6-dihydropyridin-3-yl)oxy)phenyl)-3,5-dioxo-2,3,4,5-tetrahydro-1,2,4-triazine-6-carbonitrile (706 mg, 1.57 mmol) in HCl 37% (9 eq., 1.16 mL, 14.17 mmol) and AcOH (2.35 mL, 40.95 mmol) was stirred at 120° C. under N₂ for 2 h. After cooling to rt, the reaction mixture was diluted with water. The resulting precipitate was collected by filtration, washed with water and dried under vacuum to give 2-(3,5-dichloro-4-((5-isopropyl-1-methyl-6-oxo-1,6-dihydropyridin-3-yl)oxy)phenyl)-3,5-dioxo-2,3,4,5-tetrahydro-1,2,4-triazine-6-carboxylic acid (571 mg, 78%) as an orange solid which was used as such in the next step. LC-MS: $C_{19}H_{16}Cl_2N_4O_6$ [M+H]⁺: 467.

Triethylamine (0.68 mL, 4.89 mmol) and DPPA (0.79 mL, 3.67 mmol) were added to a solution of 2-(3,5-dichloro-4-((5-isopropyl-1-methyl-6-oxo-1,6-dihydropyridin-3-yl)oxy)phenyl)-3,5-dioxo-2,3,4,5-tetrahydro-1,2,4-triazine-6-carboxylic acid (1 eq., 571 mg, 1.22 mmol) in tBuOH (18 mL) under N₂. The reaction mixture was stirred at 85° C. for 16 h, at which point extra triethylamine (4 eq., 0.68 mL, 4.89 mmol) and DPPA (3 eq., 0.79 mL, 3.67 mmol) were added and stirring at 85° C. was pursued for 5 h. After cooling to rt, the reaction mixture was diluted with sat. aq. NaHCO₃ and extracted with EA (2×). The combined organic layers were washed with water and brine and dried over Na₂SO₄. The solids were removed by filtration and the filtrate was evaporated to dryness. The crude mixture was purified by flash chromatography on silica gel (0% to 10% [MeOH/NH₄OH (9:1)]). The resulting solid was triturated in EtOH to give 6-amino-2-(3,5-dichloro-4-((5-isopropyl-1-methyl-6-oxo-1,6-dihydropyridin-3-yl)oxy)phenyl)-1,2,4-triazine-3,5(2H,4H)-dione (14) (35 mg, 7%) as a white solid. ¹H-NMR (DMSO-d₆, 400 MHz): 1.11 (d, J=6.9 Hz, 6H), 2.99-3.07 (m, 1H), 3.36 (s, 3H), 6.47 (s, 2H), 7.10 (d, J=3.4 Hz, 1H), 7.23 (d, J=3.1 Hz, 1H), 7.90 (s, 2H), 12.29 (br s, 1H) ppm. LC-MS: $C_{18}H_{17}Cl_2N_5O_4$ [M+H]⁺: 438.

Example 15

Compound 15

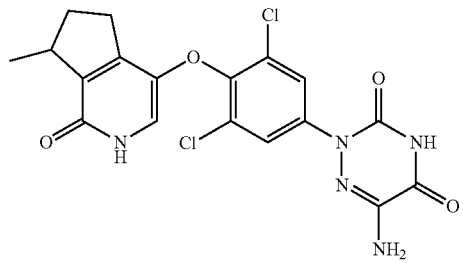

LDA (2M in THF, 9.9 mL, 19.8 mmol) was added over 5 min to a solution of 3-bromo-2-methoxy-4-methylpyridine (2 g, 9.9 mmol) in anhydrous THF (66 mL) at −78° C. under N₂. The reaction mixture was stirred at −78° C. for 1.5 h. Then, a solution of allyl bromide (3 eq., 2.58 mL, 29.7 mmol) in anhydrous THF (9.2 mL) was added over 5 min and the reaction mixture was stirred at −78° C. for 1.5 h. The reaction mixture was hydrolyzed with sat. aq. NH₄Cl and extracted with EA. The organic phase was washed with sat. aq. NH₄Cl (2×) and brine and dried over Na₂SO₄. The solids were removed by filtration and the filtrate was evaporated to dryness. The crude mixture was purified by flash chromatography on silica gel (40% DCM in CyH) to give 3-bromo-4-(but-3-en-1-yl)-2-methoxypyridine (1.8 g, 75%) as a colorless oil. $^1$H-NMR (DMSO-d$_6$, 300 MHz): 2.29-2.36 (m, 2H), 2.77-2.83 (m, 2H), 3.90 (s, 3H), 4.97-5.07 (m, 2H), 5.78-5.91 (m, 1H), 6.97 (d, J=5.1 Hz, 1H), 8.03 (d, J=5.1 Hz, 1H) ppm. LC-MS: $C_{10}H_{12}BrNO$ [M+H]$^+$: 242/244 n-BuLi 1.6M in hexane (1.2 eq., 37.11 mL, 59.38 mmol) was added to a solution of 3-bromo-4-(but-3-en-1-yl)-2-methoxypyridine (1 eq., 11.98 g, 49.48 mmol) in anhydrous THF (400 mL) at −78° C. under N$_2$. The reaction mixture was stirred at −78° C. for 1 h. Then, a solution of 12 (1.5 eq., 18.84 g, 74.22 mmol) in anhydrous THF (200 mL) was added to the reaction mixture at −78° C. The reaction mixture was allowed to warm up to rt and stirred for 1.5 h. The reaction mixture was hydrolyzed with 10% wt. aq. Na$_2$S$_2$O$_3$ and extracted with EA. The organic phase was washed with 10 wt % aq. Na$_2$S$_2$O$_3$ and brine and dried over Na$_2$SO$_4$. The solids were removed by filtration and the filtrate was evaporated to dryness. The crude mixture was purified by flash chromatography on silica gel (0% to 6% EA in CyH) to give 3-iodo-4-(but-3-en-1-yl)-2-methoxypyridine (12.56 g, 88%) as a yellow oil. $^1$H-NMR (DMSO-d$_6$, 300 MHz): 2.26-2.34 (m, 2H), 2.76-2.81 (m, 2H), 3.87 (s, 3H), 4.97-5.07 (m, 2H), 5.79-5.93 (m, 1H), 6.91 (d, J=5.1 Hz, 1H), 7.98 (d, J=5.1 Hz, 1H) ppm. LC-MS: $C_{10}H_{12}INO$ [M+H]$^+$: 290.

A solution of 3-iodo-4-(but-3-en-1-yl)-2-methoxypyridine (12.56 g, 43.44 mmol) in anhydrous MeCN (125 mL) was added to a mixture of InCl$_3$ (0.96 g, 4.34 mmol) and NaBH$_4$ (2 eq., 3.29 g, 86.89 mmol) in anhydrous MeCN (125 mL) at −78° C. under N$_2$. The reaction mixture was then stirred at rt for 20 h. The reaction mixture was quenched with sat. aq. NH$_4$Cl and extracted with EA (4×). The combined organic phases were washed with sat. aq. NH$_4$Cl (3×) and brine and dried over Na$_2$SO$_4$. The solids were removed by filtration and the filtrate was evaporated to dryness to give 1-methoxy-7-methyl-6,7-dihydro-5H-cyclopenta[c]pyridine (7.09 g, 100%) as a grey oil which was used as such in the next step. LC-MS: $C_{10}H_{13}NO$ [M+H]$^+$: 164.

A solution of NBS (11.6 g, 65.16 mmol) and 1-methoxy-7-methyl-6,7-dihydro-5H-cyclopenta[c]pyridine (7.09 g, 43.44 mmol) in anhydrous MeCN (145 mL) was stirred at rt for 16 h, at which point extra NBS (11.6 g, 65.16 mmol) was added and stirring at rt was pursued for 3 h. The reaction mixture was diluted with EA, washed with sat. aq. NaHCO$_3$ (2×) and brine and dried over Na$_2$SO$_4$. The solids were removed by filtration and the filtrate was evaporated to dryness. The crude mixture was purified by flash chromatography on silica gel (2% to 6% EA in CyH) to give 4-bromo-1-methoxy-7-methyl-6,7-dihydro-5H-cyclopenta[c]pyridine 5 (5.42 g, 52%) as a yellow oil. LC-MS: $C_{10}H_{12}BrNO$ [M+H]$^+$: 242/244.

A mixture of 4-bromo-1-methoxy-7-methyl-6,7-dihydro-5H-cyclopenta[c]pyridine (1 eq., 5.42 g, 22.39 mmol), bis(neopentyl glycolato)diboron (15.17 g, 67.16 mmol), KOAc (3 eq., 6.59 g, 67.16 mmol) and PdCl$_2$[P(o-Tol)$_3$]$_2$ (1.76 g, 2.24 mmol) in anhydrous DMSO (105 mL) was stirred at 85° C. for 2 h. After cooling to rt, the reaction mixture was diluted with EA, washed with sat. aq. NH$_4$Cl and brine (2×) and dried over Na$_2$SO$_4$. The solids were removed by filtration and the filtrate was evaporated to dryness. The crude mixture was purified by flash chromatography on silica gel (0% to 10% EA in CyH) to give 4-(5,5-dimethyl-1,3,2-dioxaborinan-2-yl)-1-methoxy-7-methyl-6,7-dihydro-5H-cyclopenta[c]pyridine (817 mg, 13%) as a yellow oil. LC-MS: $C_{15}H_{22}BNO_3$ [M(boronic acid)+H]$^+$: 208.

H$_2$O$_2$ 30% (7.58 mL, 74.23 mmol) and HOAc (25 eq., 4.25 mL, 74.23 mmol) were added to a solution of 4-(5,5-dimethyl-1,3,2-dioxaborinan-2-yl)-1-methoxy-7-methyl-6,7-dihydro-5H-cyclopenta[c]pyridine (817 mg, 2.97 mmol) in THF (16 mL) under N$_2$. The reaction mixture was stirred at rt for 1 h. The reaction mixture was quenched with sat. aq. NaHCO$_3$ and extracted with EA. The organic layer was washed with sat. aq. NaHCO$_3$ and brine (2×) and dried over Na$_2$SO$_4$. The solids were removed by filtration and the filtrate was evaporated to dryness to give 1-methoxy-7-methyl-6,7-dihydro-5H-cyclopenta[c]pyridin-4-ol 7 (532 mg, 100%) as a yellow oil which was used as such in the next step. LC-MS: $C_{10}H_{13}NO_2$ [M+H]$^+$: 180.

DIPEA (2 eq., 0.98 mL, 5.94 mmol) was added to a solution of 1-methoxy-7-methyl-6,7-dihydro-5H-cyclopenta[c]pyridin-4-ol (1 eq., 532 mg, 2.97 mmol) and 1,3-dichloro-2-fluoro-5-nitrobenzene (1 eq., 623.5 mg, 2.97 mmol) in anhydrous DMF (29 mL) under N$_2$. The reaction mixture was stirred at rt for 24 h. The reaction mixture was diluted with EA, washed with sat. aq. NH$_4$Cl (2×) and brine and dried over Na$_2$SO$_4$. The solids were removed by filtration and the filtrate was evaporated to dryness. The crude mixture was purified by flash chromatography on silica gel (2% to 5% EA in CyH) to give 4-(2,6-dichloro-4-nitrophenoxy)-1-methoxy-7-methyl-6,7-dihydro-5H-cyclopenta[c]pyridine (659 mg, 60%) as a colorless oil. LC-MS: $C_{16}H_{14}Cl_2N_2O_4$ [M+H]$^+$: 369.

A mixture of 4-(2,6-dichloro-4-nitrophenoxy)-1-methoxy-7-methyl-6,7-dihydro-5H-cyclopenta[c]pyridine (659 mg, 1.78 mmol), NH$_4$Cl (10 eq., 955 mg, 17.85 mmol) and Fe (5 eq., 498 mg, 8.92 mmol) in EtOH (12 mL) and water (6 mL) was stirred at 80° C. under N$_2$. After cooling to rt, the reaction mixture was filtered over celite. The filtrate was diluted with EA, washed with brine (2×) and dried over Na$_2$SO$_4$. The solids were removed by filtration and the filtrate was evaporated to dryness to give 3,5-dichloro-4-((1-methoxy-7-methyl-6,7-dihydro-5H-cyclopenta[c]pyridin-4-yl)oxy)aniline (232 mg, 38%) as a yellow oil which was used as such in the next step. LC-MS: $C_{16}H_{16}Cl_2N_2O_2$ [M+H]$^+$: 339.

A solution of NaNO$_2$ (99 mg, 1.44 mmol) in water (5.6 mL) was added to a solution of 3,5-dichloro-4-((1-methoxy-7-methyl-6,7-dihydro-5H-cyclopenta[c]pyridin-4-yl)oxy)aniline (232 mg, 0.68 mmol) in HCl 37% (2.4 mL), AcOH (6.8 mL) and water (5.6 mL) at 0° C. under N$_2$. The reaction mixture was stirred at 0° C. for 1 h. In parallel, a solution of ethyl N-(2-cyanoacetyl)carbamate (1.5 eq., 160 mg, 1.03 mmol) in water (6.8 mL) and pyridine (2.3 mL) was stirred at 0° C. for 15 min. The first reaction mixture was quickly added to the second one. The resulting reaction mixture was stirred at 0° C. for 1 h. The reaction mixture was diluted with more water. The precipitate was collected by filtration, washed with water, dissolved in EA and dried over Na$_2$SO$_4$. The solids were removed by filtration and the filtrate was evaporated to dryness to give ethyl (2-cyano-2-(2-(3,5-dichloro-4-((1-methoxy-7-methyl-6,7-dihydro-5H-cyclopenta[c]pyridin-4-yl)oxy)phenyl)hydrazineylidene)acetyl)carbamate (346 mg, 100%) as an orange solid which was used as such in the next step. LCMS: $C_{22}H_{21}Cl_2N_5O_5$ [M+H]$^+$: 506.

A mixture of ethyl (2-cyano-2-(2-(3,5-dichloro-4-((1-methoxy-7-methyl-6,7-dihydro-5H-cyclopenta[c]pyridin-4-yl)oxy)phenyl)hydrazineylidene)acetyl)carbamate (346 mg, 0.68 mmol) and NaOAc (224 mg, 2.74 mmol) in AcOH (7 mL) was stirred at 120° C. under N$_2$ for 1 h. After cooling to rt, the reaction mixture was diluted with water. The resulting precipitate was collected by filtration, washed with water, dissolved in EA and dried over Na$_2$SO$_4$. The solids were removed by filtration and the filtrate was evaporated to dryness to give 2-(3,5-dichloro-4-((1-methoxy-7-methyl-6,7-dihydro-5H-cyclopenta[c]pyridin-4-yl)oxy)phenyl)-3,5-dioxo-2,3,4,5-tetrahydro-1,2,4-triazine-6-carbonitrile (299 mg, 95%) as an orange solid which was used as such in the next step. LC-MS: C$_{20}$H$_{15}$Cl$_2$N$_5$O$_4$ [M+H]$^+$: 460.

HBr 48% in water (5 eq., 0.028 mL, 0.25 mmol) was added to a solution of 2-(3,5-dichloro-4-((1-methoxy-7-methyl-6,7-dihydro-5H-cyclopenta[c]pyridin-4-yl)oxy)phenyl)-3,5-dioxo-2,3,4,5-tetrahydro-1,2,4-triazine-6-carbonitrile (1 eq., 22.7 mg, 0.049 mmol) in anhydrous 1,4-dioxane (0.82 mL) under N$_2$. The reaction mixture was stirred at 60° C. for 6 h. After cooling to rt, the reaction mixture was diluted with EA, washed with sat. aq. NaHCO$_3$ and brine (2×). The aqueous phases were reextracted with EA (3×). The combined organic phases were dried over Na$_2$SO$_4$. The solids were removed by filtration and evaporated to dryness. The crude mixture was purified by Prep. HPLC (20 to 100% MeCN in 0.2 wt % NH$_3$ solution in water, 26 min) to give 2-(3,5-dichloro-4-((7-methyl-1-oxo-2,5,6,7-tetrahydro-1H-cyclopenta[c]pyridin-4-yl)oxy)phenyl)-3,5-dioxo-2,3,4,5-tetrahydro-1,2,4-triazine-6-carbonitrile (34) (2.1 mg, 10%) as a white solid. LC-MS: C$_{19}$H$_{13}$Cl$_2$N$_5$O$_4$ [M+H]$^+$: 446.

A solution of 2-(3,5-dichloro-4-((1-methoxy-7-methyl-6,7-dihydro-5H-cyclopenta[c]pyridin-4-yl)oxy)phenyl)-3,5-dioxo-2,3,4,5-tetrahydro-1,2,4-triazine-6-carbonitrile (315 mg, 0.68 mmol) in HCl 37% (1.2 mL) and AcOH (3 mL) was stirred at 120° C. under N$_2$ for 2.5 h. After cooling to rt, the reaction mixture was diluted with water. The resulting precipitate was collected by filtration, washed with water, dissolved in EA/MeOH (2:1) and dried over Na$_2$SO$_4$. The solids were removed by filtration and the filtrate was evaporated to dryness to give 2-(3,5-dichloro-4-((7-methyl-1-oxo-2,5,6,7-tetrahydro-1H-cyclopenta[c]pyridin-4-yl)oxy)phenyl)-3,5-dioxo-2,3,4,5-tetrahydro-1,2,4-triazine-6-carboxylic acid (236 mg, 74%) as an orange solid which was used as such in the next step. LC-MS: C$_{19}$H$_{14}$Cl$_2$N$_4$O$_6$ [M+H]$^+$: 465.

Triethylamine (0.27 mL, 1.93 mmol) and DPPA (0.31 mL, 1.45 mmol) were added to a solution of 2-(3,5-dichloro-4-((7-methyl-1-oxo-2,5,6,7-tetrahydro-1H-cyclopenta[c]pyridin-4-yl)oxy)phenyl)-3,5-dioxo-2,3,4,5-tetrahydro-1,2,4-triazine-6-carboxylic acid (225 mg, 0.48 mmol) in tert-butanol (7 mL) under N$_2$. The reaction mixture was stirred at 85° C. for 24 h. After cooling to rt, the reaction mixture was quenched with sat. aq. NaHCO$_3$ and extracted with EA (2×). The combined organic phases were washed with sat. aq. NaHCO$_3$ (2×) and brine and dried over Na$_2$SO$_4$. The solids were removed by filtration and the filtrate was evaporated to dryness. The crude mixture was purified by flash chromatography on silica gel (0% to 10% MeOH in DCM) to give tert-butyl (2-(3,5-dichloro-4-((7-methyl-1-oxo-2,5,6,7-tetrahydro-1H-cyclopenta[c]pyridin-4-yl)oxy)phenyl)-3,5-dioxo-2,3,4,5-tetrahydro-1,2,4-triazin-6-yl)carbamate (48 mg, 19%) as an orange solid. LC-MS: C$_{23}$H$_{23}$Cl$_2$N$_5$O$_6$ [M+H]$^+$: 536.

A solution of tert-butyl (2-(3,5-dichloro-4-((7-methyl-1-oxo-2,5,6,7-tetrahydro-1H-cyclopenta[c]pyridin-4-yl)oxy)phenyl)-3,5-dioxo-2,3,4,5-tetrahydro-1,2,4-triazin-6-yl)carbamate 13 (1 eq., 45 mg, 0.085 mmol) in HCl 4N in Dioxane (0.85 mL) was stirred at rt under N$_2$ for 3.5 h. The reaction mixture was evaporated to dryness and the crude mixture was purified by Prep. HPLC (20% to 100% MeCN in 0.2 wt % formic acid solution in water, 26 min) to give 6-amino-2-(3,5-dichloro-4-((7-methyl-1-oxo-2,5,6,7-tetrahydro-1H-cyclopenta[c]pyridin-4-yl)oxy)phenyl)-1,2,4-triazine-3,5(2H,4H)-dione (15) (10.8 mg, 29%) as a white solid. $^1$H-NMR (DMSO-d$_6$, 400 MHz): 1.20 (d, J=6.9 Hz, 3H), 1.60-1.69 (m, 1H), 2.23-2.31 (m, 1H), 2.78-3.02 (m, 3H), 6.38 (s, 1H), 6.44 (s, 2H), 7.90 (s, 2H), 11.00 (br s, 1H) ppm. LC-MS: C$_{18}$H$_{15}$Cl$_2$N$_5$O$_4$ [M+H]$^+$: 436.

Example 17

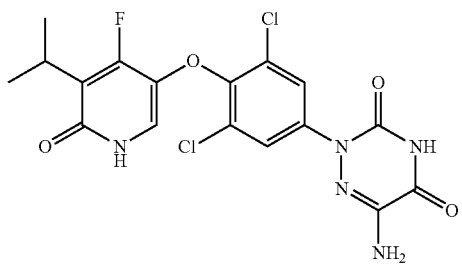

Compound 17

6-amino-2-(3,5-dichloro-4-((4-fluoro-5-isopropyl-6-oxo-1,6-dihydropyridin-3-yl)oxy)phenyl)-1,2,4-triazine-3,5(2H,4H)-dione The titled compound can be synthesized following a procedure similar to that described in the synthesis of, with the exception that 3-bromo-4-fluoro-2-methoxypyridine could be used as the starting material. Alternatively, the fluorine atom could be installed at a later stage, for example, via the Sandmeyer reaction.

Example 18

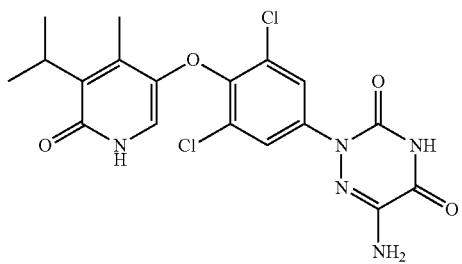

Compound 18

Pd(dppf)Cl$_2$ (3.62 g, 4.95 mmol), potassium trifluoro (prop-1-en-2-yl)borate (11.0 g, 74.24 mmol) and K$_2$CO$_3$ (34.2 g, 247.46 mmol) were added to a solution of 3-bromo-2-methoxy-4-methylpyridine (10 g, 49.49 mmol) in DME (300 mL) and H$_2$O (60 mL) under N$_2$. The reaction mixture was stirred at 90° C. for 22 h, at which point extra Potassium Trifluoro(prop-1-en-2-yl)Borate (2.75 g, 18.56 mmol), K$_2$CO$_3$ (8.55 g, 61.87 mmol) and Pd(dppf)Cl$_2$ (0.905 g, 1.24 mmol) were added to the reaction mixture. Heating at 90° C. was pursued for 2 h. The reaction mixture was cooled to rt, diluted with EA and filtered over a pad of celite. The filtrate was diluted with water and layers were separated. The aqueous layer was extracted with EA (3×). The combined organic layers were washed with brine and dried over Na₂SO₄. The solids were removed by filtration and the filtrate was evaporated to dryness. The crude product was purified by flash chromatography on silica gel (0 to 5% EA in CyH) to give 2-methoxy-4-methyl-3-(prop-1-en-2-yl)pyridine (7.4 g, 92%) as a yellow liquid. $^1$H-NMR (DMSO-$d_6$, 400 MHz): 1.91 (s, 3H), 2.19 (s, 3H), 3.81 (s, 3H), 4.75-4.77 (m, 1H), 5.24-5.27 (m, 1H), 6.84 (d, J=5.2 Hz, 1H), 7.91 (d, J=5.2 Hz, 1H) ppm. LC-MS: $C_{10}H_{13}NO$ [M+H]$^+$: 164.

A mixture of Pd/C 10% (4.82 g) and 2-methoxy-4-methyl-3-(prop-1-en-2-yl)pyridine (7.4 g, 45.34 mmol) in MeOH (100 mL) was stirred at 50° C. under a balloon of H₂ for 16 h. The reaction mixture was then filtered over a pad of celite. The filtrate was evaporated to dryness to give 3-isopropyl-2-methoxy-4-methylpyridine (6.45 g, 86%) as a yellow oil. $^1$H-NMR (DMSO-$d_6$, 400 MHz): 1.22 (d, J=7.2 Hz, 6H), 2.27 (s, 3H), 3.17-3.28 (m, 1H), 3.83 (s, 3H), 6.75 (d, J=5.2 Hz, 1H), 7.82 (d, J=5.2 Hz, 1H) ppm. LC-MS: $C_{10}H_{15}NO$ [M+H]$^+$: 166.

A solution of NBS (5.87 g, 32.98 mmol) and 3-isopropyl-2-methoxy-4-methylpyridine (5.45 g, 32.98 mmol) in anhydrous MeCN (110 mL) was stirred at rt for 20 h under N₂. The reaction mixture was evaporated to dryness and the residue was dissolved in EA. The organic phase was washed with water and brine and dried over Na₂SO₄. The solids were removed by filtration and the filtrate was evaporated to dryness. The crude mixture was purified by chromatography on silica gel (0 to 3% EA in CyH) to afford 5-bromo-3-isopropyl-2-methoxy-4-methylpyridine (7.2 g, 89%) as a yellow oil. $^1$H-NMR (DMSO-$d_6$, 400 MHz): 1.23 (d, J=6.8 Hz, 6H), 2.39 (s, 3H), 3.27-3.38 (m, 1H), 3.84 (s, 3H), 8.11 (s, 1H) ppm. LC-MS: $C_{10}H_{14}BrNO$ [M+H]$^+$: 244/246.

Bis(neopentyl glycolato)diboron (19.99 g, 88.48 mmol), KOAc (8.68 g, 88.48 mmol) and PdCl₂[P(o-Tol)₃]₂ (1.88 g, 2.39 mmol) were added to a solution of 5-bromo-3-isopropyl-2-methoxy-4-methylpyridine (7.2 g, 29.49 mmol) in anhydrous DMSO (96 mL) under N₂. The reaction mixture was stirred at 90° C. for 1 h. After cooling to rt, the reaction mixture was diluted with EA and filtered over a pad of celite. The filtrate was washed with brine and dried over Na₂SO₄. The solids were removed by filtration and the filtrate was evaporated to dryness. The crude mixture was purified by flash chromatography on silica gel (0 to 5% EA in CyH) to give 5-(5,5-dimethyl-1,3,2-dioxaborinan-2-yl)-3-isopropyl-2-methoxy-4-methylpyridine (5.24 g, 64%) as a light-yellow solid. $^1$H-NMR (DMSO-$d_6$, 400 MHz): 0.96 (s, 6H), 1.22 (d, J=7.2 Hz, 6H), 2.42 (s, 3H), 3.25-3.35 (m, 1H), 3.74 (s, 4H), 3.84 (s, 3H), 8.12 (s, 1H) ppm.

H₂O₂ 30% (19.3 mL, 189 mmol) and acetic acid (10.8 mL, 189 mmol) were added to a solution of 5-(5,5-dimethyl-1,3,2-dioxaborinan-2-yl)-3-isopropyl-2-methoxy-4-methylpyridine (5.24 g, 18.905 mmol) in THF (100 mL) under N₂. The reaction mixture was stirred at rt for 1 h. The reaction mixture was then diluted with sat. aq. Na₂CO₃ and EA. The organic phase was washed with sat. aq. Na₂CO₃ and brine and dried over Na₂SO₄. The solids were removed by filtration and the filtrate was evaporated to dryness to give 5-isopropyl-6-methoxy-4-methylpyridin-3-ol (3.43 g, 100%) as a yellow oil which was used in the next step without further purification. LC-MS: $C_{10}H_{15}NO_2$ [M+H]$^+$: 182.

DIPEA (15.5 mL, 93.8 mmol) was added to a solution of 5-isopropyl-6-methoxy-4-methylpyridin-3-ol (3.4 g, 18.76 mmol) and 1,3-dichloro-2-fluoro-5-nitrobenzene (5.91 g, 28.14 mmol) in anhydrous DMF (100 mL). The reaction mixture was stirred at rt under N₂ for 2 h, at which point extra DIPEA (3.10 mL, 18.76 mmol) was added and stirring at rt was pursued for 2 h to reach full conversion. The reaction mixture was diluted with water and EA. The organic phase was washed with brine and dried over Na₂SO₄. The solids were removed by filtration and the filtrate was evaporated to dryness. The crude mixture was purified by flash chromatography on silica gel (0 to 10% EA in CyH) to give 5-(2,6-dichloro-4-nitrophenoxy)-3-isopropyl-2-methoxy-4-methylpyridine (5.07 g, 73%) as a yellow solid. $^1$H-NMR (DMSO-$d_6$, 300 MHz): 1.27 (d, J=7.2 Hz, 6H), 2.39 (s, 3H), 3.25-3.35 (m, 1H), 3.78 (s, 3H), 7.15 (s, 1H), 8.49 (s, 2H) ppm. LC-MS: $C_{16}H_{16}Cl_2N_2O_4$ [M+H]$^+$: 371.

Iron (7.63 g, 136.58 mmol) was added to a solution of 5-(2,6-dichloro-4-nitrophenoxy)-3-isopropyl-2-methoxy-4-methylpyridine (5.07 g, 13.66 mmol) and NH₄Cl (14.61 g, 273.16 mmol) in EtOH (60 mL) and water (60 mL) under N₂. The reaction mixture stirred at 70° C. for 4 h. After cooling to rt, the reaction mixture was filtered over a pad of celite. The filtrate was concentrated to remove EtOH and extracted with EA (3×). The combined organic phases were washed with water and brine and dried over Na₂SO₄. The solids were removed by filtration and the filtrate was evaporated to dryness to give 3,5-dichloro-4-((5-isopropyl-6-methoxy-4-methylpyridin-3-yl)oxy)aniline (3.59 g, 77%) as a black oil which was used in the next step without purification. $^1$H-NMR (DMSO-$d_6$, 400 MHz): 1.26 (d, J=7.2 Hz, 6H), 2.34 (s, 3H), 3.25-3.35 (m, 1H), 3.77 (s, 3H), 5.63 (s, 2H), 6.70 (s, 2H), 6.99 (s, 1H) ppm. LC-MS: $C_{16}H_{18}Cl_2N_2O_2$ [M+H]$^+$: 341.

HCl 37% (115 mL) was added to a solution of 3,5-dichloro-4-((5-isopropyl-6-methoxy-4-methylpyridin-3-yl)oxy)aniline (4.6 g, 13.48 mmol) in acetic acid (350 mL) and water (250 mL) at 0° C. under N₂. A solution of NaNO₂ (1.95 g, 28.309 mmol) in water (250 mL) was then added and the reaction mixture was stirred at 0° C. for 1 h. Then, a solution of N-cyanoacetylurethane (3.16 g, 20.22 mmol) in pyridine (115 mL) and water (200 mL) was added. The reaction mixture was stirred at 0° C. for 2 h. The reaction mixture was warmed to rt and diluted with more water. The precipitate was collected by filtration, washed with water and co-evaporated with toluene to give ethyl-(2-cyano-2-(2-(3,5-dichloro-4-((5-isopropyl-6-methoxy-4-methyl-pyridin-3-yl)oxy)phenyl)hydrazineylidene)acetyl)carbamate (6.85 g, 100%) as an orange solid which was used as such in the next step. LC-MS: $C_{22}H_{23}Cl_2N_5O_5$ [M+H]$^+$: 508.

NaOAc (8.85 g, 107.84 mmol) was added to a mixture of ethyl-(2-cyano-2-(2-(3,5-dichloro-4-((5-isopropyl-6-methoxy-4-methylpyridin-3-yl)oxy)phenyl)hydrazineylidene)acetyl)carbamate (6.85 g, 13.48 mmol) in acetic acid (130 mL) under N₂. The reaction mixture was stirred at 120° C. for 2 h. After cooling to rt, the reaction mixture was diluted with water (100 mL). The resulting precipitate was collected by filtration, washed with water and dried under vacuum to give 2-(3,5-dichloro-4-((5-isopropyl-6-methoxy-4-methylpyridin-3-yl)oxy)phenyl)-3,5-dioxo-2,3,4,5-tetrahydro-1,2,4-triazine-6-carbonitrile (6.23 g, 100%) as a red solid which was used as such in the next step. $^1$H-NMR (DMSO-$d_6$, 400 MHz): 1.28 (d, J=7.2 Hz, 6H), 2.40 (s, 3H), 3.25-3.35 (m, 1H), 3.79 (s, 3H), 7.10 (s, 1H), 7.80 (s, 2H), 13.23 (br s, 1H) ppm. LC-MS: $C_{20}H_{17}Cl_2N_5O_4$ [M+H]$^+$: 462.

HBr (48% aq., 7.63 mL) was added to a solution of 2-(3,5-dichloro-4-((5-isopropyl-6-methoxy-4-methylpyridin-3-yl)oxy)phenyl)-3,5-dioxo-2,3,4,5-tetrahydro-1,2,4-triazine-6-carbonitrile (6.23 g, 13.48 mmol) in 1,4-dioxane (130 mL) under N₂. The reaction mixture was stirred at 60° C. for 24 h. After cooling to rt, the reaction mixture was diluted with water (50 mL) and sat. aq. Na$_2$CO$_3$ (100 mL) and extracted with EA. The layers were separated and the aqueous layer was reextracted with EA (3×). The combined organic phases were washed with sat. aq. Na$_2$CO$_3$ (2×) and brine and dried over Na$_2$SO$_4$. The solids were removed by filtration and the filtrate was evaporated to dryness to give 2-(3,5-dichloro-4-((5-isopropyl-4-methyl-6-oxo-1,6-dihydropyridin-3-yl)oxy)phenyl)-3,5-dioxo-2,3,4,5-tetrahydro-1,2,4-triazine-6-carbonitrile (5.0 g, 83%) as a yellow solid which was used in the next step without further purification. $^1$H-NMR (DMSO-d$_6$, 400 MHz): 1.28 (d, J=7.2 Hz, 6H), 2.31 (s, 3H), 3.20-3.30 (m, 1H), 6.40 (s, 1H), 7.77 (s, 2H), 10.90 (br s, 1H), 13.25 (br s, 1H) ppm. LC-MS: C$_{19}$H$_{15}$Cl$_2$N$_5$O$_4$ [M+H]$^+$: 448.

A solution of KOH (6.26 g, 111.54 mmol) in water (45 mL) was added to a solution of 2-(3,5-dichloro-4-((5-isopropyl-4-methyl-6-oxo-1,6-dihydropyridin-3-yl)oxy)phenyl)-3,5-dioxo-2,3,4,5-tetrahydro-1,2,4-triazine-6-carbonitrile (5 g, 11.15 mmol) in EtOH (45 mL). The reaction mixture was stirred at 60° C. for 40 min. After cooling to rt, the reaction mixture was diluted with more water and washed with Et$_2$O (3×). The aqueous solution was then acidified with HCl 6N to pH 1. The resulting precipitate was collected by filtration and dried under vacuum to give 2-(3,5-dichloro-4-((5-isopropyl-4-methyl-6-oxo-1,6-dihydropyridin-3-yl)oxy)phenyl)-3,5-dioxo-2,3,4,5-tetrahydro-1,2,4-triazine-6-carboxylic acid (5.2 g, 100%) as an orange solid which was used as such in the next step. LC-MS: C$_{19}$H$_{16}$Cl$_2$N$_4$O$_6$ [M+H]$^+$: 467.

Triethylamine (2.25 g, 3.09 mL, 22.25 mmol) and DPPA (4.59 g, 3.6 mL, 16.69 mmol) were added to a solution of 2-(3,5-dichloro-4-((5-isopropyl-4-methyl-6-oxo-1,6-dihydropyridin-3-yl)oxy)phenyl)-3,5-dioxo-2,3,4,5-tetrahydro-1,2,4-triazine-6-carboxylic acid (2.6 g, 5.56 mmol) in tBuOH (40 mL) under N$_2$. The reaction mixture was stirred at 85° C. for 4 h. After cooling to rt, the reaction mixture was quenched with sat. aq. NaHCO$_3$ and extracted with EA. Layers were separated and the aqueous layer was reextracted with EA (3×). The combined organic layers were washed with sat. aq. NaHCO$_3$ and brine and dried over Na$_2$SO$_4$. The solids were removed by filtration and the filtrate was evaporated to dryness. The crude mixture was purified by chromatography on silica gel (0 to 10% MeOH in DCM) to give t-butyl (2-(3,5-dichloro-4-((5-isopropyl-4-methyl-6-oxo-1,6-dihydropyridin-3-yl)oxy)phenyl)-3,5-dioxo-2,3,4,5-tetrahydro-1,2,4-triazin-6-yl)carbamate (770 mg, 26%) as an orange solid which was used as such in the next step. LC-MS: C$_{23}$H$_{25}$Cl$_2$N$_5$O$_6$ [M+H]$^+$: 538.

A solution of t-butyl (2-(3,5-dichloro-4-((5-isopropyl-4-methyl-6-oxo-1,6-dihydropyridin-3-yl)oxy)phenyl)-3,5-dioxo-2,3,4,5-tetrahydro-1,2,4-triazin-6-yl)carbamate (730 mg, 1.36 mmol) in HCl 4N in dioxane (6.78 mL, 27.12 mmol) was stirred at rt under N$_2$ for 4 h. The reaction mixture was then evaporated to dryness and the crude mixture was purified by chromatography on silica gel (0 to 10% [MeOH/NH$_4$OH (9:1)] in DCM) and by prep. HPLC (25 to 100% MeCN in water [0.2% v/v HCO$_2$H]) to give 6-amino-2-(3,5-dichloro-4-((5-isopropyl-4-methyl-6-oxo-1,6-dihydropyridin-3-yl)oxy)phenyl)-1,2,4-triazine-3,5(2H, 4H)-dione (18) (68 mg, 11%) as a white solid. $^1$H-NMR (DMSO-d$_6$, 400 MHz): 1.28 (d, J=7.0 Hz, 6H), 2.30 (s, 3H), 3.19-3.27 (m, 1H), 6.26 (s, 1H), 6.35 (s, 2H), 7.92 (s, 2H), 8.30 (s, 1H), 10.90 (br s, 1H) ppm. LC-MS: C$_{18}$H$_{17}$Cl$_2$N$_5$O$_4$ [M+H]$^+$: 438.

Example 19

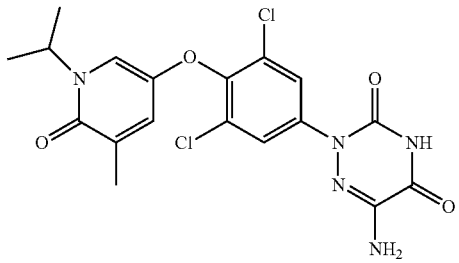

Compound 19

DIPEA (32.5 mL, 196.67 mmol) was added to a solution of 6-fluoro-5-methylpyridin-3-ol (5 g, 39.33 mmol) and 1,3-dichloro-2-fluoro-5-nitrobenzene (8.26 g, 39.33 mmol) in anhydrous DMF (175 mL) under N$_2$. The reaction mixture was stirred at rt for 1 h. The reaction mixture was diluted with water and extracted with EA (4×). The combined organic layers were washed with brine (5×) and dried over Na$_2$SO$_4$. The solids were removed by filtration and the filtrate was evaporated to dryness. The crude mixture was purified by flash chromatography on silica gel (DCM) to give 5-(2,6-dichloro-4-nitrophenoxy)-2-fluoro-3-methylpyridine (7.95 g, 64%) as a white solid. $^1$H-NMR (DMSO-d$_6$, 300 MHz): 2.22 (s, 3H), 7.54-7.60 (m, 1H), 7.78 (s, 1H), 8.56 (s, 2H) ppm. LC-MS: C$_{12}$H$_7$Cl$_2$FN$_2$O$_3$ [M+H]$^+$: 317.

A mixture of 5-(2,6-dichloro-4-nitrophenoxy)-2-fluoro-3-methylpyridine (7.95 g, 25.07 mmol) in AcOH (74 mL) and water (37 mL) was stirred at 120° C. under N$_2$ for 5 days. After cooling to rt, the reaction mixture was diluted with sat. aq. NaHCO$_3$ until pH 7. The resulting precipitate was collected by filtration to give 5-(2,6-dichloro-4-nitrophenoxy)-3-methylpyridin-2(1H)-one (7.9 g, 100%) as a yellow solid which was used in the next step without further purification. $^1$H-NMR (DMSO-d$_6$, 300 MHz): 1.99 (s, 3H), 6.90-6.93 (m, 1H), 7.32-7.35 (m, 1H), 8.48 (s, 2H), 11.60 (br s, 1H) ppm. LC-MS: C$_{12}$H$_8$Cl$_2$N$_2$O$_4$ [M+H]$^+$: 315.

K$_2$CO$_3$ (5.70 g, 41.27 mmol) was added to a solution of 5-(2,6-dichloro-4-nitrophenoxy)-3-methylpyridin-2(1H)-one (8.67 g, 27.51 mmol) in anhydrous dioxane (165 mL) under N$_2$. The reaction mixture was stirred at rt for 10 min. 2-iodopropane (7.01 g, 4.13 mL, 41.27 mmol) was added and the reaction mixture was stirred at 120° C. for 20 h. After cooling to rt, the reaction mixture was filtered and the filtrate was evaporated to dryness. The crude mixture was purified by chromatography on silica gel (0 to 40% EA in CyH) to give 5-(2,6-dichloro-4-nitrophenoxy)-1-isopropyl-3-methylpyridin-2(1H)-one (7.10 g, 72%) as a yellow solid. $^1$H-NMR (DMSO-d$_6$, 300 MHz): 1.23 (d, J=7.0 Hz, 6H), 2.00 (s, 3H), 5.01-5.10 (m, 1H), 7.21-7.24 (m, 1H), 7.29-7.32 (m, 1H), 8.50 (s, 2H) ppm. LC-MS: C$_{15}$H$_{14}$Cl$_2$N$_2$O$_4$ [M+H]$^+$: 357.

Fe (5.89 g, 105.55 mmol) was added to a solution of 5-(2,6-dichloro-4-nitrophenoxy)-1-isopropyl-3-methylpyridin-2(1H)-one (7.54 g, 21.109 mmol) and NH$_4$Cl (11.29 g, 211.092 mmol) in EtOH (20 mL) and water (20 mL) under N$_2$. The reaction mixture was stirred at 90° C. for 4 h. After cooling to rt, the reaction mixture was filtered over a pad of celite and the filtrate was evaporated to dryness. The crude mixture was purified by chromatography on silica gel (0% to 5% MeOH in DCM) to give 5-(4-amino-2,6-dichlorophenoxy)-1-isopropyl-3-methylpyridin-2(1H)-one (4.81 g, 70%) as a light brown solid. $^1$H-NMR (DMSO-d$_6$, 300 MHz): 1.21 (d, J=7.0 Hz, 6H), 1.99 (s, 3H), 4.99-5.09 (m, 1H), 5.63 (s, 2H), 6.68 (s, 2H), 7.01-7.08 (m, 2H) ppm. LC-MS: $C_{15}H_{16}Cl_2N_2O_2$ [M+H]$^+$: 327.

A solution of NaNO$_2$ (0.89 g, 12.84 mmol) in water (50 mL) was slowly added to a solution of 5-(4-amino-2,6-dichlorophenoxy)-1-isopropyl-3-methylpyridin-2(1H)-one (2 g, 6.11 mmol) in HCl 37% (21 mL), AcOH (61 mL) and water (50 mL) at 0° C. under N$_2$. The reaction mixture was stirred at 0° C. for 1 h. In parallel, a mixture of ethyl N-(2-cyanoacetyl)carbamate (1.43 g, 9.17 mmol) in water (61 mL) and pyridine (21 mL) was stirred at 0° C. for 15 min.

The first solution was quickly added to the second one. The resulting reaction mixture was stirred at 0° C. for 2 h. The reaction mixture was diluted with more water and the precipitate was collected by filtration, washed with water, dissolved in EA and dried over Na$_2$SO$_4$. The solids were removed by filtration and the filtrate was evaporated to dryness to give ethyl (2-cyano-2-(2-(3,5-dichloro-4-((1-isopropyl-5-methyl-6-oxo-1,6-dihydropyridin-3-yl)oxy)phenyl) hydrazineylidene)acetyl)carbamate (1.97 g, 65%) as an orange solid which was used as such in the next step. LC-MS: $C_{21}H_{21}Cl_2N_5O_5$ [M+H]$^+$: 494.

A solution of ethyl (2-cyano-2-(2-(3,5-dichloro-4-((1-isopropyl-5-methyl-6-oxo-1,6-dihydropyridin-3-yl)oxy)phenyl)hydrazineylidene)acetyl)carbamate (1.97 g, 3.99 mmol) and NaOAc (1.31 g, 15.94 mmol) in AcOH (40 mL) was stirred at 120° C. under N$_2$ for 2 h. After cooling to rt, the reaction mixture was diluted with water. The resulting precipitate was collected by filtration, dissolved in EA and dried over Na$_2$SO$_4$. The solids were removed by filtration and the filtrate was evaporated to dryness to give 2-(3,5-dichloro-4-((1-isopropyl-5-methyl-6-oxo-1,6-dihydropyridin-3-yl)oxy)phenyl)-3,5-dioxo-2,3,4,5-tetrahydro-1,2,4-triazine-6-carbonitrile (1.79 g, 100%) as an orange solid which was used in the next step without further purification. $^1$H-NMR (DMSO-d$_6$, 300 MHz): 1.25 (d, J=7.0 Hz, 6H), 2.00 (s, 3H), 4.99-5.10 (m, 1H), 7.14-7.16 (m, 1H), 7.31-7.33 (m, 1H), 7.77 (s, 2H) ppm. LC-MS: $C_{19}H_{15}Cl_2N_5O_4$ [M+H]$^+$: 448.

A solution of 2-(3,5-dichloro-4-((1-isopropyl-5-methyl-6-oxo-1,6-dihydropyridin-3-yl)oxy)phenyl)-3,5-dioxo-2,3,4,5-tetrahydro-1,2,4-triazine-6-carbonitrile (1.79 g, 3.99 mmol) in conc. HCl (2.95 mL, 35.94 mmol) and AcOH (5.95 mL, 103.82 mmol) was stirred at 120° C. under N$_2$ for 2 h. After cooling to rt, the reaction mixture was diluted with water. The resulting precipitate was collected by filtration, dissolved in EA and dried over Na$_2$SO$_4$. The solids were removed by filtration and the filtrate was evaporated to dryness to give 2-(3,5-dichloro-4-((1-isopropyl-5-methyl-6-oxo-1,6-dihydropyridin-3-yl)oxy)phenyl)-3,5-dioxo-2,3,4,5-tetrahydro-1,2,4-triazine-6-carboxylic acid (1.87 g, 100%) as a green solid which was used as such in the next step. LC-MS: $C_{19}H_{16}Cl_2N_4O_6$ [M+H]$^+$: 467.

Triethylamine (2.14 mL, 15.409 mmol) and DPPA (3.18 g, 2.49 mL, 11.56 mmol) were added to a solution of 2-(3,5-dichloro-4-((1-isopropyl-5-methyl-6-oxo-1,6-dihydropyridin-3-yl)oxy)phenyl)-3,5-dioxo-2,3,4,5-tetrahydro-1,2,4-triazine-6-carboxylic acid (1.8 g, 3.85 mmol) in tert-butanol (56 mL) under N$_2$. The resulting mixture was stirred at 85° C. for 22 h, at which point extra triethylamine (2.14 mL, 15.409 mmol) and DPPA (3.18 g, 2.49 mL, 11.56 mmol) were added to the reaction mixture and stirring at 85° C. was pursued for 2 h to reach full conversion. After cooling to rt, the reaction mixture was diluted with sat. aq. NaHCO$_3$ and extracted with EA. The organic phase was washed with sat. aq. NaHCO$_3$ and brine and dried over Na$_2$SO$_4$. The solids were removed by filtration and the filtrate was evaporated to dryness. The crude mixture was purified by flash chromatography on silica gel (0 to 5% MeOH in DCM) to give t-butyl (2-(3,5-dichloro-4-((1-isopropyl-5-methyl-6-oxo-1,6-dihydropyridin-3-yl)oxy)phenyl)-3,5-dioxo-2,3,4,5-tetrahydro-1,2,4-triazin-6-yl)carbamate (2.07 g, 100%) as a yellow oil. LC-MS: $C_{23}H_{25}Cl_2N_5O_6$ [M+H]$^+$: 538.

A solution of t-butyl (2-(3,5-dichloro-4-((1-isopropyl-5-methyl-6-oxo-1,6-dihydropyridin-3-yl)oxy)phenyl)-3,5-dioxo-2,3,4,5-tetrahydro-1,2,4-triazin-6-yl)carbamate (2.07 g, 3.85 mmol) in HCl (4N in dioxane, 38.5 mL) was stirred at rt under N$_2$ for 5 h. The reaction mixture was diluted with sat. aq. NaHCO$_3$ and extracted with EA. The layers were separated and the aqueous layer was extracted with EA. The combined organic layers were washed with brine and dried over Na$_2$SO$_4$. The solids were removed by filtration and the filtrate was evaporated to dryness. The crude product was purified by flash chromatography on silica gel (0% to 6% MeOH in DCM). The resulting solid was triturated in EtOH and dried under high vacuum to give 6-amino-2-(3,5-dichloro-4-((1-isopropyl-5-methyl-6-oxo-1,6-dihydropyridin-3-yl)oxy)phenyl)-1,2,4-triazine-3,5(2H,4H)-dione (19) (939 mg, 56%) as a white solid. $^1$H-NMR (DMSO-d$_6$, 400 MHz): 1.24 (d, J=7.0 Hz, 6H), 1.99 (s, 3H), 4.98-5.05 (m, 1H), 6.54 (s, 2H), 7.10-7.13 (m, 1H), 7.25-7.28 (m, 1H), 7.89 (s, 2H), 12.28 (s, 1H) ppm. LC-MS: $C_{18}H_{17}Cl_2N_5O_4$ [M+H]$^+$: 438.

Example 20

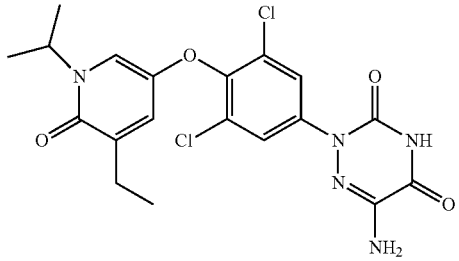

Compound 20

6-amino-2-(3,5-dichloro-4-((5-ethyl-1-isopropyl-6-oxo-1,6-dihydropyridin-3-yl)oxy)phenyl)-1,2,4-triazine-3,5(2H,4H)-dione The titled compound can be made following the procedure to make 6-amino-2-(3,5-dichloro-4-((1-isopropyl-5-methyl-6-oxo-1,6-dihydropyridin-3-yl)oxy)phenyl)-1,2,4-triazine-3,5(2H,4H)-dione and starting with 5-ethyl-6-fluoropyridin-3-ol.

Example 21

Compound 21

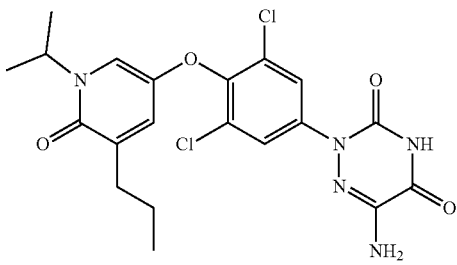

6-amino-2-(3,5-dichloro-4-((1-isopropyl-6-oxo-5-propyl-1,6-dihydropyridin-3-yl)oxy)phenyl)-1,2,4-triazine-3,5(2H,4H)-dione The titled compound can be made following the procedure to make 6-amino-2-(3,5-dichloro-4-((1-isopropyl-5-methyl-6-oxo-1,6-dihydropyridin-3-yl)oxy)phenyl)-1,2,4-triazine-3,5(2H,4H)-dione and starting with 5-(n-propyl)-6-fluoropyridin-3-ol.

Example 22

Compound 22

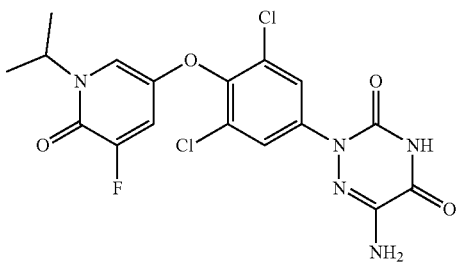

Bis(neopentyl glycolato)diboron (36.26 g, 160.5 mmol), KOAc (15.75 g, 160.5 mmol), palladium diacetate (1.20 g, 5.35 mmol) and tricyclohexylphosphine (4.50 g, 16.05 mmol) were added to a solution of 5-chloro-2,3-difluoropyridine (8 g, 53.51 mmol) in anhydrous dioxane (320 mL) under $N_2$. The reaction mixture was stirred at 90° C. for 18 h. After cooling to rt, the reaction mixture was diluted with EA, filtered on a pad of celite and evaporated to dryness. The crude mixture was purified by flash chromatography on silica gel (0 to 20% EA in CyH) to give 5-(5,5-dimethyl-1,3,2-dioxaborinan-2-yl)-2,3-difluoropyridine (10.8 g, 89%) as a pink solid. $^1$H-NMR (DMSO-$d_6$, 400 MHz): 0.96 (s, 6H), 3.78 (s, 4H), 7.99-8.06 (m, 1H), 8.22 (s, 1H) ppm.

$H_2O_2$ 30% (121 mL, 1189 mmol) and AcOH (68 mL, 1189 mmol) were added to a solution of 5-(5,5-dimethyl-1,3,2-dioxaborinan-2-yl)-2,3-difluoropyridine (10.8 g, 47.57 mmol) in THF (117 mL) under $N_2$. The reaction mixture was stirred at rt for 2 d, then diluted with water and extracted with EA (3×). Combined organic layers were washed with sat. aq. $Na_2S_2O_3$, sat. aq. $NaHCO_3$ (2×) and brine and dried over $Na_2SO_4$. The solids were removed by filtration and the filtrate was evaporated to dryness. The crude mixture was purified by flash chromatography on silica gel (0% to 20% EA in CyH) to give 5,6-difluoropyridin-3-ol (6.24 g, 100%) as a white solid. $^1$H-NMR (DMSO-$d_6$, 400 MHz): 7.34-7.43 (m, 1H), 7.52-7.54 (m, 1H), 10.45 (br s, 1H) ppm. LC-MS: $C_5H_3F_2NO$ [M+H]$^+$: 131.

DIPEA (15.7 mL, 95.21 mmol) was added to a solution of 5,6-difluoropyridin-3-ol (6.24 g, 47.60 mmol) and 1,3-dichloro-2-fluoro-5-nitrobenzene (10 g, 47.60 mmol) in anhydrous DMF (300 mL) under $N_2$. The reaction mixture was stirred at rt for 18 h. The reaction mixture was then diluted with water and extracted with EA (3×). Combined organic layers were washed with water (3×) and brine (2×) and dried over $Na_2SO_4$. The solids were removed by filtration and the filtrate was evaporated to dryness. The crude mixture was purified by chromatography on silica gel (0% to 5% EA in CyH) to give 5-(2,6-dichloro-4-nitrophenoxy)-2,3-difluoropyridine (14.55 g, 95%) as a yellow solid. $^1$H-NMR (DMSO-$d_6$, 400 MHz): 7.87-7.90 (m, 1H), 8.01-8.06 (m, 1H), 8.58 (s, 2H) ppm. LC-MS: $C_{11}H_4Cl_2F_2N_2O_3$ [M+H]$^+$: 321.

A mixture of 5-(2,6-dichloro-4-nitrophenoxy)-2,3-difluoropyridine (14.5 g, 45.16 mmol) in AcOH (139 mL) and $H_2O$ (69 mL) was stirred at 130° C. for 5 d under $N_2$. After cooling to rt, the reaction mixture was diluted with more water. The precipitate was collected by filtration, washed with water and dried under vacuum. The resulting solid was triturated in CyH/EA (95:5) and collected by filtration to give 5-(2,6-dichloro-4-nitrophenoxy)-3-fluoropyridin-2(1H)-one (8.79 g, 61%) as a beige solid. $^1$H-NMR (DMSO-$d_6$, 400 MHz): 7.04 (d, J=2.0 Hz, 1H), 7.65 (dd, J=10.4 Hz, 3.2 Hz, 1H), 8.51 (s, 2H), 12.07 (br s, 1H) ppm. LC-MS: $C_{11}H_5Cl_2FN_2O_4$ [M+H]$^+$: 319.

$K_2CO_3$ (3.25 g, 23.51 mmol) was added to a solution of 5-(2,6-dichloro-4-nitrophenoxy)-3-fluoropyridin-2(1H)-one (5 g, 15.67 mmol) in anhydrous dioxane (94 mL) under $N_2$. The reaction mixture was stirred at rt for 10 min. Then, 2-iodopropane (2.35 mL, 23.51 mmol) was added and the reaction mixture was stirred at 120° C. for 5 h, at which point extra 2-iodopropane (1.18 mL, 11.75 mmol) and $K_2CO_3$ (1.62 g, 11.75 mmol) were added and stirring at 120° C. was pursued for 24 h. After cooling to rt, the reaction mixture was filtered on a celite pad and the filtrate was evaporated to dryness. The crude mixture was purified by flash chromatography on silica gel (0 to 30% EA in CyH) to give 5-(2,6-dichloro-4-nitrophenoxy)-3-fluoro-1-isopropylpyridin-2(1H)-one (5.09 g, 90%) as a yellow solid. $^1$H-NMR (DMSO-$d_6$, 400 MHz): 1.26 (d, J=6.8 Hz, 6H), 5.02-5.12 (m, 1H), 7.38-7.40 (m, 1H), 7.56 (dd, J=10.4 Hz, 3.2 Hz, 1H), 8.52 (s, 2H) ppm. LC-MS: $C_{14}H_{11}Cl_2FN_2O_4$ [M+H]$^+$: 361.

Fe (3.49 g, 62.58 mmol) was added to a solution of 5-(2,6-dichloro-4-nitrophenoxy)-3-fluoro-1-isopropylpyridin-2(1H)-one (4.52 g, 12.52 mmol) and $NH_4Cl$ (6.69 g, 125.2 mmol) in EtOH (86 mL) and water (48 mL) under $N_2$. The reaction mixture was stirred at 80° C. for 3 h. After cooling to rt, the reaction mixture was filtered on a celite pad. The filtrate was concentrated to remove EtOH and extracted with EA (3×). Combined organic layers were washed with sat. aq. $NaHCO_3$ and brine and dried over $Na_2SO_4$. The solids were removed by filtration and the filtrate was evaporated to dryness to give 5-(4-amino-2,6-dichlorophenoxy)-3-fluoro-1-isopropylpyridin-2(1H)-one (3.52 g, 85%) as a beige solid which was used as such in the next step. $^1$H-NMR (DMSO-$d_6$, 400 MHz): 1.24 (d, J=6.8 Hz, 6H), 5.00-5.10 (m, 1H), 5.89 (s, 2H), 6.69 (s, 2H), 7.10-7.12 (m, 1H), 7.28 (dd, J=10.4 Hz, 3.2 Hz, 1H) ppm. LC-MS: $C_{14}H_{13}Cl_2FN_2O_2$ [M+H]$^+$: 331.

A solution of NaNO$_2$ (1.54 g, 22.32 mmol) in water (221 mL) was added to a solution of 5-(4-amino-2,6-dichlorophenoxy)-3-fluoro-1-isopropylpyridin-2(1H)-one (3.52 g, 10.63 mmol) in HCl 37% (92 mL), AcOH (287 mL) and water (220 mL) at 0° C. under N$_2$. The reaction mixture was stirred at 0° C. for 1 h. In parallel, a solution of ethyl N-(2-cyanoacetyl)carbamate (2.49 g, 15.94 mmol) in water (265 mL) and pyridine (88 mL) was stirred at 0° C. for 15 min. This reaction mixture was quickly added to the first one. The resulting reaction mixture was stirred at 0° C. for 1 h. The reaction mixture was then diluted with more water. The precipitate was collected by filtration, washed with water and dried under vacuum to give ethyl (2-cyano-2-(2-(3,5-dichloro-4-((5-fluoro-1-isopropyl-6-oxo-1,6-dihydropyridin-3-yl)oxy)phenyl)hydrazineylidene)acetyl) carbamate (5.3 g, 100%) as an orange solid which was used as such in the next step. LC-MS: C$_{20}$H$_{18}$Cl$_2$FN$_5$O$_5$ [M+H]$^+$: 498.

Sodium acetate (6.98 g, 85.09 mmol) was added to a solution of ethyl (2-cyano-2-(2-(3,5-dichloro-4-((5-fluoro-1-isopropyl-6-oxo-1,6-dihydropyridin-3-yl)oxy)phenyl)hydrazineylidene)acetyl)carbamate (5.3 g, 10.64 mmol) in acetic acid (103 mL) under N$_2$. The reaction mixture was stirred at 120° C. for 1 h. The reaction mixture was then cooled to 0° C., diluted with water and stirred for 30 min. The resulting precipitate was collected by filtration, washed with water and dried under vacuum to give 2-(3,5-dichloro-4-((5-fluoro-1-isopropyl-6-oxo-1,6-dihydropyridin-3-yl)oxy)phenyl)-3,5-dioxo-2,3,4,5-tetrahydro-1,2,4-triazine-6-carbonitrile (2.97 g, 62%) as a red solid which was used as such in the next step. LC-MS: C$_{18}$H$_{12}$Cl$_2$FN$_5$O$_4$ [M+H]$^+$: 452.

A mixture of 2-(3,5-dichloro-4-((5-fluoro-1-isopropyl-6-oxo-1,6-dihydropyridin-3-yl)oxy)phenyl)-3,5-dioxo-2,3,4,5-tetrahydro-1,2,4-triazine-6-carbonitrile (2.97 g, 6.57 mmol) in HCl 37% (5.4 mL) and AcOH (11.3 mL) under N$_2$ was stirred at 120° C. for 1 h. The reaction mixture was cooled to rt and diluted with water. The resulting precipitate was collected by filtration, washed with water and dried under vacuum to give 2-(3,5-dichloro-4-((5-fluoro-1-isopropyl-6-oxo-1,6-dihydropyridin-3-yl)oxy)phenyl)-3,5-dioxo-2,3,4,5-tetrahydro-1,2,4-triazine-6-carboxylic acid (2.3 g, 74%) as an orange solid which was used as such in the next step. $^1$H-NMR (DMSO-d$_6$, 400 MHz): 1.28 (d, J=6.8 Hz, 6H), 5.01-5.11 (m, 1H), 7.42-7.45 (m, 1H), 7.49 (dd, J=10.4 Hz, 2.9 Hz, 1H), 7.81 (s, 2H), 12.70 (br s, 1H) ppm. LC-MS: C$_{18}$H$_{13}$Cl$_2$FN$_4$O$_6$ [M+H]$^+$: 471.

Triethylamine (3.54 mL, 25.47 mmol) and DPPA (5.26 g, 4.12 mL, 19.1 mmol) were added to a solution of 2-(3,5-dichloro-4-((5-fluoro-1-isopropyl-6-oxo-1,6-dihydropyridin-3-yl)oxy)phenyl)-3,5-dioxo-2,3,4,5-tetrahydro-1,2,4-triazine-6-carboxylic acid (3 g, 6.37 mmol) in t-butanol (98 mL) under N$_2$. The reaction mixture was stirred at 85° C. for 16 h. After cooling to rt, the reaction mixture was diluted with sat. aq. NaHCO$_3$ and extracted with EA (3×). Combined organic layers were washed with sat. aq. NaHCO$_3$ and brine and dried over Na$_2$SO$_4$. The solids were removed by filtration and the filtrate was evaporated to dryness. The crude mixture was purified by flash chromatography on silica gel (0% to 6% MeOH in DCM) to give t-butyl (2-(3,5-dichloro-4-((5-fluoro-1-isopropyl-6-oxo-1,6-dihydropyridin-3-yl)oxy)phenyl)-3,5-dioxo-2,3,4,5-tetrahydro-1,2,4-triazin-6-yl)carbamate (1.06 g, 31%) as a yellow solid. $^1$H-NMR (DMSO-d$_6$, 400 MHz): 1.27 (d, J=6.8 Hz, 6H), 1.45 (s, 9H), 5.01-5.11 (m, 1H), 7.36-7.39 (m, 1H), 7.46 (dd, J=10.4 Hz, 2.9 Hz, 1H), 7.89 (s, 2H), 9.12 (s, 1H), 12.62 (br s, 1H) ppm. LC-MS: C$_{22}$H$_{22}$Cl$_2$FN$_5$O$_6$ [M+H]$^+$: 542.

HCl 4N in dioxane (9.2 mL, 36.9 mmol) was added to a solution of t-butyl (2-(3,5-dichloro-4-((5-fluoro-1-isopropyl-6-oxo-1,6-dihydropyridin-3-yl)oxy)phenyl)-3,5-dioxo-2,3,4,5-tetrahydro-1,2,4-triazin-6-yl)carbamate (1 g, 1.84 mmol) in anhydrous DCM (16 mL) under N$_2$. The reaction mixture was stirred at rt for 18 h and then evaporated to dryness. The crude product was purified by flash chromatography on silica gel (0 to 4% MeOH in DCM). The resulting solid was triturated in MeCN and dried under high vacuum at 45° C. to give 6-amino-2-(3,5-dichloro-4-((5-fluoro-1-isopropyl-6-oxo-1,6-dihydropyridin-3-yl)oxy)phenyl)-1,2,4-triazine-3,5(2H,4H)-dione (22) (539 mg) as a white solid. $^1$H-NMR (DMSO-d$_6$, 400 MHz): 1.27 (d, J=6.8 Hz, 6H), 5.01-5.11 (m, 1H), 6.55 (s, 2H), 7.32 (dd, J=2.9 Hz, 1.7 Hz, 1H), 7.43 (dd, J=10.4 Hz, 2.9 Hz, 1H), 7.90 (s, 2H), 12.29 (br s, 1H) ppm. LC-MS: C$_{17}$H$_{14}$Cl$_2$FN$_5$O$_4$ [M+H]$^+$: 442.

Example 23

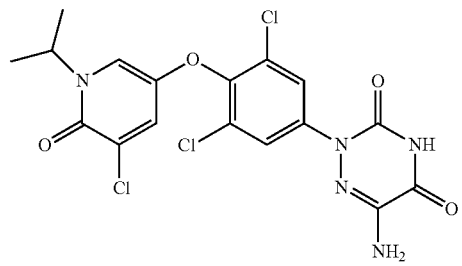

Compound 23

6-amino-2-(3,5-dichloro-4-((5-chloro-1-isopropyl-6-oxo-1,6-dihydropyridin-3-yl)oxy)phenyl)-1,2,4-triazine-3,5(2H,4H)-dione The titled compound was prepared according to the procedure to prepare 6-amino-2-(3,5-dichloro-4-((5-fluoro-1-isopropyl-6-oxo-1,6-dihydropyridin-3-yl)oxy)phenyl)-1,2,4-triazine-3,5(2H,4H)-dione, starting from 5-chloro-6-fluoropyridin-3-ol, to afford a white solid. $^1$H-NMR (DMSO-d$_6$, 400 MHz): 1.28 (d, J=6.7 Hz, 6H), 5.00-5.09 (m, 1H), 6.55 (s, 2H), 7.55 (d, J=3.1 Hz, 1H), 7.64 (d, J=3.1 Hz, 1H), 7.90 (s, 2H), 12.29 (s, 1H) ppm. LC-MS: C$_{17}$H$_{14}$Cl$_3$N$_5$O$_4$ [M+H]$^+$: 458.

Example 24

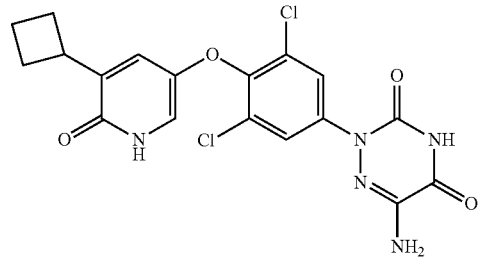

Compound 24

A solution of 3-bromo-2-methoxypyridine (5 g, 26.59 mmol) in anhydrous THF (125 mL) was added dropwise to n-BuLi 1.6M (19.9 mL, 31.91 mmol) at −78° C. under $N_2$. The reaction mixture was stirred at −78° C. for 30 min. Then, a solution of cyclobutanone (2.42 g, 2.60 mL, 34.57 mmol) in anhydrous THF (20 mL) was added dropwise and the reaction mixture was stirred at −78° C. for 30 min. The reaction mixture was warmed to rt, hydrolyzed with sat. aq. $NH_4Cl$ and extracted with EA (2×). The combined organic layers were dried over $Na_2SO_4$. The solids were removed by filtration and the filtrate was evaporated to dryness. The crude mixture was purified by chromatography on silica gel (0 to 30% EA in CyH) to give 1-(2-methoxypyridin-3-yl)cyclobutan-1-ol (4.53 g, 95%) as a colorless oil. $^1$H-NMR (DMSO-$d_6$, 300 MHz): 1.52-1.67 (m, 1H), 1.87-2.04 (m, 1H), 2.09-2.24 (m, 2H), 2.50-2.62 (m, 2H), 3.88 (s, 3H), 5.16 (s, 1H), 6.92-6.96 (m, 1H), 7.64 (dd, J=7.5 Hz, 1.5 Hz, 1H), 8.04 (dd, J=4.8 Hz, 1.2 Hz, 1H) ppm. LC-MS: $C_{10}H_{13}NO_2$ [M+H]$^+$: 180.

Triethylsilane (19.4 mL, 120 mmol) and TFA (44.6 mL, 600 mmol) were added to a solution of 1-(2-methoxypyridin-3-yl)cyclobutan-1-ol (4.3 g, 23.99 mmol) in anhydrous DCM (129 mL) under $N_2$. The reaction mixture was stirred at rt for 2 days. The reaction mixture was quenched with sat. aq. $NaHCO_3$ (sat.) and layers were separated. The aqueous layer was reextracted with DCM (3×). Combined organic layers were washed with brine (2×) and dried over $Na_2SO_4$. The solids were removed by filtration and the filtrate was evaporated to dryness. The crude mixture was purified by chromatography on silica gel (0 to 20% EA in CyH) to give 3-cyclobutyl-2-methoxypyridine (3.33 g, 85%) as a colorless oil. $^1$H-NMR (DMSO-$d_6$, 300 MHz): 1.73-1.83 (m, 1H), 1.91-2.10 (m, 3H), 2.18-2.32 (m, 2H), 3.53-3.62 (m, 1H), 3.84 (s, 3H), 6.92-6.96 (m, 1H), 7.56 (d, J=7.2 Hz, 1H), 7.97 (d, J=4.8 Hz, 1H) ppm. LC-MS: $C_{10}H_{13}NO$ [M+H]$^+$: 164.

NBS (2.04 g, 11.46 mmol) was added to a solution of 3-cyclobutyl-2-methoxypyridine (1.87 g, 11.46 mmol) in MeCN (68 mL) under $N_2$. The reaction mixture was stirred at 45° C. for 3 h. After cooling to rt, the reaction mixture was diluted with sat. aq. $Na_2S_2O_3$ and extracted with EA. The organic layer was washed with brine and dried over $Na_2SO_4$. The solids were removed by filtration and the filtrate was evaporated to dryness. The crude mixture was purified by flash chromatography on silica gel (0 to 50% EA in CyH) to give 5-bromo-3-cyclobutyl-2-methoxypyridine (1.19 g, 43%) as a colorless oil. $^1$H-NMR (CDCl$_3$, 300 MHz): 1.75-1.86 (m, 1H), 1.96-2.09 (m, 3H), 2.22-2.33 (m, 2H), 3.50-3.62 (m, 1H), 3.88 (s, 3H), 7.48 (s, 1H), 7.99 (s, 1H) ppm. LC-MS: $C_{10}H_{12}BrNO$ [M+H]$^+$: 242/244.

Bis(neopentyl glycolato)diboron (4.67 g, 20.69 mmol), potassium acetate (2.03 g, 20.69 mmol) and PdCl$_2$[P(o-Tol)$_3$]$_2$ (0.54 g, 0.69 mmol) were added to a solution of 5-bromo-3-cyclobutyl-2-methoxypyridine (1.67 g, 6.9 mmol) in anhydrous DMSO (25 mL) under $N_2$. The reaction mixture was stirred at 80° C. for 30 min. After cooling to rt, the reaction mixture was diluted with EA, filtered on a pad of celite and washed with sat. aq. $NaHCO_3$. The aqueous layer was reextracted with EA (3×). Combined organic layers were washed with water (2×) and brine (3×) and dried over $Na_2SO_4$. The solids were removed by filtration and the filtrate was evaporated to dryness. The crude mixture was purified by flash chromatography on silica gel (0 to 10% EA in CyH) to give 3-cyclobutyl-5-(5,5-dimethyl-1,3,2-dioxaborinan-2-yl)-2-methoxypyridine (1.63 g, 86%) as a yellow oil. $^1$H-NMR (CDCl$_3$, 400 MHz): 1.00 (s, 6H), 1.75-1.86 (m, 1H), 1.95-2.12 (m, 3H), 2.24-2.31 (m, 2H), 3.54-3.63 (m, 1H), 3.73 (s, 4H), 3.93 (s, 3H), 7.75 (d, J=1.6 Hz, 1H), 8.34 (d, J=1.6 Hz, 1H) ppm.

A solution of oxo(sodioperoxy)borane tetrahydrate (1.79 g, 11.63 mmol) in $H_2O$ (34 mL) was added to a solution of 3-cyclobutyl-5-(5,5-dimethyl-1,3,2-dioxaborinan-2-yl)-2-methoxypyridine (1.6 g, 5.81 mmol) in THF (68 mL) under $N_2$. The reaction mixture was stirred at rt for 1 h. The reaction mixture was quenched by sat. aq. $Na_2S_2O_3$ and extracted with EA (2×). Combined organic layers were washed with brine and dried over $Na_2SO_4$. The solids were removed by filtration and the filtrate was evaporated to dryness. The crude mixture was purified by flash chromatography on silica gel (0 to 20% EA in CyH) to give 5-cyclobutyl-6-methoxypyridin-3-ol (0.79 g, 76%) as a colorless oil. $^1$H-NMR (CDCl$_3$, 400 MHz): 1.75-1.86 (m, 1H), 1.95-2.06 (m, 3H), 2.24-2.31 (m, 2H), 3.51-3.60 (m, 1H), 3.86 (s, 3H), 6.21 (br s, 1H), 7.06 (d, J=2.4 Hz, 1.2 Hz, 1H), 7.55 (d, J=2.8 Hz, 1H) ppm. LC-MS: $C_{10}H_{13}NO_2$ [M+H]$^+$: 180.

DIPEA (1.97 mL, 11.94 mmol) was added to a solution of 5-cyclobutyl-6-methoxypyridin-3-ol (1.07 g, 5.97 mmol) and 1,3-dichloro-2-fluoro-5-nitrobenzene (1.25 g, 5.97 mmol) in anhydrous DMF (50 mL) under $N_2$. The reaction mixture was stirred at rt for 18 h. The reaction mixture was then diluted with water. The resulting precipitate was collected by filtration, washed with water and dried under vacuum to give 3-cyclobutyl-5-(2,6-dichloro-4-nitrophenoxy)-2-methoxypyridine (2.0 g, 91%) as a beige solid. $^1$H-NMR (CDCl$_3$, 400 MHz): 1.75-1.86 (m, 1H), 1.95-2.06 (m, 3H), 2.24-2.31 (m, 2H), 3.54-3.62 (m, 1H), 3.87 (s, 3H), 7.10-7.12 (m, 1H), 7.40 (d, J=2.8 Hz, 1H), 8.28 (s, 2H) ppm. LC-MS: $C_{16}H_{14}Cl_2N_2O_4$ [M+H]$^+$: 369.

Fe (1.51 g, 27.08 mmol) was added to a solution of 3-cyclobutyl-5-(2,6-dichloro-4-nitrophenoxy)-2-methoxypyridine (2 g, 5.42 mmol) and $NH_4Cl$ (2.9 g, 54.17 mmol) in EtOH (29 mL) and water (14.5 mL) under $N_2$. The reaction mixture was stirred at 70° C. for 3 h. After cooling to rt, the reaction mixture was diluted with EA and filtered on a pad of celite. The filtrate was evaporated to dryness and the residue was taken up in EA and washed with brine. The organic layer was dried over $Na_2SO_4$. The solids were removed by filtration and the filtrate was evaporated to dryness to give 3,5-dichloro-4-((5-cyclobutyl-6-methoxypyridin-3-yl)oxy)aniline (1.53 g, 83%) as a yellow solid. $^1$H-NMR (DMSO-$d_6$, 400 MHz): 1.72-1.79 (m, 1H), 1.93-2.04 (m, 3H), 2.19-2.27 (m, 2H), 3.49-3.57 (m, 1H), 3.79 (s, 3H), 5.66 (br s, 2H), 6.71 (s, 2H), 7.10-7.13 (m, 1H), 7.39 (d, J=2.8 Hz, 1H) ppm. LC-MS: $C_{16}H_{16}Cl_2N_2O_2$ [M+H]$^+$: 339.

A solution of $NaNO_2$ (97.8 mg, 1.42 mmol) in water (13 mL) was added to a solution of 3,5-dichloro-4-((5-cyclobutyl-6-methoxypyridin-3-yl)oxy)aniline (229 mg, 0.68 mmol) in HCl 37% (5.9 mL), acetic acid (18 mL) and water (13 mL) at 0° C. under $N_2$. The reaction mixture was stirred at 0° C. for 30 min. In parallel, a solution of ethyl N-(2-cyanoacetyl)carbamate (158 mg, 1.013 mmol) in water (17 mL) and pyridine (5.9 mL) was stirred at 0° C. for 15 min. The first reaction mixture was quickly added to the second one. The resulting reaction mixture was stirred at 0° C. for 1 h. The precipitate was then collected by filtration, washed with water and dried under vacuum to give ethyl (2-cyano-2-(2-(3,5-dichloro-4-((5-cyclobutyl-6-methoxypyridin-3-yl)oxy)phenyl)hydrazineylidene)acetyl)carbamate (281 mg, 82%) as a red solid which was used as such in the next step. $^1$H-NMR (DMSO-$d_6$, 400 MHz): 1.27 (t, J=7.2 Hz, 3H), 1.73-1.80 (m, 1H), 1.95-2.05 (m, 3H), 2.19-2.27 (m, 2H), 3.50-3.60 (m, 1H), 3.81 (s, 3H), 4.20 (q, J=7.2 Hz, 2H), 7.20 (dd, J=2.8 Hz, 0.8 Hz, 1H), 7.46 (d, J=2.8 Hz, 1H), 8.03 (s, 2H), 10.89 (br s, 1H) ppm. LC-MS: $C_{22}H_{21}Cl_2N_5O_5$ [M+H]$^+$: 506.

Sodium acetate (364 mg, 4.44 mmol) was added to a solution of ethyl (2-cyano-2-(2-(3,5-dichloro-4-((5-cyclobutyl-6-methoxypyridin-3-yl)oxy)phenyl)hydrazineylidene)acetyl) carbamate (281 mg, 0.55 mmol) in acetic acid (5 mL) under $N_2$. The reaction mixture was stirred at 120° C. for 30 min. The reaction mixture was then cooled at 0° C., diluted with water and stirred for 30 min. The resulting precipitate was collected by filtration, washed with water and dissolved in DCM. The organic layer was washed with brine and dried over $Na_2SO_4$. The solids were removed by filtration and the filtrate was evaporated to dryness to give 2-(3,5-dichloro-4-((5-cyclobutyl-6-methoxypyridin-3-yl)oxy)phenyl)-3,5-dioxo-2,3,4,5-tetrahydro-1,2,4-triazine-6-carbonitrile (255 mg, 100%) as a red solid which was used as such in the next step. $^1$H-NMR (DMSO-$d_6$, 400 MHz): 1.73-1.80 (m, 1H), 1.89-2.07 (m, 3H), 2.19-2.29 (m, 2H), 3.52-3.61 (m, 1H), 3.82 (s, 3H), 7.29 (d, J=3.2 Hz, 1H), 7.50 (d, J=3.2 Hz, 1H), 7.81 (s, 2H), 13.26 (br s, 1H) ppm. LC-MS: $C_{20}H_{15}Cl_2N_5O_4$ [M+H]$^+$: 460.

A solution of 2-(3,5-dichloro-4-((5-cyclobutyl-6-methoxypyridin-3-yl)oxy)phenyl)-3,5-dioxo-2,3,4,5-tetrahydro-1,2,4-triazine-6-carbonitrile (253.15 mg, 0.55 mmol) in conc. HCl (0.45 mL) and AcOH (3 mL) was stirred at 120° C. under $N_2$ for 2 h. After cooling to rt, the reaction mixture was diluted with water. The resulting precipitate was collected by filtration, washed with water and dried under vacuum to give 2-(3,5-dichloro-4-((5-cyclobutyl-6-oxo-1,6-dihydropyridin-3-yl)oxy)phenyl)-3,5-dioxo-2,3,4,5-tetrahydro-1,2,4-triazine-6-carboxylic acid (204 mg, 80%) as a beige solid which was used in the next step without further purification. $^1$H-NMR (DMSO-$d_6$, 400 MHz): 1.72-1.80 (m, 1H), 1.89-2.05 (m, 3H), 2.14-2.24 (m, 2H), 3.41-3.52 (m, 1H), 6.69 (d, J=2.4 Hz, 1H), 7.27 (d, J=2.4 Hz, 1H), 7.82 (s, 2H), 12.68 (br s, 1H) ppm. LC-MS: $C_{19}H_{14}Cl_2N_4O_6$ [M+H]$^+$: 465.

Triethylamine (0.24 mL, 1.75 mmol) and DPPA (362 mg, 0.28 mL, 1.32 mmol) were added to a solution of 2-(3,5-dichloro-4-((5-cyclobutyl-6-oxo-1,6-dihydropyridin-3-yl)oxy)phenyl)-3,5-dioxo-2,3,4,5-tetrahydro-1,2,4-triazine-6-carboxylic acid (204 mg, 0.44 mmol) in tBuOH (2 mL) under $N_2$. The reaction mixture was stirred at 85° C. for 1 h. After cooling to rt, the reaction mixture was diluted with sat. aq. $NaHCO_3$ and extracted with EA (2×). Combined organic layers were washed with sat. aq. $NaHCO_3$ and brine and dried over $Na_2SO_4$. The solids were removed by filtration and the filtrate was evaporated to dryness. The crude mixture was purified by flash chromatography on silica gel (1 to 10% MeOH in DCM) to give tert-butyl (2-(3,5-dichloro-4-((5-cyclobutyl-6-oxo-1,6-dihydropyridin-3-yl)oxy)phenyl)-3,5-dioxo-2,3,4,5-tetrahydro-1,2,4-triazin-6-yl)carbamate (91 mg, 39%) as an orange solid. LC-MS: $C_{23}H_{23}Cl_2N_5O_6$ [M+H]$^+$: 536.

HCl 4N in dioxane (0.85 mL) was added to a solution of t-butyl (2-(3,5-dichloro-4-((5-cyclobutyl-6-oxo-1,6-dihydropyridin-3-yl)oxy)phenyl)-3,5-dioxo-2,3,4,5-tetrahydro-1,2,4-triazin-6-yl)carbamate (91 mg, 0.17 mmol) in anhydrous DCM (3.9 mL) under $N_2$. The reaction mixture was stirred at rt for 24 h, at which point extra HCl 4N in dioxane (0.85 mL) was added and stirring at rt was pursued for 3 days to reach full conversion. The reaction mixture was evaporated to dryness and the crude product was purified by flash chromatography on silica gel (1% to 10% MeOH in DCM). The resulting solid was triturated in MeCN and dried under high vacuum to afford 6-amino-2-(3,5-dichloro-4-((5-cyclobutyl-6-oxo-1,6-dihydropyridin-3-yl)oxy)phenyl)-1,2,4-triazine-3,5(2H,4H)-dione (24) (37 mg, 50%) as a white solid. $^1$H-NMR (DMSO-$d_6$, 400 MHz): 1.69-1.80 (m, 1H), 1.87-2.05 (m, 3H), 2.14-2.24 (m, 2H), 3.41-3.52 (m, 1H), 6.53 (s, 2H), 6.61 (br s, 1H), 7.24 (dd, J=3.3 Hz, 1.1 Hz, 1H), 7.89 (s, 2H), 11.17 (br s, 1H), 12.28 (br s, 1H) ppm. LC-MS: $C_{18}H_{15}Cl_2N_5O_4$ [M+H]$^+$: 436.

Example 25

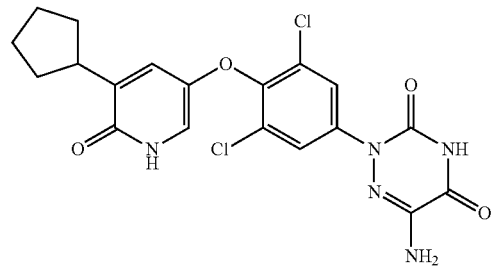

Compound 25

6-amino-2-(3,5-dichloro-4-((5-cyclopentyl-6-oxo-1, 6-dihydropyridin-3-yl)oxy)phenyl)-1,2,4-triazine-3,5 (2H,4H)-dione The titled compound can be prepared according to the procedure to prepare 6-amino-2-(3,5-dichloro-4-((5-cyclobutyl-6-oxo-1,6-dihydropyridin-3-yl)oxy)phenyl)-1,2,4-triazine-3,5(2H,4H)-dione with the exception that cyclopentanone could be used in the first step.

Example 26

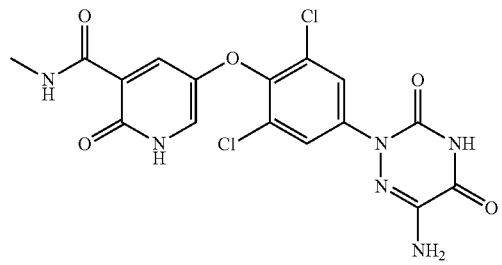

Compound 26

5-(4-(6-amino-3,5-dioxo-4,5-dihydro-1,2,4-triazin-2 (3H)-yl)-2,6-dichlorophenoxy)-N-methyl-2-oxo-1,2-dihydropyridine-3-carboxamide The titled compound could be synthesized by following the procedure used to make 5-(4-(6-amino-3,5-dioxo-4,5-dihydro-1,2,4-triazin-2(3H)-yl)-2,6-dichlorophenoxy)-N-(3, 3-difluorocyclobutyl)-2-oxo-1,2-dihydropyridine-3-carboxamide, starting from 5-(4-amino-2,6-dichlorophenoxy)-N-methyl-2-oxo-1,2-dihydropyridine-3-carboxamide.

Example 27

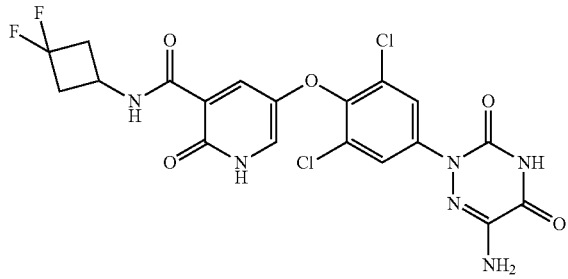

Compound 27

5-(4-(6-Amino-3,5-dioxo-4,5-dihydro-1,2,4-triazin-2 (3H)-yl)-2,6-dichlorophenoxy)-N-(3,3-difluorocyclobutyl)-2-oxo-1,2-dihydropyridine-3-carboxamide was synthesized according to the procedure described to synthesize N-(3,5-dichloro-4-((5-(methylcarbamoyl)-6-oxo-1,6-dihydropyridin-3-yl)oxy)phenyl)-5-oxo-4,5-dihydro-1,2,4-oxadiazole-3-carboxamide, with the exception that 3,3-difluorocyclobutan-1-amine was used in the first step coupling reaction. LCMS: $C_{19}H_{14}Cl_2F_2N_6O_5$ [M+H]$^+$: 515.

Example 28

Compound 28

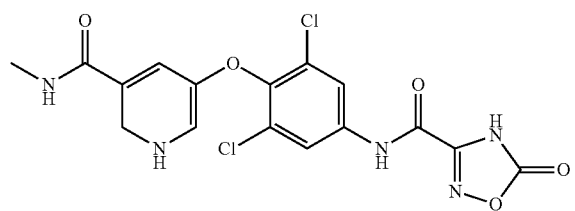

5-Bromo-2-methoxypyridine-3-carboxylic acid (1 g, 4.31 mmol), HATU (1.97 g, 5.17 mmol) and DIPEA (2.14 mL, 12.93 mmol) were added to a suspension of methylamine hydrochloride (0.29 g, 4.31 mmol) in anhydrous DCM (40 mL) under $N_2$. The reaction mixture was stirred at rt for 1 h. The reaction mixture was then diluted with sat. aq. $Na_2CO_3$ and extracted with DCM (3×). The combined organic phases were washed with water and brine and dried over $Na_2SO_4$. The solids were removed by filtration and the filtrate was evaporated to dryness. The crude mixture was purified by flash chromatography on silica gel (0 to 60% EA in CyH) to give 5-bromo-2-methoxy-N-methylnicotinamide (996 mg, 94%) as a white solid. $^1$H-NMR (DMSO-d$_6$, 300 MHz): 2.80 (d, J=4.8 Hz, 3H), 3.95 (s, 3H), 8.20 (d, J=2.4 Hz, 1H), 8.28 (br s, 1H), 8.41 (d, J=2.4 Hz, 1H) ppm. LC-MS: $C_8H_9BrN_2O_2$ [M+H]$^+$: 245/247.

A mixture of 5-bromo-2-methoxy-N-methylnicotinamide (996 mg, 4.064 mmol), bis(neopentyl glycolato)diboron (2.75 g, 12.19 mmol), KOAc (1.20 g, 12.19 mmol) and PdCl$_2$[P(o-Tol)$_3$]$_2$ (319 mg, 0.406 mmol) in anhydrous DMSO (20 mL) was stirred at 85° C. for 1 h under $N_2$. After cooling to rt, the reaction mixture was diluted with EA, washed with brine (2×) and dried over $Na_2SO_4$. The solids were removed by filtration and the filtrate was evaporated to dryness. The crude mixture was purified by flash chromatography on silica gel (0 to 80% EA in CyH) to afford 5-(5,5-dimethyl-1,3,2-dioxaborinan-2-yl)-2-methoxy-N-methylnicotinamide (1.13 g, 100%) as a white solid. $^1$H-NMR (DMSO-d$_6$, 300 MHz): 0.96 (s, 6H), 2.81 (d, J=4.5 Hz, 3H), 3.77 (s, 4H), 3.99 (s, 3H), 8.20 (br s, 1H), 8.36 (s, 1H), 8.48 (s, 1H) ppm.

$H_2O_2$ (30% aq., 10.38 mL, 101.57 mmol) and HOAc (6 mL) were added to a solution of 5-(5,5-dimethyl-1,3,2-dioxaborinan-2-yl)-2-methoxy-N-methylnicotinamide (1.13 g, 4.063 mmol) in THF (25 mL) under $N_2$. The reaction mixture was stirred at rt for 5 h, then was diluted with sat. aq. NaHCO$_3$ (150 mL) and extracted with EA (3×). The combined organic layers were washed with brine and dried over MgSO$_4$. The solids were removed by filtration and the filtrate was evaporated to dryness to afford 5-hydroxy-2-methoxy-N-methylnicotinamide (740 mg, 100%) which was used as such in the next step. $^1$H-NMR (DMSO-d$_6$, 300 MHz): 2.81 (d, J=4.5 Hz, 3H), 3.90 (s, 3H), 7.66 (d, J=3.0 Hz, 1H), 7.82 (d, J=3.0 Hz, 1H), 8.22 (br s, 1H), 9.58 (br s, 1H) ppm. LC-MS: $C_8H_{10}N_2O_3$ [M+H]$^+$: 183.

DIPEA (3.36 mL, 20.31 mmol) was added to a solution of 5-hydroxy-2-methoxy-N-methylnicotinamide (740 mg, 4.062 mmol) and 1,3-dichloro-2-fluoro-5-nitrobenzene (853 mg, 4.062 mmol) in anhydrous DMF (40 mL) under $N_2$. The reaction mixture was stirred at rt for 2 h, then diluted with water (200 mL). The resulting precipitate was collected by filtration, washed with water and dried under vacuum to give 5-(2,6-dichloro-4-nitrophenoxy)-2-methoxy-N-methylnicotinamide (1.04 g, 69%) as a beige solid which was used as such in the next step. $^1$H-NMR (DMSO-d$_6$, 300 MHz): 2.78 (d, J=4.5 Hz, 3H), 3.95 (s, 3H), 7.63 (d, J=3.0 Hz, 1H), 8.11 (d, J=3.0 Hz, 1H), 8.31 (br s, 1H), 8.55 (s, 2H) ppm. LC-MS: $C_{14}H_{11}Cl_2N_3O_5$ [M+H]$^+$: 372.

Fe (0.80 g, 14.38 mmol) was added to a solution of 5-(2,6-dichloro-4-nitrophenoxy)-2-methoxy-N-methylnicotinamide (1.07 g, 2.88 mmol) and NH$_4$Cl (1.54 g, 28.75 mmol) in EtOH (20 mL) and water (12 mL) under $N_2$. The reaction mixture was stirred at 70° C. for 20 h. After cooling to rt, the reaction mixture was diluted with EA and filtered over a pad of celite. The organic layer was washed with brine (2×) and dried over Na$_2$SO$_4$. The solids were removed by filtration and the filtrate was evaporated to dryness to give 5-(4-amino-2,6-dichlorophenoxy)-2-methoxy-N-methylnicotinamide (666 mg, 68%) as a beige solid which was used as such in the next step. $^1$H-NMR (DMSO-d$_6$, 300 MHz): 2.78 (d, J=4.5 Hz, 3H), 3.95 (s, 3H), 5.70 (s, 2H), 6.72 (s, 2H), 7.49 (d, J=3.0 Hz, 1H), 8.01 (d, J=3.0 Hz, 1H), 8.27 (br s, 1H) ppm. LC-MS: $C_{14}H_{13}Cl_2N_3O_3$ [M+H]$^+$: 342.

HBr 48% in water (0.77 mL, 6.809 mmol) was added to a solution of 5-(4-amino-2,6-dichlorophenoxy)-2-methoxy-N-methylnicotinamide (466 mg, 1.36 mmol) in 1,4-dioxane (20 mL) under $N_2$. The reaction mixture was stirred at 60° C. for 2 h, then evaporated to dryness to give 5-(4-amino-2,6-dichlorophenoxy)-N-methyl-2-oxo-1,2-dihydropyridine-3-carboxamide (446 mg, 100%) as a beige solid which was used as such in the next step. LC-MS: $C_{13}H_{11}Cl_2N_3O_3$ [M+H]$^+$: 328.

LiHMDS 1M in THF (13.6 mL, 13.59 mmol) was added to a solution of ethyl 5-oxo-4,5-dihydro-1,2,4-oxadiazole-3-carboxylate (2145 mg, 1.36 mmol) and 5-(4-amino-2,6-dichlorophenoxy)-N-methyl-2-oxo-1,2-dihydropyridine-3-carboxamide (446 mg, 1.36 mmol) in anhydrous THF (7 mL) at rt under $N_2$. The reaction mixture was stirred at rt for 6 h, at which point extra LiHMDS 1M in THF (13.6 mL, 13.59 mmol) was added and stirring at rt was pursued for 16 h. The reaction mixture was then diluted with MeOH and evaporated to dryness. The crude mixture was purified by flash chromatography on silica gel (0 to 10% [MeOH/NH₄OH (9:1)] in DCM) and by Prep. HPLC (10 to 100% MeCN in water [0.2% v/v HCO₂H]) to afford N-(3,5-dichloro-4-((5-(methylcarbamoyl)-6-oxo-1,6-dihydropyridin-3-yl)oxy)phenyl)-5-oxo-4,5-dihydro-1,2,4-oxadiazole-3-carboxamide (28) (164 mg, 27%) as a white solid. ¹H-NMR (DMSO-d₆, 400 MHz): 2.81 (d, J=4.9 Hz, 3H), 7.51 (br s, 1H), 7.96 (d, J=3.8 Hz, 1H), 8.08 (s, 2H), 9.67 (br s, 1H), 11.02 (br s, 1H), 12.59 (br s, 1H), 12.74 (br s, 1H) ppm. LC-MS: $C_{16}H_{11}Cl_2N_5O_6$ [M+H]⁺: 440.

Example 29

Compound 29

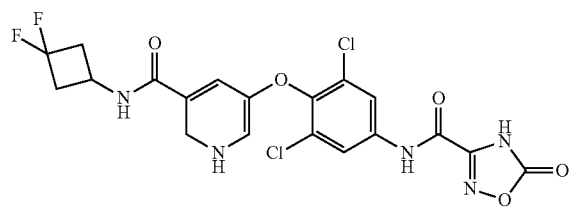

N-(3,5-dichloro-4-((5-((3,3-difluorocyclobutyl)carbamoyl)-6-oxo-1,6-dihydropyridin-3-yl)oxy)phenyl)-5-oxo-4,5-dihydro-1,2,4-oxadiazole-3-carboxamide The titled compound could be made following an analogous procedure to that described for N-(3,5-dichloro-4-((5-(methylcarbamoyl)-6-oxo-1,6-dihydropyridin-3-yl)oxy)phenyl)-5-oxo-4,5-dihydro-1,2,4-oxadiazole-3-carboxamide.

Example 30

Compound 30

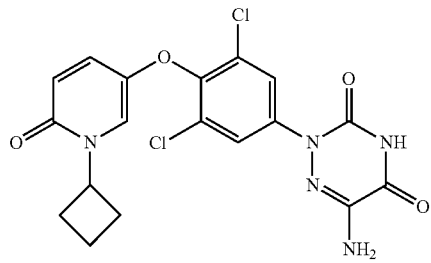

Cs₂CO₃ (36.5 g, 112.07 mmol) and cyclobutyl bromide (21.45 g, 15 mL, 158.88 mmol) were added to a solution of 5-bromo-1,2-dihydropyridin-2-one (15 g, 86.21 mmol) in DME (220 mL) under N₂. The reaction mixture was stirred at 80° C. for 4 days. After cooling to rt, the reaction mixture was diluted with EA, washed with sat. aq. NaHCO₃ and brine and dried over Na₂SO₄. The solids were removed by filtration and the filtrate was evaporated to dryness. The crude mixture was purified by flash chromatography on silica gel (0% to 5% MeOH in DCM) to give 5-bromo-1-cyclobutylpyridin-2(1H)-one (2.45 g, 12%) as a yellow oil. ¹H-NMR (DMSO-d₆, 400 MHz): 1.69-1.77 (m, 2H), 2.25-2.32 (m, 4H), 4.91-5.00 (m, 1H), 6.32 (d, J=9.6 Hz, 1H), 7.49 (dd, J=9.9 Hz, 2.8 Hz, 1H), 7.98 (d, J=2.8 Hz, 1H) ppm. LC-MS: $C_9H_{10}BrNO$ [M+H]⁺: 228/230.

Bis(neopentyl Glycolato)diboron (7.28 g, 32.22 mmol), KOAc (3.16 g, 32.22 mmol) and PdCl₂[P(o-Tol)₃]₂ (0.84 g, 1.074 mmol) were added to a solution of 5-bromo-1-cyclobutylpyridin-2(1H)-one (2.45 g, 10.74 mmol) in anhydrous DMSO (60 mL) under N₂. The reaction mixture was stirred at 85° C. for 1 h. After cooling to rt, the reaction mixture was diluted with EA, washed with brine (2×) and dried over Na₂SO₄. The solids were removed by filtration and the filtrate was evaporated to dryness. The crude product was purified by flash chromatography on silica gel (0 to 40% EA in CyH) to give 1-cyclobutyl-5-(5,5-dimethyl-1,3,2-dioxaborinan-2-yl)pyridin-2(1H)-one (2.49 g, 89%) as a yellow solid. LC-MS: $C_{14}H_{20}BNO_3$ [M(boronic acid)+H]⁺: 194.

H₂O₂ 30% (24.3 mL, 238.39 mmol) and HOAc (13.7 mL, 238.39 mmol) were added to a solution of 1-cyclobutyl-5-(5,5-dimethyl-1,3,2-dioxaborinan-2-yl)pyridin-2(1H)-one (2.49 g, 9.54 mmol) in THF (55 mL) under N₂. The reaction mixture was stirred at rt for 1 h. The reaction mixture was then diluted with sat. aq. NaHCO₃ and extracted with 15% iPrOH in EA (3×). The combined organic layers were washed with sat aq. NaHCO₃ (2×) and brine and dried over Na₂SO₄. The solids were removed by filtration and the filtrate was evaporated to dryness to give 1-cyclobutyl-5-hydroxypyridin-2(1H)-one (1.58 g, 100%) which was used as such in the next step. LC-MS: $C_9H_{11}NO_2$ [M+H]⁺: 166.

DIPEA (15.8 mL, 95.4 mmol) was added to a solution of 1-cyclobutyl-5-hydroxypyridin-2(1H)-one (1.58 g, 9.54 mmol) and 1,3-dichloro-2-fluoro-5-nitrobenzene (2.00 g, 9.54 mmol) in anhydrous DMF (55 mL) under N₂. The reaction mixture was stirred at rt for 1 h. The reaction mixture was then diluted with water and extracted with EA (3×). The combined organic phases were washed with water and brine and dried over Na₂SO₄. The solids were removed by filtration and the filtrate was evaporated to dryness. The crude product was purified by flash chromatography on silica gel (0 to 3% MeOH in DCM) to give 1-cyclobutyl-5-(2,6-dichloro-4-nitrophenoxy)pyridin-2(1H)-one (1.7 g, 50%) as a yellow solid. ¹H-NMR (DMSO-d₆, 400 MHz): 1.67-1.75 (m, 2H), 2.21-2.29 (m, 4H), 4.98-5.07 (m, 1H), 6.38 (d, J=10.0 Hz, 1H), 7.31 (dd, J=10.0 Hz, 3.2 Hz, 1H), 7.57 (d, J=3.2 Hz, 1H), 8.52 (s, 2H) ppm. LC-MS: $C_{15}H_{12}Cl_2N_2O_4$ [M+H]⁺: 355.

Iron (2.67 g, 47.86 mmol) was added to a solution of 1-cyclobutyl-5-(2,6-dichloro-4-nitrophenoxy)pyridin-2(1H)-one (1.7 g, 4.79 mmol) and NH₄Cl (5.12 g, 95.73 mmol) in EtOH (16 mL) and water (16 mL) under N₂. The reaction mixture stirred at 70° C. for 18 h. After cooling to rt, the reaction mixture was filtered over a celite pad and extracted with EA (3×). The combined organic phases were washed with water (2×) and brine and dried over Na₂SO₄. The solids were removed by filtration and the filtrate was evaporated to dryness to give 5-(4-amino-2,6-dichlorophenoxy)-1-cyclobutylpyridin-2(1H)-one (1.45 g, 93%) as a yellow oil which was used as such in the next step. LC-MS: $C_{15}H_{14}Cl_2N_2O_2$ [M+H]⁺: 325.

A solution of NaNO₂ (0.65 g, 9.36 mmol) in water (85 mL) was added to a solution of 5-(4-amino-2,6-dichlorophenoxy)-1-cyclobutylpyridin-2(1H)-one (1.45 g, 4.46 mmol) in HCl 37% (38 mL), AcOH (120 mL) and water (85 mL) at 0° C. under N₂. The reaction mixture was stirred at 0° C. for 30 min. In parallel, a solution of N-cyanoacetylurethane (1.04 g, 6.69 mmol) in pyridine (38 mL) and water (72 mL) was stirred at 0° C. for 15 min. Then, the first reaction mixture was rapidly added to this solution and the resulting reaction mixture was stirred at 0° C. for 1 h. The reaction mixture was warmed to rt and was diluted with more water. The precipitate was collected by filtration, washed with water and dried under vacuum to give ethyl (2-cyano-2-(2-(3,5-dichloro-4-((1-cyclobutyl-6-oxo-1,6-dihydropyridin-3-yl)oxy)phenyl)hydrazineylidene) acetyl) carbamate (2.2 g, 100%) as a red solid which was used as such for the next step. LC-MS: $C_{21}H_{19}Cl_2N_5O_5$ $[M+H]^+$: 492.

NaOAc (3.67 g, 44.69 mmol) was added to a mixture of ethyl (2-cyano-2-(2-(3,5-dichloro-4-((1-cyclobutyl-6-oxo-1,6-dihydropyridin-3-yl)oxy)phenyl)hydrazineylidene)acetyl) carbamate (2.2 g, 4.47 mmol) in AcOH (55 mL) under $N_2$. The reaction mixture was stirred at 120° C. for 1 h. After cooling to rt, the reaction mixture was diluted with water. The resulting precipitate was collected by filtration, washed with water and dried under vacuum to give 2-(3,5-dichloro-4-((1-cyclobutyl-6-oxo-1,6-dihydropyridin-3-yl)oxy)phenyl)-3,5-dioxo-2,3,4,5-tetrahydro-1,2,4-triazine-6-carbonitrile (620 mg, 31%) as a red solid. The filtrate was diluted with sat. aq. $NaHCO_3$ and extracted with 15% iPrOH in EA (3×). The combined organic layers were washed with sat. aq. $NaHCO_3$ (2×) and brine and dried over $Na_2SO_4$. The solids were removed by filtration and the filtrate was evaporated to dryness to give more of 2-(3,5-dichloro-4-((1-cyclobutyl-6-oxo-1,6-dihydropyridin-3-yl)oxy)phenyl)-3,5-dioxo-2,3,4,5-tetrahydro-1,2,4-triazine-6-carbonitrile (1.37 g, 69%) as a red solid. $^1$H-NMR (DMSO-$d_6$, 400 MHz): 1.70-1.77 (m, 2H), 2.21-2.29 (m, 4H), 4.96-5.06 (m, 1H), 6.35 (d, J=9.9 Hz, 1H), 7.24 (dd, J=9.9 Hz, 3.4 Hz, 1H), 7.61 (d, J=3.2 Hz, 1H), 7.79 (s, 2H), 13.27 (br s, 1H) ppm. LC-MS: $C_{19}H_{13}Cl_2N_5O_4$ $[M+H]^+$: 446.

A mixture of 2-(3,5-dichloro-4-((1-cyclobutyl-6-oxo-1,6-dihydropyridin-3-yl)oxy)phenyl)-3,5-dioxo-2,3,4,5-tetrahydro-1,2,4-triazine-6-carbonitrile (1.99 g, 4.47 mmol) and HCl 37% (3.73 mL, 44.7 mmol) in AcOH (24 mL) was stirred at 120° C. for 4 h under $N_2$. The reaction mixture was cooled to 0° C. and diluted with water. The resulting precipitate was collected by filtration, washed with water and dried under vacuum to give 2-(3,5-dichloro-4-((1-cyclobutyl-6-oxo-1,6-dihydropyridin-3-yl)oxy)phenyl)-3,5-dioxo-2,3,4,5-tetrahydro-1,2,4-triazine-6-carboxylic acid (1.20 g, 58%) as a light brown solid which was used as such in the next step. $^1$H-NMR (DMSO-$d_6$, 400 MHz): 1.68-1.77 (m, 2H), 2.18-2.34 (m, 4H), 4.96-5.06 (m, 1H), 6.35 (d, J=10.0 Hz, 1H), 7.23 (dd, J=10.0 Hz, 3.2 Hz, 1H), 7.61 (d, J=3.2 Hz, 1H), 7.82 (s, 2H), 12.68 (br s, 1H) ppm. LC-MS: $C_{19}H_{14}Cl_2N_4O_6$ $[M+H]^+$: 465.

Triethylamine (1.44 mL, 10.35 mmol) and DPPA (1.67 mL, 7.76 mmol) were added to a solution of 2-(3,5-dichloro-4-((1-cyclobutyl-6-oxo-1,6-dihydropyridin-3-yl)oxy)phenyl)-3,5-dioxo-2,3,4,5-tetrahydro-1,2,4-triazine-6-carboxylic acid (1.20 g, 2.59 mmol) in tert-butanol (12 mL) under $N_2$. The reaction mixture was stirred at 85° C. for 3 h. After cooling to rt, the reaction mixture was quenched with sat. aq. $NaHCO_3$ and extracted with EA (2×). The combined organic layers were washed sat. aq. $NaHCO_3$ (3×) and brine and dried over $Na_2SO_4$. The solids were removed by filtration and the filtrate was evaporated to dryness. The crude mixture was purified by flash chromatography on silica gel (0 to 5% MeOH in DCM) to give tert-butyl (2-(3,5-dichloro-4-((1-cyclobutyl-6-oxo-1,6-dihydropyridin-3-yl)oxy)phenyl)-3,5-dioxo-2,3,4,5-tetrahydro-1,2,4-triazin-6-yl)carbamate (976 mg, 70%) as an orange solid. $^1$H-NMR (DMSO-$d_6$, 400 MHz): 1.45 (s, 9H), 1.68-1.77 (m, 2H), 2.17-2.33 (m, 4H), 4.96-5.05 (m, 1H), 6.36 (d, J=10.0 Hz, 1H), 7.21 (dd, J=10.0 Hz, 3.2 Hz, 1H), 7.56 (d, J=3.2 Hz, 1H), 7.90 (s, 2H), 9.11 (s, 1H), 12.61 (br s, 1H) ppm. LC-MS: $C_{23}H_{23}Cl_2N_5O_6$ $[M+H]^+$: 536.

HCl 4N in dioxane (9.1 mL, 36.39 mmol) was added to a solution of tert-butyl (2-(3,5-dichloro-4-((1-cyclobutyl-6-oxo-1,6-dihydropyridin-3-yl)oxy)phenyl)-3,5-dioxo-2,3,4,5-tetrahydro-1,2,4-triazin-6-yl)carbamate (976 mg, 1.82 mmol) in anhydrous DCM (42 mL). The reaction mixture was stirred at rt for 26 h. The reaction mixture was evaporated to dryness and the crude product was purified by flash chromatography on silica gel (0 to 5% MeOH in DCM). The resulting solid was triturated with MeCN and dried under high vacuum to give 6-amino-2-(3,5-dichloro-4-((1-cyclobutyl-6-oxo-1,6-dihydropyridin-3-yl)oxy)phenyl)-1,2,4-triazine-3,5(2H,4H)-dione (30) (475 mg, 60%) as a white solid. $^1$H-NMR (DMSO-$d_6$, 400 MHz): 1.66-1.80 (m, 2H), 2.14-2.33 (m, 4H), 4.92-5.08 (m, 1H), 6.36 (d, J=9.7 Hz, 1H), 6.54 (s, 2H), 7.20 (dd, J=9.8 Hz, 3.3 Hz, 1H), 7.52 (d, J=3.3 Hz, 1H), 7.89 (s, 2H), 12.28 (br s, 1H) ppm. LC-MS: $C_{18}H_{15}Cl_2N_5O_4$ $[M+H]^+$: 436.

Example 31

Compound 31

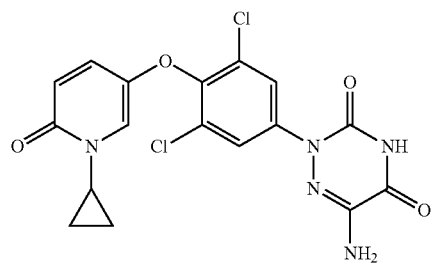

A mixture of 5-(2,6-dichloro-4-nitrophenoxy)pyridin-2(1H)-one (2.56 g, 8.50 mmol), potassium cyclopropyltrifluoroboranuide (3.77 g, 25.51 mmol), cupric acetate (0.39 g, 2.13 mmol), o-phenanthroline (0.19 g, 1.06 mmol) and $K_2CO_3$ (2.35 g, 17.00 mmol) in toluene (26 mL) and $H_2O$ (8 mL) was stirred at 70° C. under air for 3 days. After cooling to rt, the reaction mixture was diluted with sat. aq. $NaHCO_3$ and EA. The layers were separated and the aqueous layer was extracted with EA. The combined organic layers were washed with brine and dried over $Na_2SO_4$. The solids were removed by filtration and the filtrate was evaporated to dryness. The crude mixture was purified by chromatography on silica gel (up to 2% MeOH in DCM) to give 1-cyclopropyl-5-(2,6-dichloro-4-nitrophenoxy)pyridin-2(1H)-one (1.64 g, 57%) as a yellow solid. $^1$H-NMR (CDCl$_3$, 400 MHz): 0.77-0.81 (m, 2H), 1.07-1.12 (m, 2H), 3.24-3.30 (m, 1H), 6.52 (d, J=10.0 Hz, 1H), 6.88 (d, J=3.2 Hz, 1H), 7.13 (dd, J=10.0 Hz, 3.2 Hz, 1H), 8.29 (s, 2H) ppm. LC-MS: $C_{14}H_{10}C_{12}N_2O_4$ $[M+H]^+$: 341.

Fe (1.34 g, 24.04 mmol) was added to a solution of 1-cyclopropyl-5-(2,6-dichloro-4-nitrophenoxy)pyridin-2(1H)-one (1.64 g, 4.81 mmol) and $NH_4Cl$ (2.57 g, 48.07 mmol) in EtOH (26 mL) and water (13 mL) under $N_2$. The reaction mixture was stirred at 70° C. for 3 h. After cooling to rt, the reaction mixture was filtered over a pad of celite and the filtrate was evaporated to dryness. The residue was dissolved in EA, washed with brine and dried over $Na_2SO_4$. The solids were removed by filtration and the filtrate was evaporated to dryness to give 5-(4-amino-2,6-dichlorophenoxy)-1-cyclopropylpyridin-2(1H)-one (1.50 g, 100%) as an orange solid which was used as such in the next step. $^1$H-NMR (DMSO-$d_6$, 400 MHz): 0.71-0.75 (m, 2H), 0.93-0.99 (m, 2H), 3.23-3.29 (m, 1H), 5.66 (s, 2H), 6.35 (d, J=10.0 Hz, 1H), 6.68 (s, 2H), 6.97 (d, J=3.2 Hz, 1H), 7.19 (dd, J=10.0 Hz, 3.2 Hz, 1H) ppm. LC-MS: $C_{14}H_{12}Cl_2N_2O_2$ [M+H]$^+$: 311.

A solution of NaNO$_2$ (0.76 g, 11.01 mmol) in water (104 mL) was added to a solution of 5-(4-amino-2,6-dichlorophenoxy)-1-cyclopropylpyridin-2(1H)-one (1.5 g, 4.81 mmol) in HCl 37% (46 mL), acetic acid (139 mL) and water (104 mL) at 0° C. under N$_2$. The reaction mixture was stirred at 0° C. for 30 min. In parallel, a solution of ethyl N-(2-cyanoacetyl)carbamate (1.23 g, 7.88 mmol) in water (133 mL) and pyridine (46 mL) was stirred at 0° C. for 15 min. The first reaction mixture was quickly added to the second one. The resulting reaction mixture was stirred at 0° C. for 20 min. The reaction mixture was then diluted with more water. The precipitate was collected by filtration, washed with water and dried under vacuum to give ethyl (2-cyano-2-(2-(3,5-dichloro-4-((1-cyclopropyl-6-oxo-1,6-dihydropyridin-3yl)oxy)phenyl)hydrazineylidene) acetyl)carbamate (2.31 g, 100%) as a red solid which was used as such in the next step. LC-MS: $C_{20}H_{17}Cl_2N_5O_5$ [M+H]$^+$: 478.

Sodium acetate (3.18 g, 38.76 mmol) was added to a solution of (2-cyano-2-(2-(3,5-dichloro-4-((1-cyclopropyl-6-oxo-1,6-dihydropyridin-3yl)oxy)phenyl)hydrazineylidene)acetyl) carbamate (2.3 g, 4.809 mmol) in acetic acid (47 mL) under N$_2$. The reaction mixture was stirred at 120° C. for 90 min. The reaction mixture was cooled to 0° C. and diluted with water. The mixture was stirred for 30 min at 0° C. The resulting precipitate was collected by filtration and washed with water. The solid was then dissolved in DCM, washed with brine and dried over Na$_2$SO$_4$. The solids were removed by filtration and the filtrate was evaporated to dryness to afford 2-(3,5-dichloro-4-((1-cyclopropyl-6-oxo-1,6-dihydropyridin-3-yl)oxy)phenyl)-3,5-dioxo-2,3,4,5-tetrahydro-1,2,4-triazine-6-carbonitrile (1.85 g, 89%) as a red solid which was used as such in the next step. LC-MS: $C_{18}H_{11}Cl_2N_5O_4$ [M+H]$^+$: 432.

A mixture of 2-(3,5-dichloro-4-((1-cyclopropyl-6-oxo-1,6-dihydropyridin-3-yl)oxy)phenyl)-3,5-dioxo-2,3,4,5-tetrahydro-1,2,4-triazine-6-carbonitrile (1.85 g, 4.28 mmol) and HCl 37% (3.57 mL, 42.80 mmol) in AcOH (23 mL) was stirred at 120° C. for 5 days under N$_2$. The reaction mixture was cooled to 0° C. and diluted with water. The resulting precipitate was collected by filtration, washed with water and dried under vacuum to give 2-(3,5-dichloro-4-((1-cyclopropyl-6-oxo-1,6-dihydropyridin-3-yl)oxy)phenyl)-3,5-dioxo-2,3,4,5-tetrahydro-1,2,4-triazine-6-carboxylic acid (1.52 g, 79%) as a light brown solid which was used as such in the next step. LC-MS: $C_{18}H_{12}Cl_2N_4O_6$ [M+H]$^+$: 451.

Triethylamine (1.87 mL, 13.47 mmol) and DPPA (2.78 g, 2.18 mL, 10.10 mmol) were added to a solution of 2-(3,5-dichloro-4-((1-cyclopropyl-6-oxo-1,6-dihydropyridin-3-yl)oxy)phenyl)-3,5-dioxo-2,3,4,5-tetrahydro-1,2,4-triazine-6-carboxylic acid (1.52 g, 3.37 mmol) in t-butanol (15 mL) under N$_2$. The reaction mixture was stirred at 85° C. for 1 h. After cooling to rt, the reaction mixture was quenched with sat. aq. NaHCO$_3$ and extracted with EA (2×). The combined organic layers were washed with sat. aq. NaHCO$_3$ and brine and dried over Na$_2$SO$_4$. The solids were removed by filtration and the filtrate was evaporated to dryness. The crude mixture was purified by flash chromatography on silica gel (1 to 5% MeOH in DCM) to give t-butyl (2-(3,5-dichloro-4-((1-cyclopropyl-6-oxo-1,6-dihydropyridin-3-yl)oxy)phenyl)-3,5-dioxo-2,3,4,5-tetrahydro-1,2,4-triazin-6-yl)carbamate (531 mg, 30%) as a light yellow solid. $^1$H-NMR (DMSO-$d_6$, 400 MHz): 0.76-0.81 (m, 2H), 0.94-0.99 (m, 2H), 3.26-3.31 (m, 1H), 6.38 (d, J=10.0 Hz, 1H), 7.23-7.29 (m, 2H), 7.88 (s, 2H), 9.12 (s, 1H), 12.61 (s, 1H) ppm. LC-MS: $C_{22}H_{21}Cl_2N_5O_6$ [M+H]$^+$: 522.

HCl, 4N in dioxane, (5.08 mL) was added to a solution of t-butyl (2-(3,5-dichloro-4-((1-cyclopropyl-6-oxo-1,6-dihydropyridin-3-yl)oxy)phenyl)-3,5-dioxo-2,3,4,5-tetrahydro-1,2,4-triazin-6-yl)carbamate (531 mg, 1.017 mmol) in anhydrous DCM (23 mL) under N$_2$. The reaction mixture was stirred at rt for 20 h, at which point extra HCl 4N in dioxane (5.08 mL) was added and stirring at rt was pursued for 1 h to reach full conversion. The reaction mixture was evaporated to dryness and the crude product was purified by flash chromatography on silica gel (1% to 8% MeOH in DCM). The resulting light yellow solid was triturated in EtOH to give 6-amino-2-(3,5-dichloro-4-((1-cyclopropyl-6-oxo-1,6-dihydropyridin-3-yl)oxy)phenyl)-1,2,4-triazine-3,5(2H, 4H)-dione (31) (232 mg, 54%) as a white solid. $^1$H-NMR (DMSO-$d_6$, 400 MHz): 0.74-0.80 (m, 2H), 0.93-1.00 (m, 2H), 3.25-3.32 (m, 1H), 6.38 (d, J=10.0 Hz, 1H), 6.54 (s, 2H), 7.18 (d, J=3.5 Hz, 1H), 7.25 (dd, J=10.0 Hz, 3.5 Hz, 1H), 7.89 (s, 2H), 12.26 (s, 1H) ppm. LC-MS: $C_{17}H_{13}Cl_2N_5O_4$ [M+H]$^+$: 422.

Example 32

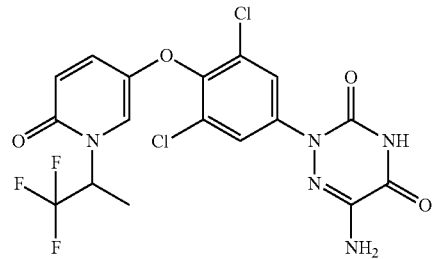

Compound 32

DIAD (10.07 g, 9.88 mL, 49.82 mmol) was added to a solution of PPh$_3$ (13.07 g, 49.82 mmol), 1,1,1-trifluoropropan-2-ol (3.79 g, 33.21 mmol) and 5-(2,6-dichloro-4-nitrophenoxy)pyridin-2(1H)-one (10 g, 33.21 mmol) in anhydrous toluene (250 mL) at 0° C. under N$_2$. The reaction mixture was stirred at 100° C. for 1 h. After cooling to rt, the reaction mixture was diluted with water and extracted with EA (3×). The combined organic layers were washed with brine and dried over Na$_2$SO$_4$. The solids were removed by filtration and the filtrate was evaporated to dryness. The crude mixture was purified by flash chromatography on silica gel (0 to 5% EA in CyH) to give 5-(2,6-dichloro-4-nitrophenoxy)-1-(1,1,1-trifluoropropan-2-yl)pyridin-2(1H)-one (3.69 g, 28%) as a white solid. $^1$H-NMR (DMSO-$d_6$, 400 MHz): 1.42 (d, J=6.6 Hz, 3H), 5.72-5.80 (m, 1H), 6.97 (d, J=9.2 Hz, 1H), 7.50 (dd, J=9.2 Hz, 3.1 Hz, 1H), 7.92 (d, J=3.1 Hz, 1H), 8.55 (s, 2H) ppm. LC-MS: $C_{14}H_9Cl_2F_3N_2O_4$ [M+H]$^+$: 397.

Iron (4.23 g, 75.79 mmol) was added to a solution of 5-(2,6-dichloro-4-nitrophenoxy)-1-(1,1,1-trifluoropropan-2-yl)pyridin-2(1H)-one (3.01 g, 7.58 mmol) and NH$_4$Cl (8.11 g, 151.6 mmol) in EtOH (20 mL) and water (20 mL) under N$_2$. The reaction mixture was stirred at 70° C. for 3 h. After cooling to rt, the reaction mixture was filtered over a pad of celite and the filtrate was extracted with EA (3×). The combined organic phases were washed with water (2×) and brine and dried over Na$_2$SO$_4$. The solids were removed by filtration and the filtrate was evaporated to dryness. The crude mixture was purified by chromatography on silica gel (0% to 10% [MeOH/NH$_4$OH (9:1)] in DCM) to give 5-(4-amino-2,6-dichlorophenoxy)-1-(1,1,1-trifluoropropan-2-yl)pyridin-2(1H)-one (1.92 g, 69%) as a white solid. $^1$H-NMR (DMSO-d$_6$, 400 MHz): 1.42 (d, J=6.6 Hz, 3H), 5.69 (s, 2H), 5.72-5.80 (m, 1H), 6.71 (s, 2H), 6.90 (d, J=9.0 Hz, 1H), 7.27 (dd, J=9.0 Hz, 3.1 Hz, 1H), 7.76 (d, J=3.1 Hz, 1H) ppm. LC-MS: C$_{14}$H$_{11}$Cl$_2$F$_3$N$_2$O$_2$ [M+H]$^+$: 367.

A solution of NaNO$_2$ (0.76 g, 10.98 mmol) in water (100 mL) was added to a solution of 5-(4-amino-2,6-dichlorophenoxy)-1-(1,1,1-trifluoropropan-2-yl)pyridin-2(1H)-one (1.92 g, 5.23 mmol) in HCl 37% (44 mL), AcOH (150 mL) and water (100 mL) at 0° C. under N$_2$. The reaction mixture was stirred at 0° C. for 45 min. In parallel, a solution of N-Cyanoacetylurethane (1.22 g, 7.84 mmol) in pyridine (44 mL) and water (85 mL) was stirred at 0° C. for 15 min, then was added to the first reaction mixture. The resulting mixture was stirred at 0° C. for 1 h and was then diluted with more water. The precipitate was collected by filtration, washed with water and dried under vacuum to give ethyl (2-cyano-2-(2-(3,5-dichloro-4-((6-oxo-1-(1,1,1-trifluoropropan-2-yl)-1,6-dihydropyridin-3-yl)oxy)phenyl)hydrazineylidene)acetyl)carbamate (2.02 g, 72%) as an orange solid which was used as such in the next step. LC-MS: C$_{20}$H$_{16}$Cl$_2$F$_3$N$_5$O$_5$ [M+H]$^+$: 534.

NaOAc (3.10 g, 37.81 mmol) was added to a solution of ethyl (2-cyano-2-(2-(3,5-dichloro-4-((6-oxo-1-(1,1,1-trifluoropropan-2-yl)-1,6-dihydropyridin-3-yl)oxy)phenyl)hydrazineylidene)acetyl)carbamate (2.02 g, 3.78 mmol) in AcOH (46 mL) under N$_2$. The reaction mixture was stirred at 120° C. for 1 h. After cooling to rt, the reaction mixture was diluted with water. The resulting precipitate was collected by filtration, washed with water and dried under vacuum to give 2-(3,5-dichloro-4-((6-oxo-1-(1,1,1-trifluoropropan-2-yl)-1,6-dihydropyridin-3-yl)oxy)phenyl)-3,5-dioxo-2,3,4,5-tetrahydro-1,2,4-triazine-6-carbonitrile (1.42 g, 77%) as an orange solid which was used as such in the next step. $^1$H-NMR (DMSO-d$_6$, 300 MHz): 1.44 (d, J=6.6 Hz, 3H), 5.72-5.80 (m, 1H), 6.94 (d, J=9.0 Hz, 1H), 7.41 (dd, J=9.0 Hz, 3.1 Hz, 1H), 7.83 (s, 2H), 7.90 (d, J=3.1 Hz, 1H), 12.01 (br s, 1H) ppm. LC-MS: C$_{18}$H$_{10}$Cl$_2$F$_3$N$_5$O$_4$ [M+H]$^+$: 488.

HCl 37% (2.42 mL, 29.09 mmol) was added to a solution of 2-(3,5-dichloro-4-((6-oxo-1-(1,1,1-trifluoropropan-2-yl)-1,6-dihydropyridin-3-yl)oxy)phenyl)-3,5-dioxo-2,3,4,5-tetrahydro-1,2,4-triazine-6-carbonitrile (1.42 g, 2.91 mmol) in AcOH (40 mL) under N$_2$. The reaction mixture was stirred at 130° C. for 24 h. After cooling to rt, the reaction mixture was diluted with water. The resulting precipitate was collected by filtration, washed with water and dried under vacuum to give 2-(3,5-dichloro-4-((6-oxo-1-(1,1,1-trifluoropropan-2-yl)-1,6-dihydropyridin-3-yl)oxy)phenyl)-3,5-dioxo-2,3,4,5-tetrahydro-1,2,4-triazine-6-carboxylic acid (1.36 g, 92%) as a red solid which was used as such in the next step. $^1$H-NMR (DMSO-d$_6$, 400 MHz): 1.44 (d, J=6.6 Hz, 3H), 5.72-5.80 (m, 1H), 6.94 (d, J=9.0 Hz, 1H), 7.42 (dd, J=9.0 Hz, 3.1 Hz, 1H), 7.86 (s, 2H), 7.92 (d, J=3.1 Hz, 1H), 12.72 (br s, 1H) ppm. LC-MS: C$_{18}$H$_{11}$Cl$_2$F$_3$N$_4$O$_6$ [M+H]$^+$: 507.

Triethylamine (2.98 mL, 21.45 mmol) and DPPA (4.43 g, 3.47 mL, 16.09 mmol) were added to a solution of 2-(3,5-dichloro-4-((6-oxo-1-(1,1,1-trifluoropropan-2-yl)-1,6-dihydropyridin-3-yl)oxy)phenyl)-3,5-dioxo-2,3,4,5-tetrahydro-1,2,4-triazine-6-carboxylic acid (1.36 g, 2.68 mmol) in tBuOH (20 mL) under N$_2$. The reaction mixture was stirred at 85° C. for 18 h, triethylamine (2.98 mL, 21.45 mmol) and DPPA (4.43 g, 3.47 mL, 16.09 mmol) were added and stirring at 85° C. was pursued for 2 h. After cooling to rt, the reaction mixture was diluted with sat. aq. NaHCO$_3$ and extracted with EA (3×). The combined organic layers were washed with sat. aq. NaHCO$_3$ and brine and dried over Na$_2$SO$_4$. The solids were removed by filtration and the filtrate was evaporated to dryness. The crude mixture was purified by flash chromatography on silica gel (0 to 10% [MeOH/NH$_4$OH (9:1)] in DCM) to give tert-butyl (2-(3,5-dichloro-4-((6-oxo-1-(1,1,1-trifluoropropan-2-yl)-1,6-dihydropyridin-3-yl)oxy)phenyl)-3,5-dioxo-2,3,4,5-tetrahydro-1,2,4-triazin-6-yl)carbamate (836 mg, 54%) as a red solid. LC-MS: C$_{22}$H$_{20}$Cl$_2$F$_3$N$_5$O$_6$ [M+H]$^+$: 578.

A solution of t-butyl (2-(3,5-dichloro-4-((6-oxo-1-(1,1,1-trifluoropropan-2-yl)-1,6-dihydropyridin-3-yl)oxy)phenyl)-3,5-dioxo-2,3,4,5-tetrahydro-1,2,4-triazin-6-yl)carbamate (836 mg, 1.45 mmol) in HCl 4N in dioxane (7.23 mL, 28.91 mmol) was stirred at rt under N$_2$ for 3 d. The reaction mixture was then evaporated to dryness and purified by flash chromatography on silica gel (0% to 10% [MeOH/NH$_4$OH (9:1)] in DCM). The resulting solid was triturated in MeCN to give 6-amino-2-(3,5-dichloro-4-((6-oxo-1-(1,1,1-trifluoropropan-2-yl)-1,6-dihydropyridin-3-yl)oxy)phenyl)-1,2,4-triazine-3,5(2H,4H)-dione (32) (220 mg, 32%) as a white solid. $^1$H-NMR (DMSO-d$_6$, 400 MHz): 1.44 (d, J=6.6 Hz, 3H), 5.67-5.87 (m, 1H), 6.55 (s, 2H), 6.94 (d, J=9.0 Hz, 1H), 7.38 (dd, J=9.0 Hz, 3.1 Hz, 1H), 7.88 (d, J=3.1 Hz, 1H), 7.93 (s, 2H), 12.29 (s, 1H) ppm. LC-MS: C$_{17}$H$_{12}$Cl$_2$F$_3$N$_5$O$_4$ [M+H]$^+$: 478.

Example 33

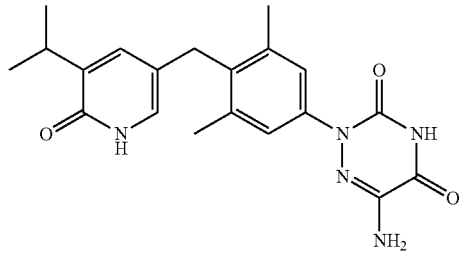

Compound 33 t-BuLi 1.7M (9.95 mL, 16.92 mmol) was added to a solution of 5-bromo-3-isopropyl-2-methoxypyridine (1.77 g, 7.69 mmol) in anhydrous THF (75 mL) at −78° C. under N$_2$. The reaction mixture was stirred at −78° C. for 20 min and was then cannulated into a solution of 2,2,2-trifluoro-N-(4-formyl-3,5-dimethylphenyl)acetamide (1.89 g, 7.69 mmol) in anhydrous THF (37 mL) at −78° C. The reaction mixture was stirred at −78° C. for 30 min and at rt for 2 h. The reaction mixture was then hydrolyzed with sat. aq. NH$_4$Cl and extracted with EA (2×). The combined organic layers were washed with brine and dried over Na$_2$SO$_4$. The solids were removed by filtration and the filtrate was evaporated to dryness. The crude mixture was purified by flash chromatography on silica gel (0 to 50% EA in CyH) to give 2,2,2-trifluoro-N-(4-(hydroxy(5-isopropyl-6-methoxypyridin-2-yl)methyl)-3,5-dimethylphenyl)acetamide (0.69 g, 22%) as a light yellow oil. $^1$H-NMR (CDCl$_3$, 400 MHz): 1.15 (d, J=6.8 Hz, 3H), 1.17 (d, J=6.8 Hz, 3H), 2.24 (d, J=4.0 Hz, 1H), 2.28 (s, 6H), 3.08-3.18 (m, 1H), 3.90 (s, 3H), 6.25

(d, J=4.0 Hz, 1H), 7.24 (s, 2H), 7.44 (d, J=2.0 Hz, 1H), 7.65-7.67 (m, 1H), 7.81 (br s, 1H) ppm. LC-MS: $C_{20}H_{23}F_3N_2O_3$ [M+H]$^+$: 397.

Triethylsilane (1.68 mL, 10.38 mmol) and trifluoroacetic acid (1.54 mL, 20.77 mmol) were added to a solution of 2,2,2-trifluoro-N-(4-(hydroxy(5-isopropyl-6-methoxypyridin-3-yl)methyl)-3,5-dimethylphenyl)acetamide (686 mg, 1.73 mmol) in anhydrous DCM (85 mL) under $N_2$. The reaction mixture was stirred at rt for 4 days, at which point extra trifluoroacetic acid (1.54 mL, 20.77 mmol) and triethylsilane (1.68 mL, 10.38 mmol) were added and stirring at rt was pursued for 2 more days. The reaction mixture was then carefully neutralized with sat. aq. NaHCO$_3$ and extracted with EA (2x). The combined organic layers were washed with sat. aq. NaHCO$_3$ and brine and dried over Na$_2$SO$_4$. The solids were removed by filtration and the filtrate was evaporated to dryness. The crude mixture was purified by flash chromatography on silica gel (2% to 25% EA in CyH) to give 2,2,2-trifluoro-N-(4-((5-isopropyl-6-methoxypyridin-3-yl)methyl)-3,5-dimethylphenyl)acetamide (0.52 g, 79%) as a light yellow oil. $^1$H-NMR (CDCl$_3$, 400 MHz): 1.13 (d, J=6.8 Hz, 6H), 2.24 (s, 6H), 3.03-3.13 (m, 1H), 3.88 (s, 3H), 3.90 (s, 2H), 7.10 (d, J=2.0 Hz, 1H), 7.26 (s, 2H), 7.50-7.52 (m, 1H), 7.80 (br s, H) ppm. LC-MS: $C_{20}H_{23}F_3N_2O_2$ [M+H]$^+$: 381.

A solution of NaOH (217 mg, 5.44 mmol) in water (5 mL) was added to a solution of 2,2,2-trifluoro-N-(4-((5-isopropyl-6-methoxypyridin-3-yl)methyl)-3,5-dimethylphenyl)acetamide (517 mg, 1.36 mmol) in MeOH (52 mL) under $N_2$. The reaction mixture was stirred at 60° C. for 17 h, at which point extra NaOH (217 mg, 5.44 mmol) in water (5 mL) was added and stirring at 60° C. was pursued for 6 h to reach full conversion. After cooling to rt, the reaction mixture was diluted with brine and extracted with EA (2x). The combined organic layers were washed with brine and dried over Na$_2$SO$_4$. The solids were removed by filtration and the filtrate was evaporated to dryness to give 4-((5-isopropyl-6-methoxypyridin-3-yl)methyl)-3,5-dimethylaniline (377 mg, 98%) as a light yellow oil which was used as such in the next step. $^1$H-NMR (DMSO-d$_6$, 400 MHz): 1.10 (d, J=6.8 Hz, 6H), 2.05 (s, 6H), 2.98-3.08 (m, 1H), 3.74 (s, 2H), 3.81 (s, 3H), 4.75 (s, 2H), 6.27 (s, 2H), 7.21 (d, J=2.0 Hz, 1H), 7.51 (d, J=2.0 Hz, 1H) ppm. LC-MS: $C_{18}H_{24}N_2O$ [M+H]$^+$: 285.

A solution of NaNO$_2$ (192 mg, 2.78 mmol) in water (26 mL) was added to a solution of 4-((5-isopropyl-6-methoxypyridin-3-yl)methyl)-3,5-dimethylaniline (377 mg, 1.33 mmol) in HCl 37% (11 mL), acetic acid (35 mL) and water (26 mL) at 0° C. under $N_2$. The reaction mixture was stirred at 0° C. for 30 min. In parallel, a solution of ethyl N-(2-cyanoacetyl)carbamate (310 mg, 1.99 mmol) in water (33 mL) and pyridine (12 mL) was stirred at 0° C. for 15 min. The first reaction mixture was quickly added to the second one. The resulting reaction mixture was stirred at 0° C. for 5 h and left to warm to rt overnight. The reaction mixture was then cooled to 0° C. and diluted with more water. The precipitate was collected by filtration and washed with water. This solid was dissolved in EA, washed with brine and dried over Na$_2$SO$_4$. The solids were removed by filtration and the filtrate was evaporated to dryness to give ethyl (2-cyano-2-(2-(4-((5-isopropyl-6-methoxypyridin-3-yl)methyl)-3,5-dimethylphenyl)hydrazineylidene)acetyl) carbamate (266 mg, 44%) as a yellow solid which was used as such in the next step. LC-MS: $C_{24}H_{29}N_5O_4$ [M+H]$^+$: 452.

Sodium acetate (378 mg, 4.61 mmol) was added to a solution of ethyl (2-cyano-2-(2-(4-((5-isopropyl-6-methoxypyridin-3-yl)methyl)-3,5-dimethylphenyl)hydrazineylidene)acetyl) carbamate (260 mg, 0.58 mmol) in acetic acid (5.6 mL) under $N_2$. The reaction mixture was stirred at 120° C. for 1 h. The reaction mixture was then cooled to 0° C., diluted with water and stirred for 30 min. The resulting precipitate was collected by filtration and washed with water. This solid was dissolved in EA, washed with brine and dried over Na$_2$SO$_4$. The solids were removed by filtration and the filtrate was evaporated to dryness to give 2-(4-((5-isopropyl-6-methoxypyridin-3-yl)methyl)-3,5-dimethylphenyl)-3,5-dioxo-2,3,4,5-tetrahydro-1,2,4-triazine-6-carbonitrile (204 mg, 87%) as an orange solid which was used as such in the next step. LC-MS: $C_{22}H_{23}N_5O_3$ [M+H]$^+$: 406.

A mixture of 2-(4-((5-isopropyl-6-methoxypyridin-3-yl)methyl)-3,5-dimethylphenyl)-3,5-dioxo-2,3,4,5-tetrahydro-1,2,4-triazine-6-carbonitrile (204 mg, 0.503 mmol) and HCl 37% (0.42 mL) in AcOH (2.7 mL) under $N_2$ was stirred at 120° C. for 20 h. The reaction mixture was cooled to 0° C. and diluted with water. The resulting precipitate was collected by filtration, washed with water and dried under vacuum to give 2-(4-((5-isopropyl-6-oxo-1,6-dihydropyridin-3-yl)methyl)-3,5-dimethylphenyl)-3,5-dioxo-2,3,4,5-tetrahydro-1,2,4-triazine-6-carboxylic acid (150 mg, 73%) as a light brown solid which was used as such in the next step. LC-MS: $C_{21}H_{22}N_4O_5$ [M+H]$^+$: 411.

Triethylamine (0.20 mL, 1.46 mmol) and DPPA (302 mg, 0.24 mL, 1.10 mmol) were added to a solution of 2-(4-((5-isopropyl-6-oxo-1,6-dihydropyridin-3-yl)methyl)-3,5-dimethylphenyl)-3,5-dioxo-2,3,4,5-tetrahydro-1,2,4-triazine-6-carboxylic acid (150 mg, 0.37 mmol) in tert-butanol (1.7 mL) under $N_2$. The reaction mixture was stirred at 85° C. for 4 h. After cooling to rt, the reaction mixture was quenched with sat. aq. NaHCO$_3$ and was extracted with EA (2x). The combined organic layers were washed with sat. aq. NaHCO$_3$, brine and dried over Na$_2$SO$_4$. The solids were removed by filtration and the filtrate was evaporated to dryness The crude mixture was purified by flash chromatography on silica gel (0 to 10% MeOH in DCM) to give t-butyl (2-(4-((5-isopropyl-6-oxo-1,6-dihydropyridin-3-yl)methyl)-3,5-dimethylphenyl)-3,5-dioxo-2,3,4,5-tetrahydro-1,2,4-triazin-6-yl)carbamate (56 mg, 32%) as a light orange solid. LC-MS: $C_{25}H_{31}N_5O_5$ [M+H]$^+$: 482.

HCl 4N in dioxane (0.52 mL, 2.077 mmol) was added to a solution of tert-butyl (2-(4-((5-isopropyl-6-oxo-1,6-dihydropyridin-3-yl)methyl)-3,5-dimethylphenyl)-3,5-dioxo-2,3,4,5-tetrahydro-1,2,4-triazin-6-yl)carbamate (50 mg, 0.104 mmol) in anhydrous DCM (0.9 mL) under $N_2$. The reaction mixture was stirred at rt for 2 days and then evaporated to dryness. The crude product was purified by chromatography on silica gel (1 to 10% MeOH in DCM) to give 6-amino-2-(4-((5-isopropyl-6-oxo-1,6-dihydropyridin-3-yl)methyl)-3,5-dimethylphenyl)-1,2,4-triazine-3,5(2H,4H)-dione (33) (6 mg, 15%) as a white solid. $^1$H-NMR (DMSO-d$_6$, 400 MHz): 1.09 (d, J=6.9 Hz, 6H), 2.22 (s, 6H), 2.87-3.01 (m, 1H), 3.73 (s, 2H), 6.30 (br s, 3H), 7.15 (d, J=2.2 Hz, 1H), 7.20 (s, 2H), 11.15 (s, 1H), 12.07 (br s, 1H) ppm. LC-MS: $C_{20}H_{23}N_5O_3$ [M+H]$^+$: 382.

Example 34

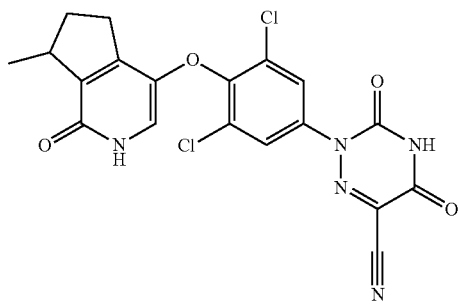

Compound 34

2-(3,5-Dichloro-4-((7-methyl-1-oxo-2,5,6,7-tetrahydro-1H-cyclopenta[c]pyridin-4-yl)oxy)phenyl)-3,5-dioxo-2,3,4,5-tetrahydro-1,2,4-triazine-6-carbonitrile The synthesis of the titled compound is described during the synthesis of 6-amino-2-[3,5-dichloro-4-[(7-methyl-1-oxo-2,5,6,7-tetrahydrocyclopenta[c]pyridin-4-yl)oxy]phenyl]-1,2,4-triazine-3,5-dione (see Example 15).

Example 35

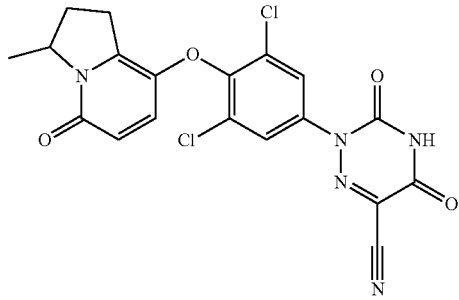

Compound 35

5-Bromo-6-methylpyridin-2-ol (10 g, 53.18 mmol) was added portionwise to a suspension of NaH 60% (2.77 g, 69.14 mmol) in anhydrous THF (200 mL) at rt under $N_2$. The reaction mixture was stirred at rt until no more $H_2$ evolution was observed, then cooled at −78° C. LDA 2M (31.91 mL, 63.82 mmol) was added dropwise over 5 minutes and the reaction mixture was stirred at −78° C. for 10 minutes. Then, allyl bromide (7.08 g, 5.09 mL, 58.50 mmol) was added dropwise and the reaction mixture was stirred at −78° C. for 1 h and was allowed to warm to rt for 1 h. The reaction mixture was hydrolyzed with sat. aq. $NH_4Cl$ and extracted with EA (2×). The combined organic layers were washed with brine and dried over $Na_2SO_4$. The solids were removed by filtration and the filtrate was evaporated to dryness. The crude mixture was purified by flash chromatography on silica gel (0% to 2.5% MeOH in DCM) to give 5-bromo-6-(but-3-en-1-yl)pyridin-2(1H)-one (7.6 g, 63%) as a white solid. $^1$H-NMR (DMSO-d$_6$, 400 MHz): 2.26-2.35 (m, 2H), 2.66-2.70 (m, 2H), 4.98-5.07 (m, 2H), 5.77-5.87 (m, 1H), 6.18 (d, J=9.6 Hz, 1H), 7.52 (d, J=9.6 Hz, 1H), 11.80 (br s, 1H) ppm. LCMS: $C_9H_{10}BrNO$ [M+H]$^+$: 228/230.

A solution of 5-bromo-6-(but-3-en-1-yl)pyridin-2(1H)-one (7.6 g, 33.32 mmol) and (Acetonitrile)[(2-biphenyl)di-tert-butylphosphine]gold(I) hexafluoroantimonate (1.29 g, 1.67 mmol) in anhydrous dioxane (64 mL) was stirred at 85° C. under $N_2$ for 3 h. The reaction mixture was then evaporated to dryness and purified by flash chromatography on silica gel (0% to 2% MeOH in DCM) to give 8-bromo-3-methyl-2,3-dihydroindolizin-5(1H)-one (5.89 g, 78%) as a colorless oil. $^1$H-NMR (DMSO-d$_6$, 400 MHz): 1.29 (d, J=6.6 Hz, 3H), 1.79-1.85 (m, 1H), 2.24-2.34 (m, 1H), 2.93-3.00 (m, 1H), 3.15-3.24 (m, 1H), 4.70-4.77 (m, 1H), 6.17 (d, J=9.6 Hz, 1H), 7.49 (d, J=9.6 Hz, 1H) ppm. LCMS: $C_9H_{10}BrNO$ [M+H]$^+$: 228/230.

Bis(neopentyl glycolato)diboron (17.5 g, 77.47 mmol), potassium acetate (7.60 g, 77.47 mmol) and Pd(P(oTolyl)$_3$)$_2$Cl$_2$ (2.03 g, 2.58 mmol) were added to a solution of 8-bromo-3-methyl-2,3-dihydroindolizin-5(1H)-one (5.89 g, 25.82 mmol) in anhydrous DMSO (94 mL) under $N_2$. The reaction mixture was stirred at 80° C. for 3 h. After cooling to rt, the reaction mixture was diluted with EA and filtered on a celite pad, then sat. aq. NaHCO$_3$ was added to the filtrate and the layers were separated. The aqueous layer was reextracted with EA. The combined organic layers were washed with water (2×) and brine and dried over Na$_2$SO$_4$. The solids were removed by filtration and the filtrate was evaporated to dryness. The crude mixture was purified by flash chromatography on silica gel (0 to 2% MeOH in DCM) to give 8-(5,5-dimethyl-1,3,2-dioxaborinan-2-yl)-3-methyl-2,3-dihydroindolizin-5(1H)-one (3.24 g, 48%) as a yellow solid which was used as such in the next step. LCMS: $C_{14}H_{20}BNO_3$ [M(boronic acid)+H]$^+$: 194.

A solution of oxo(sodioperoxy)borane tetrahydrate (3.82 g, 24.82 mmol) in water (72 mL) was added to a solution of 8-(5,5-dimethyl-1,3,2-dioxaborinan-2-yl)-3-methyl-2,3-dihydroindolizin-5(1H)-one (3.24 g, 12.41 mmol) in THF (145 mL) under $N_2$. The reaction mixture was stirred at rt for 5 h. The reaction mixture was diluted with toluene end evaporated to dryness to give 8-(2,6-dichloro-4-nitrophenoxy)-3-methyl-2,3-dihydroindolizin-5(1H)-one (2.05 g, 100%) as a yellow oil which was used as such in the next step. LC-MS: $C_9H_{11}NO_2$ [M+H]$^+$: 166.

DIPEA (4.1 mL, 24.8 mmol) was added to a solution of 8-hydroxy-3-methyl-2,3-dihydroindolizin-5(1H)-one (2.05 g, 12.4 mmol) and 1,3-dichloro-2-fluoro-5-nitrobenzene (2.60 g, 12.4 mmol) in anhydrous DMF (69 mL) under $N_2$. The reaction mixture was stirred at rt for 1 h 30. The reaction was diluted with water and extracted with EA/iPrOH (85:15). The organic layer was washed with water (2×) and brine (3×) and dried over Na$_2$SO$_4$. The solids were removed by filtration and the filtrate was evaporated to dryness. The crude mixture was purified by flash chromatography on silica gel (0 to 5% MeOH in DCM) to give 8-(2,6-dichloro-4-nitrophenoxy)-3-methyl-2,3-dihydroindolizin-5(1H)-one (1.48 g, 34%) as a white solid. $^1$H-NMR (DMSO-d$_6$, 400 MHz): 1.31 (d, J=6.6 Hz, 3H), 1.84-1.91 (m, 1H), 2.29-2.39 (m, 1H), 3.03-3.25 (m, 2H), 4.66-4.73 (m, 1H), 6.14 (d, J=9.6 Hz, 1H), 7.05 (d, J=9.6 Hz, 1H), 8.49 (s, 2H) ppm. LC-MS: $C_{15}H_{12}Cl_2N_2O_4$ [M+H]$^+$: 355.

Fe (1.16 g, 20.84 mmol) was added to a solution of 8-(2,6-dichloro-4-nitrophenoxy)-3-methyl-2,3-dihydroindolizin-5(1H)-one (1.48 g, 4.17 mmol) and NH$_4$Cl (2.23 g, 41.67 mmol) in EtOH (22 mL) and water (11 mL) under $N_2$. The reaction mixture was stirred at 70° C. for 20 h. After cooling to rt, the reaction mixture was filtered over a pad of celite. The filtrate was evaporated to dryness and the residue was dissolved in EA/iPrOH (85:15) and washed with brine. The organic layer was dried over Na$_2$SO$_4$. The solids were removed by filtration and the filtrate was evaporated to dryness. The crude mixture was purified by flash chromatography on silica gel (0% to 10% MeOH in DCM) to give 8-(4-amino-2,6-dichlorophenoxy)-3-methyl-2,3-dihydroindolizin-5(1H)-one (928 mg, 68%) as an orange solid. $^1$H-NMR (DMSO-d$_6$, 400 MHz): 1.30 (d, J=6.6 Hz, 3H), 1.83-1.89 (m, 1H), 2.25-2.35 (m, 1H), 3.05-3.22 (m, 2H), 4.63-4.70 (m, 1H), 5.62 (s, 2H), 6.11 (d, J=9.6 Hz, 1H), 6.66 (s, 2H), 6.87 (d, J=9.6 Hz, 1H) ppm. LCMS: C$_{15}$H$_{14}$Cl$_2$N$_2$O$_2$ [M+H]$^+$: 325.

A solution of NaNO$_2$ (411 mg, 5.96 mmol) in water (56 mL) was added to a solution of 8-(4-amino-2,6-dichlorophenoxy)-3-methyl-2,3-dihydroindolizin-5(1H)-one (923 mg, 2.84 mmol) in HCl 37% (25 mL), AcOH (75 mL) and water (56 mL) at 0° C. under N$_2$. The reaction mixture was stirred at 0° C. for 30 min. In parallel, a solution of ethyl N-(2-cyanoacetyl)carbamate (665 mg, 4.26 mmol) in water (72 mL) and pyridine (25 mL) was stirred at 0° C. for 15 min. The first reaction mixture was quickly added to the second one. The resulting reaction mixture was stirred at 0° C. for 1 h. The reaction mixture was diluted with more water. The precipitate was collected by filtration, washed with water and dried under vacuum to give ethyl (2-cyano-2-(2-(3,5-dichloro-4-((3-methyl-5-oxo-1,2,3,5-tetrahydroindolizin-8-yl)oxy)phenyl)hydrazineylidene)acetyl)carbamate (1.28 g, 92%) as an orange solid which was used as such in the next step. $^1$H-NMR (DMSO-d$_6$, 400 MHz): 1.27 (t, J=7.2 Hz, 3H), 1.31 (d, J=6.8 Hz, 3H), 1.85-1.93 (m, 1H), 2.27-2.41 (m, 1H), 4.20 (q, J=7.2 Hz, 2H), 4.65-4.72 (m, 1H), 6.13 (d, J=9.9 Hz, 1H), 6.95 (d, J=9.9 Hz, 1H), 8.00 (s, 2H), 10.92 (s, 1H) ppm. LC-MS: C$_{21}$H$_{19}$Cl$_2$N$_5$O$_5$ [M+H]$^+$: 492.

Sodium acetate (1.71 g, 20.8 mmol) was added to a solution of ethyl (2-cyano-2-(2-(3,5-dichloro-4-((3-methyl-5-oxo-1,2,3,5-tetrahydroindolizin-8-yl)oxy)phenyl)hydrazineylidene)acetyl)carbamate (1.28 g, 2.6 mmol) in AcOH (25 mL) under N$_2$. The reaction mixture was stirred at 120° C. for 30 min. The reaction mixture was cooled to 0° C. and diluted with water and the resulting mixture was stirred for 30 min. The precipitate was collected by filtration, washed with water and dried under vacuum to give 2-(3,5-dichloro-4-((3-methyl-5-oxo-1,2,3,5-tetrahydroindolizin-8-yl)oxy)phenyl)-3,5-dioxo-2,3,4,5-tetrahydro-1,2,4-triazine-6-carbonitrile (35) (886 mg, 76%) as a yellow solid. $^1$H-NMR (DMSO-d$_6$, 400 MHz): 1.32 (d, J=6.6 Hz, 3H), 1.85-1.93 (m, 1H), 2.27-2.41 (m, 1H), 3.07-3.27 (m, 2H), 4.66-4.75 (m, 1H), 6.13 (d, J=9.9 Hz, 1H), 7.01 (d, J=9.9 Hz, 1H), 7.77 (s, 2H) ppm. LCMS: C$_{19}$H$_{13}$Cl$_2$N$_5$O$_4$ [M+H]$^+$: 446.

Example 36

Compound 36:

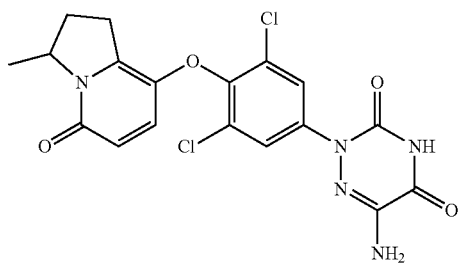

Compounds 37 and 38:

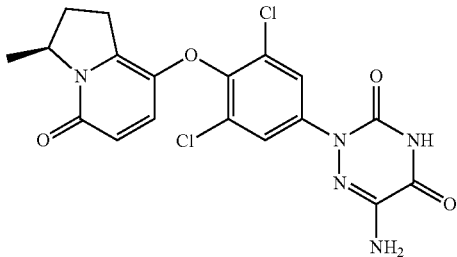

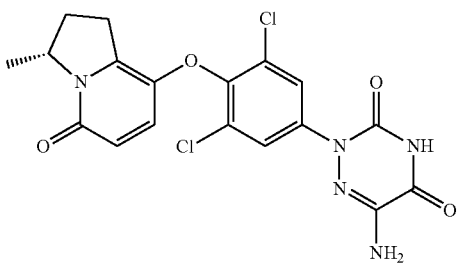

Compound 36, Compound 37, Compound 38

A mixture of 2-(3,5-dichloro-4-((3-methyl-5-oxo-1,2,3,5-tetrahydroindolizin-8-yl)oxy)phenyl)-3,5-dioxo-2,3,4,5-tetrahydro-1,2,4-triazine-6-carbonitrile (796 mg, 1.78 mmol) and HCl 37% (2.98 mL, 35.68 mmol) in AcOH (10 mL) was stirred at 120° C. under N$_2$ for 8 h. Heating was then stopped and the reaction mixture was stirred at rt over weekend. HCl 37% (1.49 mL, 17.84 mmol) was added and stirring at 120° C. was pursued for 2 h. The reaction mixture was cooled to 0° C. and diluted with water. The resulting precipitate was collected by filtration, washed with water and dried under vacuum to give 2-(3,5-dichloro-4-((3-methyl-5-oxo-1,2,3,5-tetrahydroindolizin-8-yl)oxy)phenyl)-3,5-dioxo-2,3,4,5-tetrahydro-1,2,4-triazine-6-carboxylic acid (734 mg, 88%) as a light yellow solid which was used as such in the next step. $^1$H-NMR (DMSO-d$_6$, 400 MHz): 1.32 (d, J=6.4 Hz, 3H), 1.86-1.91 (m, 1H), 2.29-2.37 (m, 1H), 3.10-3.25 (m, 2H), 4.67-4.73 (m, 1H), 6.13 (d, J=10.0 Hz, 1H), 7.00 (d, J=10.0 Hz, 1H), 7.80 (s, 2H), 12.67 (br s, 1H) ppm. LC-MS: C$_{19}$H$_{14}$Cl$_2$N$_4$O$_6$ [M+H]$^+$: 465.

Triethylamine (0.55 mL, 3.97 mmol) was added dropwise to a solution of 2-(3,5-dichloro-4-((3-methyl-5-oxo-1,2,3,5-tetrahydroindolizin-8-yl)oxy)phenyl)-3,5-dioxo-2,3,4,5-tetrahydro-1,2,4-triazine-6-carboxylic acid (615 mg, 1.32 mmol) and Diphenyl phosphoryl azide (727 mg, 0.57 mL, 2.64 mmol) in DMF (13 mL) at 0° C. under N$_2$. The reaction mixture was allowed to warm to rt and stirred for 5 h. Then, water (2.7 mL) was added and the reaction mixture was stirred at 100° C. for 18 h. The reaction mixture was diluted with sat. aq. NaHCO$_3$ and extracted with EA (2×). The combined organic layers were washed with sat. aq. NaHCO$_3$ (3×) and brine and dried over Na$_2$SO$_4$. The solids were removed by filtration and the filtrate was evaporated to dryness. The crude mixture was purified by chromatography on silica gel (0 to 10% MeOH in DCM) and by SFC (Chiralpak IG [21 mm×250 mm, 5 um], isocratic EtOH/CO$_2$ 50:50) to give two enantiomers of 6-amino-2-(3,5-dichloro-4-((3-methyl-5-oxo-1,2,3,5-tetrahydroindolizin-8-yl)oxy) phenyl)-1,2,4-triazine-3,5(2H,4H)-dione (36). The first eluting isomer (Example 37) (64 mg, 11%) and the second eluting isomer (Example 38) (64 mg, 11%), both as white solids. $^1$H-NMR (DMSO-d$_6$, 400 MHz): 1.31 (d, J=6.6 Hz, 3H), 1.84-1.93 (m, 1H), 2.27-2.40 (m, 1H), 3.06-3.27 (m, 2H), 4.63-4.74 (m, 1H), 6.13 (d, J=9.6 Hz, 1H), 6.53 (s, 2H), 6.95 (d, J=9.7 Hz, 1H), 7.86 (s, 2H), 12.27 (s, 1H) ppm. LC-MS: $C_{18}H_{15}Cl_2N_5O_4$ [M+H]$^+$: 436.

Example 39

Compound 39

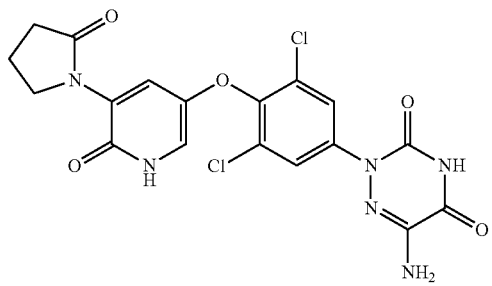

2-pyrrolidinone (4.98 g, 58.50 mmol), cesium carbonate (25.99 g, 79.78 mmol), dimethylbisdiphenylphosphinoxanthene (2 g, 3.46 mmol) and tris(dibenzylideneacetone) dipalladium (1.22 g, 1.33 mmol) were added to a solution of 3-bromo-2-methoxypyridine (10 g, 53.18 mmol) in anhydrous 1,4-dioxane (600 mL) under $N_2$. The reaction mixture was stirred at 110° C. for 22 h. After cooling to rt, the reaction mixture was diluted with EA and filtered over a pad of celite. The filtrate was evaporated to dryness and the crude mixture purified by flash chromatography on silica gel (0% to 100% EA in CyH) to give 1-(2-methoxypyridin-3-yl)pyrrolidin-2-one (9.26 g, 91%) as a brown oil. $^1$H-NMR (DMSO-d$_6$, 300 MHz): 2.04-2.13 (m, 2H), 2.37-2.42 (m, 2H), 3.66-3.71 (m, 2H), 3.88 (s, 3H), 7.04 (dd, J=7.5 Hz, 5.1 Hz, 1H), 7.66 (d, J=7.5 Hz, 1H), 8.10 (d, J=5.1 Hz, 1H) ppm. LCMS: $C_{10}H_{12}N_2O_2$ [M+H]$^+$: 193.

NBS (8.57 g, 48.17 mmol) was added to a solution of 1-(2-methoxypyridin-3-yl)pyrrolidin-2-one (9.26 g, 48.17 mmol) in anhydrous MeCN (217 mL) under $N_2$. The reaction mixture was stirred at 80° C. for 24 h, at which point extra NBS (4.29 g, 24.09 mmol) was added and stirring at 80° C. was pursued for 1 h. After cooling to rt, the reaction mixture was diluted with EA, washed with sat. aq. NaHCO$_3$ (2×) and brine and dried over Na$_2$SO$_4$. The solids were removed by filtration and the filtrate was evaporated to dryness. The crude mixture was purified by flash chromatography on silica gel (0 to 2% MeOH in DCM) to give 1-(5-bromo-2-methoxypyridin-3-yl)pyrrolidin-2-one (5.3 g, 41%) as a yellow oil. $^1$H-NMR (DMSO-d$_6$, 300 MHz): 2.04-2.13 (m, 2H), 2.37-2.42 (m, 2H), 3.68-3.73 (m, 2H), 3.88 (s, 3H), 7.94 (d, J=2.1 Hz, 1H), 8.23 (d, J=2.1 Hz, 1H) ppm. LC-MS: $C_{10}H_{11}BrN_2O_2$ [M+H]$^+$: 271/273.

A mixture of 1-(5-bromo-2-methoxypyridin-3-yl)pyrrolidin-2-one (5.3 g, 19.55 mmol), bis(neopentyl glycolato) diboron (13.25 g, 58.65 mmol), KOAc (5.76 g, 58.65 mmol) and PdCl$_2$[P(o-Tol)$_3$]$_2$ (1.54 g, 1.95 mmol) in anhydrous DMSO (90 mL) was stirred at 85° C. under $N_2$ for 1 h. After cooling to rt, the reaction mixture was diluted with EA, washed with sat. aq. NH$_4$Cl and brine (2×) and dried over Na$_2$SO$_4$. The solids were removed by filtration and the filtrate was evaporated to dryness. The crude mixture was purified by flash chromatography on silica gel (0 to 10% MeOH in DCM) to give 1-(5-(5,5-dimethyl-1,3,2-dioxaborinan-2-yl)-2-methoxypyridin-3-yl)pyrrolidin-2-one (5.13 g, 86%) as a beige solid. LC-MS: $C_{10}H_{13}BN_2O_4$ [M+H]$^+$: 237.

H$_2$O$_2$ 30% in water (44 mL, 433 mmol) and AcOH (25 mL) were added to a solution of 1-(5-(5,5-dimethyl-1,3,2-dioxaborinan-2-yl)-2-methoxypyridin-3-yl)pyrrolidin-2-one (5.27 g, 17.33 mmol) in THF (90 mL) under $N_2$. The reaction mixture was stirred at rt for 3 h. The reaction mixture was diluted with sat. aq. NaHCO$_3$ and extracted with EA (6×). The combined organic layers were washed with sat. aq. NaHCO$_3$ and brine and dried over Na$_2$SO$_4$. The solids were removed by filtration and the filtrate was evaporated to dryness. The crude mixture was purified by chromatography on silica gel (0 to 4% MeOH in DCM) to give 1-(5-hydroxy-2-methoxypyridin-3-yl)pyrrolidin-2-one (2.21 g, 61%) as a white solid. LC-MS: $C_{10}H_{12}N_2O_3$ [M+H]$^+$: 209.

DIPEA (8.77 mL, 53.07 mmol) was added to a solution of 1-(5-hydroxy-2-methoxypyridin-3-yl)pyrrolidin-2-one (2.21 g, 10.61 mmol) and 1,3-dichloro-2-fluoro-5-nitrobenzene (2.45 g, 11.68 mmol) in anhydrous DMF (48 mL) under $N_2$. The reaction mixture was stirred at rt for 1 h. The reaction mixture was then diluted with water and extracted with EA (3×). The combined organic layers were washed with brine (2×) and dried over Na$_2$SO$_4$. The solids were removed by filtration and the filtrate was evaporated to dryness. The crude mixture was purified by chromatography on silica gel (0 to 5% MeOH in DCM) to give 1-(5-(2,6-dichloro-4-nitrophenoxy)-2-methoxypyridin-3-yl)pyrrolidin-2-one (3.76 g, 89%) as a beige solid. LCMS: $C_{16}H_{13}Cl_2N_3O_5$ [M+H]$^+$: 398.

A mixture of 1-(5-(2,6-dichloro-4-nitrophenoxy)-2-methoxypyridin-3-yl)pyrrolidin-2-one (3.76 g, 9.44 mmol), NH$_4$Cl (5.05 g, 94.42 mmol) and Fe (2.64 g, 47.21 mmol) in EtOH (60 mL) and water (34 mL) was stirred at 80° C. for 4 h and at 90° C. for 3 h under $N_2$. The reaction mixture was filtered over a pad of celite and extracted with EA. The organic phase was washed with brine (2×) and dried over Na$_2$SO$_4$. The solids were removed by filtration and the filtrate was evaporated to dryness. The resulting solid was suspended in EtOH and sonicated for 5 min. The solids were then removed by filtration and the filtrate was evaporated to dryness to give 1-(5-(4-amino-2,6-dichlorophenoxy)-2-methoxypyridin-3-yl)pyrrolidin-2-one (2.62 g, 75%) as a beige solid. LCMS: $C_{16}H_{15}Cl_2N_3O_3$ [M+H]$^+$: 368.

A solution of NaNO$_2$ (1.03 g, 14.94 mmol) in water (59 mL) was added to a solution of 1-(5-(4-amino-2,6-dichlorophenoxy)-2-methoxypyridin-3-yl)pyrrolidin-2-one (2.62 g, 7.12 mmol) in HCl 37% (24 mL), AcOH (74 mL) and water (59 mL) at 0° C. under $N_2$. The reaction mixture was stirred at 0° C. for 1 h. In parallel, a solution of ethyl N-(2-cyanoacetyl)carbamate (1.67 g, 10.67 mmol) in water (74 mL) and pyridine (24 mL) was stirred at 0° C. for 15 min. The first reaction mixture was quickly added to the second one. The resulting reaction mixture was stirred at 0° C. for 2 h. The reaction mixture was diluted with more water. The precipitate was collected by filtration, dissolved in EA and dried over Na$_2$SO$_4$. The solids were removed by filtration and the filtrate was evaporated to give ethyl (2-cyano-2-(2-(3,5-dichloro-4-((6-methoxy-5-(2-oxopyrrolidin-1-yl)pyridin-3-yl)oxy)phenyl)hydrazineylidene)acetyl)carbamate (3.6 g, 95%) as an orange solid which was used as such in the next step. LC-MS: $C_{22}H_{20}Cl_2N_6O_6$ [M+H]$^+$: 535.

A mixture of ethyl (2-cyano-2-(2-(3,5-dichloro-4-((6-methoxy-5-(2-oxopyrrolidin-1-yl)pyridin-3-yl)oxy)phenyl) hydrazineylidene)acetyl)carbamate (3.6 g, 6.72 mmol) and NaOAc (2.21 g, 26.9 mmol) in AcOH (70 mL) was stirred at 120° C. for 2 h under $N_2$. After cooling to rt, the reaction mixture was diluted with water. The resulting precipitate was collected by filtration, dissolved in EA and dried over $Na_2SO_4$. The solids were removed by filtration and the filtrate was evaporated to dryness. The crude mixture was purified by flash chromatography on silica gel (0 to 10% MeOH in DCM) to give 2-(3,5-dichloro-4-((6-methoxy-5-(2-oxopyrrolidin-1-yl)pyridin-3-yl)oxy)phenyl)-3,5-dioxo-2,3,4,5-tetrahydro-1,2,4-triazine-6-carbonitrile (1.7 g, 52%) as a beige solid. LC-MS: $C_{20}H_{14}Cl_2N_6O_5$ $[M+H]^+$: 489.

KOH (3.9 g, 69.49 mmol) was added to a solution of 2-(3,5-dichloro-4-((6-methoxy-5-(2-oxopyrrolidin-1-yl)pyridin-3-yl)oxy)phenyl)-3,5-dioxo-2,3,4,5-tetrahydro-1,2,4-triazine-6-carbonitrile (1.7 g, 3.47 mmol) in water (40 mL) and EtOH (40 mL) under $N_2$. The reaction mixture was stirred at 70° C. for 15 min. After cooling to rt, the reaction mixture was acidified with HCl 1N until pH~1. The resulting precipitate was collected by filtration, washed with water and dried under vacuum to give 2-(3,5-dichloro-4-((6-methoxy-5-(2-oxopyrrolidin-1-yl)pyridin-3-yl)oxy)phenyl)-3,5-dioxo-2,3,4,5-tetrahydro-1,2,4-triazine-6-carboxylic acid (0.87 g, 49%) as a beige solid which was used as such in the next step. LCMS: $C_{20}H_{15}Cl_2N_5O_7$ $[M+H]^+$: 508.

Triethylamine (0.95 mL, 6.85 mmol) and DPPA (1.41 g, 1.11 mL, 5.14 mmol) were added to a solution of 2-(3,5-dichloro-4-((6-methoxy-5-(2-oxopyrrolidin-1-yl)pyridin-3-yl)oxy)phenyl)-3,5-dioxo-2,3,4,5-tetrahydro-1,2,4-triazine-6-carboxylic acid (0.87 g, 1.71 mmol) in tert-butanol (23 mL) under $N_2$. The reaction mixture was stirred at 85° C. for 16 h. After cooling to rt, the reaction mixture was diluted with sat. aq. $NaHCO_3$ and extracted with EA (3×). Combined organic layers were washed with sat. aq. $NaHCO_3$ and brine and dried over $Na_2SO_4$. The solids were removed by filtration and the filtrate was evaporated to dryness. The crude mixture was purified by flash chromatography on silica gel (4 to 5% MeOH in DCM) to afford t-butyl (2-(3,5-dichloro-4-((6-methoxy-5-(2-oxopyrrolidin-1-yl)pyridin-3-yl)oxy)phenyl)-3,5-dioxo-2,3,4,5-tetrahydro-1,2,4-triazin-6-yl)carbamate (0.37 g, 37%) as a yellow solid. $^1$H-NMR (DMSO-$d_6$, 400 MHz): 2.01-2.08 (m, 2H), 2.35-2.39 (m, 2H), 3.68-3.72 (m, 2H), 3.87 (s, 3H), 7.37 (d, J=2.8 Hz, 1H), 7.80 (d, J=2.1 Hz, 1H), 7.93 (s, 2H), 9.04 (br s, 1H), 12.61 (br s, 1H) ppm. LCMS: $C_{24}H_{24}Cl_2N_6O_7$ $[M+H]^+$: 579.

A solution of t-butyl (2-(3,5-dichloro-4-((6-methoxy-5-(2-oxopyrrolidin-1-yl)pyridin-3-yl)oxy)phenyl)-3,5-dioxo-2,3,4,5-tetrahydro-1,2,4-triazin-6-yl)carbamate (318 mg, 0.55 mmol) in HCl 4N in dioxane (2.74 mL, 10.98 mmol) was stirred at 60° C. for 5 h and at rt for 3 days. The reaction mixture was diluted with sat. aq. $NaHCO_3$ and extracted with EA (2×). The combined organic layers were washed with brine and dried over $Na_2SO_4$. The solids were removed by filtration and the filtrate was evaporated to dryness. The crude mixture was purified by flash chromatography on silica gel (0 to 10% MeOH in DCM) and prep. HPLC (10 to 100% MeCN in 0.2 wt % $NH_3$ solution in water) to give 6-amino-2-(3,5-dichloro-4-((6-oxo-5-(2-oxopyrrolidin-1-yl)-1,6-dihydropyridin-3-yl)oxy)phenyl)-1,2,4-triazine-3,5(2H,4H)-dione (39) (12.7 mg, 5%) as a white solid. $^1$H-NMR (DMSO-$d_6$, 400 MHz): 1.96-2.04 (m, 2H), 2.36 (t, J=7.9 Hz, 2H), 3.80 (t, J=7.2 Hz, 2H), 6.27 (s, 2H), 6.93 (s, 1H), 7.47 (d, J=3.2 Hz, 1H), 7.93 (s, 2H), 11.30 (br s, 2H) ppm. LC-MS: $C_{18}H_{14}Cl_2N_6O_5$ $[M+H]^+$: 465.

Biological Assays

THR Biochemical Assay (Assay 1)

The TR-FRET thyroid receptor beta coactivator assay is to be used. The assay uses a terbium-labeled anti-GST antibody, a glutathione-S-transferase (GST) tagged human thyroid receptor, beta or alpha, ligand-binding domain (LBD), and a fluorescein labeled SRC2-2 coactivator peptide. The antibody interacts with the LBD, where the agonist will also bind, resulting in increased affinity for the SRC2-2 coactivator peptide causing energy transfer of the acceptor fluorophore and a FRET emission shift from 495 to 520 nm. The energy transfer is detected as an increase in the fluorescence emission of the fluorescein acceptor, and a decrease in the fluorescence emission of the terbium donor. The assay is to be performed in a 384-well black plate in a final volume of 20 µL. Serial dilution of various test agonists will be performed in DMSO (1% final DMSO concentration) and added to the test plate. Thyroid receptor beta LBD will usually be added to the plate at a final concentration of 1 nM, followed by the mixture of the fluorescein labeled SRC2-2 coactivator peptide, and the terbium-labeled anti-GST antibody at final concentrations of 200 nM and 2 nM respectively. The assay will often be incubated for 1 hr at rt protected from light. The TR-FRET will then be measured on a Victor multilabel reader (Perkin Elmer) using an excitation wavelength of 340 nm with emission filters of 495 nm and 520 nm. The assay will be quantified by expressing a ratio (520:495) of the intensities, and the resulting activation curves; $EC_{50}$ values are to be generated using a sigmoidal dose response (variable slope) equation in GraphPad™ Prism 8.0.

Compounds described herein are active as THR-beta agonists as shown in Table 1, where: for Assay 1: 'A' indicates an $EC_{50}$<50 nM, 'B' indicates an $EC_{50}$ of >50 nM and <250 nM, 'C' indicates an $EC_{50}$≥250 nM and <1000 nM, 'D' indicates an $EC_{50}$≥1000 nM and <25000 nM, and 'E' indicates an $EC_{50}$>25000 nM.

TABLE 1

| Compound Number | Assay 1 |
| --- | --- |
| 1 | A |
| 2 | B |
| 3 | B |
| 4 | B |
| 5 | A |
| 6 | B |
| 7 | A |
| 8 | B |
| 9 | B |
| 10 | B |
| 13 | C |
| 14 | A |
| 15 | C |
| 18 | A |
| 19 | A |
| 22 | B |
| 23 | B |
| 24 | A |
| 27 | C |
| 28 | D |
| 30 | A |
| 31 | B |
| 32 | B |
| 33 | C |
| 34 | C |
| 35 | A |
| 36 | A |
| 37 | A |
| 38 | B |

Diet-Induced Obese (DIO) Mouse Model of NASH

C57BL/6J mice are fed a high-fat diet for 10 weeks to induce obesity and injected intraperitoneally twice weekly with carbon tetrachloride ($CCl_4$) for an additional 4 weeks to induce fibrosis. Mice fed a normal chow diet are used as healthy controls. Concomitant with $CCl_4$ dosing, mice are treated with vehicle or with a compound disclosed herein, administered by oral gavage once daily for 28 days. Drug exposure is measured in a separate experiment in lean male C57BL/6J mice. Livers of mice in the NASH study are harvested and evaluated for liver steatosis and fibrosis by histology and whole transcriptome analysis in the liver using RNA sequencing. Target engagement is confirmed by monitoring expression of TRβ-regulated genes.

Human Clinical Study: NASH

In a randomized, double-blind, placebo-controlled study, adult patients (with biopsy confirmed NASH (fibrosis stages 1-3) and hepatic fat fraction of at least 10% at baseline when assessed by MRI-proton density fat fraction (MRI-PDFF) are administered a compound disclosed herein or placebo. Serial hepatic fat measurements are obtained at weeks 12 and 36, and a second liver biopsy is obtained at week 36. The primary endpoint is relative change in MRI-PDFF assessed hepatic fat compared with placebo at week 12 in patients who have both a baseline and week 12 MRI-PDFF.

REFERENCES

1. Younossi, Z M, Koenig, A B, Abdelatif, D, Fazel, Y, Henry, L, Wymer, M. Global epidemiology of nonalcoholic fatty liver disease-Meta-analytic assessment of prevalence, incidence, and outcomes. Hepatology, 2016, 64(1):73e84.
2. Gastroenterology. 2012 June; 142(7): 1592-609. doi: 10.1053/j.gastro.2012.04.001. Epub 2012 May 15.
3. Serfaty, L., Lemoine, M. Definition and natural history of metabolic steatosis: clinical aspects of NAFLD, NASH and cirrhosis. Diabetes and Metabolism, 2008, 34 (6 Pt 2):634e637.
4. Hepatology. 2012 October; 56(4): 1580-1584. doi: 10.1002/hep.26031
5. Dulai, P S, Singh, S, Patel, J, Soni, M, Prokop, L J, Younossi, Z, et al. Increased risk of mortality by fibrosis stage in nonalcoholic fatty liver disease: systematic review and meta-analysis. Hepatology, 2017, 65(5): 1557e1565.
6. Younossi, Z M, Loomba, R, Rinella, M E, Bugianesi, E, Marchesini, G, Neuschwander-Tetri, B A, et al. Current and future therapeutic regimens for non-alcoholic fatty liver disease (NAFLD) and non-alcoholic steatohepatitis (NASH). Hepatology, 2018, 68(1):349e360.
7. Harvey C B, Williams G R. Mechanism of thyroid hormone action. Thyroid, 2002 June; 12(6):441-6.
8. Bookout A L, Jeong Y, Downes M, Yu R T, Evans R M, Mangelsdorf D J. Anatomical profiling of nuclear receptor expression reveals a hierarchical transcriptional network. Cell, 2006, 126:789-799
9. Flamant F, Baxter J D, Forrest D, Refetoff S, Samuels H H, Scanlan T S, Vennstrom B, Samarut J. International union of pharmacology. LIX. The pharmacology and classification of the nuclear receptor superfamily: thyroid hormone receptors. Pharmacol. Rev., 2006, 58:705-711
10. Haning H, Woltering M, Mueller U, Schmidt G, Schmeck C, Voehringer V, Kretschmer A, Pernerstorfer J. Bioorg. Med Chem Lett., 2005 Apr. 1, 15(7): 1835-40. Novel heterocyclic thyromimetics.
11. Hirano T, Kagechika H. Thyromimetics: a review of recent reports and patents (2004-2009). Expert Opin Ther Pat., 2010 February; 20(2):213-28. doi: 10.1517/13543770903567069.
12. Kowalik M A, Columbano A, Perra A. Thyroid Hormones, Thyromimetics and Their Metabolites in the Treatment of Liver Disease. Front Endocrinol (Lausanne), 2018 Jul. 10; 9:382. doi: 10.3389/fendo.2018.00382. eCollection 2018.
13. Erion M D, Cable E E, Ito B R, Jiang H, Fujitaki J M, Finn P D, Zhang B H, Hou J, Boyer S H, van Poelje P D, Linemeyer D L. Targeting thyroid hormone receptor-beta agonists to the liver reduces cholesterol and triglycerides and improves the therapeutic index. Proc Natl Acad Sci USA., 2007 Sep. 25; 104(39):15490-5. Epub 2007 Sep. 18.
14. Hartley M D, Kirkemo L L, Banerji T, Scanlan T S. A Thyroid Hormone-Based Strategy for Correcting the Biochemical Abnormality in X-Linked Adrenoleukodystrophy. Endocrinology 2017, 158(5), p 1328-1338. doi: 10.1210/en.2016-1842.
15. Milanesi A, Brent G A. Beam Me In: Thyroid Hormone Analog Targets Alternative Transporter in Mouse Model of X-Linked Adrenoleukodystrophy. Endocrinology 2017, 158, p 1116-1119. doi: 10.1210/en.2017-00206.

EMBODIMENTS

Embodiment P1. A compound of Formula I:

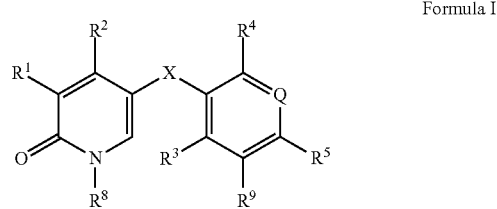

Formula I or a stereoisomer or a tautomer thereof, or a pharmaceutically acceptable salt thereof, wherein $R^1$ and $R^2$ are each independently selected from H, optionally substituted $C_1$-$C_6$ alkyl, optionally substituted $C_3$-$C_6$ cycloalkyl, and an optionally substituted non-aromatic bicyclic ring, wherein $R^1$ and $R^2$ cannot both be H; or $R^1$ and $R^2$ together with the carbon atoms to which they are attached form a $C_4$-$C_7$ monocyclic ring optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

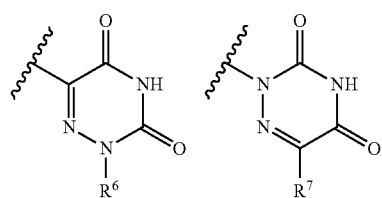

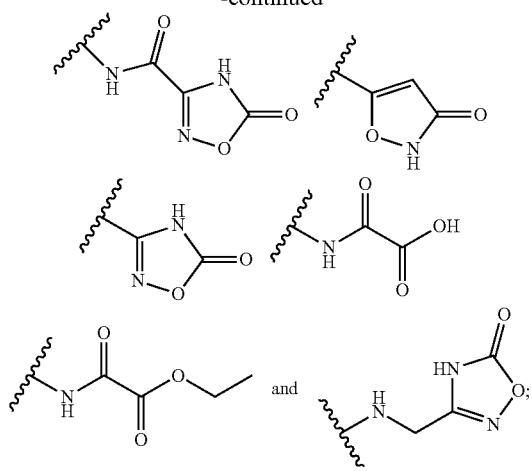

R[6] is H or $C_1$-$C_3$ alkyl;

R[7] is selected from H, —CN, $CH_3$, and —$NH_2$;

R[8] is H or $C_1$-$C_3$ alkyl optionally substituted with 1-5 halogens;

R[9] is selected from H, halogen, —CN, optionally substituted $C_1$-$C_3$ alkyl, and optionally substituted $C_1$-$C_2$ alkoxy; or R[3] and R[9] together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

Q is selected from N, CH, and CF; and

X is O or $CH_2$;

wherein 0 to 10 hydrogen atoms that are attached to one or more carbon atoms are replaced with deuterium atom(s);

with the proviso that when R[1] and R[2] together with the carbon atoms to which they are attached do not form a $C_5$-$C_7$ monocyclic ring or a polycyclic ring, then R[7] is H or —$NH_2$.

Embodiment P2. The compound of embodiment P1, or a stereoisomer or a tautomer thereof, or a pharmaceutically acceptable salt thereof, wherein R[1] and R[2] are each independently $C_1$-$C_6$ alkyl, $C_3$-$C_6$ cycloalkyl, or a non-aromatic bicyclic ring, wherein R[1] and R[2] are each optionally substituted with 1 to 3 substituents independently selected from optionally substituted $C_3$-$C_4$ cycloalkyl, optionally substituted bicyclic ring, and halogen; or R[1] or R[2] are H, but R[1] and R[2] cannot both be H.

Embodiment P3. The compound of embodiment P1 or embodiment P2, or a stereoisomer or a tautomer thereof, or a pharmaceutically acceptable salt thereof, wherein R[1] is $C_1$-$C_6$ alkyl.

Embodiment P4. The compound of any one of embodiments P1-P3, or a stereoisomer or a tautomer thereof, or a pharmaceutically acceptable salt thereof, wherein R[2] is H.

Embodiment P5. The compound of embodiment P1, or a stereoisomer or a tautomer thereof, or a pharmaceutically acceptable salt thereof, wherein R[1] and R[2] together with the carbon atoms to which they are attached form a $C_4$-$C_7$ monocyclic ring optionally substituted with 1 to 3 substituents independently selected from halogen and $C_1$-$C_6$ alkyl.

Embodiment P6. The compound of embodiment P1, or a stereoisomer or a tautomer thereof, or a pharmaceutically acceptable salt thereof, wherein R[1] and R[2] together with the carbon atoms to which they are attached form a polycyclic ring optionally substituted with 1 to 3 substituents independently selected from $C_1$-$C_6$ alkyl.

Embodiment P7. The compound of any one of embodiments P1-P6, or a stereoisomer or a tautomer thereof, or a pharmaceutically acceptable salt thereof, wherein R[3] and R[4] are each independently selected from halogen; —CN; $C_1$-$C_3$ alkyl optionally substituted with 1 to 3 substituents independently selected from halogen and $C_1$-$C_6$ alkoxy; $C_1$-$C_2$ alkoxy optionally substituted with 1 to 3 substituents independently selected from halogen; and $C_2$-$C_3$ alkenyl optionally substituted with 1 to 3 substituents independently selected from halogen and $C_1$-$C_6$ alkoxy; and cyclopropyl.

Embodiment P8. The compound of any one of embodiments P1-P7, or a stereoisomer or a tautomer thereof, or a pharmaceutically acceptable salt thereof, wherein R[3] and R[4] are each independently selected from halogen and $C_1$-$C_3$ alkyl.

Embodiment P9. The compound of any one of embodiments P1-P8, or a stereoisomer or a tautomer thereof, or a pharmaceutically acceptable salt thereof, wherein R[3] and R[4] are both halogen.

Embodiment P10. The compound of any one of embodiments P1-P8, or a stereoisomer or a tautomer thereof, or a pharmaceutically acceptable salt thereof, wherein R[3] and R[4] are both methyl.

Embodiment P11. The compound of any one of embodiments P1-P10, or a stereoisomer or a tautomer thereof, or a pharmaceutically acceptable salt thereof, wherein R[9] is selected from H; halogen; —CN; $C_1$-$C_3$ alkyl optionally substituted with 1 to 3 substituents independently selected from halogen and $C_1$-$C_2$ alkoxy; and $C_1$-$C_2$ alkoxy optionally substituted with 1 to 3 substituents independently selected from halogen.

Embodiment P12. The compound of any one of embodiments P1-P6, or a stereoisomer or a tautomer thereof, or a pharmaceutically acceptable salt thereof, wherein R[3] and R[9] together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring.

Embodiment P13. The compound of any one of embodiments P1-P12, or a stereoisomer or a tautomer thereof, or a pharmaceutically acceptable salt thereof, wherein R[5] is

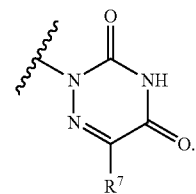

Embodiment P14. The compound of any one of embodiments P1-P13, or a stereoisomer or a tautomer thereof, or a pharmaceutically acceptable salt thereof, wherein R[7] is H.

Embodiment P15. The compound of any one of embodiments P1-P13, or a stereoisomer or a tautomer thereof, or a pharmaceutically acceptable salt thereof, wherein R[7] is —$NH_2$.

Embodiment P16. The compound of any one of embodiments P1-P13, or a stereoisomer or a tautomer thereof, or a pharmaceutically acceptable salt thereof, wherein R[7] is $CH_3$.

Embodiment P17. The compound of any one of embodiments P1-P16, or a stereoisomer or a tautomer thereof, or a pharmaceutically acceptable salt thereof, wherein X is $CH_2$.

Embodiment P18. The compound of any one of embodiments P1-P16, or a stereoisomer or a tautomer thereof, or a pharmaceutically acceptable salt thereof, wherein X is O.

Embodiment P19. The compound of any one of embodiments P1-P18, or a stereoisomer or a tautomer thereof, or a pharmaceutically acceptable salt thereof, wherein $R^8$ is H.

Embodiment P20. The compound of any one of embodiments P1-P18, or a stereoisomer or a tautomer thereof, or a pharmaceutically acceptable salt thereof, wherein $R^8$ is $C_1$-$C_3$ alkyl optionally substituted with 1-5 halogens.

Embodiment P21. A compound selected from the group consisting of:

6-amino-2-(3,5-dichloro-4-((7-methyl-1-oxo-2,5,6,7-tetrahydro-1H-cyclopenta[c]pyridin-4-yl)oxy)phenyl)-1,2,4-triazine-3,5(2H,4H)-dione;

6-amino-2-(4-chloro-5-((7-methyl-1-oxo-2,5,6,7-tetrahydro-1H-cyclopenta[c]pyridin-4-yl)oxy)bicyclo[4.2.0]octa-1,3,5-trien-2-yl)-1,2,4-triazine-3,5(2H,4H)-dione;

2-((4-chloro-5-((7-methyl-1-oxo-2,5,6,7-tetrahydro-1H-cyclopenta[c]pyridin-4-yl)oxy)bicyclo[4.2.0]octa-1,3,5-trien-2-yl)amino)-2-oxoacetic acid;

2-((7-((7-cyclopropyl-1-oxo-2,5,6,7-tetrahydro-1H-cyclopenta[c]pyridin-4-yl)oxy)-6-methyl-2,3-dihydro-1H-inden-4-yl)amino)-2-oxoacetic acid;

6-amino-2-(3,5-dichloro-4-((5-isopropyl-6-oxo-1,6-dihydropyridin-3-yl)oxy)phenyl)-1,2,4-triazine-3,5(2H,4H)-dione;

2-(3,5-dichloro-4-((7-methyl-1-oxo-2,5,6,7-tetrahydro-1H-cyclopenta[c]pyridin-4-yl)oxy)phenyl)-3,5-dioxo-2,3,4,5-tetrahydro-1,2,4-triazine-6-carbonitrile;

6-(3,5-dichloro-4-((5-isopropyl-6-oxo-1,6-dihydropyridin-3-yl)oxy)phenyl)-2-methyl-1,2,4-triazine-3,5(2H,4H)-dione;

6-amino-2-(3,5-dichloro-4-((5-(1-cyclopropylethyl)-6-hydroxypyridin-3-yl)oxy)phenyl)-1,2,4-triazine-3,5(2H,4H)-dione;

6-amino-2-(3,5-dichloro-4-((5-(1-(3,3-difluorocyclobutyl)ethyl)-6-hydroxypyridin-3-yl)oxy)phenyl)-1,2,4-triazine-3,5(2H,4H)-dione;

6-amino-2-(4-((5-(1-(bicyclo[1.1.1]pentan-2-yl)ethyl)-6-hydroxypyridin-3-yl)oxy)-3,5-dichlorophenyl)-1,2,4-triazine-3,5(2H,4H)-dione;

6-amino-2-(3,5-dichloro-4-((5-(6,6-difluorospiro[3.3]heptan-1-yl)-6-hydroxypyridin-3-yl)oxy)phenyl)-1,2,4-triazine-3,5(2H,4H)-dione;

6-amino-2-(3,5-dichloro-4-((6-hydroxy-5-(spiro[2.3]hexan-4-yl)pyridin-3-yl)oxy)phenyl)-1,2,4-triazine-3,5(2H,4H)-dione;

6-amino-2-(4-chloro-5-((6-hydroxy-5-isopropylpyridin-3-yl)oxy)-6-methylpyridin-2-yl)-1,2,4-triazine-3,5(2H,4H)-dione;

6-amino-2-(3,5-dichloro-4-((5-(1-cyclopropylethyl)-6-hydroxypyridin-3-yl)oxy)phenyl-2-d)-1,2,4-triazine-3,5(2H,4H)-dione;

6-amino-2-(3,5-dichloro-4-((6-hydroxy-5-isopropylpyridin-3-yl)oxy)phenyl-2-d)-1,2,4-triazine-3,5(2H,4H)-dione;

6-amino-2-(3,5-dichloro-4-((5-(1-cyclopropylethyl)-6-hydroxypyridin-3-yl)oxy)-2-fluorophenyl)-1,2,4-triazine-3,5(2H,4H)-dione;

6-amino-2-(3,5-dichloro-4-((8-methyl-1-oxo-1,2,5,6,7,8-hexahydro-5,8-ethanoisoquinolin-4-yl)oxy)phenyl)-1,2,4-triazine-3,5(2H,4H)-dione;

6-amino-2-(3,5-dichloro-4-((8-methyl-1-oxo-1,2,5,6,7,8-hexahydro-5,7-methanoisoquinolin-4-yl)oxy)phenyl)-1,2,4-triazine-3,5(2H,4H)-dione;

6-amino-2-(3,5-dichloro-4-((1-oxo-1,2,5,5a,6,6a-hexahydrocyclopropa[4,5]cyclopenta[1,2-c]pyridin-4-yl)oxy)phenyl)-1,2,4-triazine-3,5(2H,4H)-dione;

6-amino-2-(4-((5-isopropyl-6-oxo-1,6-dihydropyridin-3-yl)oxy)-3,5-dimethylphenyl)-1,2,4-triazine-3,5(2H,4H)-dione;

6-amino-2-(4-((5-isopropyl-6-oxo-1,6-dihydropyridin-3-yl)methyl)-3,5-dimethylphenyl)-1,2,4-triazine-3,5(2H,4H)-dione;

2-(3,5-dichloro-4-((5-isopropyl-6-oxo-1,6-dihydropyridin-3-yl)oxy)phenyl)-1,2,4-triazine-3,5(2H,4H)-dione; and 2-(4-((5-isopropyl-6-oxo-1,6-dihydropyridin-3-yl)methyl)-3,5-dimethylphenyl)-1,2,4-triazine-3,5(2H,4H)-dione;

or a stereoisomer or a tautomer thereof, or a pharmaceutically acceptable salt thereof.

Embodiment P22. A pharmaceutical composition comprising the compound of any one of embodiments P1-P21, or the stereoisomer or the tautomer thereof, or the pharmaceutically acceptable salt thereof, and at least one pharmaceutically acceptable excipient.

Embodiment P23. A method of treating a disorder or disease in a subject in need thereof, the method comprising administering to the subject a therapeutically effective amount of the compound of any one of embodiments P1-P21, or the stereoisomer or the tautomer thereof, or the pharmaceutically acceptable salt thereof, or a therapeutically effective amount of the pharmaceutical composition of embodiment P22, wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment P24. Use of the compound of any one of embodiments P1-P21, or the stereoisomer or the tautomer thereof, or the pharmaceutically acceptable salt thereof, for the manufacture of a medicament for the treatment of a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment P25. A compound of any one of embodiments P1-P21, or a stereoisomer or a tautomer thereof, or a pharmaceutically acceptable salt thereof, for use in treating a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment P26. A composition of embodiment P22 for use in treating a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment P27. A method of treating a thyroid hormone receptor related disorder in a patient, the method comprising the steps of:

identifying a patient in need of treatment for the thyroid hormone receptor related disorder, and administering to the patient, or contacting the patient with, the compound of any one of embodiments P1-P21, or the stereoisomer or the tautomer thereof, or the pharmaceutically acceptable salt thereof, or a therapeutically effective amount of the pharmaceutical composition of embodiment P22.

Embodiment P28. The method of embodiment P27, wherein the thyroid hormone receptor related disorder is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment P29. A method of selectively modulating the activity of a thyroid hormone receptor beta (THR-β) comprising contacting the compound of any one of embodiments P1-P21, or the stereoisomer or the tautomer thereof, or the pharmaceutically acceptable salt thereof, with the thyroid hormone receptor.

Embodiment P30. The method of embodiment P29, wherein the contacting is in vitro or ex vivo.

Embodiment P31. The method of embodiment P29, wherein the contacting is in vivo.

Embodiment P32. A compound of any one of embodiments P1-P21, or a stereoisomer or a tautomer thereof, or a pharmaceutically acceptable salt thereof, for use in selectively modulating the activity of a thyroid hormone receptor beta (THR-β).

Embodiment P33. A composition of embodiment P22 for use in selectively modulating the activity of a thyroid hormone receptor beta (THR-β).

Additional Embodiments

Embodiment Q1. A compound of Formula I':

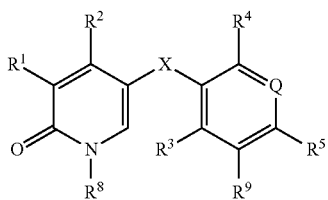

Formula I' or a stereoisomer or a tautomer thereof, or a pharmaceutically acceptable salt thereof, wherein $R^1$ and $R^2$ are each independently selected from H, halogen, —$NR^aR^b$, —$C(O)NR^aR^b$, optionally substituted $C_1$-$C_6$ alkyl, optionally substituted $C_3$-$C_6$ cycloalkyl, and an optionally substituted non-aromatic bicyclic ring, wherein $R^1$ and $R^2$ cannot both be H; or $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

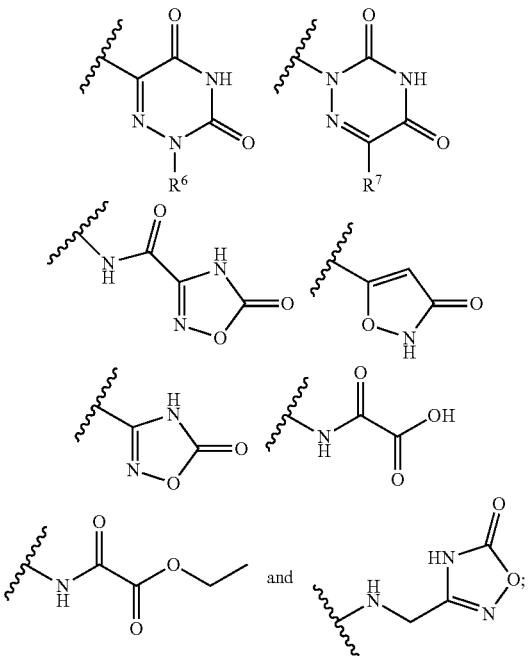

$R^6$ is H or $C_1$-$C_3$ alkyl;
$R^7$ is selected from H, —CN, $CH_3$, and —$NH_2$;
$R^8$ is H or $C_1$-$C_3$ alkyl optionally substituted with 1-5 halogens;
$R^9$ is selected from H, halogen, —CN, optionally substituted $C_1$-$C_3$ alkyl, and optionally substituted $C_1$-$C_2$ alkoxy; or $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

$R^a$ and $R^b$ are each independently selected from H, optionally substituted $C_1$-$C_6$ alkyl and optionally substituted $C_3$-$C_6$ cycloalkyl; or $R^a$ and $R^b$ together with the nitrogen atom to which they are attached form a 4- to 6-membered cyclic ring optionally substituted with 1 to 3 substituents independently selected from $C_1$-$C_3$ alkyl and halogen;

Q is selected from N, CH, and CF; and
X is O or $CH_2$;
wherein 0 to 10 hydrogen atoms that are attached to one or more carbon atoms are replaced with deuterium atom(s);
with the proviso that when $R^1$ and $R^2$ are each independently selected from H, halogen, optionally substituted $C_1$-$C_6$ alkyl, optionally substituted $C_3$-$C_6$ cycloalkyl, and an optionally substituted non-aromatic bicyclic ring; or when $R^1$ and $R^2$ together with the carbon atoms to which they are attached form a 4-membered monocyclic ring optionally substituted with 1 to 3 substituents independently selected from halogen and $C_1$-$C_6$ alkyl; then $R^7$ is H or —$NH_2$.

Embodiment Q2. The compound of embodiment Q1, or the stereoisomer or the tautomer thereof, or the pharmaceutically acceptable salt thereof, wherein $R^1$ is independently selected from H, halogen, —$NR^aR^b$, —$C(O)NR^aR^b$, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and a non-aromatic bicyclic ring optionally substituted with 1-6 halogens.

Embodiment Q3. The compound of embodiment Q1, or the stereoisomer or the tautomer thereof, or the pharmaceutically acceptable salt thereof, wherein $R^2$ is independently selected from H, halogen, $C_1$-$C_6$ alkyl optionally substituted with 1-6 halogens, $C_3$-$C_6$ cycloalkyl optionally substituted with 1-6 halogens, and a non-aromatic bicyclic ring optionally substituted with 1-6 halogens.

Embodiment Q4. The compound of embodiment Q1, or the stereoisomer or the tautomer thereof, or the pharmaceutically acceptable salt thereof, wherein $R^1$ is independently selected from H, optionally substituted $C_1$-$C_6$ alkyl, optionally substituted $C_3$-$C_6$ cycloalkyl, and an optionally substituted non-aromatic bicyclic ring; and $R^2$ is independently selected from H, halogen, optionally substituted $C_1$-$C_6$ alkyl, optionally substituted $C_3$-$C_6$ cycloalkyl, and an optionally substituted non-aromatic bicyclic ring.

Embodiment Q5. The compound of embodiment Q1, or the stereoisomer or the tautomer thereof, or the pharmaceutically acceptable salt thereof, wherein $R^1$ is independently selected from H, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and a non-aromatic bicyclic ring optionally substituted with 1-6 halogens; and $R^2$ is independently selected from H, halogen, $C_1$-$C_6$ alkyl optionally substituted with 1-6 halogens, $C_3$-$C_6$ cycloalkyl optionally substituted with 1-6 halogens, and a non-aromatic bicyclic ring optionally substituted with 1-6 halogens.

Embodiment Q6. The compound of embodiment Q1, or the stereoisomer or the tautomer thereof, or the pharmaceutically acceptable salt thereof, wherein $R^1$ is —$NR^aR^b$ or $C_1$-$C_6$ alkyl optionally substituted with 1 to 5 substituents independently selected from halogen and $C_3$-$C_4$cycloalkyl.

Embodiment Q7. The compound of embodiment Q1, or the stereoisomer or the tautomer thereof, or the pharmaceutically acceptable salt thereof, wherein $R^1$ is —$C(O)NR^aR^b$.

Embodiment Q8. The compound of any one of embodiments Q1, Q2, Q6, or Q7, or the stereoisomer or the tautomer thereof, or the pharmaceutically acceptable salt thereof, wherein $R^a$ and $R^b$ are each independently selected from $C_1$-$C_3$ alkyl.

Embodiment Q9. The compound of any one of embodiments Q1, Q2, Q6, or Q7, or the stereoisomer or the tautomer thereof, or the pharmaceutically acceptable salt thereof, wherein $R^a$ is H; and $R^b$ is $C_1$-$C_3$ alkyl optionally substituted with 1 to 3 halogens, or $C_3$-$C_6$ cycloalkyl optionally substituted with 1-5 halogens.

Embodiment Q10. A compound of Formula I:

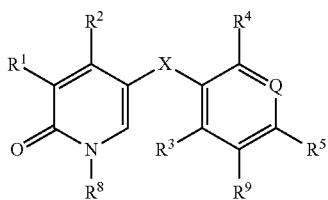

Formula I or a stereoisomer or a tautomer thereof, or a pharmaceutically acceptable salt thereof, wherein $R^1$ and $R^2$ are each independently selected from H, optionally substituted $C_1$-$C_6$ alkyl, optionally substituted $C_3$-$C_6$ cycloalkyl, and an optionally substituted non-aromatic bicyclic ring, wherein $R^1$ and $R^2$ cannot both be H; or $R^1$ and $R^2$ together with the carbon atoms to which they are attached form a $C_4$-$C_7$ monocyclic ring optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

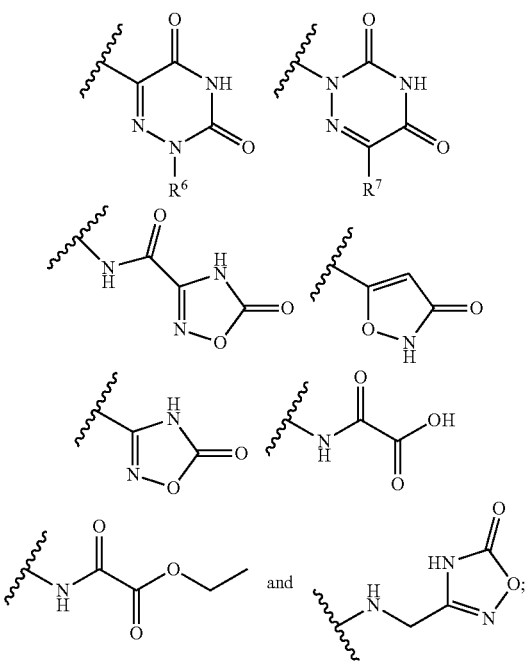

$R^6$ is H or $C_1$-$C_3$ alkyl;

$R^7$ is selected from H, —CN, $CH_3$, and —$NH_2$;

$R^8$ is H or $C_1$-$C_3$ alkyl optionally substituted with 1-5 halogens;

$R^9$ is selected from H, halogen, —CN, optionally substituted $C_1$-$C_3$ alkyl, and optionally substituted $C_1$-$C_2$ alkoxy; or $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

Q is selected from N, CH, and CF; and

X is O or $CH_2$;

wherein 0 to 10 hydrogen atoms that are attached to one or more carbon atoms are replaced with deuterium atom(s);

with the proviso that when $R^1$ and $R^2$ together with the carbon atoms to which they are attached do not form a $C_5$-$C_7$ monocyclic ring or a polycyclic ring, then $R^7$ is H or —$NH_2$.

Embodiment Q11. The compound of embodiment Q10, or the stereoisomer or the tautomer thereof, or the pharmaceutically acceptable salt thereof, wherein $R^8$ is hydrogen.

Embodiment Q12. A compound of Formula IA:

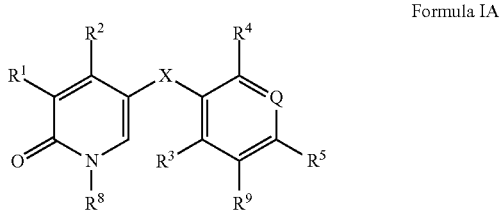

Formula IA or a stereoisomer or a tautomer thereof, or a pharmaceutically acceptable salt thereof, wherein $R^1$ and $R^2$ are each independently selected from H, halogen, —$NR^aR^b$, —$C(O)NR^aR^b$, optionally substituted $C_1$-$C_6$ alkyl, optionally substituted $C_3$-$C_6$ cycloalkyl, and an optionally substituted non-aromatic bicyclic ring; or $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

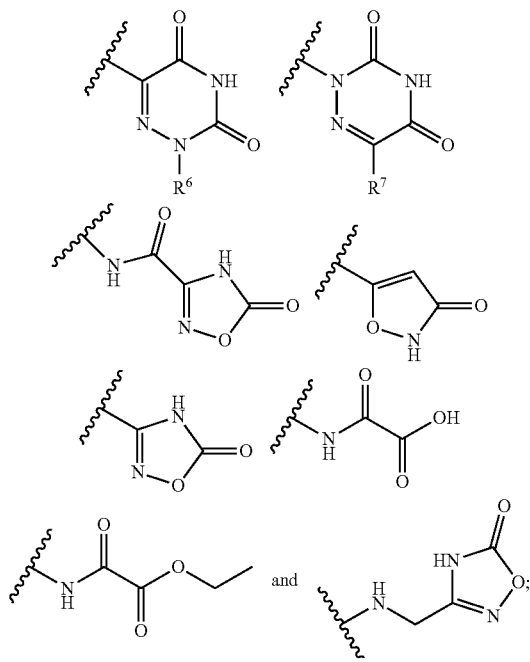

$R^6$ is H or $C_1$-$C_3$ alkyl;
$R^7$ is selected from H, —CN, $CH_3$, and —$NH_2$;
$R^8$ is $C_1$-$C_3$ alkyl optionally substituted with 1-5 halogens or optionally substituted $C_3$-$C_5$ cycloalkyl;

$R^9$ is selected from H, halogen, —CN, optionally substituted $C_1$-$C_3$ alkyl, and optionally substituted $C_1$-$C_2$ alkoxy; or $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

$R^a$ and $R^b$ are each independently selected from H, optionally substituted $C_1$-$C_6$ alkyl and optionally substituted $C_3$-$C_6$ cycloalkyl; or $R^a$ and $R^b$ together with the nitrogen atom to which they are attached form a 4- to 6-membered cyclic ring optionally substituted with 1 to 3 substituents independently selected from $C_1$-$C_3$ alkyl and halogen;

Q is selected from N, CH, and CF; and
X is O or $CH_2$;
wherein 0 to 10 hydrogen atoms that are attached to one or more carbon atoms are replaced with deuterium atom(s);
with the proviso that the compound is not:
2-(3,5-dichloro-4-((1-isopropyl-6-oxo-1,6-dihydropyridin-3-yl)oxy)phenyl)-1,2,4-triazine-3,5(2H,4H)-dione; or
2-(3,5-dichloro-4-((1-isopropyl-6-oxo-1,6-dihydropyridin-3-yl)oxy)phenyl)-3,5-dioxo-2,3,4,5-tetrahydro-1,2,4-triazine-6-carbonitrile.

Embodiment Q13. The compound of embodiment Q12, having the chemical structure of:

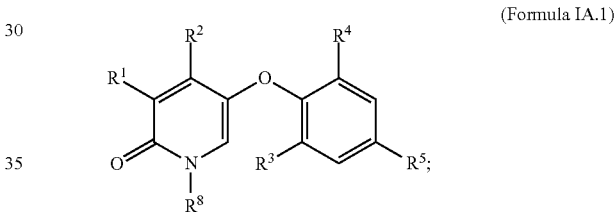

(Formula IA.1)

or the stereoisomer or the tautomer thereof, or the pharmaceutically acceptable salt thereof.

Embodiment Q14. The compound of embodiment Q12 or embodiment Q13, or the stereoisomer or the tautomer thereof, or the pharmaceutically acceptable salt thereof, wherein $R^1$ is independently selected from H, halogen, —$NR^aR^b$, —$C(O)NR^aR^b$, $C_1$-$C_6$ alkyl optionally substituted with 1-6 substituents independently selected from halogen and $C_3$-$C_4$ cycloalkyl optionally substituted with 1-6 halogens, $C_3$-$C_6$ cycloalkyl optionally substituted with 1-6 halogens, and an non-aromatic bicyclic ring optionally substituted with 1-6 halogens.

Embodiment Q15. The compound of embodiment Q12 or embodiment Q13, or the stereoisomer or the tautomer thereof, or the pharmaceutically acceptable salt thereof, wherein $R^2$ is independently selected from H, halogen, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and an non-aromatic bicyclic ring optionally substituted with 1-6 halogens.

Embodiment Q16. The compound of embodiment Q12 or embodiment Q13, or the stereoisomer or the tautomer thereof, or the pharmaceutically acceptable salt thereof, wherein $R^1$ is independently selected from H, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and a non-aromatic bicyclic ring optionally substituted with 1-6 halogens; and $R^2$ is independently selected from H, halogen, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and a non-aromatic bicyclic ring optionally substituted with 1-6 halogens.

Embodiment Q17. The compound of embodiment Q12 or embodiment Q13, or the stereoisomer or the tautomer thereof, or the pharmaceutically acceptable salt thereof, wherein $R^1$ is —$NR^aR^b$ or $C_1$-$C_6$ alkyl optionally substituted with 1 to 5 halogens.

Embodiment Q18. The compound of embodiment Q12 or embodiment Q13, or the stereoisomer or the tautomer thereof, or the pharmaceutically acceptable salt thereof, wherein $R^1$ is —$C(O)NR^aR^b$.

Embodiment Q19. The compound of any one of embodiments Q12, Q13, Q14, Q17, or Q18, or the stereoisomer or the tautomer thereof, or the pharmaceutically acceptable salt thereof, wherein $R^a$ and $R^b$ are each independently selected from $C_1$-$C_3$ alkyl.

Embodiment Q20. The compound of any one of embodiments Q12, Q13, Q14, Q17, or Q18, or the stereoisomer or the tautomer thereof, or the pharmaceutically acceptable salt thereof, wherein $R^a$ is H; and $R^b$ is $C_1$-$C_3$ alkyl optionally substituted with 1 to 3 halogens, or $C_3$-$C_6$ cycloalkyl optionally substituted with 1-5 halogens.

Embodiment Q21. The compound of any one of embodiments Q12, Q13, Q14, Q17, or Q18, or the stereoisomer or the tautomer thereof, or the pharmaceutically acceptable salt thereof, wherein $R^a$ and $R^b$ together with the nitrogen atom to which they are attached form a 4- to 6-membered cyclic ring optionally substituted with 1 to 3 substituents independently selected from $C_1$-$C_3$ alkyl and halogen.

Embodiment Q22. The compound of any one of embodiments Q1, Q10, Q12, or Q13, or the stereoisomer or the tautomer thereof, or the pharmaceutically acceptable salt thereof, wherein $R^1$ and $R^2$ are H;

$R^5$ is

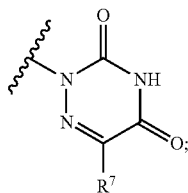

$R^7$ is —$NH_2$; and $R^8$ is isopropyl, optionally substituted with 1-5 halogens.

Embodiment Q23. The compound of any one of embodiments Q1, Q10, Q12, or Q13, or the stereoisomer or the tautomer thereof, or the pharmaceutically acceptable salt thereof, wherein $R^5$ is

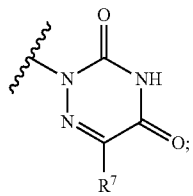

$R^7$ is $CH_3$ or —$NH_2$; and $R^8$ is $C_1$-$C_3$ alkyl.

Embodiment Q24. The compound of any one of embodiments Q1-Q11, having the chemical structure of:

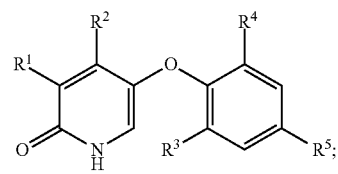

(Formula I.1)

or a stereoisomer or a tautomer thereof, or a pharmaceutically acceptable salt thereof.

Embodiment Q25. The compound of any one of embodiments Q1, Q10, Q12, or Q13, or the stereoisomer or the tautomer thereof, or the pharmaceutically acceptable salt thereof, wherein $R^1$ is $CH_3$; $R^8$ is isopropyl; $R^5$ is

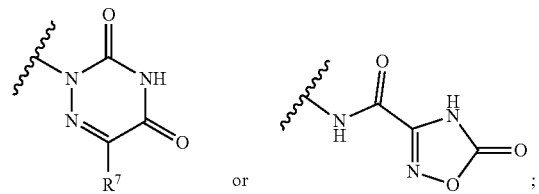

and $R^7$ is —$NH_2$.

Embodiment Q26. The compound of any one of embodiments Q1, Q10, Q12, or Q13, or the stereoisomer or the tautomer thereof, or the pharmaceutically acceptable salt thereof, wherein $R^1$ and $R^2$ are each independently $C_1$-$C_6$ alkyl, $C_3$-$C_6$ cycloalkyl, or a non-aromatic bicyclic ring, wherein $R^1$ and $R^2$ are each optionally substituted with 1 to 3 substituents independently selected from optionally substituted $C_3$-$C_4$ cycloalkyl, optionally substituted bicyclic ring, and halogen; or $R^1$ or $R^2$ are H, but $R^1$ and $R^2$ cannot both be H.

Embodiment Q27. The compound of any one of embodiments Q1, Q10, Q12, or Q13, or the stereoisomer or the tautomer thereof, or the pharmaceutically acceptable salt thereof, wherein $R^1$ and $R^2$ are each independently $C_1$-$C_6$ alkyl, $C_3$-$C_6$ cycloalkyl, or a non-aromatic bicyclic ring, wherein $R^1$ and $R^2$ are each optionally substituted with 1 to 3 substituents independently selected from $C_3$-$C_4$ cycloalkyl optionally substituted with 1 to 3 substituents independently selected from halogen and $C_1$-$C_3$ alkyl; bicyclic ring optionally substituted with 1 to 3 substituents independently selected from halogen and $C_1$-$C_3$ alkyl; and halogen; or $R^1$ or $R^2$ are H, but $R^1$ and $R^2$ cannot both be H.

Embodiment Q28. The compound of any one of embodiments Q1, Q10, Q12, or Q13, or the stereoisomer or the tautomer thereof, or the pharmaceutically acceptable salt thereof, wherein $R^1$ is $C_1$-$C_6$ alkyl.

Embodiment Q29. The compound of any one of embodiments Q1, Q2, Q4-Q14, Q16-Q21, Q23-Q25, or Q28, or the stereoisomer or the tautomer thereof, or the pharmaceutically acceptable salt thereof, wherein $R^2$ is H.

Embodiment Q30. The compound of any one of embodiments Q1, Q10, Q12, or Q13, or the stereoisomer or the tautomer thereof, or the pharmaceutically acceptable salt thereof, wherein $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl.

Embodiment Q31. The compound of any one of embodiments Q1, Q10, Q12, or Q13, or the stereoisomer or the tautomer thereof, or the pharmaceutically acceptable salt thereof, wherein $R^1$ and $R^2$ together with the carbon atoms to which they are attached form a $C_4$-$C_7$ monocyclic ring optionally substituted with 1 to 3 substituents independently selected from halogen and $C_1$-$C_6$ alkyl.

Embodiment Q32. The compound of any one of embodiments Q1, Q10, Q12, or Q13, or the stereoisomer or the tautomer thereof, or the pharmaceutically acceptable salt thereof, wherein $R^1$ and $R^2$ together with the carbon atoms to which they are attached form a polycyclic ring optionally substituted with 1 to 3 substituents independently selected from $C_1$-$C_6$ alkyl.

Embodiment Q33. The compound of any one of embodiments Q1-Q32, or the stereoisomer or the tautomer thereof, or the pharmaceutically acceptable salt thereof, wherein $R^3$ and $R^4$ are each independently selected from halogen; —CN; $C_1$-$C_3$ alkyl optionally substituted with 1 to 3 substituents independently selected from halogen and $C_1$-$C_6$ alkoxy; $C_1$-$C_2$ alkoxy optionally substituted with 1 to 3 substituents independently selected from halogen; and $C_2$-$C_3$ alkenyl optionally substituted with 1 to 3 substituents independently selected from halogen and $C_1$-$C_6$ alkoxy; and cyclopropyl.

Embodiment Q34. The compound of any one of embodiments Q1-Q32, or the stereoisomer or the tautomer thereof, or the pharmaceutically acceptable salt thereof, wherein $R^3$ and $R^4$ are each independently selected from halogen and $C_1$-$C_3$ alkyl.

Embodiment Q35. The compound of any one of embodiments Q1-Q32, or the stereoisomer or the tautomer thereof, or the pharmaceutically acceptable salt thereof, wherein $R^3$ and $R^4$ are both halogen.

Embodiment Q36. The compound of any one of embodiments Q1-Q32, or the stereoisomer or the tautomer thereof, or the pharmaceutically acceptable salt thereof, wherein $R^3$ and $R^4$ are both —Cl.

Embodiment Q37. The compound of any one of embodiments Q1-Q32, or the stereoisomer or the tautomer thereof, or the pharmaceutically acceptable salt thereof, wherein $R^3$ and $R^4$ are both methyl.

Embodiment Q38. The compound of any one of embodiments Q1-Q37, or the stereoisomer or the tautomer thereof, or the pharmaceutically acceptable salt thereof, wherein $R^9$ is selected from H; halogen; —CN; $C_1$-$C_3$ alkyl optionally substituted with 1 to 3 substituents independently selected from halogen and $C_1$-$C_2$ alkoxy; and $C_1$-$C_2$ alkoxy optionally substituted with 1 to 3 substituents independently selected from halogen.

Embodiment Q39. The compound of any one of embodiments Q1-Q37, or the stereoisomer or the tautomer thereof, or the pharmaceutically acceptable salt thereof, wherein $R^9$ is H.

Embodiment Q40. The compound of any one of embodiments Q1-Q32, or the stereoisomer or the tautomer thereof, or the pharmaceutically acceptable salt thereof, wherein $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring.

Embodiment Q41. The compound of any one of embodiments Q1-Q21, Q24, or Q26-Q40, or the stereoisomer or the tautomer thereof, or the pharmaceutically acceptable salt thereof, wherein $R^5$ is

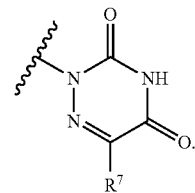

Embodiment Q42. The compound of any one of embodiments Q1-Q21, Q24, or Q26-Q40, or the stereoisomer or the tautomer thereof, or the pharmaceutically acceptable salt thereof, wherein $R^5$ is

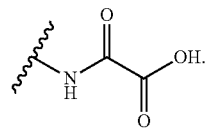

Embodiment Q43. The compound of any one of embodiments Q1-Q21, Q24, or Q26-Q40, or the stereoisomer or the tautomer thereof, or the pharmaceutically acceptable salt thereof, wherein $R^5$ is

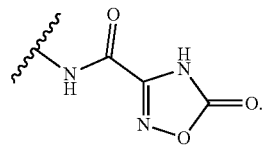 [SMILES: *NC(=O)c1noc(=O)[nH]1]

Embodiment Q44. The compound of any one of embodiments Q1-Q21, Q24, or Q26-Q40, or the stereoisomer or the tautomer thereof, or the pharmaceutically acceptable salt thereof, wherein $R^7$ is H.

Embodiment Q45. The compound of any one of embodiments Q1-Q21, Q24, or Q26-Q40, or the stereoisomer or the tautomer thereof, or the pharmaceutically acceptable salt thereof, wherein $R^7$ is —$NH_2$.

Embodiment Q46. The compound of any one of embodiments Q1-Q21, Q24, or Q26-Q40, or the stereoisomer or the tautomer thereof, or the pharmaceutically acceptable salt thereof, wherein $R^7$ is $CH_3$.

Embodiment Q47. The compound of any one of embodiments Q1-Q21, Q24, or Q26-Q40, or the stereoisomer or the tautomer thereof, or the pharmaceutically acceptable salt thereof, wherein $R^7$ is —CN.

Embodiment Q48. The compound of any one of embodiments Q1-Q47, or the stereoisomer or the tautomer thereof, or the pharmaceutically acceptable salt thereof, wherein Q is CH.

Embodiment Q49. The compound of any one of embodiments Q1-Q48, or the stereoisomer or the tautomer thereof, or the pharmaceutically acceptable salt thereof, wherein X is $CH_2$.

Embodiment Q50. The compound of any one of embodiments Q1-Q48, or the stereoisomer or the tautomer thereof, or the pharmaceutically acceptable salt thereof, wherein X is O.

Embodiment Q51. A compound selected from the group consisting of:
6-amino-2-(3,5-dichloro-4-((7-methyl-1-oxo-2,5,6,7-tetrahydro-1H-cyclopenta[c]pyridin-4-yl)oxy)phenyl)-1,2,4-triazine-3,5(2H,4H)-dione;
6-amino-2-(4-chloro-5-((7-methyl-1-oxo-2,5,6,7-tetrahydro-1H-cyclopenta[c]pyridin-4-yl)oxy)bicyclo[4.2.0]octa-1,3,5-trien-2-yl)-1,2,4-triazine-3,5(2H,4H)-dione;
2-((4-chloro-5-((7-methyl-1-oxo-2,5,6,7-tetrahydro-1H-cyclopenta[c]pyridin-4-yl)oxy)bicyclo[4.2.0]octa-1,3,5-trien-2-yl)amino)-2-oxoacetic acid;
2-((7-((7-cyclopropyl-1-oxo-2,5,6,7-tetrahydro-1H-cyclopenta[c]pyridin-4-yl)oxy)-6-methyl-2,3-dihydro-1H-inden-4-yl)amino)-2-oxoacetic acid;
6-amino-2-(3,5-dichloro-4-((5-isopropyl-6-oxo-1,6-dihydropyridin-3-yl)oxy)phenyl)-1,2,4-triazine-3,5(2H,4H)-dione;
2-(3,5-dichloro-4-((7-methyl-1-oxo-2,5,6,7-tetrahydro-1H-cyclopenta[c]pyridin-4-yl)oxy)phenyl)-3,5-dioxo-2,3,4,5-tetrahydro-1,2,4-triazine-6-carbonitrile;
6-(3,5-dichloro-4-((5-isopropyl-6-oxo-1,6-dihydropyridin-3-yl)oxy)phenyl)-2-methyl-1,2,4-triazine-3,5(2H,4H)-dione;
6-amino-2-(3,5-dichloro-4-((5-(1-cyclopropylethyl)-6-hydroxypyridin-3-yl)oxy)phenyl)-1,2,4-triazine-3,5(2H,4H)-dione;
6-amino-2-(3,5-dichloro-4-((5-(1-(3,3-difluorocyclobutyl)ethyl)-6-hydroxypyridin-3-yl)oxy)phenyl)-1,2,4-triazine-3,5(2H,4H)-dione;
6-amino-2-(4-((5-(1-(bicyclo[1.1.1]pentan-2-yl)ethyl)-6-hydroxypyridin-3-yl)oxy)-3,5-dichlorophenyl)-1,2,4-triazine-3,5(2H,4H)-dione;
6-amino-2-(3,5-dichloro-4-((5-(6,6-difluorospiro[3.3]heptan-1-yl)-6-hydroxypyridin-3-yl)oxy)phenyl)-1,2,4-triazine-3,5(2H,4H)-dione;
6-amino-2-(3,5-dichloro-4-((6-hydroxy-5-(spiro[2.3]hexan-4-yl)pyridin-3-yl)oxy)phenyl)-1,2,4-triazine-3,5(2H,4H)-dione;
6-amino-2-(4-chloro-5-((6-hydroxy-5-isopropylpyridin-3-yl)oxy)-6-methylpyridin-2-yl)-1,2,4-triazine-3,5(2H,4H)-dione;
6-amino-2-(3,5-dichloro-4-((5-(1-cyclopropylethyl)-6-hydroxypyridin-3-yl)oxy)phenyl-2-d)-1,2,4-triazine-3,5(2H,4H)-dione;
6-amino-2-(3,5-dichloro-4-((6-hydroxy-5-isopropylpyridin-3-yl)oxy)phenyl-2-d)-1,2,4-triazine-3,5(2H,4H)-dione;
6-amino-2-(3,5-dichloro-4-((5-(1-cyclopropylethyl)-6-hydroxypyridin-3-yl)oxy)-2-fluorophenyl)-1,2,4-triazine-3,5(2H,4H)-dione;
6-amino-2-(3,5-dichloro-4-((8-methyl-1-oxo-1,2,5,6,7,8-hexahydro-5,8-ethanoisoquinolin-4-yl)oxy)phenyl)-1,2,4-triazine-3,5(2H,4H)-dione;
6-amino-2-(3,5-dichloro-4-((8-methyl-1-oxo-1,2,5,6,7,8-hexahydro-5,7-methanoisoquinolin-4-yl)oxy)phenyl)-1,2,4-triazine-3,5(2H,4H)-dione;
6-amino-2-(3,5-dichloro-4-((1-oxo-1,2,5,5a,6,6a-hexahydrocyclopropa[4,5]cyclopenta[1,2-c]pyridin-4-yl)oxy)phenyl)-1,2,4-triazine-3,5(2H,4H)-dione;
6-amino-2-(4-((5-isopropyl-6-oxo-1,6-dihydropyridin-3-yl)oxy)-3,5-dimethylphenyl)-1,2,4-triazine-3,5(2H,4H)-dione;
6-amino-2-(4-((5-isopropyl-6-oxo-1,6-dihydropyridin-3-yl)methyl)-3,5-dimethylphenyl)-1,2,4-triazine-3,5(2H,4H)-dione;
2-(3,5-dichloro-4-((5-isopropyl-6-oxo-1,6-dihydropyridin-3-yl)oxy)phenyl)-1,2,4-triazine-3,5(2H,4H)-dione; and
2-(4-((5-isopropyl-6-oxo-1,6-dihydropyridin-3-yl)methyl)-3,5-dimethylphenyl)-1,2,4-triazine-3,5(2H,4H)-dione;
or a stereoisomer or a tautomer thereof, or a pharmaceutically acceptable salt thereof.

Embodiment Q52. A compound selected from the group consisting of:
6-amino-2-(3,5-dichloro-4-((7-methyl-1-oxo-2,5,6,7-tetrahydro-1H-cyclopenta[c]pyridin-4-yl)oxy)phenyl)-1,2,4-triazine-3,5(2H,4H)-dione;
6-amino-2-(4-chloro-5-((7-methyl-1-oxo-2,5,6,7-tetrahydro-1H-cyclopenta[c]pyridin-4-yl)oxy)bicyclo[4.2.0]octa-1,3,5-trien-2-yl)-1,2,4-triazine-3,5(2H,4H)-dione;
2-((4-chloro-5-((7-methyl-1-oxo-2,5,6,7-tetrahydro-1H-cyclopenta[c]pyridin-4-yl)oxy)bicyclo[4.2.0]octa-1,3,5-trien-2-yl)amino)-2-oxoacetic acid;
2-((7-((7-cyclopropyl-1-oxo-2,5,6,7-tetrahydro-1H-cyclopenta[c]pyridin-4-yl)oxy)-6-methyl-2,3-dihydro-1H-inden-4-yl)amino)-2-oxoacetic acid;
6-amino-2-(3,5-dichloro-4-((5-isopropyl-6-oxo-1,6-dihydropyridin-3-yl)oxy)phenyl)-1,2,4-triazine-3,5(2H,4H)-dione;
2-(3,5-dichloro-4-((7-methyl-1-oxo-2,5,6,7-tetrahydro-1H-cyclopenta[c]pyridin-4-yl)oxy)phenyl)-3,5-dioxo-2,3,4,5-tetrahydro-1,2,4-triazine-6-carbonitrile;
6-(3,5-dichloro-4-((5-isopropyl-6-oxo-1,6-dihydropyridin-3-yl)oxy)phenyl)-2-methyl-1,2,4-triazine-3,5(2H,4H)-dione;
6-amino-2-(3,5-dichloro-4-((5-(1-cyclopropylethyl)-6-hydroxypyridin-3-yl)oxy)phenyl)-1,2,4-triazine-3,5(2H,4H)-dione;
6-amino-2-(3,5-dichloro-4-((5-(1-(3,3-difluorocyclobutyl)ethyl)-6-hydroxypyridin-3-yl)oxy)phenyl)-1,2,4-triazine-3,5(2H,4H)-dione;
6-amino-2-(4-((5-(1-(bicyclo[1.1.1]pentan-2-yl)ethyl)-6-hydroxypyridin-3-yl)oxy)-3,5-dichlorophenyl)-1,2,4-triazine-3,5(2H,4H)-dione;
6-amino-2-(3,5-dichloro-4-((5-(6,6-difluorospiro[3.3]heptan-1-yl)-6-hydroxypyridin-3-yl)oxy)phenyl)-1,2,4-triazine-3,5(2H,4H)-dione;
6-amino-2-(3,5-dichloro-4-((6-hydroxy-5-(spiro[2.3]hexan-4-yl)pyridin-3-yl)oxy)phenyl)-1,2,4-triazine-3,5(2H,4H)-dione;
6-amino-2-(4-chloro-5-((6-hydroxy-5-isopropylpyridin-3-yl)oxy)-6-methylpyridin-2-yl)-1,2,4-triazine-3,5(2H,4H)-dione;
6-amino-2-(3,5-dichloro-4-((5-(1-cyclopropylethyl)-6-hydroxypyridin-3-yl)oxy)phenyl-2-d)-1,2,4-triazine-3,5(2H,4H)-dione;
6-amino-2-(3,5-dichloro-4-((6-hydroxy-5-isopropylpyridin-3-yl)oxy)phenyl-2-d)-1,2,4-triazine-3,5(2H,4H)-dione;
6-amino-2-(3,5-dichloro-4-((5-(1-cyclopropylethyl)-6-hydroxypyridin-3-yl)oxy)-2-fluorophenyl)-1,2,4-triazine-3,5(2H,4H)-dione;
6-amino-2-(3,5-dichloro-4-((8-methyl-1-oxo-1,2,5,6,7,8-hexahydro-5,8-ethanoisoquinolin-4-yl)oxy)phenyl)-1,2,4-triazine-3,5(2H,4H)-dione;
6-amino-2-(3,5-dichloro-4-((8-methyl-1-oxo-1,2,5,6,7,8-hexahydro-5,7-methanoisoquinolin-4-yl)oxy)phenyl)-1,2,4-triazine-3,5(2H,4H)-dione;
6-amino-2-(3,5-dichloro-4-((1-oxo-1,2,5,5a,6,6a-hexahydrocyclopropa[4,5]cyclopenta[1,2-c]pyridin-4-yl)oxy)phenyl)-1,2,4-triazine-3,5(2H,4H)-dione;
6-amino-2-(4-((5-isopropyl-6-oxo-1,6-dihydropyridin-3-yl)oxy)-3,5-dimethylphenyl)-1,2,4-triazine-3,5(2H,4H)-dione;

6-amino-2-(4-((5-isopropyl-6-oxo-1,6-dihydropyridin-3-yl)methyl)-3,5-dimethylphenyl)-1,2,4-triazine-3,5(2H,4H)-dione;
2-(3,5-dichloro-4-((5-isopropyl-6-oxo-1,6-dihydropyridin-3-yl)oxy)phenyl)-1,2,4-triazine-3,5(2H,4H)-dione;
2-(4-((5-isopropyl-6-oxo-1,6-dihydropyridin-3-yl)methyl)-3,5-dimethylphenyl)-1,2,4-triazine-3,5(2H,4H)-dione;
2-((3,5-dichloro-4-((5-isopropyl-6-oxo-1,6-dihydropyridin-3-yl)oxy)phenyl)amino)-2-oxoacetic acid;
N-(3,5-dichloro-4-((5-isopropyl-6-oxo-1,6-dihydropyridin-3-yl)oxy)phenyl)-5-oxo-4,5-dihydro-1,2,4-oxadiazole-3-carboxamide;
N-(3,5-dichloro-4-((1-isopropyl-6-oxo-1,6-dihydropyridin-3-yl)oxy)phenyl)-5-oxo-4,5-dihydro-1,2,4-oxadiazole-3-carboxamide; and
6-amino-2-(3,5-dichloro-4-((1-isopropyl-6-oxo-1,6-dihydropyridin-3-yl)oxy)phenyl)-1,2,4-triazine-3,5(2H,4H)-dione;
6-amino-2-(3,5-dichloro-4-((5-(1-cyclopropylethyl)-6-oxo-1,6-dihydropyridin-3-yl)oxy)phenyl)-1,2,4-triazine-3,5(2H,4H)-dione;
6-amino-2-(3,5-dichloro-4-((5-(isopropyl(methyl)amino)-6-oxo-1,6-dihydropyridin-3-yl)oxy)phenyl)-1,2,4-triazine-3,5(2H,4H)-dione;
6-amino-2-(3,5-dichloro-4-((5-(dimethylamino)-6-oxo-1,6-dihydropyridin-3-yl)oxy)phenyl)-1,2,4-triazine-3,5(2H,4H)-dione;
6-amino-2-(3,5-dichloro-4-((5-isopropyl-1-methyl-6-oxo-1,6-dihydropyridin-3-yl)oxy)phenyl)-1,2,4-triazine-3,5(2H,4H)-dione;
6-amino-2-(3,5-dichloro-4-((4-fluoro-5-isopropyl-6-oxo-1,6-dihydropyridin-3-yl)oxy)phenyl)-1,2,4-triazine-3,5(2H,4H)-dione;
6-amino-2-(3,5-dichloro-4-((5-isopropyl-4-methyl-6-oxo-1,6-dihydropyridin-3-yl)oxy)phenyl)-1,2,4-triazine-3,5(2H,4H)-dione;
6-amino-2-(3,5-dichloro-4-((1-isopropyl-5-methyl-6-oxo-1,6-dihydropyridin-3-yl)oxy)phenyl)-1,2,4-triazine-3,5(2H,4H)-dione;
6-amino-2-(3,5-dichloro-4-((5-ethyl-1-isopropyl-6-oxo-1,6-dihydropyridin-3-yl)oxy)phenyl)-1,2,4-triazine-3,5(2H,4H)-dione;
6-amino-2-(3,5-dichloro-4-((1-isopropyl-6-oxo-5-propyl-1,6-dihydropyridin-3-yl)oxy)phenyl)-1,2,4-triazine-3,5(2H,4H)-dione;
6-amino-2-(3,5-dichloro-4-((5-fluoro-1-isopropyl-6-oxo-1,6-dihydropyridin-3-yl)oxy)phenyl)-1,2,4-triazine-3,5(2H,4H)-dione;
6-amino-2-(3,5-dichloro-4-((5-chloro-1-isopropyl-6-oxo-1,6-dihydropyridin-3-yl)oxy)phenyl)-1,2,4-triazine-3,5(2H,4H)-dione;
6-amino-2-(3,5-dichloro-4-((5-cyclobutyl-6-oxo-1,6-dihydropyridin-3-yl)oxy)phenyl)-1,2,4-triazine-3,5(2H,4H)-dione;
6-amino-2-(3,5-dichloro-4-((5-cyclopentyl-6-oxo-1,6-dihydropyridin-3-yl)oxy)phenyl)-1,2,4-triazine-3,5(2H,4H)-dione;
5-(4-(6-amino-3,5-dioxo-4,5-dihydro-1,2,4-triazin-2(3H)-yl)-2,6-dichlorophenoxy)-N-methyl-2-oxo-1,2-dihydropyridine-3-carboxamide;
5-(4-(6-amino-3,5-dioxo-4,5-dihydro-1,2,4-triazin-2(3H)-yl)-2,6-dichlorophenoxy)-N-(3,3-difluorocyclobutyl)-2-oxo-1,2-dihydropyridine-3-carboxamide;
N-(3,5-dichloro-4-((5-(methylcarbamoyl)-6-oxo-1,6-dihydropyridin-3-yl)oxy)phenyl)-5-oxo-4,5-dihydro-1,2,4-oxadiazole-3-carboxamide; and
N-(3,5-dichloro-4-((5-((3,3-difluorocyclobutyl)carbamoyl)-6-oxo-1,6-dihydropyridin-3-yl)oxy)phenyl)-5-oxo-4,5-dihydro-1,2,4-oxadiazole-3-carboxamide;
or a stereoisomer or a tautomer thereof, or a pharmaceutically acceptable salt thereof.

Embodiment Q53. A pharmaceutical composition comprising the compound of any one of embodiments Q1-Q52, or the stereoisomer or the tautomer thereof, or the pharmaceutically acceptable salt thereof, and at least one pharmaceutically acceptable excipient.

Embodiment Q54. A method of treating a disorder or disease in a subject in need thereof, the method comprising administering to the subject a therapeutically effective amount of the compound of any one of embodiments Q1-Q52, or the stereoisomer or the tautomer thereof, or the pharmaceutically acceptable salt thereof, or a therapeutically effective amount of the pharmaceutical composition of embodiment Q53, wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment Q55. Use of the compound of any one of embodiments Q1-Q52, or the stereoisomer or the tautomer thereof, or the pharmaceutically acceptable salt thereof, for the manufacture of a medicament for the treatment of a disorder or disease selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment Q56. A compound of any one of embodiments Q1-Q52, or the stereoisomer or the tautomer thereof, or the pharmaceutically acceptable salt thereof, for use in treating a disorder or disease selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment Q57. A composition of embodiment Q53 for use in treating a disorder or disease selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment Q58. A method of treating a thyroid hormone receptor related disorder in a patient, the method comprising the steps of:
identifying a patient in need of treatment for the thyroid hormone receptor related disorder, and
administering to the patient, or contacting the patient with, the compound of any one of embodiments Q1-Q52, or the stereoisomer or the tautomer thereof, or the pharmaceutically acceptable salt thereof, or a therapeutically effective amount of the pharmaceutical composition of embodiment Q53.

Embodiment Q59. The method of embodiment Q58, wherein the thyroid hormone receptor related disorder is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment Q60. A method of selectively modulating the activity of a thyroid hormone receptor beta (THR-β) comprising contacting the compound of any one of embodiments Q1-Q52, or the stereoisomer or the tautomer thereof, or the pharmaceutically acceptable salt thereof, with the thyroid hormone receptor.

Embodiment Q61. The method of embodiment Q60, wherein the contacting is in vitro or ex vivo.

Embodiment Q62. The method of embodiment Q60, wherein the contacting is in vivo.

Embodiment Q63. A compound of any one of embodiments Q1-Q52, or the stereoisomer or the tautomer thereof, or the pharmaceutically acceptable salt thereof, for use in selectively modulating the activity of a thyroid hormone receptor beta (THR-β).

Embodiment Q64. A composition of embodiment Q53 for use in selectively modulating the activity of a thyroid hormone receptor beta (THR-β).

Further Embodiments

Embodiment 1. A compound of Formula I":

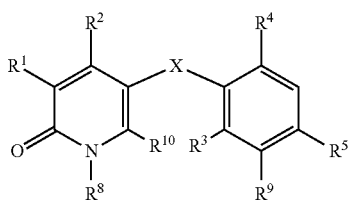

Formula I"

or a stereoisomer or a tautomer thereof, or a pharmaceutically acceptable salt thereof, wherein $R^1$ and $R^2$ are each independently selected from H, halogen, —$NR^aR^b$, —$C(O)NR^aR^b$, optionally substituted $C_1$-$C_6$ alkyl, optionally substituted $C_3$-$C_6$ cycloalkyl, and an optionally substituted non-aromatic bicyclic ring, wherein $R^1$ and $R^2$ cannot both be H; or $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

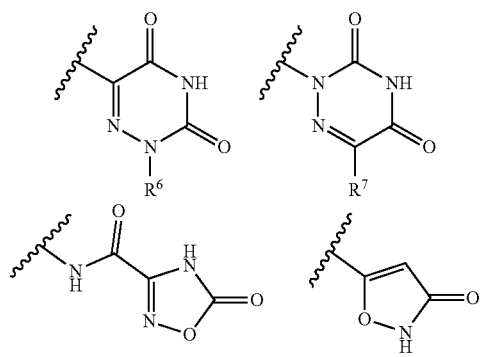

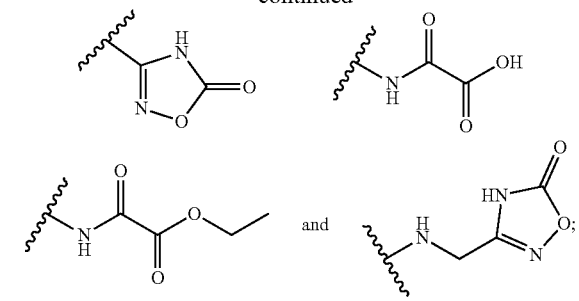

$R^6$ is H or $C_1$-$C_3$ alkyl;

$R^7$ is selected from H, —CN, $CH_3$, and —$NH_2$;

$R^8$ is H, $C_1$-$C_3$ alkyl optionally substituted with 1-5 halogens, or $C_3$-$C_6$ cycloalkyl optionally substituted with 1-6 halogens;

$R^9$ is selected from H, halogen, —CN, optionally substituted $C_1$-$C_3$ alkyl, and optionally substituted $C_1$-$C_2$ alkoxy; or $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

$R^{10}$ is selected from H, halogen, or optionally substituted $C_1$-$C_3$ alkyl, or $R^8$ and $R^{10}$ together with the atoms to which they are attached form 4- to 6-membered cyclic ring optionally substituted with 1 to 3 substituents independently selected from $C_1$-$C_3$ alkyl and halogen;

$R^a$ and $R^b$ are each independently selected from H, optionally substituted $C_1$-$C_6$ alkyl and optionally substituted $C_3$-$C_6$ cycloalkyl; or $R^a$ and $R^b$ together with the nitrogen atom to which they are attached form a 4- to 6-membered cyclic ring optionally substituted with 1 to 3 substituents independently selected from $C_1$-$C_3$ alkyl, halogen, and =O;

Q is selected from N, CH, and CF; and

X is O or $CH_2$;

wherein 0 to 10 hydrogen atoms that are attached to one or more carbon atoms are replaced with deuterium atom(s);

with the proviso that when $R^1$ and $R^2$ are each independently selected from H, halogen, optionally substituted $C_1$-$C_6$ alkyl, optionally substituted $C_3$-$C_6$ cycloalkyl, and an optionally substituted non-aromatic bicyclic ring; or when $R^1$ and $R^2$ together with the carbon atoms to which they are attached form a 4-membered monocyclic ring optionally substituted with 1 to 3 substituents independently selected from halogen and $C_1$-$C_6$ alkyl; then $R^7$ is H or —$NH_2$.

Embodiment 2. A compound of Formula I':

Formula I' or a stereoisomer or a tautomer thereof, or a pharmaceutically acceptable salt thereof, wherein $R^1$ and $R^2$ are each independently selected from H, halogen, $-NR^aR^b$, $-C(O)NR^aR^b$, optionally substituted $C_1$-$C_6$ alkyl, optionally substituted $C_3$-$C_6$ cycloalkyl, and an optionally substituted non-aromatic bicyclic ring, wherein $R^1$ and $R^2$ cannot both be H; or $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, $-CN$, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

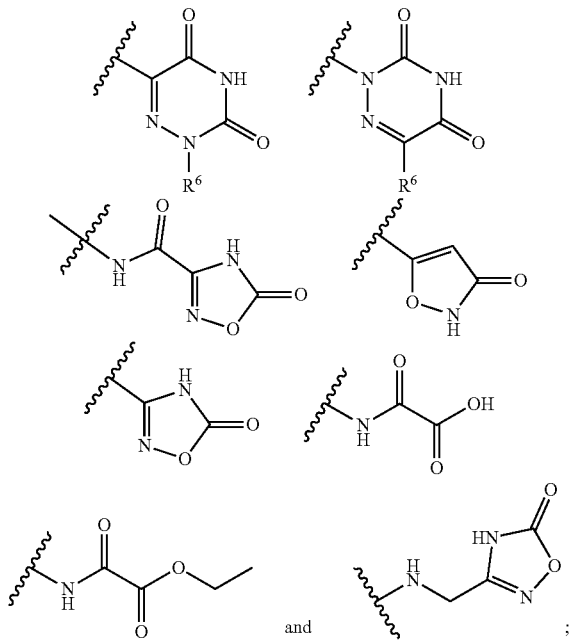

$R^6$ is H or $C_1$-$C_3$ alkyl;

$R^7$ is selected from H, $-CN$, $CH_3$, and $-NH_2$;

$R^8$ is H or $C_1$-$C_3$ alkyl optionally substituted with 1-5 halogens;

$R^9$ is selected from H, halogen, $-CN$, optionally substituted $C_1$-$C_3$ alkyl, and optionally substituted $C_1$-$C_2$ alkoxy; or $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

$R^a$ and $R^b$ are each independently selected from H, optionally substituted $C_1$-$C_6$ alkyl and optionally substituted $C_3$-$C_6$ cycloalkyl; or $R^a$ and $R^b$ together with the nitrogen atom to which they are attached form a 4- to 6-membered cyclic ring optionally substituted with 1 to 3 substituents independently selected from $C_1$-$C_3$ alkyl and halogen;

Q is selected from N, CH, and CF; and

X is O or $CH_2$;

wherein 0 to 10 hydrogen atoms that are attached to one or more carbon atoms are replaced with deuterium atom(s);

with the proviso that when $R^1$ and $R^2$ are each independently selected from H, halogen, optionally substituted $C_1$-$C_6$ alkyl, optionally substituted $C_3$-$C_6$ cycloalkyl, and an optionally substituted non-aromatic bicyclic ring; or when $R^1$ and $R^2$ together with the carbon atoms to which they are attached form a 4-membered monocyclic ring optionally substituted with 1 to 3 substituents independently selected from halogen and $C_1$-$C_6$ alkyl; then $R^7$ is H or $-NH_2$.

Embodiment 3. A compound of Formula I:

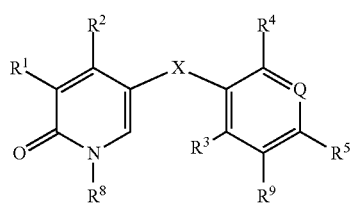

Formula I or a stereoisomer or a tautomer thereof, or a pharmaceutically acceptable salt thereof, wherein $R^1$ and $R^2$ are each independently selected from H, optionally substituted $C_1$-$C_6$ alkyl, optionally substituted $C_3$-$C_6$ cycloalkyl, and an optionally substituted non-aromatic bicyclic ring, wherein $R^1$ and $R^2$ cannot both be H; or $R^1$ and $R^2$ together with the carbon atoms to which they are attached form a $C_4$-$C_7$ monocyclic ring optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, $-CN$, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

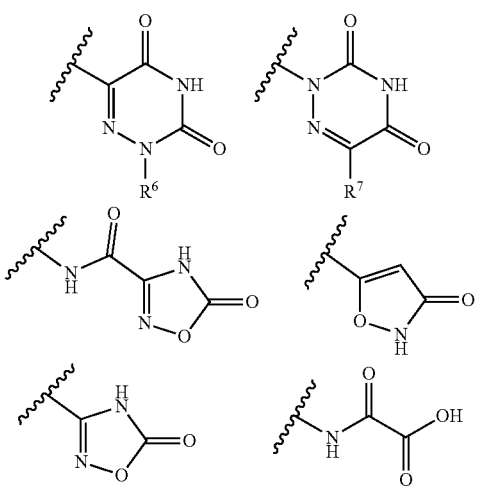

175

-continued

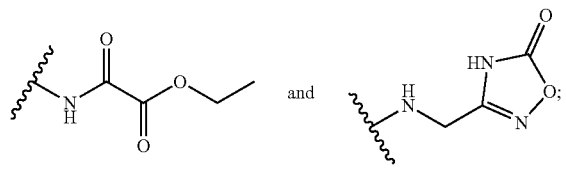

and

R[6] is H or $C_1$-$C_3$ alkyl;

R[7] is selected from H, —CN, CH$_3$, and —NH$_2$;

R[8] is H or $C_1$-$C_3$ alkyl optionally substituted with 1-5 halogens;

R[9] is selected from H, halogen, —CN, optionally substituted $C_1$-$C_3$ alkyl, and optionally substituted $C_1$-$C_2$ alkoxy; or R[3] and R[9] together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

Q is selected from N, CH, and CF; and

X is O or CH$_2$;

wherein 0 to 10 hydrogen atoms that are attached to one or more carbon atoms are replaced with deuterium atom(s);

with the proviso that when R[1] and R[2] together with the carbon atoms to which they are attached do not form a $C_5$-$C_7$ monocyclic ring or a polycyclic ring, then R[7] is H or —NH$_2$.

Embodiment 4. A compound of Formula IA":

Formula IA"

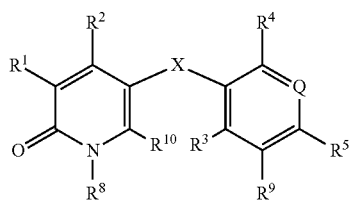

or a stereoisomer or a tautomer thereof, or a pharmaceutically acceptable salt thereof, wherein R[1] and R[2] are each independently selected from H, halogen, —NR$^a$R$^b$, —C(O)NR$^a$R$^b$, optionally substituted $C_1$-$C_6$ alkyl, optionally substituted $C_3$-$C_6$ cycloalkyl, and an optionally substituted non-aromatic bicyclic ring; or R[1] and R[2] together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl; or R[1] and R[2] together with the carbon atoms to which they are attached form a polycyclic ring optionally substituted with 1 to 3 substituents independently selected from halogen and $C_1$-$C_6$ alkyl;

R[3] and R[4] are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

176

R[5] is selected from:

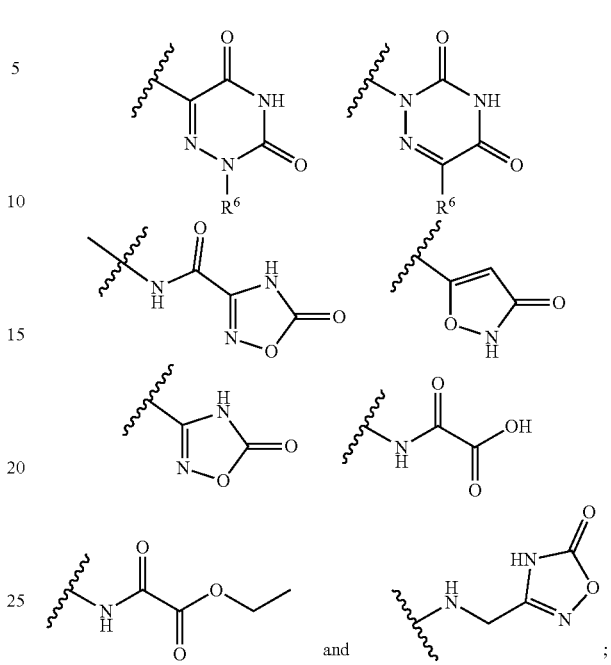

and

R[6] is H or $C_1$-$C_3$ alkyl;

R[7] is selected from H, —CN, CH$_3$, and —NH$_2$;

R[8] is $C_1$-$C_3$ alkyl optionally substituted with 1-5 halogens or optionally substituted $C_3$-$C_5$ cycloalkyl, or $C_3$-$C_6$ cycloalkyl optionally substituted with 1-6 halogens;

R[9] is selected from H, halogen, —CN, optionally substituted $C_1$-$C_3$ alkyl, and optionally substituted $C_1$-$C_2$ alkoxy; or R[3] and R[9] together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

R[10] is selected from H, halogen, or optionally substituted $C_1$-$C_3$ alkyl, or R[8] and R[10] together with the atoms to which they are attached form 4- to 6-membered cyclic ring optionally substituted with 1 to 3 substituents independently selected from $C_1$-$C_3$ alkyl and halogen;

R$^a$ and R$^b$ are each independently selected from H, optionally substituted $C_1$-$C_6$ alkyl and optionally substituted $C_3$-$C_6$ cycloalkyl; or R$^a$ and R$^b$ together with the nitrogen atom to which they are attached form a 4- to 6-membered cyclic ring optionally substituted with 1 to 3 substituents independently selected from $C_1$-$C_3$ alkyl, halogen, and =O;

Q is selected from N, CH, and CF; and

X is O or CH$_2$;

wherein 0 to 10 hydrogen atoms that are attached to one or more carbon atoms are replaced with deuterium atom(s);

with the proviso that the compound is not:

2-(3,5-dichloro-4-((1-isopropyl-6-oxo-1,6-dihydropyridin-3-yl)oxy)phenyl)-1,2,4-triazine-3,5(2H,4H)-dione;

2-(3,5-dichloro-4-((1-isopropyl-6-oxo-1,6-dihydropyridin-3-yl)oxy)phenyl)-3,5-dioxo-2,3,4,5-tetrahydro-1,2,4-triazine-6-carbonitrile; or 2-(3,5-dichloro-4-((1-cyclopropyl-6-oxo-1,6-dihydropyridin-3-yl)oxy)phenyl)-3,5-dioxo-2,3,4,5-tetrahydro-1,2,4-triazine-6-carbonitrile.

Embodiment 5. A compound of Formula IA:

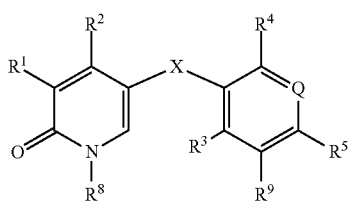

Formula IA or a stereoisomer or a tautomer thereof, or a pharmaceutically acceptable salt thereof, wherein $R^1$ and $R^2$ are each independently selected from H, halogen, —$NR^aR^b$, —$C(O)NR^aR^b$, optionally substituted $C_1$-$C_6$ alkyl, optionally substituted $C_3$-$C_6$ cycloalkyl, and an optionally substituted non-aromatic bicyclic ring; or $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

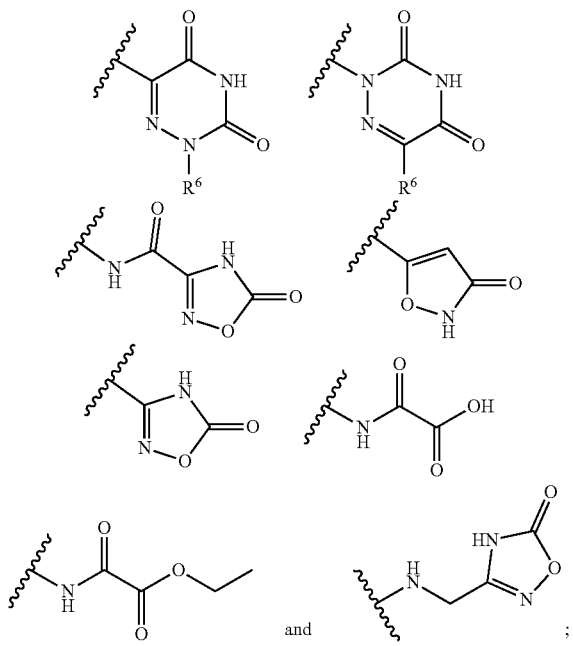

$R^6$ is H or $C_1$-$C_3$ alkyl;

$R^7$ is selected from H, —CN, $CH_3$, and —$NH_2$;

$R^8$ is $C_1$-$C_3$ alkyl optionally substituted with 1-5 halogens or optionally substituted $C_3$-$C_5$ cycloalkyl;

$R^9$ is selected from H, halogen, —CN, optionally substituted $C_1$-$C_3$ alkyl, and optionally substituted $C_1$-$C_2$ alkoxy; or $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

$R^a$ and $R^b$ are each independently selected from H, optionally substituted $C_1$-$C_6$ alkyl and optionally substituted $C_3$-$C_6$ cycloalkyl; or $R^a$ and $R^b$ together with the nitrogen atom to which they are attached form a 4- to 6-membered cyclic ring optionally substituted with 1 to 3 substituents independently selected from $C_1$-$C_3$ alkyl and halogen;

Q is selected from N, CH, and CF; and

X is O or $CH_2$;

wherein 0 to 10 hydrogen atoms that are attached to one or more carbon atoms are replaced with deuterium atom(s);

with the proviso that the compound is not:

2-(3,5-dichloro-4-((1-isopropyl-6-oxo-1,6-dihydropyridin-3-yl)oxy)phenyl)-1,2,4-triazine-3,5(2H,4H)-dione; or 2-(3,5-dichloro-4-((1-isopropyl-6-oxo-1,6-dihydropyridin-3-yl)oxy)phenyl)-3,5-dioxo-2,3,4,5-tetrahydro-1,2,4-triazine-6-carbonitrile.

Embodiment 6. The compound of any one of embodiments 1-5, having the chemical structure of:

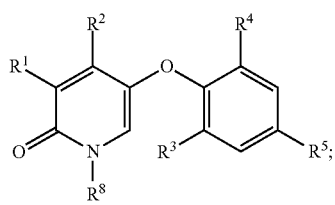

(Formula IA.1)

or the stereoisomer or the tautomer thereof, or the pharmaceutically acceptable salt thereof.

Embodiment 7. The compound of any one of embodiments 1-3, or the stereoisomer or the tautomer thereof, or the pharmaceutically acceptable salt thereof, wherein $R^8$ is H.

Embodiment 8. The compound of any one of embodiments 1-6, or the stereoisomer or the tautomer thereof, or the pharmaceutically acceptable salt thereof, wherein $R^8$ is $C_1$-$C_3$ alkyl optionally substituted with 1-5 halogens.

Embodiment 9. The compound of any one of embodiments 1, 4, or 6, or the stereoisomer or the tautomer thereof, or the pharmaceutically acceptable salt thereof, wherein $R^8$ is $C_3$-$C_6$ cycloalkyl optionally substituted with 1-6 halogens.

Embodiment 10. The compound of embodiment 4, or the stereoisomer or the tautomer thereof, wherein $R^8$ and $R^{10}$ together with the atoms to which they are attached form 4- to 6-membered cyclic ring optionally substituted with 1 to 3 substituents independently selected from $C_1$-$C_3$ alkyl and halogen.

Embodiment 11. The compound of any one of embodiments 1, 2, or 4-10, or the stereoisomer or the tautomer thereof, or the pharmaceutically acceptable salt thereof, wherein $R^1$ and $R^2$ are each independently selected from H, halogen, —$NR^aR^b$, optionally substituted $C_1$-$C_6$ alkyl, optionally substituted $C_3$-$C_6$ cycloalkyl, and an optionally substituted non-aromatic bicyclic ring.

Embodiment 12. The compound of any one of embodiments 1, 2, or 4-10, or the stereoisomer or the tautomer thereof, or the pharmaceutically acceptable salt thereof, wherein $R^1$ is independently selected from H, halogen, —$NR^aR^b$, —$C(O)NR^aR^b$, $C_1$-$C_6$ alkyl optionally substituted with 1-6 substituents independently selected from halogen and $C_3$-$C_4$ cycloalkyl optionally substituted with 1-6 halogens, $C_3$-$C_6$ cycloalkyl optionally substituted with 1-6 halogens, and an non-aromatic bicyclic ring optionally substituted with 1-6 halogens.

Embodiment 13. The compound of any one of embodiments 1-10, or the stereoisomer or the tautomer thereof, or the pharmaceutically acceptable salt thereof, wherein $R^2$ is independently selected from H, halogen, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and a non-aromatic bicyclic ring optionally substituted with 1-6 halogens.

Embodiment 14. The compound of any one of embodiments 1-13, or the stereoisomer or the tautomer thereof, or the pharmaceutically acceptable salt thereof, wherein $R^2$ is H.

Embodiment 15. The compound of any one of embodiments 1-10, or the stereoisomer or the tautomer thereof, or the pharmaceutically acceptable salt thereof, wherein $R^1$ is independently selected from H, optionally substituted $C_1$-$C_6$ alkyl, optionally substituted $C_3$-$C_6$ cycloalkyl, and an optionally substituted non-aromatic bicyclic ring; and $R^2$ is independently selected from H, halogen, optionally substituted $C_1$-$C_6$ alkyl, optionally substituted $C_3$-$C_6$ cycloalkyl, and an optionally substituted non-aromatic bicyclic ring.

Embodiment 16. The compound of any one of embodiments 1-10, or the stereoisomer or the tautomer thereof, or the pharmaceutically acceptable salt thereof, wherein $R^1$ is independently selected from H, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and a non-aromatic bicyclic ring optionally substituted with 1-6 halogens; and $R^2$ is independently selected from H, halogen, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and a non-aromatic bicyclic ring optionally substituted with 1-6 halogens.

Embodiment 17. The compound of any one of embodiments 1, 2, or 4-10, or the stereoisomer or the tautomer thereof, or the pharmaceutically acceptable salt thereof, wherein $R^1$ is —$NR^aR^b$ or $C_1$-$C_6$ alkyl optionally substituted with 1 to 5 substituents independently selected from halogen and $C_3$-$C_4$ cycloalkyl.

Embodiment 18. The compound of any one of embodiments 1-10, or the stereoisomer or the tautomer thereof, or the pharmaceutically acceptable salt thereof, wherein $R^1$ is $C_1$-$C_6$ alkyl.

Embodiment 19. The compound of any one of embodiments 1-10, or the stereoisomer or the tautomer thereof, or the pharmaceutically acceptable salt thereof, wherein $R^1$ is halogen.

Embodiment 20. The compound of any one of embodiments 1-10, or the stereoisomer or the tautomer thereof, or the pharmaceutically acceptable salt thereof, wherein $R^1$ is $C_3$-$C_6$ cycloalkyl optionally substituted with 1-6 halogens.

Embodiment 21. The compound of any one of embodiments 1, 2, or 4-10, or the stereoisomer or the tautomer thereof, or the pharmaceutically acceptable salt thereof, wherein $R^1$ is —$C(O)NR^aR^b$.

Embodiment 22. The compound of any one of embodiments 1, 2, 4-14, 17, or 21, or the stereoisomer or the tautomer thereof, or the pharmaceutically acceptable salt thereof, wherein $R^a$ and $R^b$ are each independently selected from $C_1$-$C_3$ alkyl.

Embodiment 23. The compound of any one of embodiments 1, 2, 4-14, 17, or 21, or the stereoisomer or the tautomer thereof, or the pharmaceutically acceptable salt thereof, wherein $R^a$ is H; and $R^b$ is $C_1$-$C_3$ alkyl optionally substituted with 1 to 3 halogens, or $C_3$-$C_6$ cycloalkyl optionally substituted with 1-5 halogens.

Embodiment 24. The compound of any one of embodiments 1, 2, 4-14, 17, or 21, or the stereoisomer or the tautomer thereof, or the pharmaceutically acceptable salt thereof, wherein $R^a$ is H; and $R^b$ is a 4- to 6-membered cyclic ring optionally substituted with 2 halogens.

Embodiment 25. The compound of any one of embodiments 1, 4, 6-14, 17, or 21, or the stereoisomer or the tautomer thereof, or the pharmaceutically acceptable salt thereof, wherein $R^a$ and $R^b$ together with the nitrogen atom to which they are attached form a 4- to 6-membered cyclic ring optionally substituted with 1 to 3 substituents independently selected from $C_1$-$C_3$ alkyl, halogen and =O.

Embodiment 26. The compound of any one of embodiments 1-3, 6, 7, or 11-25, having the chemical structure of:

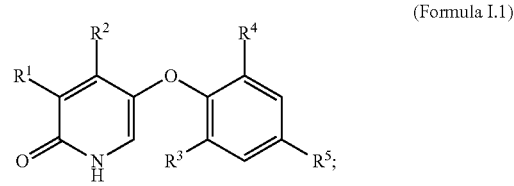

(Formula I.1)

or a stereoisomer or a tautomer thereof, or a pharmaceutically acceptable salt thereof.

Embodiment 27. The compound of any one of embodiments 1-10 or 26, or the stereoisomer or the tautomer thereof, or the pharmaceutically acceptable salt thereof, wherein $R^1$ and $R^2$ are each independently $C_1$-$C_6$ alkyl, $C_3$-$C_6$ cycloalkyl, or a non-aromatic bicyclic ring, wherein $R^1$ and $R^2$ are each optionally substituted with 1 to 3 substituents independently selected from optionally substituted $C_3$-$C_4$ cycloalkyl, optionally substituted bicyclic ring, and halogen; or $R^1$ or $R^2$ are H, but $R^1$ and $R^2$ cannot both be H.

Embodiment 28. The compound of any one of embodiments 1-10 or 26, or the stereoisomer or the tautomer thereof, or the pharmaceutically acceptable salt thereof, wherein $R^1$ and $R^2$ are each independently $C_1$-$C_6$ alkyl, $C_3$-$C_6$ cycloalkyl, or a non-aromatic bicyclic ring, wherein $R^1$ and $R^2$ are each optionally substituted with 1 to 3 substituents independently selected from $C_3$-$C_4$ cycloalkyl optionally substituted with 1 to 3 substituents independently selected from halogen and $C_1$-$C_3$ alkyl; bicyclic ring optionally substituted with 1 to 3 substituents independently selected from halogen and $C_1$-$C_3$ alkyl; and halogen; or $R^1$ or $R^2$ are H, but $R^1$ and $R^2$ cannot both be H.

Embodiment 29. The compound of any one of embodiments 1-2, 4-10, or 26, or the stereoisomer or the tautomer thereof, or the pharmaceutically acceptable salt thereof, wherein $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl.

Embodiment 30. The compound of any one of embodiments 3, 6-7, or 26, or the stereoisomer or the tautomer thereof, or the pharmaceutically acceptable salt thereof, wherein $R^1$ and $R^2$ together with the carbon atoms to which they are attached form a $C_4$-$C_7$ monocyclic ring optionally substituted with 1 to 3 substituents independently selected from halogen and $C_1$-$C_6$ alkyl.

Embodiment 31. The compound of any one of embodiments 1-10 or 26, or the stereoisomer or the tautomer thereof, or the pharmaceutically acceptable salt thereof, wherein $R^1$ and $R^2$ together with the carbon atoms to which they are attached form a polycyclic ring optionally substituted with 1 to 3 substituents independently selected from $C_1$-$C_6$ alkyl.

Embodiment 32. The compound of any one of embodiments 1-31, or the stereoisomer or the tautomer thereof, or the pharmaceutically acceptable salt thereof, wherein $R^3$ and $R^4$ are each independently selected from halogen; —CN; $C_1$-$C_3$ alkyl optionally substituted with 1 to 3 substituents independently selected from halogen and $C_1$-$C_6$ alkoxy; $C_1$-$C_2$ alkoxy optionally substituted with 1 to 3 substituents independently selected from halogen; and $C_2$-$C_3$ alkenyl optionally substituted with 1 to 3 substituents independently selected from halogen and $C_1$-$C_6$ alkoxy; and cyclopropyl.

Embodiment 33. The compound of any one of embodiments 1-31, or the stereoisomer or the tautomer thereof, or the pharmaceutically acceptable salt thereof, wherein $R^3$ and $R^4$ are each independently selected from halogen and $C_1$-$C_3$ alkyl.

Embodiment 34. The compound of any one of embodiments 1-31, or the stereoisomer or the tautomer thereof, or the pharmaceutically acceptable salt thereof, wherein $R^3$ and $R^4$ are both halogen.

Embodiment 35. The compound of any one of embodiments 1-31, or the stereoisomer or the tautomer thereof, or the pharmaceutically acceptable salt thereof, wherein $R^3$ and $R^4$ are both —Cl.

Embodiment 36. The compound of any one of embodiments 1-31, or the stereoisomer or the tautomer thereof, or the pharmaceutically acceptable salt thereof, wherein $R^3$ and $R^4$ are both methyl.

Embodiment 37. The compound of any one of embodiments 1-36, or the stereoisomer or the tautomer thereof, or the pharmaceutically acceptable salt thereof, wherein $R^9$ is selected from H; halogen; —CN; $C_1$-$C_3$ alkyl optionally substituted with 1 to 3 substituents independently selected from halogen and $C_1$-$C_2$ alkoxy; and $C_1$-$C_2$ alkoxy optionally substituted with 1 to 3 substituents independently selected from halogen.

Embodiment 38. The compound of any one of embodiments 1-37, or the stereoisomer or the tautomer thereof, or the pharmaceutically acceptable salt thereof, wherein $R^9$ is H.

Embodiment 39. The compound of any one of embodiments 1-31, or the stereoisomer or the tautomer thereof, or the pharmaceutically acceptable salt thereof, wherein $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring.

Embodiment 40. The compound of any one of embodiments 1-39, or the stereoisomer or the tautomer thereof, or the pharmaceutically acceptable salt thereof, wherein $R^5$ is

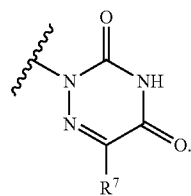

Embodiment 41. The compound of any one of embodiments 1-40, or the stereoisomer or the tautomer thereof, or the pharmaceutically acceptable salt thereof, wherein $R^7$ is H.

Embodiment 42. The compound of any one of embodiments 1-40, or the stereoisomer or the tautomer thereof, or the pharmaceutically acceptable salt thereof, wherein $R^7$ is —$NH_2$.

Embodiment 43. The compound of any one of embodiments 1-40, or the stereoisomer or the tautomer thereof, or the pharmaceutically acceptable salt thereof, wherein $R^7$ is $CH_3$.

Embodiment 44. The compound of any one of embodiments 1-40, or the stereoisomer or the tautomer thereof, or the pharmaceutically acceptable salt thereof, wherein $R^7$ is —CN.

Embodiment 45. The compound of any one of embodiments 1-39, or the stereoisomer or the tautomer thereof, or the pharmaceutically acceptable salt thereof, wherein $R^5$ is

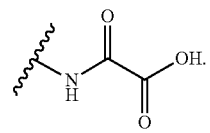 [SMILES: *NC(=O)C(=O)O]

Embodiment 46. The compound of any one of embodiments 1-39, or the stereoisomer or the tautomer thereof, or the pharmaceutically acceptable salt thereof, wherein $R^5$ is

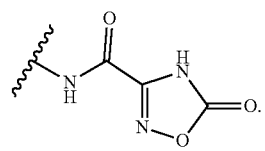 [SMILES: *NC(=O)c1noc(=O)[nH]1]

Embodiment 47. The compound of any one of embodiments 4-6 or 8-16, or the stereoisomer or the tautomer thereof, or the pharmaceutically acceptable salt thereof, wherein $R^1$ and $R^2$ are H;

$R^5$ is

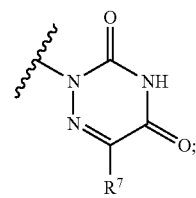

$R^7$ is —$NH_2$; and $R^8$ is isopropyl, optionally substituted with 1-5 halogens.

Embodiment 48. The compound of any one of embodiments 1-6 or 8-20, or the stereoisomer or the tautomer thereof, or the pharmaceutically acceptable salt thereof, wherein $R^5$ is

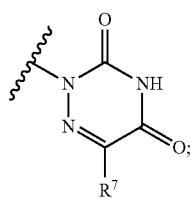

R[7] is CH$_3$ or —NH$_2$; and R[8] is C$_1$-C$_3$ alkyl.

Embodiment 49. The compound of any one of embodiments 1-3, 6, or 11-18, or the stereoisomer or the tautomer thereof, or the pharmaceutically acceptable salt thereof, wherein R[1] is CH$_3$; R[8] is isopropyl; R[5] is

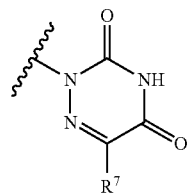 or 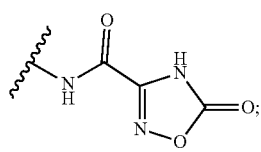

and R[7] is —NH$_2$.

Embodiment 50. The compound of any one of embodiments 1-5, 7-27, and 29-49, or the stereoisomer or the tautomer thereof, or the pharmaceutically acceptable salt thereof, wherein Q is CH.

Embodiment 51. The compound of any one of embodiments 1-5, 7-27, and 29-50, or the stereoisomer or the tautomer thereof, or the pharmaceutically acceptable salt thereof, wherein X is CH$_2$.

Embodiment 52. The compound of any one of embodiments 1-50, or the stereoisomer or the tautomer thereof, or the pharmaceutically acceptable salt thereof, wherein X is O.

Embodiment 53. A compound selected from the group consisting of:

6-amino-2-(3,5-dichloro-4-((7-methyl-1-oxo-2,5,6,7-tetrahydro-1H-cyclopenta[c]pyridin-4-yl)oxy)phenyl)-1,2,4-triazine-3,5(2H,4H)-dione;

6-amino-2-(4-chloro-5-((7-methyl-1-oxo-2,5,6,7-tetrahydro-1H-cyclopenta[c]pyridin-4-yl)oxy)bicyclo[4.2.0]octa-1,3,5-trien-2-yl)-1,2,4-triazine-3,5(2H,4H)-dione;

2-((4-chloro-5-((7-methyl-1-oxo-2,5,6,7-tetrahydro-1H-cyclopenta[c]pyridin-4-yl)oxy)bicyclo[4.2.0]octa-1,3,5-trien-2-yl)amino)-2-oxoacetic acid;

2-((7-((7-cyclopropyl-1-oxo-2,5,6,7-tetrahydro-1H-cyclopenta[c]pyridin-4-yl)oxy)-6-methyl-2,3-dihydro-1H-inden-4-yl)amino)-2-oxoacetic acid;

6-amino-2-(3,5-dichloro-4-((5-isopropyl-6-oxo-1,6-dihydropyridin-3-yl)oxy)phenyl)-1,2,4-triazine-3,5(2H,4H)-dione;

2-(3,5-dichloro-4-((7-methyl-1-oxo-2,5,6,7-tetrahydro-1H-cyclopenta[c]pyridin-4-yl)oxy)phenyl)-3,5-dioxo-2,3,4,5-tetrahydro-1,2,4-triazine-6-carbonitrile;

6-(3,5-dichloro-4-((5-isopropyl-6-oxo-1,6-dihydropyridin-3-yl)oxy)phenyl)-2-methyl-1,2,4-triazine-3,5(2H,4H)-dione;

6-amino-2-(3,5-dichloro-4-((5-(1-cyclopropylethyl)-6-hydroxypyridin-3-yl)oxy)phenyl)-1,2,4-triazine-3,5(2H,4H)-dione;

6-amino-2-(3,5-dichloro-4-((5-(1-(3,3-difluorocyclobutyl)ethyl)-6-hydroxypyridin-3-yl)oxy)phenyl)-1,2,4-triazine-3,5(2H,4H)-dione;

6-amino-2-(4-((5-(1-(bicyclo[1.1.1]pentan-2-yl)ethyl)-6-hydroxypyridin-3-yl)oxy)-3,5-dichlorophenyl)-1,2,4-triazine-3,5(2H,4H)-dione;

6-amino-2-(3,5-dichloro-4-((5-(6,6-difluorospiro[3.3]heptan-1-yl)-6-hydroxypyridin-3-yl)oxy)phenyl)-1,2,4-triazine-3,5(2H,4H)-dione;

6-amino-2-(3,5-dichloro-4-((6-hydroxy-5-(spiro[2.3]hexan-4-yl)pyridin-3-yl)oxy)phenyl)-1,2,4-triazine-3,5(2H,4H)-dione;

6-amino-2-(4-chloro-5-((6-hydroxy-5-isopropylpyridin-3-yl)oxy)-6-methylpyridin-2-yl)-1,2,4-triazine-3,5(2H,4H)-dione;

6-amino-2-(3,5-dichloro-4-((5-(1-cyclopropylethyl)-6-hydroxypyridin-3-yl)oxy)phenyl-2-d)-1,2,4-triazine-3,5(2H,4H)-dione;

6-amino-2-(3,5-dichloro-4-((6-hydroxy-5-isopropylpyridin-3-yl)oxy)phenyl-2-d)-1,2,4-triazine-3,5(2H,4H)-dione;

6-amino-2-(3,5-dichloro-4-((5-(1-cyclopropylethyl)-6-hydroxypyridin-3-yl)oxy)-2-fluorophenyl)-1,2,4-triazine-3,5(2H,4H)-dione;

6-amino-2-(3,5-dichloro-4-((8-methyl-1-oxo-1,2,5,6,7,8-hexahydro-5,8-ethanoisoquinolin-4-yl)oxy)phenyl)-1,2,4-triazine-3,5(2H,4H)-dione;

6-amino-2-(3,5-dichloro-4-((8-methyl-1-oxo-1,2,5,6,7,8-hexahydro-5,7-methanoisoquinolin-4-yl)oxy)phenyl)-1,2,4-triazine-3,5(2H,4H)-dione;

6-amino-2-(3,5-dichloro-4-((1-oxo-1,2,5,5a,6,6a-hexahydrocyclopropa[4,5]cyclopenta[1,2-c]pyridin-4-yl)oxy)phenyl)-1,2,4-triazine-3,5(2H,4H)-dione;

6-amino-2-(4-((5-isopropyl-6-oxo-1,6-dihydropyridin-3-yl)oxy)-3,5-dimethylphenyl)-1,2,4-triazine-3,5(2H,4H)-dione;

6-amino-2-(4-((5-isopropyl-6-oxo-1,6-dihydropyridin-3-yl)methyl)-3,5-dimethylphenyl)-1,2,4-triazine-3,5(2H,4H)-dione;

2-(3,5-dichloro-4-((5-isopropyl-6-oxo-1,6-dihydropyridin-3-yl)oxy)phenyl)-1,2,4-triazine-3,5(2H,4H)-dione;

2-(4-((5-isopropyl-6-oxo-1,6-dihydropyridin-3-yl)methyl)-3,5-dimethylphenyl)-1,2,4-triazine-3,5(2H,4H)-dione;

2-((3,5-dichloro-4-((5-isopropyl-6-oxo-1,6-dihydropyridin-3-yl)oxy)phenyl)amino)-2-oxoacetic acid;

N-(3,5-dichloro-4-((5-isopropyl-6-oxo-1,6-dihydropyridin-3-yl)oxy)phenyl)-5-oxo-4,5-dihydro-1,2,4-oxadiazole-3-carboxamide;

N-(3,5-dichloro-4-((1-isopropyl-6-oxo-1,6-dihydropyridin-3-yl)oxy)phenyl)-5-oxo-4,5-dihydro-1,2,4-oxadiazole-3-carboxamide; and 6-amino-2-(3,5-dichloro-4-((1-isopropyl-6-oxo-1,6-dihydropyridin-3-yl)oxy)phenyl)-1,2,4-triazine-3,5(2H,4H)-dione;

6-amino-2-(3,5-dichloro-4-((5-(1-cyclopropylethyl)-6-oxo-1,6-dihydropyridin-3-yl)oxy)phenyl)-1,2,4-triazine-3,5(2H,4H)-dione;

6-amino-2-(3,5-dichloro-4-((5-(isopropyl(methyl)amino)-6-oxo-1,6-dihydropyridin-3-yl)oxy)phenyl)-1,2,4-triazine-3,5(2H,4H)-dione;

6-amino-2-(3,5-dichloro-4-((5-(dimethylamino)-6-oxo-1,6-dihydropyridin-3-yl)oxy)phenyl)-1,2,4-triazine-3,5(2H,4H)-dione;

6-amino-2-(3,5-dichloro-4-((5-isopropyl-1-methyl-6-oxo-1,6-dihydropyridin-3-yl)oxy)phenyl)-1,2,4-triazine-3,5(2H,4H)-dione;

6-amino-2-(3,5-dichloro-4-((4-fluoro-5-isopropyl-6-oxo-1,6-dihydropyridin-3-yl)oxy)phenyl)-1,2,4-triazine-3,5(2H,4H)-dione;

6-amino-2-(3,5-dichloro-4-((5-isopropyl-4-methyl-6-oxo-1,6-dihydropyridin-3-yl)oxy)phenyl)-1,2,4-triazine-3,5(2H,4H)-dione;

6-amino-2-(3,5-dichloro-4-((1-isopropyl-5-methyl-6-oxo-1,6-dihydropyridin-3-yl)oxy)phenyl)-1,2,4-triazine-3,5(2H,4H)-dione;

6-amino-2-(3,5-dichloro-4-((5-ethyl-1-isopropyl-6-oxo-1,6-dihydropyridin-3-yl)oxy)phenyl)-1,2,4-triazine-3,5(2H,4H)-dione;

6-amino-2-(3,5-dichloro-4-((1-isopropyl-6-oxo-5-propyl-1,6-dihydropyridin-3-yl)oxy)phenyl)-1,2,4-triazine-3,5(2H,4H)-dione;

6-amino-2-(3,5-dichloro-4-((5-fluoro-1-isopropyl-6-oxo-1,6-dihydropyridin-3-yl)oxy)phenyl)-1,2,4-triazine-3,5(2H,4H)-dione;

6-amino-2-(3,5-dichloro-4-((5-chloro-1-isopropyl-6-oxo-1,6-dihydropyridin-3-yl)oxy)phenyl)-1,2,4-triazine-3,5(2H,4H)-dione;

6-amino-2-(3,5-dichloro-4-((5-cyclobutyl-6-oxo-1,6-dihydropyridin-3-yl)oxy)phenyl)-1,2,4-triazine-3,5(2H,4H)-dione;

6-amino-2-(3,5-dichloro-4-((5-cyclopentyl-6-oxo-1,6-dihydropyridin-3-yl)oxy)phenyl)-1,2,4-triazine-3,5(2H,4H)-dione;

5-(4-(6-amino-3,5-dioxo-4,5-dihydro-1,2,4-triazin-2(3H)-yl)-2,6-dichlorophenoxy)-N-methyl-2-oxo-1,2-dihydropyridine-3-carboxamide;

5-(4-(6-amino-3,5-dioxo-4,5-dihydro-1,2,4-triazin-2(3H)-yl)-2,6-dichlorophenoxy)-N-(3,3-difluorocyclobutyl)-2-oxo-1,2-dihydropyridine-3-carboxamide;

N-(3,5-dichloro-4-((5-(methylcarbamoyl)-6-oxo-1,6-dihydropyridin-3-yl)oxy)phenyl)-5-oxo-4,5-dihydro-1,2,4-oxadiazole-3-carboxamide;

N-(3,5-dichloro-4-((5-((3,3-difluorocyclobutyl)carbamoyl)-6-oxo-1,6-dihydropyridin-3-yl)oxy)phenyl)-5-oxo-4,5-dihydro-1,2,4-oxadiazole-3-carboxamide;

6-amino-2-(3,5-dichloro-4-((1-cyclobutyl-6-oxo-1,6-dihydropyridin-3-yl)oxy)phenyl)-1,2,4-triazine-3,5(2H,4H)-dione;

6-amino-2-(3,5-dichloro-4-((1-cyclopropyl-6-oxo-1,6-dihydropyridin-3-yl)oxy)phenyl)-1,2,4-triazine-3,5(2H,4H)-dione;

6-amino-2-(3,5-dichloro-4-((6-oxo-1-(1,1,1-trifluoropropan-2-yl)-1,6-dihydropyridin-3-yl)oxy)phenyl)-1,2,4-triazine-3,5(2H,4H)-dione;

2-(3,5-dichloro-4-((3-methyl-5-oxo-1,2,3,5-tetrahydroindolizin-8-yl)oxy)phenyl)-3,5-dioxo-2,3,4,5-tetrahydro-1,2,4-triazine-6-carbonitrile;

6-amino-2-(3,5-dichloro-4-((3-methyl-5-oxo-1,2,3,5-tetrahydroindolizin-8-yl)oxy)phenyl)-1,2,4-triazine-3,5(2H,4H)-dione;

(S)-6-amino-2-(3,5-dichloro-4-((3-methyl-5-oxo-1,2,3,5-tetrahydroindolizin-8-yl)oxy)phenyl)-1,2,4-triazine-3,5(2H,4H)-dione;

(R)-6-amino-2-(3,5-dichloro-4-((3-methyl-5-oxo-1,2,3,5-tetrahydroindolizin-8-yl)oxy)phenyl)-1,2,4-triazine-3,5(2H,4H)-dione; and 6-amino-2-(3,5-dichloro-4-((6-oxo-5-(2-oxopyrrolidin-1-yl)-1,6-dihydropyridin-3-yl)oxy)phenyl)-1,2,4-triazine-3,5(2H,4H)-dione;

or a stereoisomer or a tautomer thereof, or a pharmaceutically acceptable salt thereof.

Embodiment 54. A pharmaceutical composition comprising the compound of any one of embodiments 1-52, or the stereoisomer or the tautomer thereof, or the pharmaceutically acceptable salt thereof, and at least one pharmaceutically acceptable excipient.

Embodiment 55. A method of treating a disorder or disease in a subject in need thereof, the method comprising administering to the subject a therapeutically effective amount of the compound of any one of embodiments 1-53, or the stereoisomer or the tautomer thereof, or the pharmaceutically acceptable salt thereof, or a therapeutically effective amount of the pharmaceutical composition of embodiment 54, wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 56. Use of the compound of any one of embodiments 1-53, or the stereoisomer or the tautomer thereof, or the pharmaceutically acceptable salt thereof, for the manufacture of a medicament for the treatment of a disorder or disease selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 57. A compound of any one of embodiments 1-53, or the stereoisomer or the tautomer thereof, or the pharmaceutically acceptable salt thereof, for use in treating a disorder or disease selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 58. A composition of embodiment 54 for use in treating a disorder or disease selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 59. A method of treating a thyroid hormone receptor related disorder in a patient, the method comprising the steps of:

identifying a patient in need of treatment for the thyroid hormone receptor related disorder, and administering to the patient, or contacting the patient with, the compound of any one of embodiments 1-53, or the stereoisomer or the tautomer thereof, or the pharmaceutically acceptable salt thereof, or a therapeutically effective amount of the pharmaceutical composition of embodiment 54.

Embodiment 60. The method of embodiment 59, wherein the thyroid hormone receptor related disorder is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 61. A method of selectively modulating the activity of a thyroid hormone receptor beta (THR-β) comprising contacting the compound of any one of embodiments 1-53, or the stereoisomer or the tautomer thereof, or the pharmaceutically acceptable salt thereof, with the thyroid hormone receptor.

Embodiment 62. The method of embodiment 61, wherein the contacting is in vitro or ex vivo.

Embodiment 63. The method of embodiment 61, wherein the contacting is in vivo.

Embodiment 64. A compound of any one of embodiments 1-53, or the stereoisomer or the tautomer thereof, or the pharmaceutically acceptable salt thereof, for use in selectively modulating the activity of a thyroid hormone receptor beta (THR-β).

Embodiment 65. A composition of embodiment 54 for use in selectively modulating the activity of a thyroid hormone receptor beta (THR-β).

Embodiment 66. The method of embodiments 55, 59, or 60, wherein the compound of any one of embodiments 1-53 or the stereoisomer or the tautomer thereof, or the pharmaceutically acceptable salt thereof, or a therapeutically effective amount of the pharmaceutical composition of embodiment 54, is administered in combination with a KHK inhibitor, an FXR agonist, a SSAO inhibitor, a FASN inhibitor, or a SCD1 modulator Embodiment 67. The method of embodiment 66, wherein the KHK inhibitor is PF-06835919; the FXR agonist is TERN-101 (LY2562175), Tropifexor, obeticholic acid (OCA), or ASC42; the SSAO inhibitor is TERN-201; the FASN inhibitor is ASC40; and the SCD1 modulator is aramchol.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

What is claimed is:

1. A compound of Formula I":

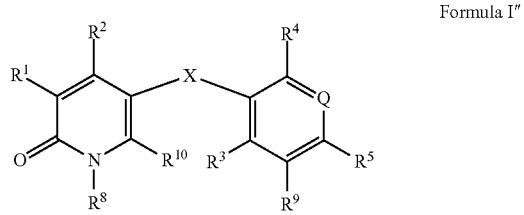

or a stereoisomer or a tautomer thereof, or a pharmaceutically acceptable salt thereof, wherein $R^1$ and $R^2$ are each independently selected from H, halogen, —$NR^aR^b$, —$C(O)NR^aR^b$, optionally substituted $C_1$-$C_6$ alkyl, optionally substituted $C_3$-$C_6$ cycloalkyl, and an optionally substituted non-aromatic bicyclic ring, wherein $R^1$ and $R^2$ cannot both be H; or $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

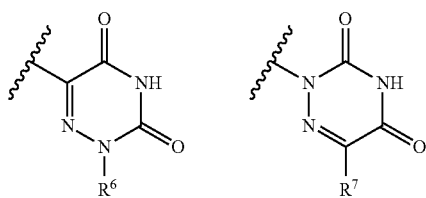

-continued $R^6$ is H or $C_1$-$C_3$ alkyl;

$R^7$ is selected from H, —CN, CH₃, and —NH₂;

$R^8$ is H, $C_1$-$C_3$ alkyl optionally substituted with 1-5 halogens, or $C_3$-$C_6$ cycloalkyl optionally substituted with 1-6 halogens;

$R^9$ is selected from H, halogen, —CN, optionally substituted $C_1$-$C_3$ alkyl, and optionally substituted $C_1$-$C_2$ alkoxy; or $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

$R^{10}$ is selected from H, halogen, or optionally substituted $C_1$-$C_3$ alkyl, or $R^8$ and $R^{10}$ together with the atoms to which they are attached form 4- to 6-membered cyclic ring optionally substituted with 1 to 3 substituents independently selected from $C_1$-$C_3$ alkyl and halogen;

$R^a$ and $R^b$ are each independently selected from H, optionally substituted $C_1$-$C_6$ alkyl and optionally substituted $C_3$-$C_6$ cycloalkyl; or $R^a$ and $R^b$ together with the nitrogen atom to which they are attached form a 4- to 6-membered cyclic ring optionally substituted with 1 to 3 substituents independently selected from $C_1$-$C_3$ alkyl, halogen, and =O;

Q) is selected from N, CH, and CF; and

X is O or $CH_2$;

wherein 0 to 10 hydrogen atoms that are attached to one or more carbon atoms are replaced with deuterium atom(s);

with the proviso that when $R^1$ and $R^2$ are each independently selected from H, halogen, optionally substituted $C_1$-$C_6$ alkyl, optionally substituted $C_3$-$C_6$ cycloalkyl, and an optionally substituted non-aromatic bicyclic ring; or when $R^1$ and $R^2$ together with the carbon atoms to which they are attached form a 4-membered monocyclic ring optionally substituted with 1 to 3 substituents independently selected from halogen and $C_1$-$C_6$ alkyl; then $R^7$ is H or —NH₂.

2. A compound of Formula IA":

Formula IA"

or a stereoisomer or a tautomer thereof, or a pharmaceutically acceptable salt thereof, wherein $R^1$ and $R^2$ are each independently selected from H, halogen, —NR$^a$R$^b$, —C(O)NR$^a$R$^b$, optionally substituted $C_1$-$C_6$ alkyl, optionally substituted $C_3$-$C_6$ cycloalkyl, and an optionally substituted non-aromatic bicyclic ring; or $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl; or $R^1$ and $R^2$ together with the carbon atoms to which they are attached form a polycyclic ring optionally substituted with 1 to 3 substituents independently selected from halogen and $C_1$-$C_6$ alkyl;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

$R^6$ is H or $C_1$-$C_3$ alkyl;

$R^7$ is selected from H, —CN, CH₃, and —NH₂;

$R^8$ is $C_1$-$C_3$ alkyl optionally substituted with 1-5 halogens or optionally substituted $C_3$-$C_5$ cycloalkyl, or $C_3$-$C_6$ cycloalkyl optionally substituted with 1-6 halogens;

$R^9$ is selected from H, halogen, —CN, optionally substituted $C_1$-$C_3$ alkyl, and optionally substituted $C_1$-$C_2$ alkoxy; or $R^3$ and $R^9$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;

$R^{10}$ is selected from H, halogen, and optionally substituted $C_1$-$C_3$ alkyl, or $R^8$ and $R^{10}$ together with the atoms to which they are attached form 4- to 6-membered cyclic ring optionally substituted with 1 to 3 substituents independently selected from $C_1$-$C_3$ alkyl and halogen;

$R^a$ and $R^b$ are each independently selected from H, optionally substituted $C_1$-$C_6$ alkyl and optionally substituted $C_3$-$C_6$ cycloalkyl; or $R^a$ and $R^b$ together with the nitrogen atom to which they are attached form a 4- to 6-membered cyclic ring optionally substituted with 1 to 3 substituents independently selected from $C_1$-$C_3$ alkyl, halogen, and =O;

Q) is selected from N, CH, and CF; and

X is O or $CH_2$;

wherein 0 to 10 hydrogen atoms that are attached to one or more carbon atoms are replaced with deuterium atom(s);

with the proviso that the compound is not:
2-(3,5-dichloro-4-((1-isopropyl-6-oxo-1,6-dihydropyridin-3-yl)oxy)phenyl)-1,2,4-triazine-3,5(2H,4H)-dione;
2-(3,5-dichloro-4-((1-isopropyl-6-oxo-1,6-dihydropyridin-3-yl)oxy)phenyl)-3,5-dioxo-2,3,4,5-tetrahydro-1,2,4-triazine-6-carbonitrile; or
2-(3,5-dichloro-4-((1-cyclopropyl-6-oxo-1,6-dihydropyridin-3-yl)oxy)phenyl)-3,5-dioxo-2,3,4,5-tetrahydro-1,2,4-triazine-6-carbonitrile.

3. The compound of claim 1, or the stereoisomer or the tautomer thereof, or the pharmaceutically acceptable salt thereof, wherein $R^8$ is H.

4. The compound of claim 1, or the stereoisomer or the tautomer thereof, or the pharmaceutically acceptable salt thereof, wherein $R^8$ is $C_1$-$C_3$ alkyl optionally substituted with 1-5 halogens, or $C_3$-$C_6$ cycloalkyl optionally substituted with 1-6 halogens.

5. The compound of claim 2, or the stereoisomer or the tautomer thereof, wherein $R^8$ and $R^{10}$ together with the atoms to which they are attached form 4- to 6-membered cyclic ring optionally substituted with 1 to 3 substituents independently selected from $C_1$-$C_3$ alkyl and halogen.

6. The compound of claim 1, or the stereoisomer or the tautomer thereof, or the pharmaceutically acceptable salt thereof, wherein $R^1$ and $R^2$ are each independently selected from H, halogen, —$NR^aR^b$, optionally substituted $C_1$-$C_6$ alkyl, optionally substituted $C_3$-$C_6$ cycloalkyl, and an optionally substituted non-aromatic bicyclic ring.

7. The compound of claim 1, or the stereoisomer or the tautomer thereof, or the pharmaceutically acceptable salt thereof, wherein $R^1$ is independently selected from H, halogen, —$NR^aR^b$, —$C(O)NR^aR^b$, $C_1$-$C_6$ alkyl optionally substituted with 1-6 substituents independently selected from halogen and $C_3$-$C_4$ cycloalkyl optionally substituted with 1-6 halogens, $C_3$-$C_6$ cycloalkyl optionally substituted with 1-6 halogens, and an non-aromatic bicyclic ring optionally substituted with 1-6 halogens.

8. The compound of claim 1, or the stereoisomer or the tautomer thereof, or the pharmaceutically acceptable salt thereof, wherein $R^2$ is independently selected from H, halogen, $C_1$-$C_6$ alkyl optionally substituted with 1-6 substituents independently selected from halogen and $C_3$-$C_4$ cycloalkyl, $C_3$-$C_6$ cycloalkyl optionally substituted with 1-6 halogens, and a non-aromatic bicyclic ring optionally substituted with 1-6 halogens.

9. The compound of claim 1, or the stereoisomer or the tautomer thereof, or the pharmaceutically acceptable salt thereof, wherein $R^1$ and $R^2$ together with the carbon atoms to which they are attached form a 4- to 7-membered monocyclic ring optionally containing 1 or 2 ring heteroatoms independently selected from N, O, and S, and wherein the monocyclic ring is optionally substituted with 1 to 3 substituents independently selected from halogen and $C_1$-$C_6$ alkyl.

10. The compound of claim 1, or the stereoisomer or the tautomer thereof, or the pharmaceutically acceptable salt thereof, wherein $R^3$ and $R^4$ are each independently selected from halogen and $C_1$-$C_3$ alkyl.

11. The compound of claim 1, or the stereoisomer or the tautomer thereof, or the pharmaceutically acceptable salt thereof, wherein $R^9$ is H.

12. The compound of claim 1, or the stereoisomer or the tautomer thereof, or the pharmaceutically acceptable salt thereof, wherein $R^5$ is

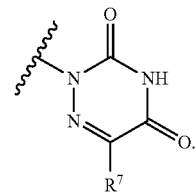

13. The compound of claim 1, or the stereoisomer or the tautomer thereof, or the pharmaceutically acceptable salt thereof, wherein $R^7$ is H or —$NH_2$.

14. The compound of claim 1, or the stereoisomer or the tautomer thereof, or the pharmaceutically acceptable salt thereof, wherein $R^5$ is

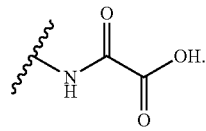

15. The compound of claim 1, or the stereoisomer or the tautomer thereof, or the pharmaceutically acceptable salt thereof, wherein $R^5$ is

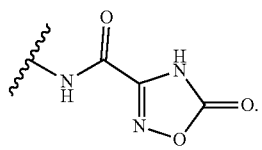 [SMILES: *NC(=O)c1noc(=O)[nH]1]

16. The compound of claim 2, or the stereoisomer or the tautomer thereof, or the pharmaceutically acceptable salt thereof, wherein $R^1$ and $R^2$ are H;

R⁵ is

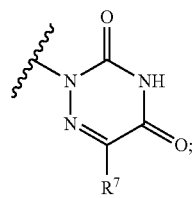

R⁷ is —NH₂; and
R⁸ is isopropyl, optionally substituted with 1-5 halogens.

17. The compound of claim 1, or the stereoisomer or the tautomer thereof, or the pharmaceutically acceptable salt thereof, wherein Q is CH.

18. A compound selected from the group consisting of:
6-amino-2-(3,5-dichloro-4-((7-methyl-1-oxo-2,5,6,7-tetrahydro-1H-cyclopenta[c]pyridin-4-yl)oxy)phenyl)-1,2,4-triazine-3,5(2H,4H)-dione;
6-amino-2-(4-chloro-5-((7-methyl-1-oxo-2,5,6,7-tetrahydro-1H-cyclopenta[c]pyridin-4-yl)oxy)bicyclo[4.2.0]octa-1,3,5-trien-2-yl)-1,2,4-triazine-3,5(2H,4H)-dione;
2-((4-chloro-5-((7-methyl-1-oxo-2,5,6,7-tetrahydro-1H-cyclopenta[c]pyridin-4-yl)oxy)bicyclo[4.2.0]octa-1,3,5-trien-2-yl)amino)-2-oxoacetic acid;
2-((7-((7-cyclopropyl-1-oxo-2,5,6,7-tetrahydro-1H-cyclopenta[c]pyridin-4-yl)oxy)-6-methyl-2,3-dihydro-1H-inden-4-yl)amino)-2-oxoacetic acid;
6-amino-2-(3,5-dichloro-4-((5-isopropyl-6-oxo-1,6-dihydropyridin-3-yl)oxy)phenyl)-1,2,4-triazine-3,5(2H,4H)-dione;
2-(3,5-dichloro-4-((7-methyl-1-oxo-2,5,6,7-tetrahydro-1H-cyclopenta[c]pyridin-4-yl)oxy)phenyl)-3,5-dioxo-2,3,4,5-tetrahydro-1,2,4-triazine-6-carbonitrile;
6-(3,5-dichloro-4-((5-isopropyl-6-oxo-1,6-dihydropyridin-3-yl)oxy)phenyl)-2-methyl-1,2,4-triazine-3,5(2H,4H)-dione;
6-amino-2-(3,5-dichloro-4-((5-(1-cyclopropylethyl)-6-hydroxypyridin-3-yl)oxy)phenyl)-1,2,4-triazine-3,5(2H,4H)-dione;
6-amino-2-(3,5-dichloro-4-((5-(1-(3,3-difluorocyclobutyl)ethyl)-6-hydroxypyridin-3-yl)oxy)phenyl)-1,2,4-triazine-3,5(2H,4H)-dione;
6-amino-2-(4-((5-(1-(bicyclo[1.1.1]pentan-2-yl)ethyl)-6-hydroxypyridin-3-yl)oxy)-3,5-dichlorophenyl)-1,2,4-triazine-3,5(2H,4H)-dione;
6-amino-2-(3,5-dichloro-4-((5-(6,6-difluorospiro[3.3]heptan-1-yl)-6-hydroxypyridin-3-yl)oxy)phenyl)-1,2,4-triazine-3,5(2H,4H)-dione;
6-amino-2-(3,5-dichloro-4-((6-hydroxy-5-(spiro[2.3]hexan-4-yl)pyridin-3-yl)oxy)phenyl)-1,2,4-triazine-3,5(2H,4H)-dione;
6-amino-2-(4-chloro-5-((6-hydroxy-5-isopropylpyridin-3-yl)oxy)-6-methylpyridin-2-yl)-1,2,4-triazine-3,5(2H,4H)-dione;
6-amino-2-(3,5-dichloro-4-((5-(1-cyclopropylethyl)-6-hydroxypyridin-3-yl)oxy)phenyl-2-d)-1,2,4-triazine-3,5(2H,4H)-dione;
6-amino-2-(3,5-dichloro-4-((6-hydroxy-5-isopropylpyridin-3-yl)oxy)phenyl-2-d)-1,2,4-triazine-3,5(2H,4H)-dione;
6-amino-2-(3,5-dichloro-4-((5-(1-cyclopropylethyl)-6-hydroxypyridin-3-yl)oxy)-2-fluorophenyl)-1,2,4-triazine-3,5(2H,4H)-dione;
6-amino-2-(3,5-dichloro-4-((8-methyl-1-oxo-1,2,5,6,7,8-hexahydro-5,8-ethanoisoquinolin-4-yl)oxy)phenyl)-1,2,4-triazine-3,5(2H,4H)-dione;
6-amino-2-(3,5-dichloro-4-((8-methyl-1-oxo-1,2,5,6,7,8-hexahydro-5,7-methanoisoquinolin-4-yl)oxy)phenyl)-1,2,4-triazine-3,5(2H,4H)-dione;
6-amino-2-(3,5-dichloro-4-((1-oxo-1,2,5,5a,6,6a-hexahydrocyclopropa[4,5]cyclopenta[1,2-c]pyridin-4-yl)oxy)phenyl)-1,2,4-triazine-3,5(2H,4H)-dione;
6-amino-2-(4-((5-isopropyl-6-oxo-1,6-dihydropyridin-3-yl)oxy)-3,5-dimethylphenyl)-1,2,4-triazine-3,5(2H,4H)-dione;
6-amino-2-(4-((5-isopropyl-6-oxo-1,6-dihydropyridin-3-yl)methyl)-3,5-dimethylphenyl)-1,2,4-triazine-3,5(2H,4H)-dione;
2-(3,5-dichloro-4-((5-isopropyl-6-oxo-1,6-dihydropyridin-3-yl)oxy)phenyl)-1,2,4-triazine-3,5(2H,4H)-dione;
2-(4-((5-isopropyl-6-oxo-1,6-dihydropyridin-3-yl)methyl)-3,5-dimethylphenyl)-1,2,4-triazine-3,5(2H,4H)-dione;
2-((3,5-dichloro-4-((5-isopropyl-6-oxo-1,6-dihydropyridin-3-yl)oxy)phenyl)amino)-2-oxoacetic acid;
N-(3,5-dichloro-4-((5-isopropyl-6-oxo-1,6-dihydropyridin-3-yl)oxy)phenyl)-5-oxo-4,5-dihydro-1,2,4-oxadiazole-3-carboxamide;
N-(3,5-dichloro-4-((1-isopropyl-6-oxo-1,6-dihydropyridin-3-yl)oxy)phenyl)-5-oxo-4,5-dihydro-1,2,4-oxadiazole-3-carboxamide; and
6-amino-2-(3,5-dichloro-4-((1-isopropyl-6-oxo-1,6-dihydropyridin-3-yl)oxy)phenyl)-1,2,4-triazine-3,5(2H,4H)-dione;
6-amino-2-(3,5-dichloro-4-((5-(1-cyclopropylethyl)-6-oxo-1,6-dihydropyridin-3-yl)oxy)phenyl)-1,2,4-triazine-3,5(2H,4H)-dione;
6-amino-2-(3,5-dichloro-4-((5-(isopropyl(methyl)amino)-6-oxo-1,6-dihydropyridin-3-yl)oxy)phenyl)-1,2,4-triazine-3,5(2H,4H)-dione;
6-amino-2-(3,5-dichloro-4-((5-(dimethylamino)-6-oxo-1,6-dihydropyridin-3-yl)oxy)phenyl)-1,2,4-triazine-3,5(2H,4H)-dione;
6-amino-2-(3,5-dichloro-4-((5-isopropyl-1-methyl-6-oxo-1,6-dihydropyridin-3-yl)oxy)phenyl)-1,2,4-triazine-3,5(2H,4H)-dione;
6-amino-2-(3,5-dichloro-4-((4-fluoro-5-isopropyl-6-oxo-1,6-dihydropyridin-3-yl)oxy)phenyl)-1,2,4-triazine-3,5(2H,4H)-dione;
6-amino-2-(3,5-dichloro-4-((5-isopropyl-4-methyl-6-oxo-1,6-dihydropyridin-3-yl)oxy)phenyl)-1,2,4-triazine-3,5(2H,4H)-dione;
6-amino-2-(3,5-dichloro-4-((1-isopropyl-5-methyl-6-oxo-1,6-dihydropyridin-3-yl)oxy)phenyl)-1,2,4-triazine-3,5(2H,4H)-dione;
6-amino-2-(3,5-dichloro-4-((5-ethyl-1-isopropyl-6-oxo-1,6-dihydropyridin-3-yl)oxy)phenyl)-1,2,4-triazine-3,5(2H,4H)-dione;
6-amino-2-(3,5-dichloro-4-((1-isopropyl-6-oxo-5-propyl-1,6-dihydropyridin-3-yl)oxy)phenyl)-1,2,4-triazine-3,5(2H,4H)-dione;
6-amino-2-(3,5-dichloro-4-((5-fluoro-1-isopropyl-6-oxo-1,6-dihydropyridin-3-yl)oxy)phenyl)-1,2,4-triazine-3,5(2H,4H)-dione;
6-amino-2-(3,5-dichloro-4-((5-chloro-1-isopropyl-6-oxo-1,6-dihydropyridin-3-yl)oxy)phenyl)-1,2,4-triazine-3,5(2H,4H)-dione;
6-amino-2-(3,5-dichloro-4-((5-cyclobutyl-6-oxo-1,6-dihydropyridin-3-yl)oxy)phenyl)-1,2,4-triazine-3,5(2H,4H)-dione;

6-amino-2-(3,5-dichloro-4-((5-cyclopentyl-6-oxo-1,6-dihydropyridin-3-yl)oxy)phenyl)-1,2,4-triazine-3,5(2H,4H)-dione;

5-(4-(6-amino-3,5-dioxo-4,5-dihydro-1,2,4-triazin-2 (3H)-yl)-2,6-dichlorophenoxy)-N-methyl-2-oxo-1,2-dihydropyridine-3-carboxamide;

5-(4-(6-amino-3,5-dioxo-4,5-dihydro-1,2,4-triazin-2 (3H)-yl)-2,6-dichlorophenoxy)-N-(3,3-difluorocyclobutyl)-2-oxo-1,2-dihydropyridine-3-carboxamide;

N-(3,5-dichloro-4-((5-(methylcarbamoyl)-6-oxo-1,6-dihydropyridin-3-yl)oxy)phenyl)-5-oxo-4,5-dihydro-1,2,4-oxadiazole-3-carboxamide;

N-(3,5-dichloro-4-((5-((3,3-difluorocyclobutyl)carbamoyl)-6-oxo-1,6-dihydropyridin-3-yl)oxy)phenyl)-5-oxo-4,5-dihydro-1,2,4-oxadiazole-3-carboxamide;

6-amino-2-(3,5-dichloro-4-((1-cyclobutyl-6-oxo-1,6-dihydropyridin-3-yl)oxy)phenyl)-1,2,4-triazine-3,5(2H,4H)-dione;

6-amino-2-(3,5-dichloro-4-((1-cyclopropyl-6-oxo-1,6-dihydropyridin-3-yl)oxy)phenyl)-1,2,4-triazine-3,5(2H,4H)-dione;

6-amino-2-(3,5-dichloro-4-((6-oxo-1-(1,1,1-trifluoropropan-2-yl)-1,6-dihydropyridin-3-yl)oxy)phenyl)-1,2,4-triazine-3,5(2H,4H)-dione;

2-(3,5-dichloro-4-((3-methyl-5-oxo-1,2,3,5-tetrahydroindolizin-8-yl)oxy)phenyl)-3,5-dioxo-2,3,4,5-tetrahydro-1,2,4-triazine-6-carbonitrile;

6-amino-2-(3,5-dichloro-4-((3-methyl-5-oxo-1,2,3,5-tetrahydroindolizin-8-yl)oxy)phenyl)-1,2,4-triazine-3,5 (2H,4H)-dione;

(S)-6-amino-2-(3,5-dichloro-4-((3-methyl-5-oxo-1,2,3,5-tetrahydroindolizin-8-yl)oxy)phenyl)-1,2,4-triazine-3,5(2H,4H)-dione;

(R)-6-amino-2-(3,5-dichloro-4-((3-methyl-5-oxo-1,2,3,5-tetrahydroindolizin-8-yl)oxy)phenyl)-1,2,4-triazine-3,5(2H,4H)-dione; and 6-amino-2-(3,5-dichloro-4-((6-oxo-5-(2-oxopyrrolidin-1-yl)-1,6-dihydropyridin-3-yl)oxy)phenyl)-1,2,4-triazine-3,5(2H,4H)-dione;

or a stereoisomer or a tautomer thereof, or a pharmaceutically acceptable salt thereof.

19. A pharmaceutical composition comprising the compound of claim 1, or the stereoisomer or the tautomer thereof, or the pharmaceutically acceptable salt thereof, and at least one pharmaceutically acceptable excipient.

* * * * *